（12）United States Patent
Tang et al.

(10) Patent No.: US 11,267,874 B2
(45) Date of Patent: Mar. 8, 2022

(54) SENSOR SYSTEMS FOR TARGET LIGANDS AND USES THEREOF

(71) Applicant: PRESIDENT AND FELLOWS OF HARVARD COLLEGE, Cambridge, MA (US)

(72) Inventors: Chung Yiu Jonathan Tang, Boston, MA (US); Constance Cepko, Newton, MA (US); Eugene Drokhlyansky, Westwood, MA (US); Sui Wang, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 54 days.

(21) Appl. No.: 15/566,798

(22) PCT Filed: Apr. 15, 2016

(86) PCT No.: PCT/US2016/027749
§ 371 (c)(1),
(2) Date: Oct. 16, 2017

(87) PCT Pub. No.: WO2016/168594
PCT Pub. Date: Oct. 20, 2016

(65) Prior Publication Data
US 2018/0118818 A1 May 3, 2018

Related U.S. Application Data

(60) Provisional application No. 62/148,595, filed on Apr. 16, 2015.

(51) Int. Cl.
| | | |
|---|---|---|
| *C12N 15/63* | (2006.01) | |
| *C07K 16/18* | (2006.01) | |
| *C07K 16/10* | (2006.01) | |
| *C07K 16/12* | (2006.01) | |
| *C12N 9/22* | (2006.01) | |
| *G01N 33/542* | (2006.01) | |
| *C12N 9/00* | (2006.01) | |
| *G01N 33/569* | (2006.01) | |
| *C12N 9/96* | (2006.01) | |
| *C12N 15/11* | (2006.01) | |
| *G01N 33/53* | (2006.01) | |
| *G01N 33/573* | (2006.01) | |
| *A61K 39/00* | (2006.01) | |
| *A61K 38/00* | (2006.01) | |

(52) U.S. Cl.
CPC .......... *C07K 16/18* (2013.01); *C07K 16/1063* (2013.01); *C07K 16/1232* (2013.01); *C12N 9/00* (2013.01); *C12N 9/22* (2013.01); *C12N 9/96* (2013.01); *C12N 15/11* (2013.01); *C12N 15/63* (2013.01); *G01N 33/5306* (2013.01); *G01N 33/542* (2013.01); *G01N 33/56916* (2013.01); *G01N 33/56966* (2013.01); *G01N 33/56983* (2013.01); *G01N 33/573* (2013.01); *A61K 38/00* (2013.01); *A61K 2039/505* (2013.01); *C07K 2317/22* (2013.01); *C07K 2317/565* (2013.01); *C07K 2317/567* (2013.01); *C07K 2317/569* (2013.01); *C07K 2317/70* (2013.01); *C07K 2317/77* (2013.01); *C07K 2317/92* (2013.01); *C07K 2317/94* (2013.01); *C07K 2319/00* (2013.01); *C07K 2319/33* (2013.01); *C07K 2319/43* (2013.01); *C07K 2319/55* (2013.01); *C07K 2319/60* (2013.01); *C12N 2310/20* (2017.05); *C12N 2750/14143* (2013.01)

(58) Field of Classification Search
CPC ........ C12N 2310/20; C12N 9/00; C12N 9/22; C12N 9/96; C12N 15/11; C12N 15/63; C07K 16/18; C07K 16/1063; C07K 16/1232; C07K 2317/22; C07K 2317/565; C07K 2317/567; C07K 2317/569; C07K 2317/77; C07K 2319/33; C07K 2319/43; C07K 2319/60; G01N 33/5306; G01N 33/542; G01N 33/56916; G01N 33/56966; G01N 33/56983; G01N 33/573; A61K 38/00
See application file for complete search history.

(56) References Cited

U.S. PATENT DOCUMENTS

| | | | |
|---|---|---|---|
| 2013/0230863 | A1 | 9/2013 | Tang et al. |
| 2014/0189896 | A1* | 7/2014 | Zhang ....................... C12N 9/22 800/18 |
| 2016/0264665 | A1* | 9/2016 | Lim ........................ C07K 19/00 |

OTHER PUBLICATIONS

Tang in "Co-opting Intracellular Proteins for Cell-Specific Gene Manipulation" (Harvard University Dissertation Nov. 2014; IDS reference). (Year: 2014).*
Tang, "Co-opting Intracellular Proteins for Cell-Specific Gene Manipulation", Harvard University: Dissertation (2014). Web. <URL: https://dash.harvard.edu/handle/1/14226052>.
Tang et al., "Detection and Manipulation of Live Antigen-Expressing Cells Using conditionally Stable Nanobodies", eLife 5:1-27 (2016).
Auslander et al. "A general design strategy for protein-responsive riboswitches in mammalian cells." Nat Methods 11(11): 1154-1160 (2014).
Banaszynski et al. "A rapid, reversible, and tunable method to regulate protein function in living cells using synthetic small molecules." Cell 126(5): 995-1004 (2006).

(Continued)

*Primary Examiner* — Catherine S Hibbert
(74) *Attorney, Agent, or Firm* — Nixon Peabody LLP; Mark J. Fitzgerald; Jeanne Jodoin

(57) ABSTRACT

Disclosed herein are sensor systems, compositions comprising the sensor systems, and methods of using the same. In particular aspects, disclosed herein are sensor systems for a target intracellular ligand and uses thereof, e.g., in detection assays or in cell manipulation or therapeutic applications.

16 Claims, 32 Drawing Sheets
Specification includes a Sequence Listing.

(56) References Cited

OTHER PUBLICATIONS

Feil et al. "Regulation of Cre recombinase activity by mutated estrogen receptor ligand-binding domains." Biochemical and Biophysical Research Communications 237(3): 752-757 (1997).
Irannejad et al. "Conformational biosensors reveal GPCR signalling from endosomes." Nature 495(7442): 534-538 (2013).
Kennedy et al. "Protein-responsive ribozyme switches in eukaryotic cells." Nucleic Acids Res 42(19): 12306-12321 (2014).
Kirchhofer et al. "Modulation of protein properties in living cells using nanobodies." Nat Strct Mol Biol 17(1): 133-138 (2010).
Oyen et al. "Mechanistic analysis of allosteric and non-allosteric effects arising from nanobody binding to two epitopes of the dihydrofolate reductase of *Escherichia coli*." Biochim Biophys Acta 1834(10): 2147-2157 (2013).
Rothbauer et al. "A versatile nanotrap for biochemical and functional studies with fluorescent fusion proteins." Mol Cell Proteomics 7(2): 282-289 (2008).
Rothbauer et al. "Targeting and tracing antigens in live cells with fluorescent nanobodies." Nat Methods 3(11): 887-889 (2006).
Saito et al. "Synthetic human cell fate regulation by protein-driven RNA switches." Nat Commun 2: 160 (2011).
Tang et al. "A nanobody-based system using fluorescent proteins as scaffolds for cell-specific gene manipulation." Cell 154(4): 928-939 (2013).
Tang et al. "Cell type-specific manipulation with GFP-dependent Cre recombinase." Nat. Neurosci. 18(9): 1334-1341 (2015).
Wurch et al. "Novel protein scaffolds as emerging therapeutic proteins: from discovery to clinical proof-of-concept." Trends Biotechnol 30(11): 575-582 (2012).

\* cited by examiner

A

B

5mPx330
(5' modified Px330)

C

D

5' to cas9

3 components
+ GFP 2 components
+ GFP

| | Position of dGBP1 mutation | | | | | |
|---|---|---|---|---|---|---|
| | A25V | E63V | S73R | C/S98Y | Q109H | S117F |
| Nbs with identical residue to GBP1, % (n) | 79 (60) | 1 (1) | 99 (75) | 100 (76) | 86 (65) | 100 (76) |

Total Nbs analyzed = 76. Conserved residue at C/S98Y position is C. For S73R position the lone mismatching Nb has a S→T difference.

B

| | Position of dGBP1 mutation | | | | | |
|---|---|---|---|---|---|---|
| | A25V | E63V | S73R | C/S98Y | Q109H | S117F |
| Nbs with residue position located outside Nb-antigen interface, % (n) | 100 (76) | 22 (17) | 100 (76) | 100 (76) | 99 (75) | 100 (76) |

Total Nbs analyzed = 76.

Figs. 19A-19B

Figs. 23A-23D
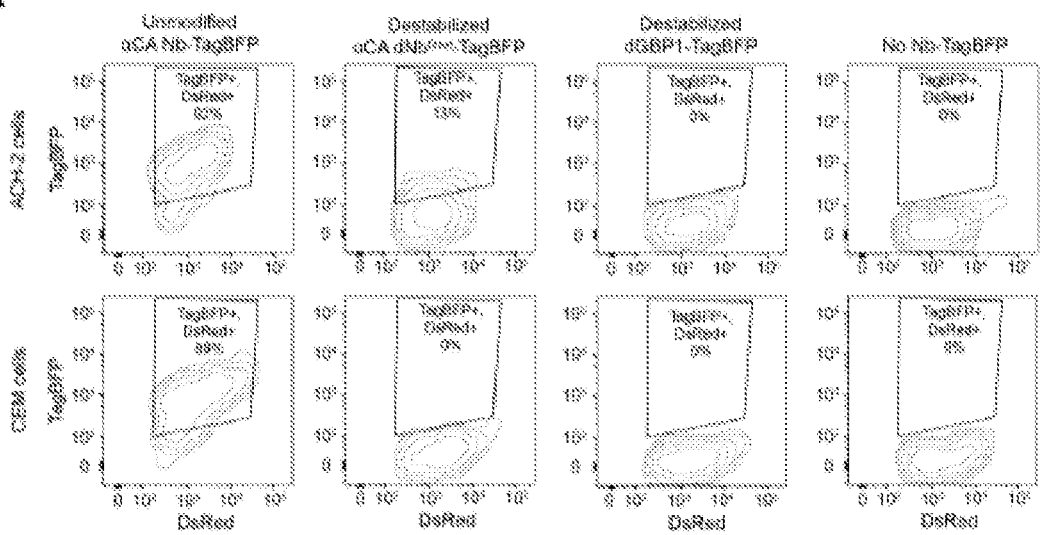
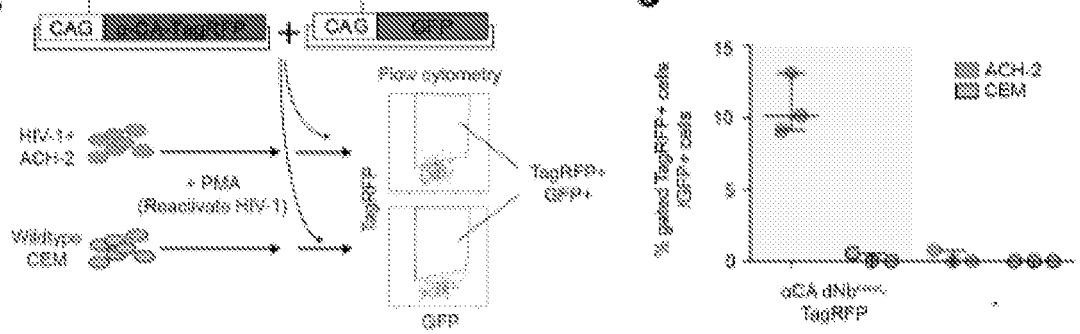
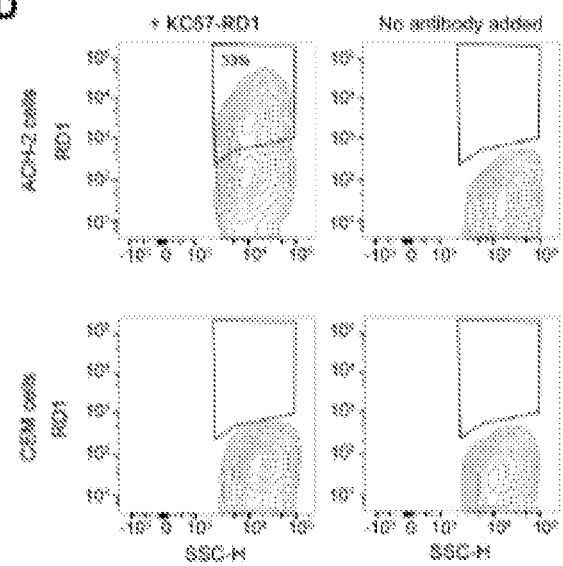

Fig. 24

| Nanobody PDB code | Species of origin | Tested Antigen | Antigen species/pathogen | Endogenous location of epitope |
|---|---|---|---|---|
| 3K1K | C. dromedarius | GFP | Aequorea victoria | Intracellular |
| | | YFP | Aequorea victoria | Intracellular |
| | | YFP-FLAG | Aequorea victoria | Intracellular |
| 2XV6 | V. pacos | Capsid protein p24 C-terminal domain, residues 278-352 of gag polyprotein | HIV-1 | Intracellular |
| | | Capsid protein p24 | HIV-1 | Intracellular |
| 4EIG | L. glama | Dihydrofolate reductase | Escherichia coli | Intracellular |
| 4TVS | V. pacos | Torsin-1A-interacting protein 1, UNP residues 356-583 | Homo sapiens | Intracellular |
| 4EIZ | L. glama | Dihydrofolate reductase | Escherichia coli | Intracellular |
| 4FHB | L. glama | Dihydrofolate reductase | Escherichia coli | Intracellular |
| 4QO1 | L. glama | Cellular tumor antigen p53 DBD, UNP residues 92-312 | Homo sapiens | Intracellular |
| 3K7U | L. glama | MP18 RNA editing protein | Trypanosoma brucei | Intracellular |
| 4GFT | L. glama | Myosin A tail domain interacting protein C-terminal domain, UNP residues 137-204 | Plasmodium falciparum | Intracellular |
| 4C57 | L. glama | Cyclin-G associated kinase, kinase domain residues 14-351 | Homo sapiens | Intracellular |

C. dro - Camelus dromedarius. L. glama - Lama glama. V. pacos - Vicugna pacos.

*Fig. 25*

|  | FR1 | CDR1 | FR2 | CDR2 |
|---|---|---|---|---|
| ChickenVH-PDBno-4P48 | ALTLDESGGGLQTPGGALSLVCKASGFTFSSYQMQWVRQAPGKGLEWVAGIQNDDT-GTY |
| ChickenVH-PDBno-4P49 | AVTLDESGGGLQTPGGALSLVCKASGFTFSSYAMGWVRQAPGKGLEWVAGISDDGDSYIS |
| CamelidVHH-PDBno-3K1K | DVQLVESGGALVQPGGSLRLSCAASGPPVNRYSMRWYRQAPGKEREWVAGMSSAGD-RSS |
| CamelidVHH-PDBno-2XT1 | QVQLVESGGGLVQAGGSLRLSCAASGSFFMSNVMAWYRQAPGKARELIAAIRGGDN-STV |
| HumanVH-PDBno-3B9V | EVQLVESGGGLVQPGGSLRLSCAASGFNIKDTYIGWVRRAPGKGEEWVASIYPTNG-YTR |
| HumanVH-PDBno-3EBL | EVQLVESGGGLVQPGGSLRLSCAASGFTFSSYAMGWVRQAPGKGFEWVSLISGSGG-STW |
| HumanVH-PDBno-1T2J | QVQLQESGGGLVQPGGSLRLSCAASGFTFSNSAMSWVRQAPGKGLEWVSSISGSGG-RTY |
| CamelidVHH-PDBno-4EIG | QVQLQESGGGSVQAGGSLRLSCAASGIIFSVYKMPWYRQAPGKERELVALIFT-NN-NYN |
| CamelidVHH-PDBno-3G9A | DVQLQESGGGSVQAGGSLRLSCAASGSFFSSYSNAWFRQAPGKECELVSNILR-DG-TTT |
| MouseVH-PDBno-3UMT | QVQLQQSGLELVKPGASVKISCKTSGYTFTEYTMHWVQSHRFKSLEWIGGINPNNG-GTS |
| MouseVH-PDBno-1QOK | QVKLQQSGAELVRSGTSVKLSCTASGPNIKDSYMHWLRQKPEQGLEWIGWIDPENG-DTE |

|  | 79 FR3 | 104 CDR3 |
|---|---|---|
| ChickenVH-PDBno-4P48 | YGAAVKGRATISRDNGQSTVRLQLNNLRAEDTGYYCANDASSDKGYQS-----------DGI |
| ChickenVH-PDBno-4P49 | YATAVKGRATISRDNGQSTVRLQLNNLRAEDTATYYCARSHCG-GCRNA--------ALI |
| CamelidVHH-PDBno-3K1K | YEDSVKGRFTISRDDARNTVYLQMNSLKPEDTAVYYCNVNV------------------GF |
| CamelidVHH-PDBno-2XT1 | YDDSVKGRFTISRDDDKNILYLQMNDLKPEDTAMYYCKASG------------------- |
| HumanVH-PDBno-3B9V | YADSVKGRFTISRDTSKNTAYLQMNSLRAEDTAVYYCARWGGDG-------------FYAM |
| HumanVH-PDBno-3EBL | YDDSVKGRFTISRDNSKNLLYLQMNSLRAEDTAVYYCANHAP-S-----------TEAP |
| HumanVH-PDBno-1T2J | SADSVKGRFTISRDNAKNSLYLQMNSLRAEDTAVYYCARDRY---------------GN |
| CamelidVHH-PDBno-4EIG | TVDSVKGRFTISRDNVQNTVYLEMNSLKPEDTAVYYCRANRGLA---------------GP |
| CamelidVHH-PDBno-3G9A | YAGSVKGRFTISRDDARNTVYLQMNVNLRSEDTARYYCAADSGTQLGYVGAVGLSCLDYYR |
| MouseVH-PDBno-3UMT | YNQKFKGKAILTVDKSSSTAYLELRSLTSEDSAVYYCARDD-RY-------------PANF |
| MouseVH-PDBno-1QOK | YAPKFQGKATFTTDTSSNTAYLQLSSLTSEDTAVYYCNEGTPTG-------------PYYF |

|  | CDR3 FR4 128 |
|---|---|
| ChickenVH-PDBno-4P48 | DAWGHGTEVIVSS |
| ChickenVH-PDBno-4P49 | DAWGHGTEVIVSS |
| CamelidVHH-PDBno-3K1K | EYWGQGTQVTVSS |
| CamelidVHH-PDBno-2XT1 | SSWGQGTQVTVSS |
| HumanVH-PDBno-3B9V | DYWGQGTLVTVSS |
| HumanVH-PDBno-3EBL | DYWGQGTLVTVSS |
| HumanVH-PDBno-1T2J | DYWGQGTTVTVSS |
| CamelidVHH-PDBno-4EIG | AYWGQGTQVTVSS |
| CamelidVHH-PDBno-3G9A | DYWGKGTQVTVSS |
| MouseVH-PDBno-3UMT | AYWGQGTTVTVSS |
| MouseVH-PDBno-1QOK | DYWGQGTTVTVSS |

SEQUENCE LISTING

```
<160> NUMBER OF SEQ ID NOS: 39

<210> SEQ ID NO 1
<211> LENGTH: 117
<212> TYPE: PRT
<213> ORGANISM: Unknown
<220> FEATURE:
<223> OTHER INFORMATION: Description of Unknown: Wild type GBP1 protein
      sequence

<400> SEQUENCE: 1

Met Ala Asp Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
            20                  25                  30

Arg Tyr Ser Met Arg Trp Tyr Arg Gln Ala Pro Gly Lys Glu Arg Glu
        35                  40                  45

Trp Val Ala Gly Met Ser Ser Ala Gly Asp Arg Ser Ser Tyr Glu Asp
    50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Ser Asn Val Asn Val Gly Phe Glu Tyr Trp Gly Gln Gly Thr Gln
                100                 105                 110

Val Thr Val Ser Ser
        115

<210> SEQ ID NO 2
<211> LENGTH: 115
<212> TYPE: PRT
<213> ORGANISM: Human immunodeficiency virus

<400> SEQUENCE: 2

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Ser Phe Phe Met
            20                  25                  30

Ser Asn Val Met Ala Trp Tyr Arg Gln Ala Pro Gly Lys Ala Arg Glu
        35                  40                  45

Leu Ile Ala Ala Ile Arg Gly Gly Asp Met Ser Thr Val Tyr Asp Asp
    50                  55                  60
```

Ser Val Lys Gly Arg Phe Thr Ile Thr Arg Asp Asp Lys Asn Ile
65                  70                  75                  80

Leu Tyr Leu Gln Met Asn Asp Leu Lys Pro Glu Asp Thr Ala Met Tyr
                85                  90                  95

Tyr Cys Lys Ala Ser Gly Ser Ser Trp Gly Gln Gly Thr Gln Val Thr
            100                 105                 110

Val Ser Ser
        115

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaccatcctc tagactgccg gatccgccac catggccgac gtgcagctcg tggaat      56

<210> SEQ ID NO 4
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgttctcctt aatcagctcg ctcatgcatg cagaactaac agtcacttgt gtgccc      56

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaccatcctc tagactgccg gatccgccac c                                 31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgttctcctt aatcagctcg ctcatgcatg c                                 31

<210> SEQ ID NO 7
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
ggaagtggca gtggtatggc gcaggtgcag ctggtggaaa gcggcggcgg cctggtgcag   60
gcgggcggca gcctgcgcct gagctgcgtg gcgagcggca gcttttttat gagcaacgtg  120

```
atggcgtggt atcgccaggc gccgggcaaa gcgcgcgaac tgattgcggc gattcgcggc    180
ggcgatatga gcaccgtgta tgtggatagc gtgaaaggcc gctttaccat tcgccgcgat    240
gatgataaaa acattctgta tctgcagatg aacgatctga accggaaga taccgcgatg     300 tattattata agcgagcgg cagcagctgg gccatggcc cccaggtgac cgtgagcttt      360
gcatgcatgg ctcaagtcca actcgtcgag tctggtggcg gactggtgca ggctggcgga    420
tctctgagac tgagctgtgt cgccagcggc agcttcttca tgtccaacgt catggcctgg    480
tacagacagg cccctggcaa ggccagagag ctgatcgctg ctatcagagg cggcgacatg    540
agcaccgtgt acgtcgacag cgtgaagggc agattcacca tccggaggga cgacgacaag    600
aacatcctgt acctgcaaat gaacgacctg aagcccgagg acaccgccat gtactactac    660
aaggcctccg gcagctcttg ggggcacgga acacaagtca cggtctcctt c             711
```

<210> SEQ ID NO 8
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
aatcactttt tttcaggttg gactcgagaa ttgtacaatg gactataagg accacgacg     59
```

<210> SEQ ID NO 9
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
cgtcgtggtc cttatagtcc attgtacaat tctcgagtcc aacctgaaaa aaagtgatt    59
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
ggaagtggca gtggtatggc gc                                              22
```

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
tccagaacca ctgccgaagg ag                                              22
```

<210> SEQ ID NO 12
<211> LENGTH: 38
<212> TYPE: DNA
<213> ORGANISM: Artificial Sequence
<220> FEATURE:

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
aattctcgag gccaccatgg cgcaggtgca gctggtgg          38

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
aatttgtaca gcatgcgaag gagaccgtga cttgtgtt          38

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gacctttggt cgcccggcct          20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gagttggcca ctccctctct gc          22

<210> SEQ ID NO 16
<211> LENGTH: 115
<212> TYPE: PRT
<213> ORGANISM: Camelus dromedarius
<220> FEATURE:
<221> NAME/KEY: MOD_RES
<222> LOCATION: (23)..(23)
<223> OTHER INFORMATION: Ala or Val
<220> FEATURE:
<221> NAME/KEY: MOD_RES
<222> LOCATION: (61)..(61)
<223> OTHER INFORMATION: Glu or Val
<220> FEATURE:
<221> NAME/KEY: MOD_RES
<222> LOCATION: (71)..(71)
<223> OTHER INFORMATION: Ser or Arg
<220> FEATURE:
<221> NAME/KEY: MOD_RES
<222> LOCATION: (96)..(96)
<223> OTHER INFORMATION: Ser or Tyr
<220> FEATURE:
<221> NAME/KEY: MOD_RES
<222> LOCATION: (107)..(107)
<223> OTHER INFORMATION: Gln or His
<220> FEATURE:
<221> NAME/KEY: MOD_RES
<222> LOCATION: (115)..(115)
<223> OTHER INFORMATION: Ser or Phe

<400> SEQUENCE: 16

Asp Val Gln Leu Val Glu Ser Gly Gly Ala Leu Val Gln Pro Gly Gly

```
1               5                   10                  15
Ser Leu Arg Leu Ser Cys Xaa Ala Ser Gly Phe Pro Val Asn Arg Tyr
            20                  25                  30

Ser Met Arg Trp Tyr Arg Gln Ala Pro Gly Lys Glu Arg Glu Trp Val
            35                  40                  45

Ala Gly Met Ser Ser Ala Gly Asp Arg Ser Ser Tyr Xaa Asp Ser Val
            50                  55                  60

Lys Gly Arg Phe Thr Ile Xaa Arg Asp Asp Ala Arg Asn Thr Val Tyr
 65                 70                  75                  80

Leu Gln Met Asn Ser Leu Lys Pro Glu Asp Thr Ala Val Tyr Tyr Xaa
            85                  90                  95

Asn Val Asn Val Gly Phe Glu Tyr Trp Gly Xaa Gly Thr Gln Val Thr
            100                 105                 110

Val Ser Xaa
            115
```

<210> SEQ ID NO 17
<211> LENGTH: 113
<212> TYPE: PRT
<213> ORGANISM: Vicugna pacos
<220> FEATURE:
<221> NAME/KEY: MOD_RES
<222> LOCATION: (23)..(23)
<223> OTHER INFORMATION: Ala or Val
<220> FEATURE:
<221> NAME/KEY: MOD_RES
<222> LOCATION: (61)..(61)
<223> OTHER INFORMATION: Asp or Val
<220> FEATURE:
<221> NAME/KEY: MOD_RES
<222> LOCATION: (71)..(71)
<223> OTHER INFORMATION: Thr or Arg
<220> FEATURE:
<221> NAME/KEY: MOD_RES
<222> LOCATION: (96)..(96)
<223> OTHER INFORMATION: Cys or Tyr
<220> FEATURE:
<221> NAME/KEY: MOD_RES
<222> LOCATION: (105)..(105)
<223> OTHER INFORMATION: Gln or His
<220> FEATURE:
<221> NAME/KEY: MOD_RES
<222> LOCATION: (113)..(113)
<223> OTHER INFORMATION: Ser or Phe

<400> SEQUENCE: 17

```
Gln Val Gln Leu Val Glu Ser Gly Gly Gly Leu Val Gln Ala Gly Gly
 1               5                   10                  15

Ser Leu Arg Leu Ser Cys Xaa Ala Ser Gly Ser Phe Phe Met Ser Asn
            20                  25                  30

Val Met Ala Trp Tyr Arg Gln Ala Pro Gly Lys Ala Arg Glu Leu Ile
            35                  40                  45

Ala Ala Ile Arg Gly Gly Asp Met Ser Thr Val Tyr Xaa Asp Ser Val
            50                  55                  60

Lys Gly Arg Phe Thr Ile Xaa Arg Asp Asp Lys Asn Ile Leu Tyr
 65                 70                  75                  80

Leu Gln Met Asn Asp Leu Lys Pro Glu Asp Thr Ala Met Tyr Tyr Xaa
            85                  90                  95

Lys Ala Ser Gly Ser Ser Trp Gly Xaa Gly Thr Gln Val Thr Val Ser
            100                 105                 110

Xaa
```

-continued

```
<210> SEQ ID NO 18
<211> LENGTH: 117
<212> TYPE: PRT
<213> ORGANISM: Lama glama
<220> FEATURE:
<221> NAME/KEY: MOD_RES
<222> LOCATION: (23)..(23)
<223> OTHER INFORMATION: Lys or Val
<220> FEATURE:
<221> NAME/KEY: MOD_RES
<222> LOCATION: (70)..(70)
<223> OTHER INFORMATION: Ser or Arg
<220> FEATURE:
<221> NAME/KEY: MOD_RES
<222> LOCATION: (95)..(95)
<223> OTHER INFORMATION: Cys or Tyr
<220> FEATURE:
<221> NAME/KEY: MOD_RES
<222> LOCATION: (109)..(109)
<223> OTHER INFORMATION: Gln or His
<220> FEATURE:
<221> NAME/KEY: MOD_RES
<222> LOCATION: (117)..(117)
<223> OTHER INFORMATION: Ser or Phe

<400> SEQUENCE: 18

Gln Val Gln Leu Gln Glu Ser Gly Gly Gly Leu Val Gln Ala Gly Gly
1               5                   10                  15

Ser Leu Arg Leu Ser Cys Xaa Ala Ser Gly Ile Ile Phe Ser Val Tyr
            20                  25                  30

Lys Met Thr Trp Tyr Arg Gln Ala Pro Gly Lys Glu Arg Glu Leu Val
        35                  40                  45

Ala Leu Ile Thr Thr Asn Asn Asn Thr Met Thr Val Asp Ser Val Lys
    50                  55                  60

Gly Arg Phe Thr Ile Xaa Arg Asp Asn Val Gln Asn Thr Val Tyr Leu
65                  70                  75                  80

Glu Met Asn Asn Leu Lys Pro Glu Asp Thr Ala Val Tyr Tyr Xaa Asn
                85                  90                  95

Ala Asn Arg Gly Leu Ala Gly Pro Ala Tyr Trp Gly Xaa Gly Thr Gln
            100                 105                 110

Val Thr Val Ser Xaa
        115

<210> SEQ ID NO 19
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Ser Phe Phe Met
            20                  25                  30

Ser Asn Val Met Ala Trp Tyr Arg Gln Ala Pro Gly Lys Ala Arg Glu
        35                  40                  45

Leu Ile Ala Ala Ile Arg Gly Gly Asp Met Ser Thr Val Tyr Asp Asp
    50                  55                  60

Ser Val Lys Gly Arg Phe Thr Ile Thr Arg Asp Asp Lys Asn Ile
65                  70                  75                  80

Leu Tyr Leu Gln Met Asn Asp Leu Lys Pro Glu Asp Thr Ala Met Tyr
                85                  90                  95
```

```
Tyr Cys Lys Ala Ser Gly Ser Ser Trp Gly Gln Gly Thr Gln Val Thr
                100                 105                 110

Val Ser Ser
        115

<210> SEQ ID NO 20
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Ala Asp Val Gln Leu Val Glu Ser Gly Gly Ala Leu Val Gln Pro
1               5                   10                  15

Gly Gly Ser Leu Arg Leu Ser Cys Ala Ala Ser Gly Phe Pro Val Asn
                20                  25                  30

Arg Tyr Ser Met Arg Trp Tyr Arg Gln Ala Pro Gly Lys Glu Arg Glu
            35                  40                  45

Trp Val Ala Gly Met Ser Ser Ala Gly Asp Arg Ser Ser Tyr Glu Asp
    50                  55                  60

Ser Val Lys Gly Arg Phe Thr Ile Ser Arg Asp Asp Ala Arg Asn Thr
65                  70                  75                  80

Val Tyr Leu Gln Met Asn Ser Leu Lys Pro Glu Asp Thr Ala Val Tyr
                85                  90                  95

Tyr Ser Asn Val Asn Val Gly Phe Glu Tyr Trp Gly Gln Gly Thr Gln
                100                 105                 110

Val Thr Val Ser Ser
        115

<210> SEQ ID NO 21
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Ala Gln Val Gln Leu Gln Glu Ser Gly Gly Gly Leu Val Gln Ala
1               5                   10                  15

Gly Ala Ser Leu Arg Leu Ser Cys Ala Ala Ser Glu Arg Leu Thr Val
                20                  25                  30

Asp Tyr Ala Ile Gly Trp Phe Arg Gln Ala Pro Gly Lys Glu Arg Glu
            35                  40                  45

Phe Val Ala Ala Ile Ser Trp Gly Gly Gly Leu Thr Val Tyr Gly Glu
    50                  55                  60

Ser Val Glu Gly Arg Phe Thr Ile Ser Arg Asp Ile Ala Lys Asn Thr
65                  70                  75                  80

Met Asn Leu Gln Met Asn Val Leu Arg Pro Glu Asp Thr Ala Asn Tyr
                85                  90                  95

Tyr Cys Ala Ala Ser Arg Ile Ser Tyr Arg Val Trp Asn Thr Ile Pro
                100                 105                 110

Tyr Asn Lys Leu Thr Leu Trp Gly Arg Gly Thr Gln Val Thr Val Ser
        115                 120                 125

Ser
```

<210> SEQ ID NO 22
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ala Gln Val Gln Leu Gln Glu Ser Gly Gly Gly Thr Val Gln Pro
1               5                   10                  15

Gly Gly Ser Leu Lys Leu Ser Cys Ser Ala Ala Pro Glu Arg Ala Phe
            20                  25                  30

Ser Asn Tyr Ala Met Gly Trp Phe Arg Gln Ala Pro Gly Gln Glu Arg
        35                  40                  45

Glu Phe Val Ala Gly Ile Thr Gly Ser Gly Arg Ser Gln Tyr Tyr Ala
    50                  55                  60

Asp Ser Val Lys Gly Arg Phe Thr Ile Ser Arg Asp Asn Ala Met Asn
65                  70                  75                  80

Ala Val Tyr Leu Gln Met Asn Ser Val Lys Ala Glu Asp Thr Ala Val
                85                  90                  95

Tyr Tyr Cys Ala Ala Arg Val Val Pro Val Phe Ser Asp Ser Thr Lys
            100                 105                 110

Gly Tyr Val Tyr Trp Gly Gln Gly Thr Gln Val Thr Val Ser Ser
        115                 120                 125

<210> SEQ ID NO 23
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Gln Val Gln Leu Val Glu Ser Gly Gly Gly Leu Val Gln Ala
1               5                   10                  15

Gly Gly Ser Leu Arg Leu Ser Cys Ala Ala Ser Gly Ser Ile Val Asn
            20                  25                  30

Phe Glu Thr Met Gly Trp Tyr Arg Gln Ala Pro Gly Lys Glu Arg Glu
        35                  40                  45

Leu Val Ala Thr Ile Thr Asn Glu Gly Ser Ser Asn Tyr Ala Asp Ser
    50                  55                  60

Val Lys Gly Arg Phe Thr Ile Ser Gly Asp Asn Ala Lys Asn Thr Val
65                  70                  75                  80

Ser Leu Gln Met Asn Ser Leu Lys Pro Glu Asp Thr Ala Val Tyr Tyr
                85                  90                  95

Cys Ser Ala Thr Phe Gly Ser Arg Trp Pro Tyr Ala His Ser Asp His
            100                 105                 110

Trp Gly Gln Gly Thr Gln Val Thr Val Ser Ser
        115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 24

Met Ala Val Gln Leu Val Glu Ser Gly Gly Gly Leu Val Gln Pro Gly
1               5                   10                  15

Gly Ser Leu Arg Leu His Cys Ala Ala Ser Gly Ser Ile Ala Ser Ile
            20                  25                  30

Tyr Arg Thr Cys Trp Tyr Arg Gln Gly Thr Gly Lys Gln Arg Glu Leu
        35                  40                  45

Val Ala Ala Ile Thr Ser Gly Gly Asn Thr Tyr Tyr Ala Asp Ser Val
    50                  55                  60

Lys Gly Arg Phe Thr Ile Ser Arg Asp Asn Ala Lys Asn Thr Ile Asp
65                  70                  75                  80

Leu Gln Met Asn Ser Leu Lys Pro Glu Asp Thr Ala Val Tyr Tyr Cys
                85                  90                  95

Asn Ala Asp Glu Ala Gly Ile Gly Phe Asn Asp Tyr Trp Gly Gln
            100                 105                 110

Gly Thr Gln Val Thr Val Ser Ser
        115                 120

<210> SEQ ID NO 25
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Ala Gln Val Gln Leu Val Glu Thr Gly Gly Gly Thr Val Gln Thr
1               5                   10                  15

Gly Gly Ser Leu Arg Leu Ser Cys Ser Ala Ser Gly Ser Phe Ser
            20                  25                  30

Arg Asn Ala Met Gly Trp Phe Arg Gln Ala Pro Gly Lys Glu Arg Glu
        35                  40                  45

Phe Val Ala Ala Ile Asn Trp Ser Ala Ser Thr Tyr Tyr Arg Asp
    50                  55                  60

Ser Val Lys Gly Arg Phe Thr Val Ser Arg Asp Asn Ala Lys Asn Thr
65                  70                  75                  80

Val Tyr Leu His Leu Asn Ser Leu Lys Leu Glu Asp Thr Ala Ala Tyr
                85                  90                  95

Tyr Cys Ala Gly Ser Ser Val Tyr Ala Glu Met Pro Tyr Ala Asp Ser
            100                 105                 110

Val Lys Ala Thr Ser Tyr Asn Tyr Trp Gly Gln Gly Thr Gln Val Thr
        115                 120                 125

Val Ser Ser
    130

<210> SEQ ID NO 26
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Gln Val Gln Leu Val Glu Ser Gly Gly Gly Leu Val Gln Ala
1               5                   10                  15

Gly Gly Ser Leu Ser Leu Ser Cys Ala Ala Ser Gly Gly Asp Phe Ser
```

```
            20                  25                  30
Arg Asn Ala Met Ala Trp Phe Arg Gln Ala Pro Gly Lys Glu Arg Glu
        35                  40                  45

Phe Val Ala Ser Ile Asn Trp Thr Gly Ser Gly Thr Tyr Tyr Leu Asp
    50                  55                  60

Ser Val Lys Gly Arg Phe Thr Ile Ser Arg Asp Asn Ala Lys Asn Ala
65                  70                  75                  80

Leu Tyr Leu Gln Met Asn Asn Leu Lys Pro Glu Asp Thr Ala Val Tyr
                85                  90                  95

Tyr Cys Ala Arg Ser Thr Val Phe Ala Glu Ile Thr Gly Leu Ala Gly
            100                 105                 110

Tyr Gln Ser Gly Ser Tyr Asp Tyr Trp Gly Gln Gly Thr Gln Val Thr
        115                 120                 125

Val Ser Ser
        130

<210> SEQ ID NO 27
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Ala Gln Val Gln Leu Val Glu Thr Gly Gly Gly Leu Val Gln Pro
1               5                   10                  15

Gly Gly Ser Leu Thr Leu Ser Cys Ala Gly Ser Gly Gly Thr Leu Glu
            20                  25                  30

His Tyr Ala Ile Gly Trp Phe Arg Gln Ala Pro Gly Lys Glu His Glu
        35                  40                  45

Trp Leu Val Cys Asn Arg Gly Glu Tyr Gly Ser Thr Val Tyr Val Asp
    50                  55                  60

Ser Val Lys Gly Arg Phe Thr Ala Ser Arg Asp Asn Ala Lys Asn Thr
65                  70                  75                  80

Val Tyr Leu Gln Leu Asn Ser Leu Lys Pro Asp Asp Thr Gly Ile Tyr
                85                  90                  95

Tyr Cys Val Ser Gly Cys Tyr Ser Trp Arg Gly Pro Trp Gly Gln Gly
            100                 105                 110

Thr Gln Val Thr Val Ser Ser
        115

<210> SEQ ID NO 28
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Ala Gln Val Gln Leu Gln Glu Ser Gly Gly Gly Leu Val Gln Pro
1               5                   10                  15

Gly Gly Ser Leu Arg Leu Ser Cys Ser Ala Ser Gly Phe Lys Phe Asn
            20                  25                  30

Asp Ser Tyr Met Ser Trp Val Arg Arg Val Pro Gly Lys Gly Leu Glu
        35                  40                  45

Trp Val Ala Gly Ile Trp Glu Asp Ser Ser Ala Ala His Tyr Arg Asp
```

```
                    50                  55                  60
Ser Val Lys Gly Arg Phe Thr Ile Ser Arg Asp Asn Ala Lys Asn Met
 65                  70                  75                  80

Leu Tyr Leu Gln Met Ser Ser Leu Lys Ser Asp Asp Thr Gly Leu Tyr
                     85                  90                  95

Tyr Cys Val Arg Arg Gly Tyr Ser Gly Asp Tyr Arg Pro Ile Asn Asn
                    100                 105                 110

Pro Ser Ser Gln Gly Thr Gln Val Thr Val Ser Ser
                    115                 120
```

<210> SEQ ID NO 29
<211> LENGTH: 124
<212> TYPE: PRT
<213> ORGANISM: Gallus gallus

<400> SEQUENCE: 29

```
Ala Leu Thr Leu Asp Glu Ser Gly Gly Leu Gln Thr Pro Gly Gly
 1               5                  10                  15

Ala Leu Ser Leu Val Cys Lys Ala Ser Gly Phe Thr Phe Ser Ser Tyr
                20                  25                  30

Gly Met Gln Trp Val Arg Gln Ala Pro Gly Lys Gly Leu Glu Trp Val
                 35                  40                  45

Ala Gly Ile Gln Asn Asp Asp Thr Gly Thr Tyr Tyr Gly Ala Ala Val
            50                  55                  60

Lys Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Tyr Cys
                     85                  90                  95

Ala Lys Asp Ala Ser Ser Asp Gly Gly Tyr Gly Gly Asp Ser Ile Asp
                    100                 105                 110

Ala Trp Gly His Gly Thr Glu Val Ile Val Ser Ser
                    115                 120
```

<210> SEQ ID NO 30
<211> LENGTH: 124
<212> TYPE: PRT
<213> ORGANISM: Gallus gallus

<400> SEQUENCE: 30

```
Ala Val Thr Leu Asp Glu Ser Gly Gly Leu Gln Thr Pro Gly Gly
 1               5                  10                  15

Ala Leu Ser Leu Val Cys Lys Ala Ser Gly Phe Thr Phe Ser Ser Tyr
                20                  25                  30

Ala Met Gly Trp Val Arg Gln Ala Pro Gly Lys Gly Leu Glu Trp Val
                 35                  40                  45

Ala Gly Ile Ser Asp Asp Gly Asp Ser Tyr Ile Ser Tyr Ala Thr Ala
            50                  55                  60

Val Lys Gly Arg Ala Thr Ile Ser Arg Asp Asn Gly Gln Ser Thr Val
 65                  70                  75                  80

Arg Leu Gln Leu Asn Asn Leu Arg Ala Glu Asp Thr Ala Thr Tyr Tyr
                     85                  90                  95

Cys Ala Arg Ser His Cys Ser Gly Cys Arg Asn Ala Ala Leu Ile Asp
                    100                 105                 110

Ala Trp Gly His Gly Thr Glu Val Ile Val Ser Ser
                    115                 120
```

-continued

```
<210> SEQ ID NO 31
<211> LENGTH: 115
<212> TYPE: PRT
<213> ORGANISM: Camelus dromedarius

<400> SEQUENCE: 31

Asp Val Gln Leu Val Glu Ser Gly Gly Ala Leu Val Gln Pro Gly Gly
1               5                   10                  15

Ser Leu Arg Leu Ser Cys Ala Ala Ser Gly Phe Pro Val Asn Arg Tyr
            20                  25                  30

Ser Met Arg Trp Tyr Arg Gln Ala Pro Gly Lys Glu Arg Glu Trp Val
        35                  40                  45

Ala Gly Met Ser Ser Ala Gly Asp Arg Ser Ser Tyr Glu Asp Ser Val
    50                  55                  60

Lys Gly Arg Phe Thr Ile Ser Arg Asp Asp Ala Arg Asn Thr Val Tyr
65                  70                  75                  80

Leu Gln Met Asn Ser Leu Lys Pro Glu Asp Thr Ala Val Tyr Tyr Cys
                85                  90                  95

Asn Val Asn Val Gly Phe Glu Tyr Trp Gly Gln Gly Thr Gln Val Thr
            100                 105                 110

Val Ser Ser
        115

<210> SEQ ID NO 32
<211> LENGTH: 113
<212> TYPE: PRT
<213> ORGANISM: Camelus dromedarius

<400> SEQUENCE: 32

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Phe Phe Met Ser Asn
            20                  25                  30

Val Met Ala Trp Tyr Arg Gln Ala Pro Gly Lys Ala Arg Glu Leu Ile
        35                  40                  45

Ala Ala Ile Arg Gly Gly Asp Met Ser Thr Val Tyr Asp Asp Ser Val
    50                  55                  60

Lys Gly Arg Phe Thr Ile Thr Arg Asp Asp Lys Asn Ile Leu Tyr
65                  70                  75                  80

Leu Gln Met Asn Asp Leu Lys Pro Glu Asp Thr Ala Met Tyr Tyr Cys
                85                  90                  95

Lys Ala Ser Gly Ser Ser Trp Gly Gln Gly Thr Gln Val Thr Val Ser
            100                 105                 110

Ser

<210> SEQ ID NO 33
<211> LENGTH: 120
<212> TYPE: PRT
<213> ORGANISM: Homo sapiens

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile Gly Trp Val Arg Arg Ala Pro Gly Lys Gly Glu Glu Trp Val
        35                  40                  45
```

-continued

Ala Ser Ile Tyr Pro Thr Asn Gly Tyr Thr Arg Tyr Ala Asp Ser Val
       50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 34
<211> LENGTH: 119
<212> TYPE: PRT
<213> ORGANISM: Homo sapiens

<400> SEQUENCE: 34

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Gly Trp Val Arg Gln Ala Pro Gly Lys Gly Pro Glu Trp Val
         35                  40                  45

Ser Leu Ile Ser Gly Ser Gly Ser Thr Trp Tyr Asp Asp Ser Val
     50                  55                  60

Lys Gly Arg Phe Thr Ile Ser Arg Asp Asn Ser Lys Asn Leu Leu Tyr
 65                  70                  75                  80

Leu Gln Met Asn Ser Leu Arg Ala Glu Asp Thr Ala Val Tyr Tyr Cys
                 85                  90                  95

Ala Arg His Ala Pro Ser Thr Glu Ala Pro Asp Tyr Trp Gly Gln Gly
            100                 105                 110

Thr Leu Val Thr Val Ser Ser
            115

<210> SEQ ID NO 35
<211> LENGTH: 116
<212> TYPE: PRT
<213> ORGANISM: Homo sapiens

<400> SEQUENCE: 35

Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Ser
             20                  25                  30

Ala Met Ser Trp Val Arg Gln Ala Pro Gly Lys Gly Leu Glu Trp Val
         35                  40                  45

Ser Ser Ile Ser Gly Ser Gly Gly Asn Thr Tyr Ser Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Trp Tyr Gly Met Asp Val Trp Gly Gln Gly Thr Thr Val
            100                 105                 110

Thr Val Ser Ser
            115

-continued

<210> SEQ ID NO 36
<211> LENGTH: 117
<212> TYPE: PRT
<213> ORGANISM: Camelus dromedarius

<400> SEQUENCE: 36

Gln Val Gln Leu Gln Glu Ser Gly Gly Gly Leu Val Gln Ala Gly Gly
1               5                   10                  15

Ser Leu Arg Leu Ser Cys Lys Ala Ser Gly Ile Ile Phe Ser Val Tyr
            20                  25                  30

Lys Met Thr Trp Tyr Arg Gln Ala Pro Gly Lys Glu Arg Glu Leu Val
        35                  40                  45

Ala Leu Ile Thr Thr Asn Asn Asn Thr Met Thr Val Asp Ser Val Lys
    50                  55                  60

Gly Arg Phe Thr Ile Ser Arg Asp Asn Val Gln Asn Thr Val Tyr Leu
65                  70                  75                  80

Glu Met Asn Asn Leu Lys Pro Glu Asp Thr Ala Val Tyr Tyr Cys Asn
                85                  90                  95

Ala Asn Arg Gly Leu Ala Gly Pro Ala Tyr Trp Gly Gln Gly Thr Gln
            100                 105                 110

Val Thr Val Ser Ser
        115

<210> SEQ ID NO 37
<211> LENGTH: 131
<212> TYPE: PRT
<213> ORGANISM: Camelus dromedarius

<400> SEQUENCE: 37

Asp Val Gln Leu Gln Glu Ser Gly Gly Gly Ser Val Gln Ala Gly Gly
1               5                   10                  15

Ser Leu Arg Leu Ser Cys Ala Ala Ser Gly Asp Thr Phe Ser Ser Tyr
            20                  25                  30

Ser Met Ala Trp Phe Arg Gln Ala Pro Gly Lys Glu Cys Glu Leu Val
        35                  40                  45

Ser Asn Ile Leu Arg Asp Gly Thr Thr Thr Tyr Ala Gly Ser Val Lys
    50                  55                  60

Gly Arg Phe Thr Ile Ser Arg Asp Asp Ala Lys Asn Thr Val Tyr Leu
65                  70                  75                  80

Gln Met Val Asn Leu Lys Ser Glu Asp Thr Ala Arg Tyr Tyr Cys Ala
                85                  90                  95

Ala Asp Ser Gly Thr Gln Leu Gly Tyr Val Gly Ala Val Gly Leu Ser
            100                 105                 110

Cys Leu Asp Tyr Val Met Asp Tyr Trp Gly Lys Gly Thr Gln Val Thr
        115                 120                 125

Val Ser Ser
    130

<210> SEQ ID NO 38
<211> LENGTH: 119
<212> TYPE: PRT
<213> ORGANISM: Mus musculus

<400> SEQUENCE: 38

Gln Val Gln Leu Gln Gln Ser Gly Leu Glu Leu Val Lys Pro Gly Ala
1               5                   10                  15

Ser Val Lys Ile Ser Cys Lys Thr Ser Gly Tyr Thr Phe Thr Glu Tyr

```
                       20                  25                  30

Thr Met His Trp Val Lys Gln Ser His Gly Lys Ser Leu Glu Trp Ile
        35                  40                  45

Gly Gly Ile Asn Pro Asn Asn Gly Gly Thr Ser Tyr Asn Gln Lys Phe
        50                  55                  60

Lys Gly Lys Ala Ile Leu Thr Val Asp Lys Ser Ser Thr Ala Tyr
 65                  70                  75                  80

Leu Glu Leu Arg Ser Leu Thr Ser Glu Asp Ser Ala Val Tyr Tyr Cys
                85                  90                  95

Ala Arg Asp Asp Arg Tyr Pro Ala Trp Phe Ala Tyr Trp Gly Gln Gly
                100                 105                 110

Thr Thr Val Thr Val Ser Ser
            115

<210> SEQ ID NO 39
<211> LENGTH: 120
<212> TYPE: PRT
<213> ORGANISM: Mus musculus

<400> SEQUENCE: 39

Gln Val Lys Leu Gln Gln Ser Gly Ala Glu Leu Val Arg Ser Gly Thr
 1               5                  10                  15

Ser Val Lys Leu Ser Cys Thr Ala Ser Gly Phe Asn Ile Lys Asp Ser
                20                  25                  30

Tyr Met His Trp Leu Arg Gln Gly Pro Glu Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Lys Ala Thr Phe Thr Thr Asp Thr Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
                100                 105                 110

Gly Thr Thr Val Thr Val Ser Ser
            115                 120
```

SENSOR SYSTEMS FOR TARGET LIGANDS AND USES THEREOF

This Application is a 35 U.S.C. § 371 National Phase Entry Application of International Application No. PCT/US2016/027749 filed Apr. 15, 2016, which designates the U.S. and which claims benefit under 35 U.S.C. § 119(e) of the U.S. Provisional Application No. 62/148,595 filed Apr. 16, 2015, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 25, 2016, is named 002806-083591-PCT_SL.txt and is 34,550 bytes in size.

FIELD OF THE INVENTION

Embodiments of various aspects described herein relate to biological sensor systems, compositions comprising the sensor systems, and methods of using the same. In particular aspects, described herein are sensor systems for a target intracellular ligand and uses thereof, e.g., in detection assays or in cell manipulation or therapeutic applications.

BACKGROUND

The ability to target specific cell populations based upon expression of an intracellular biomolecule, or on specific molecular modifications, would greatly facilitate studies of basic biology, as well as therapeutic applications. For example, in developmental biology and neuroscience there are many studies that focus on tracing and manipulating the activity of specific cell types defined by their unique molecular profiles. In biomedicine, such approaches could provide ways to selectively target and manipulate healthy or diseased cells of interest. Genetic manipulation is routinely performed on model organisms for which transgenesis and transient gene delivery methods are well established. For example, a common strategy for controlling specific cell types involves placing a coding sequence of a gene of interest under the control of cis-regulatory sequences in the genome or at the DNA level. However, it is often not clear which genomic loci or cis-regulatory sequence one could use to confer cell specificity in expression. Alternatively, cells can be targeted using cell-targeting moieties that interact with cell surface proteins for delivering cargos, e.g., via viruses, but this approach is limited to the existence of cell-specific surface receptors.

Binary expression strategies provide a powerful means of manipulating specific cell populations. In such strategies, a "driver" molecule is expressed under a cell-type specific promoter, and it interacts with a responder element to drive target gene expression. For example, the driver molecule can be a transcription factor that binds its cognate upstream activating sequence (UAS), resulting in transcription of a target gene under UAS control. Examples of the drive molecule-based control systems are the GAL4/UAS system (Brand and Perrimon, 1993), LexAop (Butala et al., 2009) and TetON/OFF systems (Schonig et al., 2010). The driver molecule can also be a site-specific DNA recombinase that recognizes its cognate binding sequences to induce DNA recombination events, leading to outcomes such as gene activation or deletion. Site-specific DNA recombinases have become the predominant driver molecules of choice in the mouse research community, with the most popular versions being the Cre/LoxP (Orban et al., 1992) and Flp/FRT systems (Dymecki, 1996).

Binary systems are powerful for a number of reasons. First, since expression of the driver molecule is separated from that of the target gene, different cell-specific driver constructs can be combined with different responder-target gene constructs to perform a wide variety of experiments. This modularity greatly reduces the number of genetic constructs needed to be generated for each experiment. Second, in the context of transgenic animals, the use of a default and innocuous driver molecule to create cell-specific driver lines makes it more likely that the resultant transgenic animals would be viable, with normal development and behaviors. Third, driver molecules can amplify the expression level of the target gene, as one driver molecule may catalyze or induce production of multiple target molecules. However, small molecules have been traditionally selected as driver molecules for their desired, natural biological activities, and are usually exogenous to the system of study.

To expand the ability of manipulating or targeting specific cell types beyond use of cell surface proteins, new genetic tools need to be developed. Accordingly, there is a need to develop novel and versatile sensor systems for detecting, targeting, and/or manipulating specific cell types.

SUMMARY

Aspects described herein stem from, at least in part, engineering a synthetic biological switch that enables spatial control of an effector activity in a cell. The synthetic biological switch comprises: a fusion protein comprising an intracellular target ligand-binding recognition domain linked to an effector domain, wherein the effector domain is active upon stabilization of an intracellular target ligand-binding recognition domain in the presence of an intracellular target ligand; or the effector domain is not active due to destabilization or degradation of the target ligand-binding recognition domain in the absence of the intracellular target ligand. In particular, the inventors have demonstrated inter alia that intracellular molecules, endogenously expressed or exogenously introduced, can be used as stabilizing ligands to permit spatial control of the stability and/or activity of an effector domain with cellular precision. In some embodiments and as a proof of principle, the inventors have developed a binary system using green fluorescent protein (GFP), an intracellular ligand, to induce stabilization of a destabilizing target ligand-binding recognition domain (e.g., mutant GFP-binding nanobody (GBP1)) and such that an effector domain (e.g., a fluorescent molecule) fused to the target ligand-binding recognition is active and generates a detectable output (e.g., a fluorescent signal) inside a cell (e.g., a mammalian cell). The inventors have also showed that the mutant nanobody could be applied in vivo (e.g., in a murine model) for intracellular ligand (e.g., GFP)-dependent and cell-specific regulation of an effector domain. In one embodiment, the inventors have showed that an intracellular ligand (exemplified by, e.g., GFP) can control the spatial expression pattern of GBP1 fusion proteins in the mouse retina.

The concept of using a destabilizing target ligand-binding recognition domain/stabilizing target ligand system as a biological switch to control activity of an effector domain in a cell (e.g., a mammalian cell) can be extended to any other target ligand-binding recognition domain and/or any other effector domain. As the destabilizing mutations identified in the GBP1 nanobody scatter along the highly conserved framework of nanobodies, the inventors have demonstrated that, in one embodiment, transfer of at least one or more of the GBP1 nanobody mutations to another nanobody targeting other proteins of interest, e.g., the HIV C-terminal domain (CTD) capsid or *E. coli* Dihydrofolate reductase (DHFR) enzyme, resulted in CTD-inducible or DHFR-inducible stabilization of nanobody fusion protein. Further, the inventors have shown use of the same destabilizing nanobody scaffold to control activity of different effector domains by fusing a different effector domain of interest (e.g., a fluorescent protein, a recombinase, or a bacterial enzyme) to the destabilizing nanobody scaffold. In addition, the inventors have demonstrated that mutations identified to destabilize a nanobody from one species (e.g., camels) can be mapped to nanobodies of other species (e.g., but not limited to alpaca and llama) and exert target-ligand-dependent stabilization effects as well. Indeed, the sites that provide target ligand-dependent stabilization effects in camelid antibodies can be mapped to corresponding conserved sites in other species, including human, as described herein below. Accordingly, the inventors have developed novel and versatile sensor systems that can be generalized for rapid design of protein-responsive sensors and effectors with an amino acid residue code that can be grafted across conserved binding protein scaffolds regardless of antigen/target ligand identity. As such, embodiments of various aspects described herein relate to sensor systems, compositions comprising the sensor systems, and methods of using the same. In particular aspects, described herein are sensor systems for a target intracellular ligand and uses thereof, e.g., in detection assays or in cell manipulation or therapeutic applications.

One aspect described herein relates to a sensor system for an intracellular target ligand. The sensor system comprises: a fusion molecule comprising at least one target ligand-binding recognition domain linked to an effector domain, wherein the target ligand-binding recognition domain is selected for specific binding to an intracellular target ligand and is configured such that (i) in the absence of the target ligand, the target ligand-binding recognition domain is destabilized and such that the fusion protein is destabilized and the effector domain is not active, or (ii) in the presence of the target ligand, the target ligand-binding recognition domain is stabilized upon binding of the target ligand, and the effector domain is active.

In some embodiments, the intracellular target ligand can be an endogenous, intracellular ligand (i.e., inherently expressed by a host cell). In some embodiments, the intracellular target ligand can be a ligand exogenously introduced into a cell, e.g., a viral antigen in an infected cell. Thus, the sensor systems described herein can provide a spatial control of an effector domain activity in a cell based on spatial expression of an intracellular ligand of interest in the cell. Accordingly, the sensor systems described herein are cell-controlled, i.e., the activity of the sensor systems are controlled by the spatial expression of an intracellular ligand of interest in a cell.

In some embodiments, at least two target ligand-binding recognition domains can be linked to an effector domain. In some embodiments, the two target ligand-binding recognition domains can target the same intracellular target ligand. In some embodiments, the two target ligand-binding recognition domains can target different intracellular target ligands. This can be beneficial for reducing the background and/or non-specific activity of the effector domain when at least one target ligand is absent. Accordingly, another aspect described herein relates to a sensor system comprising a fusion molecule with at least two target ligand-binding recognition domains linked to an effector domain. The sensor system comprises: a fusion molecule comprising: (a) an effector domain; (b) a first target ligand-binding recognition domain linked to the effector domain, wherein the first target ligand-binding recognition domain specifically binds a first intracellular target ligand and is configured such that (i) in the absence of the first target ligand, the first target ligand-binding recognition domain is destabilized and such that the fusion protein is destabilized, or (ii) in the presence of the target ligand, the target ligand-binding recognition domain is stabilized upon binding of the target ligand; and (c) a second target ligand-binding recognition domain linked to the effector domain; wherein the second target ligand-binding recognition domain specifically binds a second intracellular target ligand and is configured such that (i) in the absence of the second target ligand, the second target ligand-binding recognition domain is destabilized and such that the fusion protein is destabilized, or (ii) in the presence of the second target ligand, the second target ligand-binding recognition domain is stabilized upon binding of the second target ligand. In this aspect, the effector domain displays a higher activity (e.g., at least about 30% or more) in the presence of the first target ligand and the second target ligand than when either the first target ligand or the second target ligand is present.

The target ligand-binding recognition domain of the sensor systems described herein can be a protein, a peptide, a nucleic acid, an antibody, an antibody fragment, a nanobody, a single-domain antibody, a scaffold protein, or combinations thereof. In some embodiments, the target ligand-binding recognition domain is a nanobody.

To configure the target ligand-binding recognition domain to have a desirable ligand-dependent stabilization effect, in some embodiments, the target ligand-binding recognition domain can be configured or engineered to comprise at least one or more (including, e.g., at least two or more, at least three or more) target ligand-dependent destabilizing mutations, as compared to a wild-type target ligand-binding recognition domain.

In some embodiments, the wild-type target ligand-binding recognition domain can be a naturally occurring destabilizing target ligand-binding recognition domain. Without wishing to be bound by theory, addition of one or more destabilizing mutations can tune the responsiveness of such target ligand-binding recognition domain to ligand-dependent stabilization effects. For example, addition of one or more destabilizing mutations can further destabilize the naturally occurring destabilizing target ligand-binding recognition domain in the absence of target ligands, and/or promote stabilization of the naturally occurring destabilizing target ligand-binding recognition domain in the presence of target ligands.

In some embodiments, the wild-type target ligand-binding recognition domain can be naturally a stable molecule. By adding at least one or more destabilizing mutations, the stable molecule can be engineered to be a biological switch with target ligand-dependent stabilization effects.

Destabilizing mutations can be identified through a combination of art-recognized mutagenesis methods and screening assays for ligand-dependent effector domain activity, for example, as described in Example 1. In some embodiments, the target ligand-dependent destabilizing mutation can be one or a combination of two or more mutations highlighted in FIG. 5A, FIG. 14A or FIG. 18, with respect to the conserved framework sequence of nanobodies and other antigen-binding immunoglobulin protein constructs. In some embodiments, the target ligand-dependent destabilizing mutation can be a mutation of S73R, S/C98Y, S117F (wherein the amino acid numbering is according to the IMGT numbering system), or a combination thereof with respect to SEQ ID NOs. 1 and 2. It is demonstrated herein that mutation of the residues corresponding to S73R, C/S98Y, and/or S117F of the dGBP1 camelid antibody can confer the ligand-sensitive stabilization effect upon other camelid antibodies and that these sites are conserved in other mammalian antibody $V_H$ proteins.

The effector domain can be any molecule selected to suit the needs of a desired application provided that the effector domain produces, directly or indirectly, a detectable output signal when it is active. By way of example only, for detecting the presence of an endogenous, intracellular ligand in a cell, the effector domain can be a detectable agent. For delivering a therapeutic agent to a diseased cell, the effector domain can be a therapeutic agent. In some embodiments, the effector domain can be an enzyme or a protein, whose function can be activated in a cell in the presence of an intracellular target ligand. Accordingly, the effector domain can be, without limitations, a protein, an enzyme, a nucleic acid, a therapeutic agent, a detectable agent, a DNA nuclease enzyme (e.g., a DNA endonuclease enzyme) and combinations thereof. In some embodiments, the effector domain can be a DNA nuclease enzyme. In some embodiments, the effector domain can be a recombinase enzyme. In some embodiments, the effector domain can be a toxin. In some embodiments, the effector domain can be a fluorescent protein. In some embodiments, the effector domain can be a DNA nuclease enzyme, e.g., a DNA endonuclease enzyme. In some embodiments, the DNA endonuclease enzyme can be an RNA-guided endonuclease enzyme (e.g., but not limited to CRISPR associated protein).

In some embodiments, the sensor systems described herein can further comprise an intracellular target ligand.

Expression vectors comprising a nucleotide sequence encoding one or more embodiments of the sensor systems described herein are also provided. In the expression vectors, the target ligand-binding recognition domain can be inserted in frame to the effector domain. In some embodiments, at least one target ligand-binding recognition domain can be inserted upstream to the effector domain. In other embodiments, at least one target ligand-binding recognition domain can be inserted downstream to the effector domain.

Any expression vector known in the art and effective for expression in a desired cell type can be used to express the sensor systems described herein. An exemplary expression vector is a viral vector.

Another aspect provides a pharmaceutical composition comprising (i) the sensor system according to one or more embodiments described herein or the sensor system-encoding expression vectors according to one or more embodiments described herein, and (ii) a pharmaceutically acceptable carrier.

The sensor systems, expression vectors encoding the same, and pharmaceutical compositions described herein can be used in various applications. In some embodiments, the sensor systems, expression vectors encoding the same, and pharmaceutical compositions described herein can be used to detect an intracellular target ligand in a cell. Accordingly, in one aspect, methods for detecting an intracellular target ligand in a cell are also provided herein. The method comprises (a) introducing to a cell the sensor system described herein; (b) detecting a detectable signal of the effector domain of the sensor system; and (c) determining the presence of an intracellular target ligand if a detectable signal of the effector domain is detected; or determining the absence of the target ligand if a detectable signal of the effector domain is not detected. In some embodiments, the target ligand can be an intracellular, endogenous ligand.

In some embodiments, the sensor systems, expression vectors encoding the same, and pharmaceutical compositions described herein can be used to control or regulate activity of an effector molecule in a cell or limit activity of an effector molecule to a specific cell. Accordingly, another aspect described herein provides a method of controlling activation of an effector protein in a manner that depends on the presence of a target intracellular ligand in a cell. The method comprises: introducing to a cell the sensor system described herein or the sensor system-encoding expression vector described herein, wherein the effector domain of the sensor system is an effector protein, wherein: in the absence of the target intracellular ligand, the target ligand-binding recognition domain is destabilized and such that the fusion protein is destabilized and the effector protein is not active in the cell, or in the presence of the target intracellular ligand, the target ligand-binding recognition domain is stabilized upon binding of the target intracellular ligand, and the effector protein is active in the cell.

In some embodiments, the effector protein can be a DNA nuclease enzyme or a recombinase enzyme. In these embodiments, the target ligand can be a viral protein. Thus, the activity of DNA nuclease enzyme or recombinase enzyme can be limited to cells that contains or are infected with a viral protein.

In some embodiments, the method can further comprise introducing to the cell an intracellular target ligand selected for the sensor system.

In some embodiments, the sensor systems, expression vectors encoding the same, and pharmaceutical compositions described herein can be used for targeted therapy. Accordingly, methods for delivery of a therapeutic agent or pro-drug agent to a target cell in a subject are also provided herein. The method comprises administering to a subject in need thereof the sensor system-comprising pharmaceutical composition described herein, wherein the effector domain of the sensor system is a therapeutic agent or pro-drug agent; and the target ligand-binding recognition domain of the sensor system is selected for specific binding to an intracellular ligand of a target cell to be treated. In a non-target cell without the intracellular ligand, the target ligand-binding recognition domain is destabilized and such that the fusion protein is destabilized and the therapeutic agent or pro-drug agent is not active in the non-target cell. In a target cell with the intracellular ligand, the target ligand-binding recognition domain is stabilized upon binding of the intracellular ligand, and the therapeutic agent or pro-drug agent is active in the target cell.

In some embodiments, the inventors have fused destabilized nanobodies to Cas9 to perform genome targeting and editing under the control of desired antigens (e.g., FIGS. 7A-7D). Accordingly, a system for genome editing is also described herein. The system comprises (a) a nucleic acid guide designed to be complementary to a target sequence to be cut; and (b) a fusion molecule comprising: at least one target ligand-binding recognition domain linked to a nucleic acid-guided DNA endonuclease enzyme, wherein the target ligand-binding recognition domain specifically binds an intracellular target ligand and is configured such that (i) in the absence of the target ligand, the target ligand-binding recognition domain is destabilized and such that the fusion protein is destabilized and the DNA endonuclease enzyme is not active, or (ii) in the presence of the target ligand, the target ligand-binding recognition domain is stabilized upon binding of the target ligand, and the DNA endonuclease enzyme is active.

In some embodiments, the nucleic acid can be RNA.

In some embodiments, the nucleic acid-guided endonuclease enzyme can be CRISPR associated protein (e.g., but not limited to Cas9).

Components of the systems for genome editing, e.g., the nucleic acid guide and fusion molecule as described herein, can be introduced into cells by any art-recognized nucleic acid delivery methods or as described herein. For example, the nucleic acid guide and fusion molecule can be independently introduced into cells using expression vectors. Thus, expression vector systems comprising a nucleotide sequence encoding the nucleic acid guide, and a nucleotide sequence encoding the fusion molecule are also described herein. Alternatively, the nucleic acid guide and fusion molecule can be independently coupled to or encapsulated in a cell-permeable carrier prior to administration. An exemplary cell-permeable carrier is a liposome or a nanoparticle.

Detection of intracellular antigens for genome editing can be used to activate genome editing on in cells expressing a pathogenic antigen, for effects such as triggering apoptosis or activation of cellular mechanisms to counteract pathogen activity. Accordingly, a method of treating a disease or disorder caused by a mutation in a gene is also described herein. The method comprises introducing into cells a pharmaceutical composition comprising: (a) a nucleic acid guide designed to be complementary to a target sequence comprising a disease-causing mutation or a pathogen gene; and (b) a fusion molecule comprising: at least one pathogenic antigen-binding recognition domain linked to a nucleic acid-guided DNA endonuclease enzyme, wherein the pathogenic antigen-binding recognition domain specifically binds an intracellular pathogenic antigen and is configured such that (i) in the absence of the pathogenic antigen, the pathogenic antigen-binding recognition domain is destabilized and such that the fusion protein is destabilized and the DNA endonuclease enzyme is not activated to cut the target sequence, or (ii) in the presence of the pathogenic antigen, the pathogenic antigen-binding recognition domain is stabilized upon binding of the pathogenic antigen, and the DNA endonuclease enzyme is active to cut the target sequence.

The pharmaceutical composition of any aspects described herein can be administered to the subject in need thereof by any methods known in the art. For example, the sensor system-encoding expression vectors can be administered by any DNA delivery methods, including, e.g., but not limited to, virus-based delivery, plasmid-based delivery, and/or electroporation-based delivery. In some embodiments, the sensor systems described herein can be coupled to or encapsulated in a cell-permeable carrier prior to administration to the subject in need thereof. An exemplary cell-permeable carrier is a liposome or a nanoparticle.

Another aspect provided herein relates to a method for preparing a destabilized antibody/ligand pair, the method comprising: (i) introducing a destabilizing mutation at at least one amino acid residue outside of the ligand binding region, (ii) measuring antibody stability in the presence and absence of ligand, wherein in the absence of the ligand, the antibody is destabilized, or in the presence of the ligand, the antibody is stabilized upon binding of the target ligand, thereby preparing a destabilized antibody/ligand pair.

In one embodiment of this aspect and all other aspects provided herein, the method further comprises a step of determining the amino acid residue to be mutated. In some embodiments, the step of determining the amino acid residue comprises aligning the amino acid sequence of the antibody with dGBP1 as described herein in the working Examples and identifying the corresponding residue to the 3 major mutations described for dGBP1. Alternatively, the amino acid sequence of the antibody can be numbered according to the IMGT numbering system to determine the residue to be mutated.

In another embodiment of this aspect and all other aspects provided herein, the $V_H$ amino acid residue to mutate to render an antibody unstable in the absence of target ligand is selected from the group consisting of: A25, E63, S73, C/S98, Q109, and S117, wherein the numbering of the amino acid residues is according to the IMGT numbering system.

In another embodiment of this aspect and all other aspects provided herein, the destabilizing mutation is introduced to at least three amino acid residues.

In another embodiment of this aspect and all other aspects provided herein, the at least three amino acid residues of an antibody are S73, C/598, and S117 or sites corresponding to them, and wherein the numbering of the amino acid residues is according to the IMGT numbering system.

In another embodiment of this aspect and all other aspects provided herein, the destabilizing mutations are S73R, C/S98Y, and S117F, and wherein the numbering of the amino acid residues is according to the IMGT numbering system.

BRIEF DESCRIPTION OF THE DRAWINGS

(FIG. 1A) Concept of antigen-controlled protein stabilization. Output protein (OP) (or also referred to as "effector domain" herein) fused to a destabilized binding protein (or also referred to as "target ligand-binding recognition domain" herein) is degraded or inactive until binding of destabilized binding protein to input antigen (IA) (or also referred to as a "target ligand" or a "target intracellular ligand" herein). (FIG. 1B) Strategy for isolating destabilized nanobodies. Mutagenized nanobody, in this case GBP1, is cloned into a Mouse Moloney Leukemia Viral (MMLV) TagBFP-IRES-t-HcRed vector. Multi-step FACS protocol adding GFP antigen in latter steps results in selection of GBP1 variants stabilized by GFP binding. LTR—Long Terminal Repeat. (FIG. 1C) Model for GFP-regulated stabilization of TagBFP. (FIGS. 1D-1E) dGBP1, but not wildtype GBP1, destabilizes the TagBFP fusion partner in cells. 293T cells were transfected with plasmids encoding the GFP derivative YFP or filler plasmids along with the dGBP1-TagBFP or GBP1-TagBFP MMLV constructs. (FIG. 1D) Western blot for TagBFP and βgal (a transfection control) shows GFP-dependent stabilization of both wildtype and destabilized GBP1. Harvested 2 days post-transfection. Image is representative of 3 independent experiments. (FIG. 1E) Representative images showing GFP-dependent fluorescence of dGBP1-TagBFP. Cells were imaged 32 hours after transfection. t-HcRed labels cells with the TagBFP fusion constructs. Scale bar, 100 μm. Consistent results were observed across triplicates and confirmed in at least four independent experiments. See also FIG. 8 and FIG. 1H. (FIG. 1F) Dependence of dGBP1-TagBFP protein level on YFP dose in transfected 293T cells. (FIG. 1G) The ubiquitin proteasome pathway is involved in degradation of dGBP1. Transfected 293T cells were treated with drugs for 20 h.

BTZ, Bortezomib. All results are representative of three independent experiments, for 3 biological replicates. (FIG. 1H) YFP-dependent dGBP1-TagBFP stabilization in cells. Quantification of results from FIG. 1E. Transfected cells were identified by expression of either YFP or t-HcRed. Plot shows median and maximum-to-minimum range. Data are from 3 independent experiments, for 3 biological replicates.

(FIG. 2A) Schematic of electroporation experiment. Plasmid encoding promoter-GFP or CAG-driven DsRed is co-electroporated with CAG-driven dGBP1-TagBFP to the murine retina at postnatal day 0 (P0). Retinas were harvested at P14. (FIG. 2B) GFP, but not DsRed, induces dGBP1-TagBFP fluorescence in the mouse retina. ONL, outer nuclear layer; INL, outer nuclear layer. (FIG. 2C) The expression pattern of TagBFP protein, as detected by Anti-TagBFP, can be altered by changing the GFP expression pattern with broadly active (CAG) or rod photoreceptor-specific (Rho) promoters. Anti-TagBFP was not used in (A) as it cross-reacts with DsRed. Scale bar is 20 μm. Sample size (retinas): n=3 for all conditions. See also FIGS. 9A-9E. (FIG. 2D) Tight coupling of GFP expression and Anti-TagBFP staining from ONL cells in the +CAG-GFP condition. Scale bar is 20 μm. (FIGS. 2E-2H). Quantification of electroporation results. (FIG. 2E) GFP-dependency of TagBFP expression. Counted cells from ONL. Plotted % TagBFP+ cells given GFP+ (from +CAG-GFP) or DsRed+ cells (from +CAG-DsRed). (FIG. 2F) Efficiency of GFP-dependent protein stabilization. Efficiency is % Anti-TagBFP+ cells given GFP+ (FIG. 2G) GFP-specificity of system, as determined by % GFP+ cells given Anti-TagBFP+ cells. (FIG. 2H) dGBP1-TagBFP expression pattern closely matches that of GFP. All electroporated cells, as defined by GFP or TagBFP expression, were quantified across a 20 μm retinal section and represented as % of total number of cells counted. Graphs and values shown are as mean±standard deviation. Biological replicates (retinas): n=3 for all conditions.

(FIGS. 3A and 3D) Schematic of dGBP1-Cre (FIG. 3A) or dGBP1-Flpo (FIG. 3D). (FIGS. 3B and 3E) GFP-dependent Cre or Flpo recombination of LNL- (FIG. 3B) or FNF- (FIG. 3E) DsRed, respectively. Cells images at 24-36 hr post-transfection. (FIGS. 3C and 3F) GFP-independent background recombinase activity can be suppressed by increasing the number of dGBP1 fused to Cre (FIG. 3C) or Flpo (FIG. 3F). Reporter is LNL- (FIG. 3C) or FNF- (FIG. 3F) luc2. Cells harvested at 15 hr (FIG. 3C) or 36 hr (FIG. 3F) post-transfection. Luciferase plots are mean+/− standard deviation. Scale bar is 200 μm in (FIG. 3A) and 100 μm in (FIG. 3B). All reporter results were representative of 3 independent experiments. Sample size per condition is n=12 (FIG. 3C) and n=18 (FIG. 3E). (FIG. 3G) Rapid generation of a C-CA-dependent Flpo by transfer of dGBP1 mutations to aCA Nb. Schematic of C-CA-dependent Flpo (left). C-CA can promote Flpo recombination in the mouse retina (right). n-Bgal was an electroporation marker. Scale bar, 20 μm. (FIG. 3H) Quantification of C-CA-dependent Flpo activity. In (FIGS. 3G, 3H), 4 and 3 electroporated retinas were analyzed for +C-CA and +GFP conditions, respectively.

(FIG. 4A) Schematic of electroporation experiment. CAG-nlacZ is an electroporation marker. (FIG. 4B) Electroporation of CAG-driven dGBP1×2-Flpo into Tg(CRX-GFP) retinas resulted in strong activation of FNF-DsRed reporter. DsRed was not detected in electroporated wildtype retinas. Scale bar, 20 μm. (FIG. 4C) Quantification of GFP-dependent Flpo recombination in the outer nuclear layer (ONL) of Tg(CRX-GFP) or wildtype retinas. Sample size, n=4 for GFP+ condition, n=3 for GFP negative condition. Plots were mean+/− standard deviation. Consistent results were obtained in independent experiments.

(FIG. 5A) Protein alignment of nanobodies against GFP (GBP1, SEQ ID NO: 16), HIV C-CA (VHH9, SEQ ID NO: 17) and E. coli DHFR (CA1698; SEQ ID NO: 18). Amino acid positions were numbered according to the ImMunoGeneTics information system (IMGT). FR, framework. CDR, complementarity determining region. Purple and green highlighted residues were sites of dGBP1 mutation. Green residues have the strongest destabilizing effects. (FIGS. 5B-5E) Transfer of dGBP1 mutations to other nanobodies. Plasmids transfection in 293T cells, imaged 16 hours post-transfection and harvested 24 hours for western blot post-transfection. Relative to their respective wildtype nanobodies, destabilized VHH9 (FIGS. 5B and 5C) and CA1698 (FIGS. 5D and 5E) showed antigen-dependent fluorescence (FIGS. 5B and 5D) as well as protein expression (FIGS. 5C and 5E). DsRed was used as transfection marker in (FIG. 5B) and (FIG. 5D) to control for negative TagBFP results. Scale bar, 50 μm. Consistent results were obtained in 3 independent experiments. (FIG. 5F) A dNb generated by mutation transfer was degraded by the UPS. aCA-dNb6mut 446-TagBFP showed an increase in protein level when transfected 293T cells were treated with MG132 for 6 h. Results representative of 3 independent experiments. (FIG. 5G) Heat map showing median TagBFP fluorescence intensity of Nb-TagBFP fusions. All Nbs shown recognize epitopes of intracellular origin. Fluorescent readings were normalized to that of unmodified Nb (no antigen) condition, which was set to 100. n=3 biological replicates pooled from 3 independent experiments per Nb. Each biological replicate result is shown as a horizontal bar in the heat map. Bar graphs indicate median and maximum-to-minimum range.

(FIG. 6A) Schematic of double destabilized nanobody fusion system for coincidence detection of antigen. OP, output protein. (FIG. 6B) destabilized nanobodies were fused to Flpo at the N-terminal in succession. (FIGS. 6C and 6D) 293T luciferase assay using Flp-dependent luc2 construct, CAFNF-luc2. Cells harvested 16 hours post-transfection. Results show dependence of Flpo activity on the presence of both GFP and C-CA (FIG. 6C) or GFP and DHFR (FIG. 6D). n=6 per condition in (FIG. 6C) and n=9 per condition in (FIG. 6D). Consistent results were obtained in 3 independent experiments.

(FIG. 7A) Schematic of Cas9 fusion protein inducible by C-CA binding. (FIG. 7B) Fusion configuration of tandemly repeated C-CA nanobody to Cas9, giving dCC-Cas9. (FIG. 7C) dCC-Cas9 activity was assayed for βgal expression in a human TE671 cell line engineered to contain a lacZ reporter inactive in expression due to a loxP-STOP-loxP transcriptional termination cassette. gRNA targets both loxP sequences for Cas9 cleavage and STOP removal. (FIG. 7D) dCC-Cas9 shows C-CA-dependent activity. Cas9 activity is represented as number of βgal+ cells induced as a percentage of unfused Cas9 activity (100%). Plots were mean+/− standard deviation. n=3 or 5 per condition. Consistent results were obtained in 3 independent experiments.

(FIG. 9A) Tight coupling of GFP expression and Anti-TagBFP staining from ONL cells in the +CAG-GFP condition. Scale bar is 20 μm (FIGS. 9B-9E) Quantification of electroporation results. (FIG. 9B) GFP-dependency of TagBFP expression. Counted cells from ONL. Plotted % TagBFP+ cells given GFP+ (from +CAG-GFP) or DsRed+ cells (from +CAG-DsRed). (FIG. 9C) Efficiency of GFP-dependent protein stabilization. Efficiency is % Anti-TagBFP+ cells given GFP+ cells. (FIG. 9D) GFP-specificity of system, as determined by % GFP+ cells given Anti-TagBFP+ cells. (FIG. 9E) dGBP1-TagBFP expression pattern closely matches that of GFP. All electroporated cells, as defined by GFP or TagBFP expression, are quantified across a 20 μm retinal section and represented as % of total number of cells counted. Graphs and values shown are as mean±standard deviation. Sample size (retinas): n=3 for all conditions.

(FIGS. 10A and 10B) Cre and Flpo were each individually fused to either GBP1, dGBP1-GBP1, or dGBP1×2, respectively (see schematic diagram). dGBP1×2, but not dGBP1-GBP1 fusion to recombinase suppresses background activity. O/E: overexposed. Cells imaged at 22 hr (FIG. 10A) or 50 hr (FIG. 10B) post-transfection. Images representative of three independent experiments. Scale bar, 100 μm. (FIG. 10C) GFP dose dependency of GFP-dependent Flpo. n=6. Data pooled from 3 independent experiments. (FIG. 10D) C-CA dose dependency of C-CA-dependent Flpo. n=6. Data pooled from 3 independent experiments. In (FIGS. 10C, 10D), Boxplots indicate maximum-to-minimum range. Box boundaries range from 25th to 75th percentile. The line in box indicates median.

(FIG. 11A) Representative images showing expression of GBP1 variants tagged with mCherry in 293T cells. Images taken 15 hours post transfection. Scale bar, 50 μm. (FIG. 11B) Semi-quantitative summary of mCherry fluorescence intensity as well as cellular solubility phenotype. Sol, soluble. Agg, aggregate. Plot is mean+/− standard deviation. Asterisk indicates mutations which showed clear increase in fluorescence compared to dGBP1-mCherry. n=4 to 5 per condition. Consistent results were obtained in at least 3 independent experiments.

(FIG. 12A) Representative images showing expression of GBP1 variants tagged with mCherry in 293T cells. Images taken 17 hours post transfection. Scale bar, 50 μm. (FIG. 12B) Semi-quantitative summary of mCherry fluorescence intensity as well as cellular solubility phenotype. Sol, soluble. Agg, aggregate. Plot is mean+/− standard deviation. Asterisk indicates clearly destabilized mutations compared to GBP1-mCherry. n=6 per condition except GBP1 control (n=3). Consistent results were obtained in at least 3 independent experiments.

(FIGS. 13A-13C) Two different views of crystal structure complexes of: (FIG. 13A) HIV C-terminal domain (CTD) bound to its nanobody (CTD Nb). (FIG. 13B) GFP bound to GBP1. (FIG. 13C) GFP (orange) bound to GBP4 (wheat). Note the arrow denotes the end of the CDR3 loop in GBP1 in (FIG. 13B). GBP4 has an elongated loop, pushing the GFP antigen away from the backbone structure, whereas CTD Nb and GBP1 do not. (FIG. 13D) Superimposition of CTD/CTD Nb complex on top of GFP/GBP1 complex. (FIG. 13E) Superimposition of CTD/CTD Nb complex on top of GFP/GBP4 complex. (FIG. 13F) Superimposition of GFP/GBP1 complex on top of GFP/GBP4 complex.

(FIG. 14A) Protein alignment of CTD nanobody (CTDNb; SEQ ID NO: 19) against GBP1 (SEQ ID NO: 20). Black box highlights GBP1 residues mutated in dGBP1. Noted mutation positions correspond to dGBP1. Note that position 98 is originally cysteine in GBP1 as well, but was changed to serine in the version used. (FIG. 14B) Transfer of dGBP1 mutations to CTD Nb generates destabilized CTD nanobody (dCTD Nb). Both dCTD Nb-mCherry and dGBP1-mCherry construct increases in fluorescence in the presence of its respective antigen. Images taken from transfected 293T cells, 16 hours post-transfection. 1.5:1 DNA weight ratio of CAG-driven antigen plasmid to nanobody-mCherry plasmid. Scale bar, 100 μm. Consistent results were obtained in 3 independent experiments. (FIG. 14C) Close up view of cells from experiment in (FIG. 14B), taken 22 hour post transfection. Note aggregation of mCherry in "No Antigen" condition. For top panels, the antigen was CTD. For bottom panels, the antigen was GFP. Scale bar, 40 μm. (FIG. 14D) Sub-mapping of dGBP1 mutations involved in CTD Nb destabilizing phenotype. S98Y, Q109H and S117F appear to be involved in CTD Nb destabilization. Images taken 16 hours post-transfection. 1:1 DNA weight ratio of antigen to nanobody-mCherry plasmid transfected. Scale bar, 100 μm. All experiments were done in duplicates or triplicates, and consistent results were obtained in at least 2 independent experiments. (FIG. 14E) Western blot confirming CTD-inducible stabilization of dCTD Nb, but not wildtype CTD Nb, in transfected 293T cells. Harvested 1 day post-transfection. βgal is a transfection control. Image representative of triplicate transfection sets.

(FIG. 15A) Original Cas9 and guide RNA encoding vector. (FIG. 15B) Modified vector bearing XhoI and BsrGI restriction site. (FIG. 15C) Amplification of dCTDx2 with specified primers. (FIG. 15D) Cloning of XhoI/BsrGI flanked dCTDx2 PCR product into px300 using specified primers.

FIG. 18 shows protein alignment of GBP1 with example nanobodies targeting other proteins. GBP1 (or GBP1s shown in the figure; SEQ ID NO: 1) residues mutated in destabilized GBP1 mutants were also highly conserved across multiple nanobodies targeting other proteins. GBP1 was aligned against nanobodies selected against DHFR (4I13_B, SEQ ID NO: 21), MTIF (4GFT_B, SEQ ID NO: 22) and ricin. Multiple ricin nanobodies are listed in the figure: 4LHJ_B, SEQ ID NO: 23; 4LGR_B, SEQ ID NO: 24; ricin8, SEQ ID NO: 25; ricin4, SEQ ID NO: 26. 4GLP_D, SEQ ID NO 27; and 4C57 D, SEQ ID NO: 28. The rectangle box (labeled as "Green") highlights destabilizing mutations that are highly conserved.

FIGS. 19A-19B shows generation of dNbs by mutation transfer. (FIG. 19A) Conservation of dGBP1 mutations across 76 Nbs derived from *Camelus dromedaries*, *Lama glama* and *Vicugna pacos*. (FIG. 19B) Mapping of Nb destabilizing positions in relation to binding interfaces across Nb-Antigen complexes.

(FIG. 20A) AAV reagents for (FIGS. 20B-20D). (FIG. 20B) Schematic showing delivery of AAVs to the mouse cerebellum for cell type-specific manipulation in Tg(GAD67-GFP) animals. (FIG. 20C) Representative image showing that AAV-encoded, GFP-dependent Flpo activates ChR2-mCherry expression selectively in the cerebellar cortex of Tg(GAD67-GFP) (n=4), but not wildtype (n=2) animals. ZsGreen is unrelated to GFP and was used as an infection marker for GFP-negative animals. Scale bar, 50 μm. (FIG. 20D) Optogenetic manipulation of GFP+, ChR2-mCherry+ cells. A pulse of blue light evoked a photocurrent at −60 mV holding potential, and an inhibitory synaptic current at 0 mV that was blocked by 5 μM of the GABAA receptor antagonist SR-95531, indicating activation of mCherry−ChR2+ cells synapsing onto the recorded PC. No photocurrents or synaptic currents were detected in GFP+/mCherry− PCs (n=12 cells) from Tg(GAD67-GFP) animals as well as ZsGreen+/mCherry− PCs (n=9 cells) from wildtype animals. 2-photon images show cells identified live for optogenetic manipulation and physiology. Bright ZsGreen aggregates were sometimes detected as faint signals in the mCherry channel. Scale bar, 10 μm. ZsG, ZsGreen; mC, mCherry.

(FIG. 21A) Reagents for (FIGS. 21B-21D). (FIG. 21B) Schematic showing delivery of AAVs and green fluorescent beads to the mouse cerebellum for cell type-specific manipulation in Tg(GAD67-GFP) animals. (FIG. 21C) AAV-delivered, Flp-DOG activated ChR2-mCherry expression selectively in the cerebellar cortex of GFP+, but not GFP-negative animals. Fluorescent beads mark the site of infection. Pictures representative of 2 injected animals per condition. Scale bar, 50 μm. (FIG. 21D) Quantification of Flpo activity with regards to (FIG. 21B-21C). Plots show number of mCherry+ (mC+) cells counted in whole brain slices labeled with beads. All mCherry+ cells were counted in 9 and 7 whole brain sections with highest bead density, for Tg(GAD67-GFP) and GFP-negative brains, respectively. n=2 animals per condition. (FIG. 21E) Quantification of Flpo activity in Tg(GAD67-GFP) animals injected with AAV-EF1α-Flp-DOG and AAV-FLEXFRT-ChR2-mCherry, as well as in wildtype animals injected with AAV-EF1a-ZsGreen, AAV-EF1a-Flp-DOG and AAV FLEXFRT-ChR2-mCherry. Plot shows percentage of GFP+ PCs expressing ChR2-mCherry (335 cells counted, 15 sections, 4 Gad67-GFP+ animals), and percentage of mCherry+ PCs in ZsGreen+ PCs (108 cells counted, 8 sections, 2 wildtype animals). (FIG. 21F) Input resistance and spontaneous firing frequency measured in GFP+, mCherry+ PCs (39+/−6 MO, n=21; 62+/−11 Hz, n=10) and GFP+, mCherry− PCs (50+/−10 MO, n=12; 65+/−12 Hz, n=7) of AAV-injected Tg(GAD67-GFP) animals, as well as in ZsGreen+/mCherry− PCs of AAV-injected wildtype animals (51+/−5 MO, n=9; 81+/−13 Hz, n=8), were not significantly different (p=0.433 for comparisons of input resistance, p=0.522 for comparisons of spontaneous frequency, 1-way ANOVA). Values are listed as mean+/− SEM. All plots show median and interquartile range (FIG. 22A) Schematic showing isolation of HIV-1 cells via flow cytometry using αCA-specific, dNb sensor. Both ACH-2 (HIV+) and CEM (HIV-) cells were treated with 10 nM PMA prior to transfection of sensors. CAG-DsRed was a transfection marker. (FIG. 22B) Destabilized, but not unmodified aCA Nb enabled selective isolation of reactivated HIV-1 cells using flow cytometry (P=0.0009 for comparison between destabilized aCA, ACH-2 vs. CEM). Plot shows median and maximum-to-minimum range. The number of biological replicates (equal to number of independent experiments) for each condition is shown in parentheses. ** P<10-3, Mann-Whitney test.

FIGS. 23A-23D dNb sensor against HIV-1 CA enables detection and isolation of reactivated HIV-1+ cells with flow cytometry. (FIG. 23A) Example of flow cytometry gating to isolate HIV-1 cells based on expression of CA. Cell populations are represented as log contour maps. Percentages of DsRed+ cells that are TagBFP+ are indicated for each condition. All cell populations were gated for DsRed expression. Results shown are representative of the following number of biological replicates (equal to number of independent experiments): Unmodified αCA-TagBFP in both ACH-2 and CEM cells (4), Destabilized αCA-Nb6mut 654 TagBFP in both cell types (8), Destabilized GBP1-TagBFP in both cell types (4), No Nb-TagBFP in both cell types (6). (FIG. 23B) Schematic showing isolation of HIV-1 cells via flow cytometry using HIV-1 CA-specific, red fluorescent sensor. (FIG. 23C) Destabilized, but not unmodified aCA Nb enabled selective isolation of reactivated HIV-1 cells using red fluorescence in flow cytometry. Plot shows median and maximum-to-minimum range. 3 independent experiments were performed for each condition, yielding 3 biological replicate values. (FIG. 23D) Confirmation of CA immunoreactivity in PMA-stimulated ACH-2, but not CEM cells. KC57-RD1 is a RD1 dye-conjugated, mouse monoclonal antibody that recognizes CA protein. Cell populations are represented as log contour maps. Unlike αCA-Nb6mut 663 TagBFP, immunostaining for KC57-RD1 requires cell fixation and membrane permeabilization.

FIG. 24 is a Table showing a list of tested nanobodies and their associated antigens.

FIG. 25 is a protein alignment showing that amino acid identities of the 3 major destabilizing positions are highly conserved across heavy chain portions of antibodies. Clustal omega protein alignment of heavy chain portions of antibodies from chicken (*Gallus gallus*; ChickenVH-PDBno-4P48, SEQ ID NO: 29; ChickenVH-PDBno-4P49, SEQ ID NO: 30), camelid (*Camelus dromedarius*; CamelidVHH-PDBno-3K1K, SEQ ID NO: 31; CamelidVHH-PDBno-2XT1, SEQ ID NO: 32; CamelidVHH-PDBno-4EIG, SEQ ID NO: 36; CamelidVHH-PDBno-3G9A, SEQ ID NO: 37), human (*Homo sapiens*; HumanVH-PDBno-3B9V, SEQ ID NO: 33; HumanVH-PDBno-3ZHL, SEQ ID NO: 34; HumanVH-PBDno-1T2J, SEQ ID NO: 35) and mouse (*Mus musculus*; MouseVH-PDBno-3UMT, SEQ ID NO: 38; MouseVH-PDBno-1QOK, SEQ ID NO 39). Only the portion of human, chicken and mouse heavy chains that aligns with the camelid VHH sequences is indicated. Indicated amino acid positions are numbered according to the ImMunoGeneTics information system (IMGT). The camelid VHHs derived from PDB number (PDBno) 3K1K, 2XT1, and 4EIG could tolerate destabilizing mutations at the 3 major destabilizing positions (emphasized with black rectangles and numbered according to the IMGT system). FR framework. CDR complementarity determining region. CDR sequences are expected to be more variable, as they were selected for antigen binding.

DETAILED DESCRIPTION OF THE INVENTION

Figures 1A, 1B, 1C, 1D, 1E:
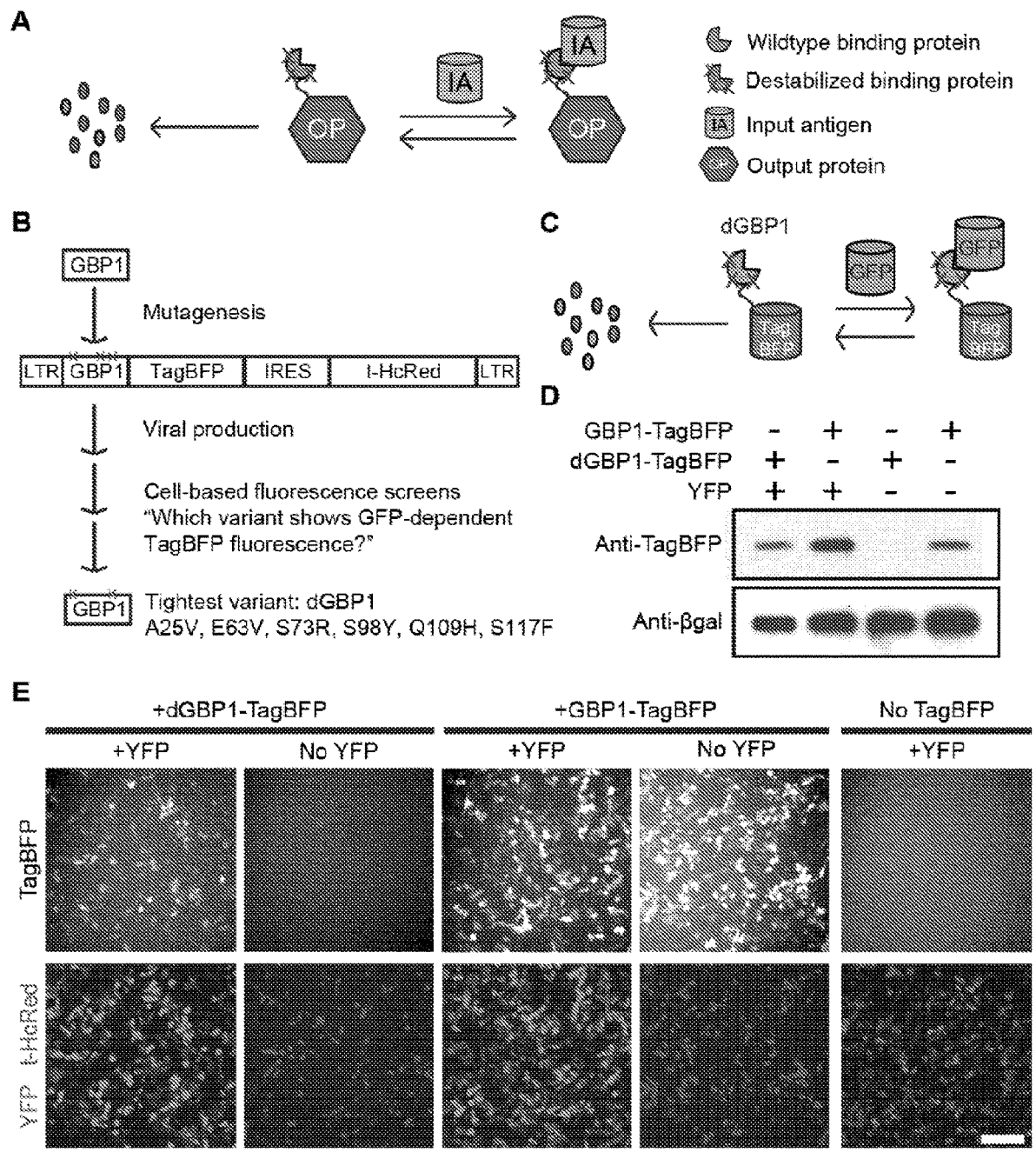
FIGS. 1A-1H show schematic diagrams and associated experimental data depicting isolation of a strongly destabilized nanobody whose protein level depends on antigen binding.

Embodiments of various aspects described herein relate to sensor systems, compositions comprising the sensor systems, and methods of using the same. In particular aspects, described herein are sensor systems for a target intracellular ligand and uses thereof, e.g., in detection assays or in cell manipulation or therapeutic applications. Aspects described herein stem from, at least in part, engineering a synthetic biological switch that enables spatial control of an effector activity in a cell. The synthetic biological switch comprises: a fusion protein comprising an intracellular target ligand-binding recognition domain linked to an effector domain, wherein the effector domain is active upon stabilization of an intracellular target ligand-binding recognition domain in the presence of an intracellular target ligand; or the effector domain is not active due to destabilization or degradation of the target ligand-binding recognition domain in the absence of the target ligand. In particular, inventors have demonstrated inter alia that intracellular molecules, endogenously expressed or exogenously introduced, can be used as stabilizing ligands to enable spatial control of the stability and/or activity of an effector domain with cellular precision. In some embodiments, the inventors have developed a binary system using green fluorescent protein (GFP), an intracellular ligand, to induce stabilization of a destabilizing target ligand-binding recognition domain (e.g., mutant GFP-binding nanobody (GBP1)) and such that an effector domain (e.g., a fluorescent molecule) fused to the target ligand-binding recognition is active and generates a detectable output (e.g., a fluorescent signal) inside a cell (e.g., a mammalian cell). The inventors have also showed that the mutant nanobody could be applied in vivo (e.g., in a murine model) for intracellular ligand (e.g., GFP)-dependent and cell-specific regulation of an effector domain. In one embodiment, the inventors have showed that an intracellular ligand (e.g., GFP) can control the spatial expression pattern of GBP1 fusion proteins in the mouse retina.

The concept of using a destabilizing target ligand-binding recognition domain/stabilizing target ligand system as a biological switch to control activity of an effector domain in a cell (e.g., a mammalian cell) can be extended to any other target ligand-binding recognition domain and/or any other effector domain. As the destabilizing mutations identified in the GBP1 nanobody scatter along the highly conserved framework of nanobodies, the inventors have demonstrated that, in one embodiment, transfer of at least one or more of the GBP1 nanobody mutations to another nanobody targeting other proteins of interest, e.g., the HIV C-terminal domain (CTD), resulted in CTD-inducible stabilization of nanobody fusion protein. Further, the inventors have shown use of the same destabilizing nanobody scaffold to control activity of different effector domains by fusing a different effector domain of interest (e.g., a fluorescent protein, a recombinase, or a bacterial enzyme) to the destabilizing nanobody scaffold. Accordingly, the inventors have developed novel and versatile sensor systems that can be generalized for rapid design of protein-responsive sensors and effectors with an amino acid residue code that can be grafted across conserved binding protein scaffolds regardless of antigen identity.

Figure 17A:
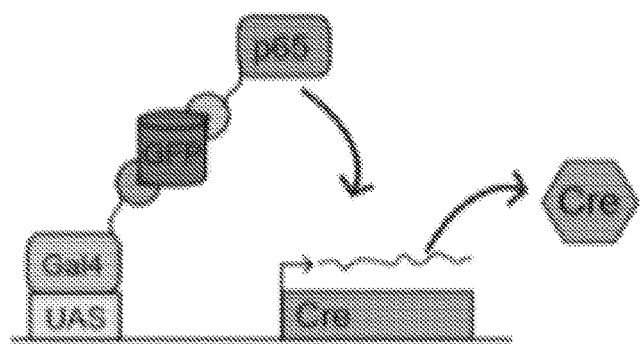
FIGS. 17A-17B show example embodiments of Transcription Devices Dependent on GFP (T-DDOG) (FIG. 17A) as described in Tang et al. (Cell (2013) 154: 928-939) and in U.S. Patent Application No. US 2013/0230863 or CRE-DOG system (as shown in FIG. 17B). In order for GFP to induce transcription of Cre, at least 3 components must be delivered and expressed in GFP-labeled cells in the T-DDOG system (FIG. 17A), and at least 2 components have to be delivered in the CRE-DOG system to create Cre activity (FIG. 17B).
Figure 17B:
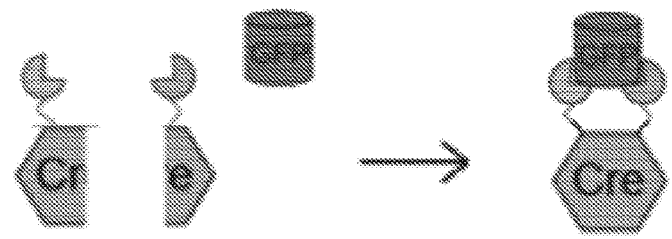

The sensor systems described herein are different from Transcription Devices Dependent on GFP (T-DDOG) (FIG. 17A) as described in Tang et al. (Cell (2013) 154: 928-939) and in U.S. Patent Application No. US 2013/0230863 or CRE-DOG system (as shown in FIG. 17B). By way of example only, in order for GFP to induce transcription of Cre, at least 3 components must be delivered and expressed in GFP-labeled cells in the T-DDOG system (FIG. 17A), and at least 2 components have to be delivered in the CRE-DOG system to create Cre activity (FIG. 17B). Also, these dimerizer systems suffered from a caveat that at concentrations in which the intracellular product of interest is in far excess of the split components, the activity of the system could be inhibited. In contrast, the sensor systems described herein (e.g., as shown in FIG. 1A) is a simple binary system, in which an intracellular ligand (e.g., GFP) interacts with a single component to directly induce activity of a protein of interest (e.g., Cre). Further, unlike other existing small molecule or light-inducible sensor systems that provide only temporal control over activity of an effector (Banaszynski et al., 2006; Bonger et al., 2014), the sensor systems described herein provide spatial control of stability of a destabilizable protein which in turn regulates activity of the fused effector protein.

Sensor Systems

One aspect described herein relates to a sensor system for at least one intracellular target ligand. The sensor system comprises: a fusion molecule comprising at least one target ligand-binding recognition domain linked to an effector domain, wherein the target ligand-binding recognition domain is selected for specific binding to an intracellular target ligand and is configured to be destabilizable such that (i) in the absence of the target ligand, the target ligand-binding recognition domain is destabilized or degraded and such that the fusion molecule is destabilized or degraded and the effector domain is not active, or (ii) in the presence of the target ligand, the target ligand-binding recognition domain is stabilized upon binding of the target ligand, and the effector domain is active. As such, the sensor systems described herein are cell-controlled, i.e., the activity of the sensor systems are controlled by the spatial expression of an intracellular ligand of interest in a cell.

Intracellular target ligands: While the sensor systems described herein can be applied to any types of ligand, e.g., cell surface-binding ligands or intracellular ligands, the sensor systems described herein are generally designed for an intracellular target ligand. As used interchangeably herein, the term "intracellular target ligand" or "intracellular ligand" refers to a ligand inside a cell (e.g., in the cytoplasm and/or nucleus of a cell). A ligand is generally a molecule with an affinity to bind to second molecule (e.g., an intracellular target ligand-binding recognition domain). An intracellular ligand can be a naturally-occurring, mutant, or synthetic molecule. The intracellular ligand can be an endogenous ligand (i.e., inherently expressed inside a host cell), or a ligand exogenously introduced into a cell, e.g., a viral antigen in an infected cell. Examples of an intracellular ligand include, but are not limited to, a protein, a peptide, a nucleic acid, a viral protein, a bacterium, a metabolite, a lipid, a carbohydrate (e.g., monosaccharide, disaccharides, oligosaccharides, and polysaccharides), an enzyme (e.g., but not limited to RNA polymerase II), and combinations thereof. As used herein, intracellular target ligands do not encompass cell-permeable small molecules.

In some embodiments, an intracellular ligand can be an oncogene or oncogenic protein. The term "oncogene" as used herein refers to a nucleic acid sequence encoding, or the polypeptide encoded by a mutated and/or overexpressed version of a normal gene that in a dominant fashion can release the cell from normal restraints on growth and thus alone or in concert with other changes, contribute to a cell's tumorigenicity. Examples of oncogenes include; gp40 (v-fms); p21 (ras); p55 (v-myc); p65 (gag-jun); pp60 (v-src); v-abl; v-erb; v-erba; v-fos etc. A proto-oncogene refers to the normal expression of a nucleic acid expressing the normal, cellular equivalent of an oncogene, typically these genes are usually a gene involved in the signaling or regulation of cell growth.

In some embodiments, an intracellular ligand can be a mutant protein expressed by a host cell.

In some embodiments, an intracellular ligand can be a nucleic acid or protein from or introduced by an infectious agent (e.g., an agent that infects a cell such as a virus).

As intracellular ligand(s), unlike extracellular ligands, are used as signals for specifying the spatial expression pattern of the destabilizable target ligand-binding recognition domain, the sensor systems described herein provide a spatial control of an effector domain activity in a cell based on spatial expression of an intracellular ligand of interest in the cell.

In some embodiments, the sensor fusion can further comprise a small molecule-binding recognition domain linked to an effector domain. By regulating exogenous introduction of a cell-permeable small molecule into a cell, the activity of the effector domain can also be controlled in a temporal manner. Accordingly, in some embodiments, the sensor systems described herein can provide both spatial and temporal controls of an effector domain activity in a cell based on both spatial expressions of an intracellular ligand of interest in the cell and temporal introduction of a small molecule into the cell. Examples of small molecule-binding recognition domain for temporal control of an effector domain activity are described in U.S. Pat. No. 8,173,792, the content of which is incorporated herein by reference.

As used herein, the term "fusion molecule" refers to a molecule comprising at least two components that are directly or indirectly fused together and do not occur in a fused form in a nature. In some embodiments, the fusion molecule can be a fusion protein. The components are fused together by at least one linker in the fusion molecule. As used herein, the term "linker" generally refers to an entity that can directly or indirectly connect at two parts of a composition, e.g., at least one target ligand-binding recognition domain and an effector domain. Examples of a linker include, but are not limited to, a chemical bond, a chemical functional group, an atom, a small molecule, a peptide or oligopeptide, an amino acid residue, a nucleic acid, and combinations thereof. In some embodiments, at least one target ligand-binding recognition domain can be linked to an effector domain by a cleavable linker. In some embodiments, at least one target ligand-binding recognition domain can be linked to an effector domain by a non-cleavable linker.

Cleavable linkers are susceptible to cleavage agents, e.g., hydrolysis, pH, redox potential or the presence of degradative molecules such as enzymes. Exemplary cleavable linking groups include, but are not limited to, hydrolyzable linkers, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease.

In some embodiments, at least two or more (e.g., 2, 3, 4 or more) target ligand-binding recognition domains can be linked to an effector domain. The two or more target ligand-binding recognition domains can be the same or different. In some embodiments, the two or more target ligand-binding recognition domains can be destabilizable in response to the same target intracellular ligand. In some embodiments, the two or more target ligand-binding recognition domains can each be destabilizable in response to a different target intracellular ligand. In some embodiments where two or more target ligand-binding recognition domains are linked to an effector protein, the fusion molecule is stabilized when at least one or more of the destabilizable target ligand-binding recognition domains is stabilized upon binding to a respective intracellular ligand. In some embodiments, the fusion molecule is stabilized when all of the destabilizable target ligand-binding recognition domains are stabilized upon binding to their respective intracellular ligands.

Accordingly, another aspect described herein relates to a sensor system comprising a fusion molecule with at least two target ligand-binding recognition domains linked to an effector domain. The sensor system comprises: a fusion molecule comprising: (a) an effector domain; (b) a first target ligand-binding recognition domain linked to the effector domain, wherein the first target ligand-binding recognition domain specifically binds a first intracellular target ligand and is configured such that (i) in the absence of the first target ligand, the first target ligand-binding recognition domain is destabilized and such that the fusion protein is destabilized, or (ii) in the presence of the target ligand, the target ligand-binding recognition domain is stabilized upon binding of the target ligand; and (c) a second target ligand-binding recognition domain linked to the effector domain; wherein the second target ligand-binding recognition domain specifically binds a second intracellular target ligand and is configured such that (i) in the absence of the second target ligand, the second target ligand-binding recognition domain is destabilized and such that the fusion protein is destabilized, or (ii) in the presence of the second target ligand, the second target ligand-binding recognition domain is stabilized upon binding of the second target ligand. In some embodiments, the effector domain can display a higher activity (e.g., at least about 30% or more, including, e.g., at least about 40%, at least about 50%, at least about 60%, at least about 70%, at least about 80%, at least about 90%, at least about 95% or more) in the presence of the first target ligand and the second target ligand than when either the first target ligand or the second target ligand is present, but not both. In some embodiments, the effector domain can display a higher activity by at least about 1.1-fold or more, including, e.g., at least about 1.5-fold, at least about 2-fold, at least about 3-fold, at least about 4-fold, at least about 5-fold, at least about 6-fold, at least about 7-fold or more) in the presence of the first target ligand and the second target ligand than when either the first target ligand or the second target ligand is present, but not both. In some embodiments, the effector domain can be activated only when all the target ligand-binding recognition domains of the fusion protein are stabilized upon binding to their corresponding target ligands.

Figure 10A:
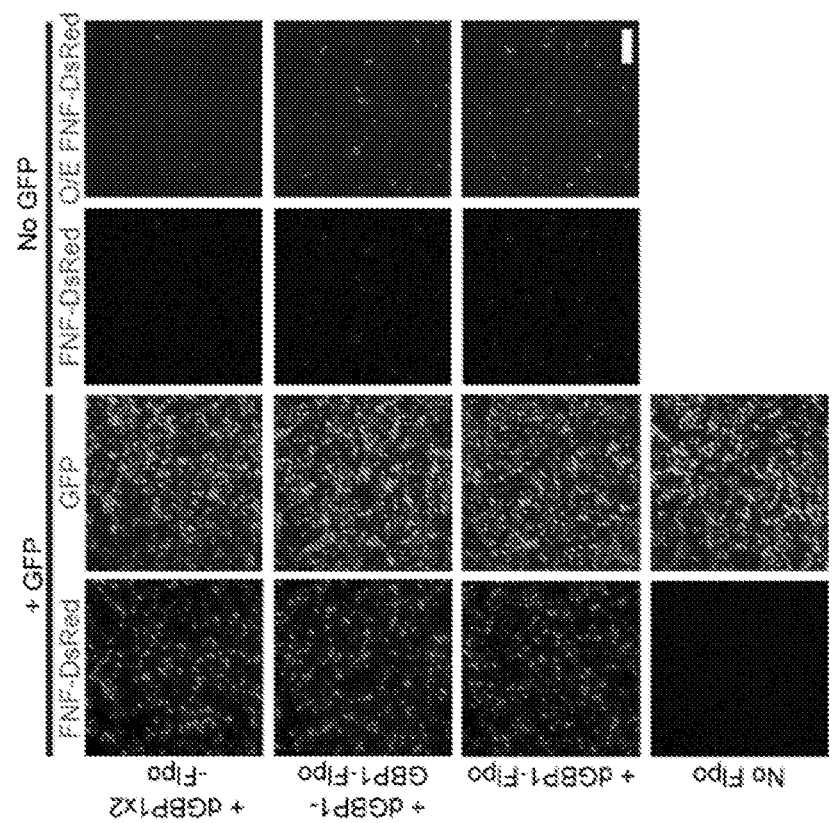
FIGS. 10A-10D show effect of double dGBP1 fusion on Cre and Flpo recombination. Refer to FIGS. 3A-3F and Methods for experimental setup. Plasmids encoding wildtype or destabilized GBP1 fusion to Cre or Flpo were transfected into 293T cells along with loxP-Neo-loxP- (LNL-) or FRT-Neo-FRT- (FNF-) DsRed.
Figure 10B:
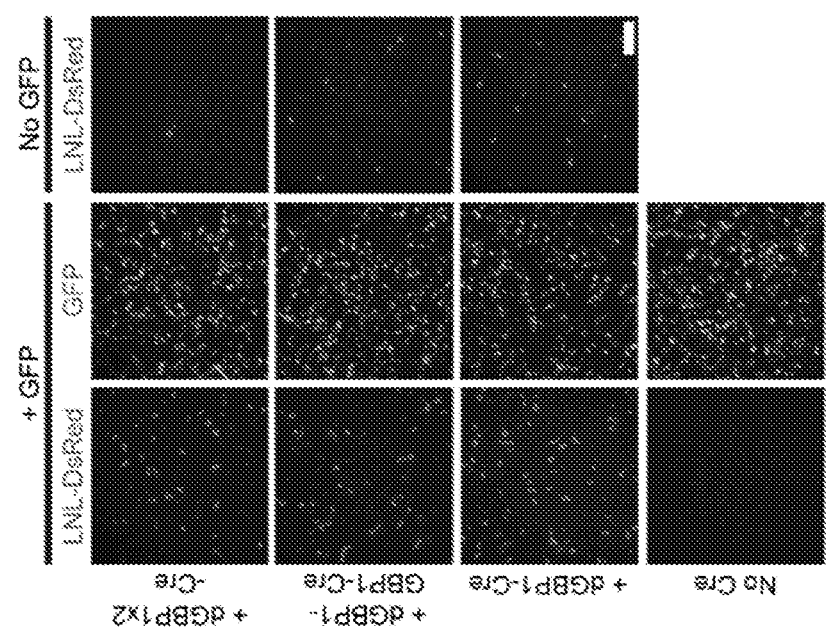
Figure 10C:
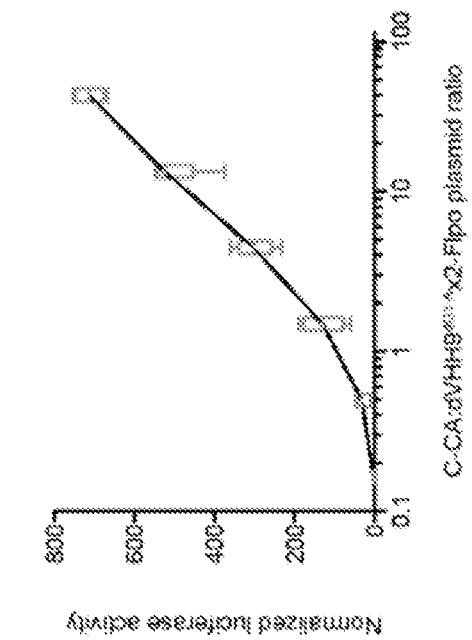
Figure 10D:
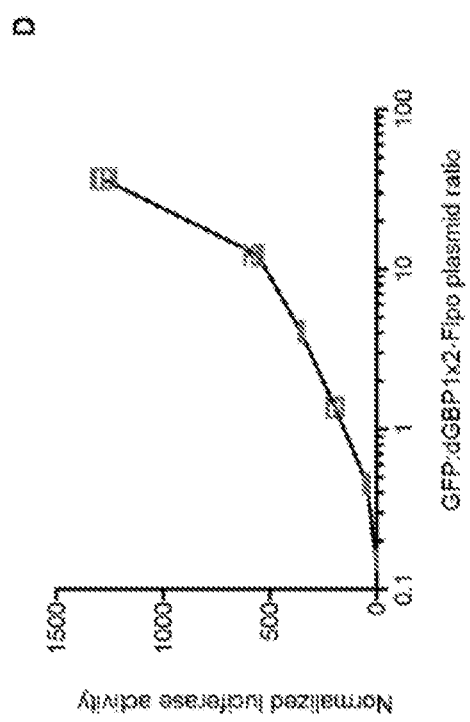
Figure 11A:
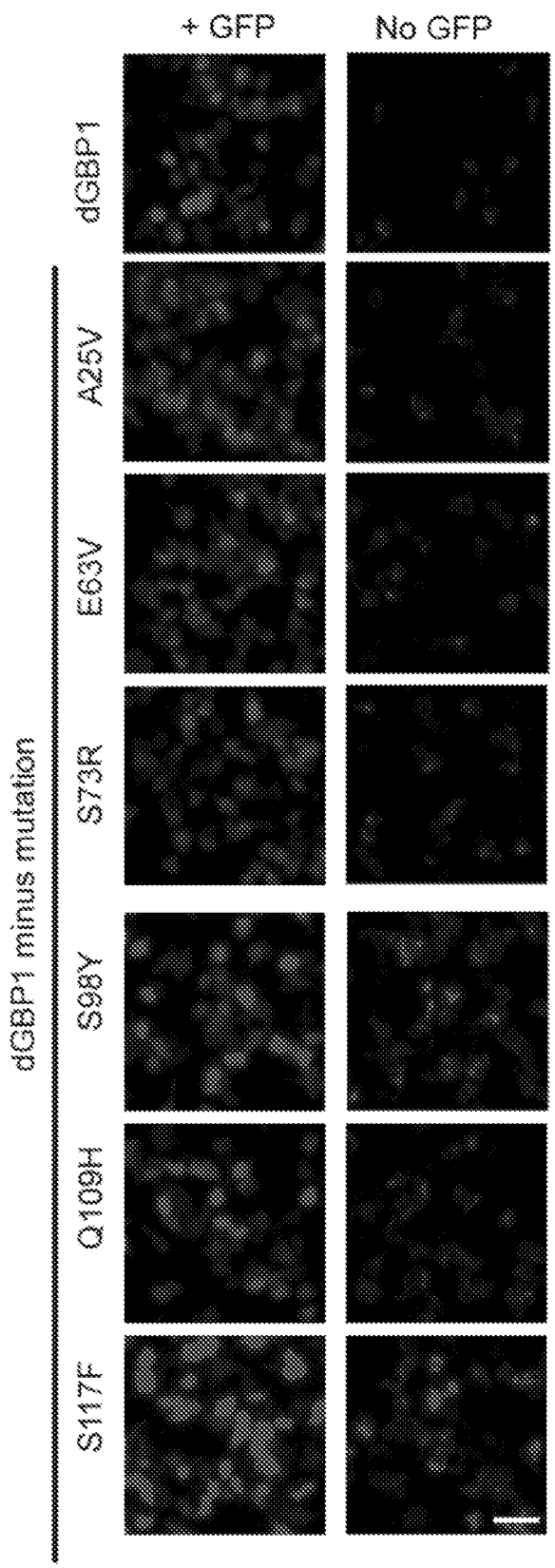
FIGS. 11A-11B show mapping of mutations necessary for dGBP1 destabilization.
Figure 11B:
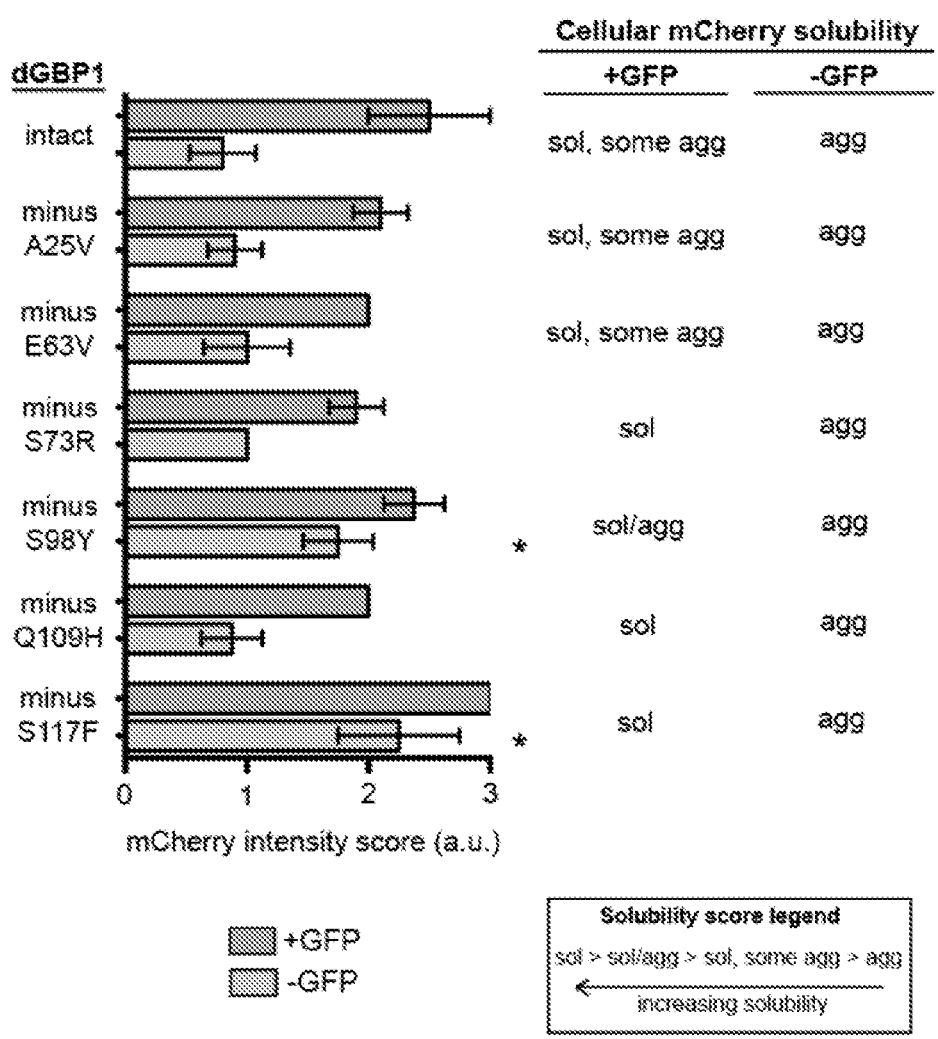

Without wishing to be bound by theory, increasing the number of target ligand-binding recognition domains linked to an effector domain can be beneficial for reducing the background and/or non-specific activity of the effector domain when the target ligand is absent. As shown in the Examples herein the inventors have shown that two target ligand-binding recognition domains linked to an effector domain (e.g., a recombinase) can reduce an intracellular target ligand-independent activity of an effector domain and/or enhance the efficiency of degradation of the sensor systems described herein the absence of an intracellular target ligand, as compared to one target ligand-binding recognition domain linked to an effector domain. This approach has been shown to suppress leakage of Cre and especially Flpo activity (FIGS. 10A-10B).

Target-ligand-binding recognition domain: As used herein, the term "target ligand-binding recognition domain" refers to a region or regions having an ability to directly and specifically bind an intracellular target ligand. Upon a ligand binding, the target ligand-binding recognition domain can be in full or partial contact with the ligand. In some embodiments, the target ligand-binding recognition domain can comprise a linear epitope or conformational epitope. A linear epitope generally refers to a continuous binding region, while a conformational epitope generally comprises discontinuous binding regions. If the target ligand-binding recognition domain is a conformational epitope, the target ligand is generally recognized by the three-dimensional structure of the target ligand-binding recognition domain.

As used herein, the term "specifically bind" or "specific binding" when used in reference to binding of a ligand to an intracellular target ligand-binding recognition domain is a term well understood in the art, and methods to determine such specific or preferential binding are also well known in the art. An intracellular target ligand-binding recognition domain is said to exhibit "specific binding" or "preferential binding" if it reacts or associates more frequently, more rapidly, with greater duration and/or with greater affinity with an intracellular target ligand than it does with non-target ligands. For example, an intracellular target ligand-binding recognition domain "specifically binds" or "preferentially binds" to an intracellular target ligand if it binds with greater affinity, avidity, more readily, and/or with greater duration than it binds to other non-target ligands. Accordingly, as used herein, "selectively binds" or "specifically binds" refers to the ability of a polypeptide domain described herein to bind to a target ligand, with a $K_D$ $10^{-5}$ M (10000 nM) or less, e.g., $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less. For example, if a polypeptide agent described herein binds to a first target ligand with a $K_D$ of $10^{-5}$ M or lower, but not to a second, lower affinity target ligand, then the agent is said to specifically bind the first target ligand. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

The target ligand-binding recognition domain of the sensor systems described herein can be a protein, a peptide, a nucleic acid, an antibody, an antibody fragment, a nanobody, a single-domain antibody, a peptidomimetic, a scaffold protein (e.g., fibronectin), or combinations thereof.

The term "antibody" as used herein refers to immunoglobulin molecules and immunologically active portions of immunoglobulin molecules (molecules that contain an antigen binding site which specifically binds an antigen), including monoclonal antibodies (including full length monoclonal antibodies), polyclonal antibodies, multispecific antibodies (for example, bispecific antibodies), chimeric antibodies, humanized antibodies, human antibodies, and single chain antibodies (scFvs).

As used herein, the term "antibody fragment," as used herein, refers to a protein fragment that comprises only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_{H1}$ domains; (ii) the Fab' fragment, which is a Fab fragment having one or more cysteine residues at the C-terminus of the $C_{H1}$ domain; (iii) the Fd fragment having $V_H$ and $C_{H1}$ domains; (iv) the Fd' fragment having $V_H$ and $C_{H1}$ domains and one or more cysteine residues at the C-terminus of the $C_{H1}$ domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_{H1}$-$V_H$-$C_{H1}$) which, together with complementary light chain polypeptides, form a pair of antigen binding regions (Zapata et al. Protein Eng. 8(10):1057-1062 (1995); and U.S. Pat. No. 5,641,870).

In some embodiments, the target ligand-binding recognition domain is a single-domain antibody. By the term "single-domain antibody" or "sdAb", it is meant an antibody fragment comprising a single protein domain. Single domain antibodies can comprise any variable fragment, including $V_L$, $V_H$, $V_{HH}$, and $V_{NAR}$, and can be naturally-occurring or produced by recombinant technologies. For example, $V_H$, $V_L$, $V_{HH}$, and $V_{NAR}$ domains can be generated by techniques well known in the art (Holt, et al., 2003; Jespers, et al., 2004a; Jespers, et al., 2004b; Tanha, et al., 2001; Tanha, et al., 2002; Tanha, et al., 2006; Revets, et al., 2005; Holliger, et al., 2005; Harmsen, et al., 2007; Liu, et al., 2007; Dooley, et al., 2003; Nuttall, et al., 2001; Nuttall, et al., 2000; Hoogenboom, 2005; Arbabi-Ghahroudi et al., 2008). In the recombinant DNA technology approach, libraries of sdAbs can be constructed in a variety of ways, "displayed" in a variety of formats such as phage display, yeast display, ribosome display, and subjected to selection to isolate binders to the targets of interest (panning). Examples of libraries include immune libraries derived from llama, shark or human immunized with the target antigen; non-immune/naïve libraries derived from non-immunized llama, camel, shark or human; or synthetic or semi-synthetic libraries such as $V_H$, $V_L$, $V_{HH}$ or $V_{NAR}$ libraries. In one embodiment, the sdAb can be a heavy variable domain ($V_H$).

In some embodiments, the target ligand-binding recognition domain is a nanobody. A nanobody (Nb) is single variable domain ($V_H$H) of a naturally occurring single-chain antibody and is known to the person skilled in the art. They are generally derived from heavy chain only antibodies, for example, in camelids, alpacas, llamas, and sharks. The term "Camelids" refers to old world camelids (*Camelus bactrianus* and *Camelus dromedarius*) and new world carnelids (for example, *Lama paccos, Lama glans, Lama guanicoe* and *Lama vicugna*). The small size and unique biophysical properties of Nbs exceed conventional antibody fragments for the recognition of uncommon or hidden epitopes and for binding into cavities or active sites of protein targets. Further, Nbs can be designed as multi-specific and multivalent antibodies or attached to reporter molecules. Certain Nbs and Nb variants can survive the gastro-intestinal system and Nbs can easily be manufactured, Therefore, Nbs can be used in many applications including drug discovery and therapy, but also as a versatile and valuable tool for purification, functional study and crystallization of proteins.

The nanobodies generally comprise a single amino acid chain that can be considered to comprise four "framework regions" or FRs and three "complementarity determining regions" or CDRs. The term "complementarity determining region" or "CDR" refers to variable regions in nanobodies and contains the amino acid sequences capable of specifically binding to antigenic targets. These CDR regions account for the basic specificity of the nanbody for a particular antigenic determinant structure. Such regions are also referred to as "hypervariable regions." The nanobodies have three CDR regions, each non-contiguous with the others (termed CDR1, CDR2, CDR3).

In some embodiments, the target ligand-binding recognition domain can be a nanobody against a GFP protein. In some embodiments, the target ligand-binding recognition domain can be a nanobody against HIV C-terminal domain (CTD). In some embodiments, the target ligand-binding recognition domain can be dihydrofolate reductase.

Destabilizing mutations: To configure the target ligand-binding recognition domain to have a desirable ligand-dependent stabilization effect, in some embodiments, the target ligand-binding recognition domain can be configured to be destabilizable. As used herein, the term "destabilizable" refers to an ability of a target ligand-binding recognition domain to switch between the state of destabilization and the state of stabilization. In the absence of an intracellular target ligand, the target ligand-binding recognition is destabilized and/or degraded, which in turn leads to destabilization and/or degradation of the corresponding fusion molecule and inactivation of the effector domain. In the presence of an intracellular target ligand, the target ligand-binding recognition is stabilized upon its binding to the target ligand, which in turn leads to activation of the effector domain.

For example, a destabilizable target ligand-binding recognition domain can comprise at least one or more (including, e.g., at least two or more, at least three or more) target ligand-dependent destabilizing mutations, as compared to a wild-type target ligand-binding recognition domain.

In some embodiments, the wild-type target ligand-binding recognition domain can be a naturally occurring destabilizing target ligand-binding recognition domain. Without wishing to be bound by theory, addition of one or more destabilizing mutations can tune the responsiveness of such target ligand-binding recognition domain to ligand-dependent stabilization effects. For example, addition of one or more destabilizing mutations can further destabilize the naturally occurring destabilizing target ligand-binding recognition domain in the absence of target ligands, and/or promote stabilization of the naturally occurring destabilizing target ligand-binding recognition domain in the presence of target ligands.

In some embodiments, the wild-type target ligand-binding recognition domain can be naturally a stable molecule. By adding at least one or more destabilizing mutations, the stable molecule can be engineered to be a biological switch with target ligand-dependent stabilization effects.

The amino acid residues useful for introducing a destabilizing mutation are referred to herein by the ImMunoGeneTics (IMGT) numbering system, as described in Lefranc, M. et al. *Dev Comp Immunol* (2003) 27(1):55-77, the contents of which are herein incorporated by reference in their entirety. This system readily permits the identification of amino acid residues that correspond from one antibody to another.

In some embodiments, the destabilizing mutations can be selected such that the destabilizable target ligand-binding recognition domain has a half-life of no more than 30 minutes or less (including, e.g., no more than 20 minutes, no more than 10 minutes, no more than 5 minutes, or less), when an intracellular target ligand is absent.

In some embodiments, the destabilizing mutations can be selected such that they are located within a conserved framework region of a nanobody scaffold, and/or a region that is not involved in antigen or ligand binding. As such, the destabilizing mutations identified in one nanobody can be mapped to other nanobodies for generation of ligand-dependent sensors and effectors without undue experimentation to select and/or screen for a destabilized nanobody of interest.

Destabilizing mutations can be identified through a combination of art-recognized mutagenesis methods and screening assays for ligand-dependent effector domain activity, for example as described in Example 1. For example, the coding sequence of a wild-type target ligand-binding recognition domain can be mutagenized and the mutants can be cloned into an expression vector (e.g., a viral vector). The target ligand-binding recognition domain mutant (referred to as "RDmutant" hereafter) can be inserted upstream or downstream and in frame to an effector domain of interest. The RDmutant-effector domain sequence can be also part of a bicistronic cassette, in which a detectable label (e.g., a fluorescent protein) is expressed via an internal ribosomal entry site (IRES). Cells such as 293T cells are then transfected with the expression vector encoding the RDmutant-effector domain sequence, and the cells are selected for high expression of the detectable label and low activity of the effector domain. In some embodiments, the cells can be selected by fluorescence-activating cell sorting (FACS). The selected cells are then transfected with a second expression vector expressing the corresponding target ligand, followed by selection of cells for high activity of the effector domain and high expression of the detectable label. The selected cells with high activity of the effector domain and high expression of the detectable label are subjected to genomic extraction and polymerase chain reaction (PCR) to isolate RDmutant-effector domain fusion molecules that are responsive to the target ligand of interest. The target ligand-dependent RDmutant-effector domain fusion molecules are then re-cloned into an expression vector (e.g., a viral vector), and then screened individually for enhanced expression and activity of the effector domain in the presence of the target ligand, as compared to fusion molecules comprising a wild-type target ligand-binding recognition domain being contacted with the same target ligand. Destabilizing mutation(s) can then be determined from the clone(s) that shows an enhanced expression and activity of the effector domain in the presence of the target ligand, e.g., by at least about 30% or more (including, e.g., at least about 40%, at least about 50%, at least about 60%, at least about 70%, at least about 80%, at least about 90%, or more), as compared to fusion molecules comprising wild-type target ligand-binding recognition domain being contacted with the same target ligand.

If multiple mutations occur in the target ligand-binding recognition domain, one can determine the "necessary and sufficient" mutation(s) by creating clones with each individual mutation removed one at a time, and/or by creating clones with each individual mutation alone, followed by characterization of the ligand-dependent stabilization effects (in the presence of an intracellular target ligand vs. in the absence of an intracellular target ligand), for example, as described in the Examples.

As a proof-of-concept, single chain antigen recognition domains derived from Camelid antibodies, or nanobodies, were selected and modified to form a destabilizable target ligand-binding recognition domain of the sensor system according to one embodiment described herein. For example, for ease of detecting an intracellular target ligand and activity of an effector domain, the inventors have selected GFP-GBP1 complex (Kirchhofer et al., 2010) to construct a sensor system as described in the Examples and to identify destabilizing mutation(s). In some embodiments, the target ligand-dependent destabilizing mutation can be at least one mutation or a combination of two or more mutations of a nanobody of SEQ ID NO: 1 (wild-type GBP1) selected from the group consisting of A25V, E63V, S73R, S/C98Y, Q109H, and S117F. In some embodiments, the target ligand-dependent destabilizing mutation can be at least one mutation or a combination of two or more mutations of a nanobody of SEQ ID NO: 1 (wild-type GBP1) selected from the group consisting of S73R, S/C98Y and S117F. In some embodiments, the target ligand-dependent destabilizing mutation can be at least one mutation of a nanobody of SEQ ID NO: 1 (wild-type GBP1) selected from S/C98Y and S117F, or a combination thereof. These destabilizing mutations identified in a nanobody targeting a specific ligand can be transferred to other nanobodies targeting a different ligand.

The destabilizing mutations identified in a GBP1 nanobody are located within the conserved framework regions of the nanbody scaffold, and the mutated resides do not appear to be involved in antigen or ligand binding. Given the conserved protein backbone structure of nanobodies (e.g., see FIGS. 5A, 14A, and 18) and potential to be selected to bind a variety of antigens in living cells (Muyldermans, 2013), and the destabilizing mutations identified in the GBP1 occur in the relatively conserved framework regions of the nanobody, it is contemplated that the identified destabilizing mutations can be transferred to other nanobodies against different target ligands (e.g., target intracellular ligands). Indeed, the inventors have showed that the destabilizing mutations identified in the GBP1 can be transferred to a nanobody against a different intracellular target ligand, e.g., HIV C-terminal domain (CTD) capsid protein or *E. coli* Dihydrofolate reductase (DHFR) enzyme, and still confer desirable target ligand-dependent stabilization effects of the nanobody. In some embodiments, the target ligand-dependent destabilizing mutation can be at least one mutation or a combination of two or more mutations of a nanobody of SEQ ID NO: 2 (wild-type HIV CTD) selected from the group consisting of A25V, E63V, S73R, S/C98Y, Q109H, and S117F. These destabilizing mutations identified in a nanobody targeting a specific ligand can be transferred to other nanobodies targeting a different ligand.

In addition, the inventors have surprisingly discovered that mutations identified to destabilize a nanobody from one species can be mapped to nanobodies of other species (e.g., but not limited to from camel to alpaca or llama) and exert target-ligand-dependent stabilization effects as well (e.g., FIGS. 5A-5E). Accordingly, in some embodiments, the destabilizing mutations described herein identified in nanobodies of one species can be transferred to nanobodies of different species. Nanobodies can be generated from various species, including, e.g., but not limited to, camels, dromedaries, llama, alpacas, and sharks.

In some embodiments, the destabilizing mutations described herein can be transferred to other nanobodies that have similar mode/configuration of ligand-nanobody binding as observed in the crystal structures of GFP-GBP1 (FIG. 13B) complex or CTD-HIV CTD Nb complex (FIG. 13A).

To determine effects of destabilizing mutations on antigen-nanobody binding modes, one can repeat the mutagenesis screen on selected candidates within each clade of complexes, and then to compare and contrast isolated mutations within clade and across clades. Upon arrival at a common set of residues and residue mutations within and between clades, single, and/or combinations of mutations can be grafted between nanobodies to assess whether a Glade-specific or universal mutation codes can be arrived at for generating antigen/ligand-inducible protein stabilization. The approach of comparing crystal structures can identify residues likely to permit ligand-dependent stabilization/destabilization when mutated in orthologs or homologs of a given ligand-binding protein.

Figures 5A, 5B, 5C, 5D, 5E:
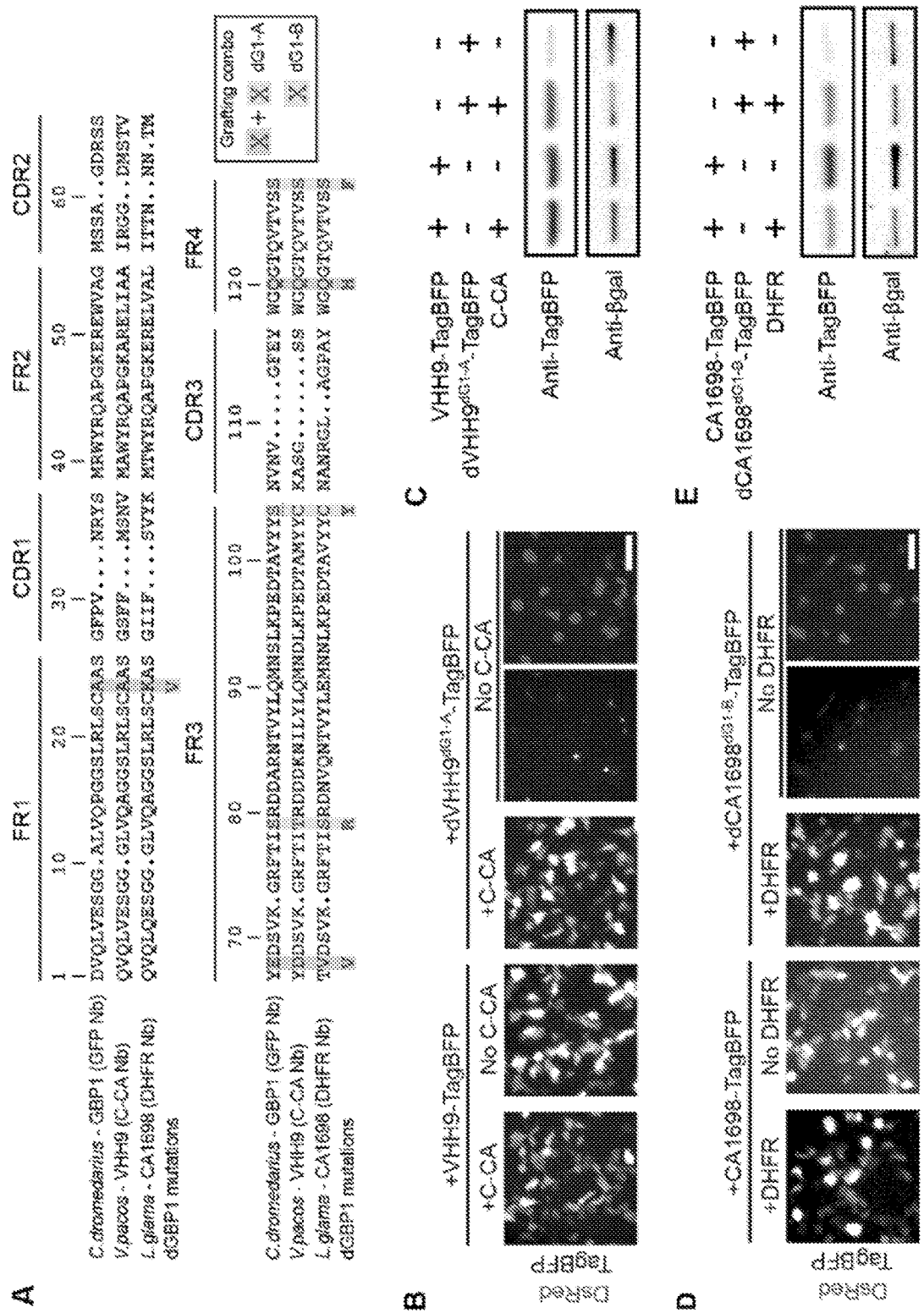
FIGS. 5A-5G show conserved effects of dGBP1 destabilizing mutations on other nanobodies derived from different species.
Figures 5F, 5G:
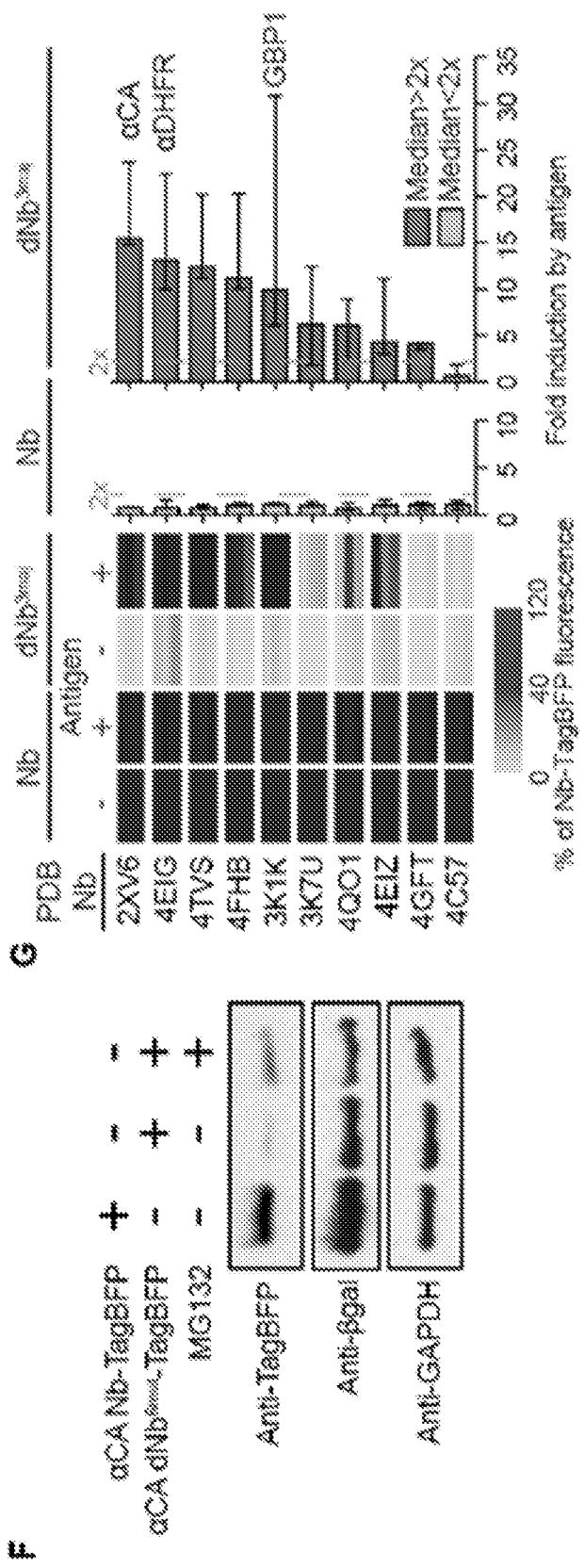
Figures 14A, 14B, 14C, 14D, 14E:
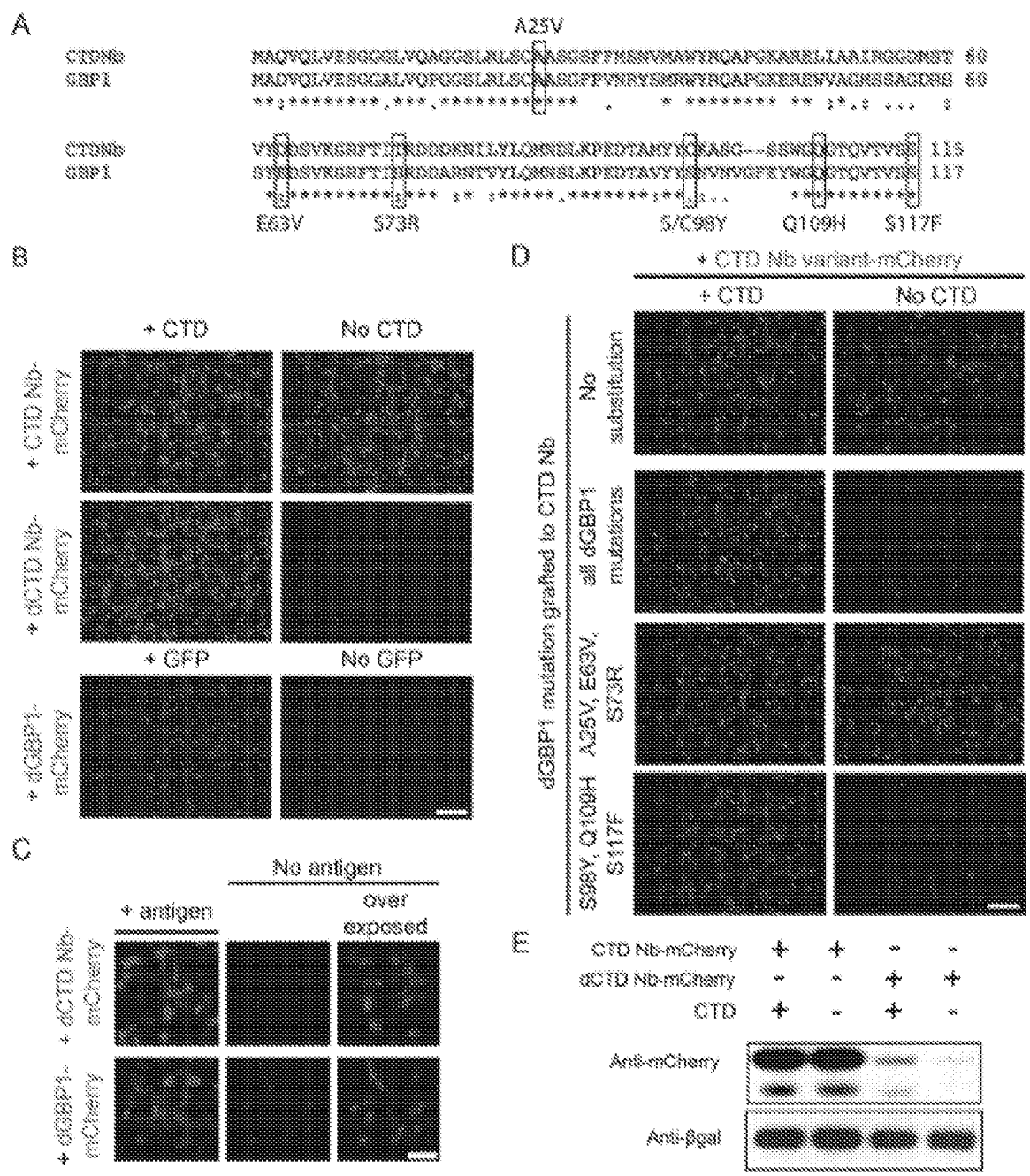
FIGS. 14A-14E contain experimental data showing destabilized CTD nanobody generated by grafting the destabilizing mutations from dGBP1.
Figure 15A:
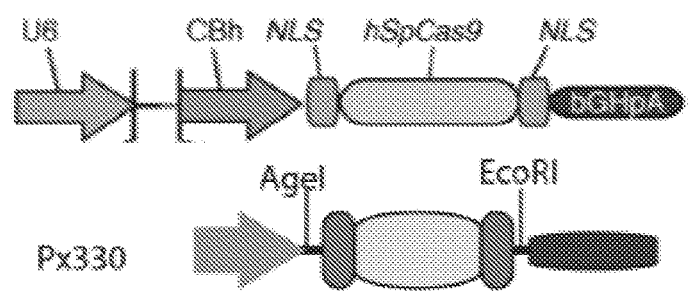
FIGS. 15A-15D are schematic diagrams showing design of dCTDx2-Cas9 fusion construct.
Figure 15B:
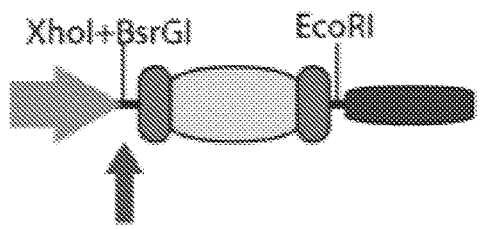
Figure 15C:
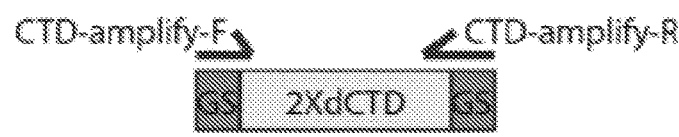
Figure 15D:
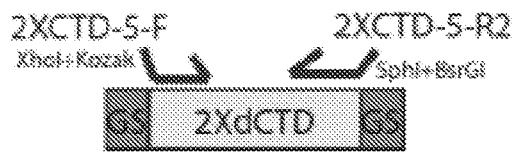
Figure 16:
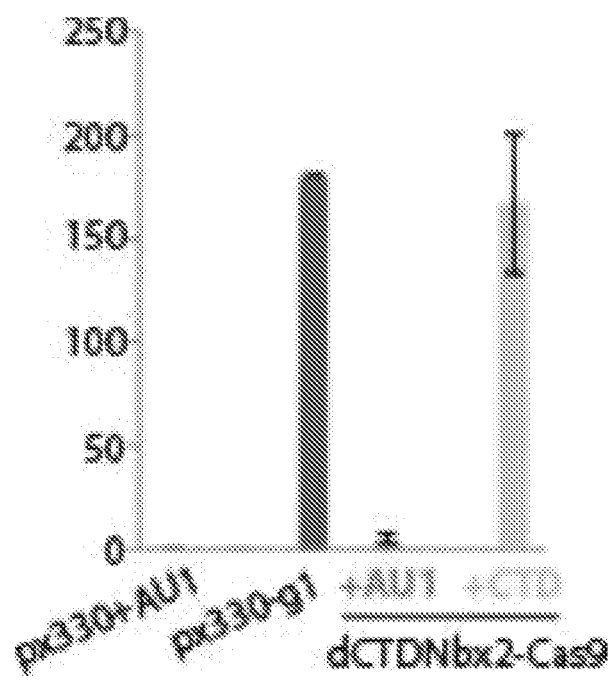
FIG. 16 is a data graph showing CTD-inducible genome editing in human cells. Plasmid encoding unfused or dCTD Nb fused Cas9 and guide RNA were transfected into a modified human cell line, LoxLacZ, to remove a transcriptional stop cassette from an exogenously introduced locus, loxP-STOP-loxP-lacZ. Wildtype Cas9 encoding plasmid (px330) did not induce detectable Cas9 activity. dCTDx2 fused Cas9 (dCTDNbx2-Cas9) did induce lacZ expression with CTD antigen expression, but not with the negative control expression of AU1 peptide. Y axis represents the number of mCherry+ and X-gal+ cells counted in a transfected well. Cells were harvested.
Figure 18:
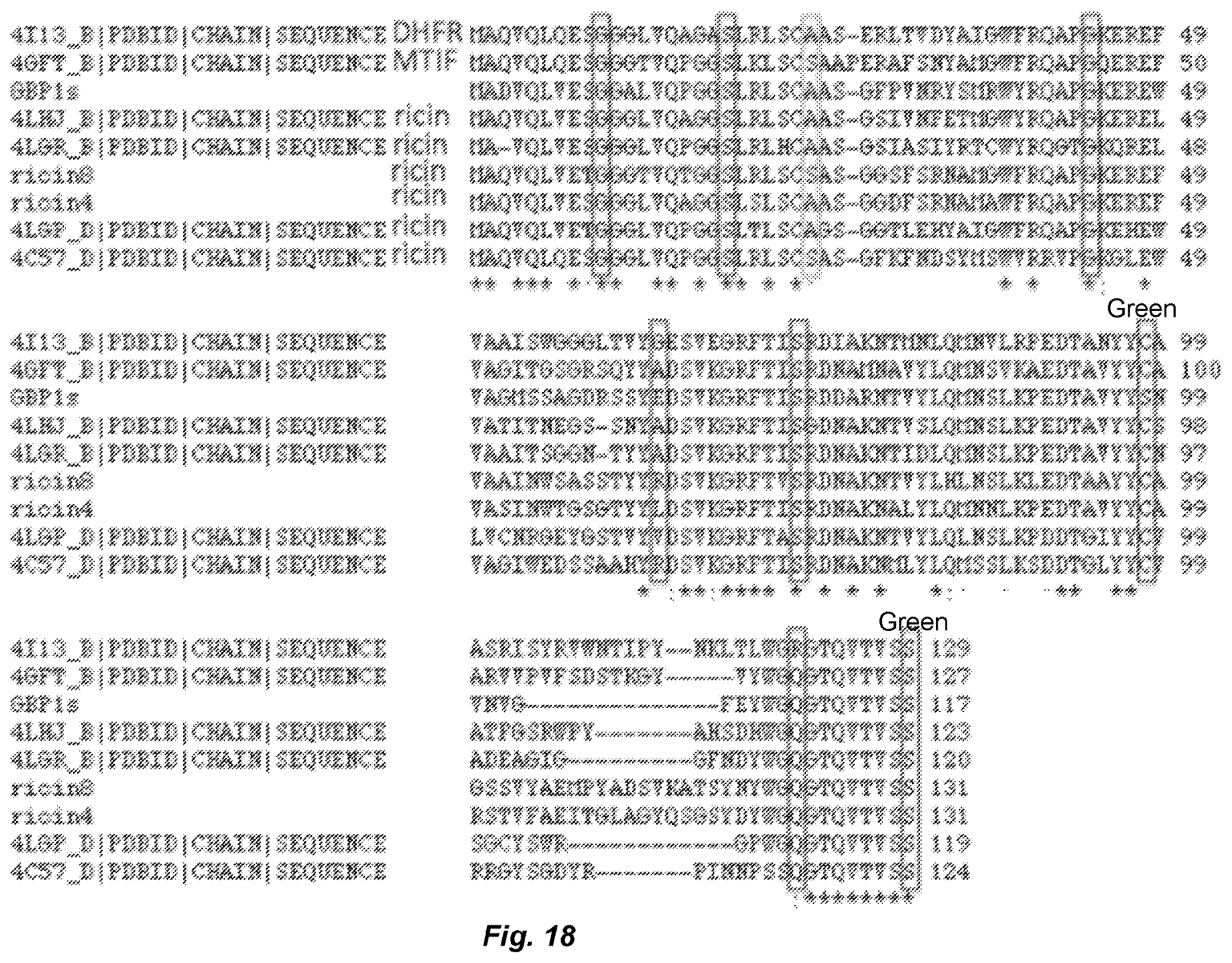

To predict effects of destabilizing mutations mapped from a reference nanobody to a nanobody of interest, one can compare the primary amino acid sequence and crystal structures of the nanobody of interest/ligand complex to those of the reference nanobody. For example, if the identified destabilizing mutations from a reference nanobody fall in the relatively conserved framework region of a nanobody scaffold, and/or are not involved in antigen or ligand binding, the destabilizing mutations can be likely transferred to a nanobody of interest with a similar conserved framework region, e.g., as shown in FIGS. 5A, 14A and 18, to produce target ligand-dependent stabilization effects. Additionally or alternatively, one can compare and analyze the crystal structures of ligand-nanobody complexes to determine if it shares a similar binding relationship as between a reference nanobody and its corresponding ligand. If a candidate nanobody shares a similar binding interaction (e.g., involving a similar interaction surface) as seen in the reference nanobody, it indicates that the candidate nanobody is likely to be more responsive to receiving the destabilizing mutations identified in the reference nanobody. For example, as shown in Example 2, a nanobody structure can be divided into multiple secondary structure regions such as loops, alpha helices and beta strands. The crystal structure of antigen-nanobody complexes (e.g., accessible online at www.pdb.org) can be analyzed to create a matrix and each nanobody secondary structure region for putative contact sites with the antigen can be scored. Statistical analysis, e.g., principal component analysis, can be used to analyze and cluster antigen-nanobody complexes, e.g., separating nanobodies that would likely acquire ligand-dependent stabilization characteristics upon introduction of the identified destabilizing mutations, from nanobodies that would unlikely respond. Such example analysis can provide a guide for choosing nanobodies for introducing destabilizing mutations identified from a reference nanobody.

An alternative way to design a universal destabilized nanobody scaffold can be to graft the hypervariable CDR loops onto a common destabilized scaffold.

In certain embodiments, methods are provided for generating a destabilized antibody from a desired antibody (e.g., a human antibody against a desired target) by mutating at least one amino acid residue (e.g., 1, 2 or 3 (i.e., all)) selected from the group consisting of: S79, C/S98 and S117 as numbered according to the ImMunoGeneTics numbering system (IMGT). In other embodiments, the destabilizing mutations are S73R (or a conservative substitution of R), C/S98Y (or a conservative substitution of Y), and/or S117F (or a conservative substitution of F). Other residues that can be mutated include, but are not limited to, A25, E63, S73, and SQ109. Exemplary mutations for these residues include A25 V (or a conservative substitution of V), E63V (or a conservative substitution of V), S73R (or a conservative substitution of R), and Q109H (or a conservative substitution of H). It should be self-evident that a "conservative mutation" in this context does not include substitution that restores the wild-type amino acid.

As well-known in the art, a "conservative substitution" of an amino acid or a "conservative substitution variant" of a polypeptide refers to an amino acid substitution which maintains: 1) the structure of the backbone of the polypeptide (e.g. a beta sheet or alpha-helical structure); 2) the charge or hydrophobicity of the amino acid; or 3) the bulkiness of the side chain. More specifically, the well-known terminologies "hydrophilic residues" relate to serine or threonine. "Hydrophobic residues" refer to leucine, isoleucine, phenylalanine, valine or alanine. "Positively charged residues" relate to lysine, arginine or histidine. "Negatively charged residues" refer to aspartic acid or glutamic acid. Residues having "bulky side chains" refer to phenylalanine, tryptophan or tyrosine. For example, the term "D144N" or similar terms specifying other specific amino acid substitutions means that the Asp (D) at position 144 is substituted with Asn (N). A "conservative substitution variant" of D144N would substitute a conservative amino acid variant of Asn (N) that is not D.

The terminology "conservative amino acid substitutions" is well known in the art, which relates to substitution of a particular amino acid by one having a similar characteristic (e.g., similar charge or hydrophobicity, similar bulkiness). Examples include aspartic acid for glutamic acid, or isoleucine for leucine. A list of exemplary conservative amino acid substitutions is given in the table below. A conservative substitution mutant or variant of a conditionally destabilized antibody will 1) have only conservative amino acid substitutions relative to the destabilized parent sequence, 2) will have at least 90% sequence identity with respect to the parent sequence, preferably at least 95% identity, 96% identity, 97% identity, 98% identity or 99% or greater identity; and 3) will retain conditional destabilization of the antibody protein.

| CONSERVATIVE AMINO ACID REPLACEMENTS | | |
|---|---|---|
| For Amino Acid | Code | Replace With |
| Alanine | A, Ala | D-ala, Gly, Aib, β-Ala, Acp, L-Cys, D-Cys |
| Arginine | R, Arg | D-Arg, Lys, D-Lys, homo-Arg, D-homo-Arg, Met, Ile, D-Met, D-Ile, Orn, D-Orn |
| Asparagine | N, Asn | D-Asn, Asp, D-Asp, Glu, D-Glu, Gln, D-Gln |
| Aspartic Acid | D, Asp | D-Asp, D-Asn, Asn, Glu, D-Glu, Gln, D-Gln |
| Cysteine | C, Cys | D-Cys, S-Me-Cys, Met, D-Met, Thr, D-Thr |
| Glutamine | Q, Gln | D-Gln, Asn, D-Asn, Glu, D-Glu, Asp, D-Asp |
| Glutamic Acid | E, Glu | D-Glu, D-Asp, Asp, Asn, D-Asn, Gln, D-Gln |
| Glycine | G, Gly | Ala, D-Ala, Pro, D-Pro, Aib, β-Ala, Acp |
| Histidine | H, His | Arg, Asn, Gln, Tyr, Phe |
| Isoleucine | I, Ile | D-Ile, Val, D-Val, AdaA, AdaG, Leu, D-Leu, Met, D-Met |
| Leucine | L, Leu | D-Leu, Val, D-Val, AdaA, AdaG, Leu, D-Leu, Met, D-Met |
| Lysine | K, Lys | D-Lys, Arg, D-Arg, homo-Arg, D-homo-Arg, Met, D-Met, Ile, D-Ile, Orn, D-Orn |

CONSERVATIVE AMINO ACID REPLACEMENTS

| For Amino Acid | Code | Replace With |
| --- | --- | --- |
| Methionine | M, Met | D-Met, S-Me-Cys, Ile, D-Ile, Leu, D-Leu, Val, D-Val |
| Phenylalanine | F, Phe | D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, D-Bpa |
| Proline | P, Pro | D-Pro, L-I-thioazolidine-4-carboxylic acid, D-or-L-1-oxazolidine-4-carboxylic acid (Kauer, U.S. Pat. No. (4,511,390) |
| Serine | S, Ser | D-Ser, Thr, D-Thr, allo-Thr, Met, D-Met, Met (O), D-Met (O), L-Cys, D-Cys |
| Threonine | T, Thr | D-Thr, Ser, D-Ser, allo-Thr, Met, D-Met, Met (O), D-Met (O), Val, D-Val |
| Tyrosine | Y, Tyr | D-Tyr, Phe, D-Phe, L-Dopa, His, D-His |
| Valine | V, Val | D-Val, Leu, D-Leu, Ile, D-Ile, Met, D-Met, AdaA, AdaG |

Effector domain: The effector domain is linked directly or indirectly to at least one target ligand-binding recognition domain. As used herein, the term "effector domain" refers to any molecule or a portion thereof, or combination of molecules whose functional activity is desired to be induced in and/or be localized in a cell. Thus, an effector domain can be any molecule(s) or portions thereof selected to suit the needs of a desired application provided that the effector domain produces, directly or indirectly, a detectable output signal when it is active. Examples of a detectable output signal include, but are not limited to, optical signals, therapeutic effects (e.g., apoptosis or killing of a diseased cell), effector responses (e.g., biological response of an effector domain), gene editing, changes in cell phenotype, viability, and/or metabolism, changes in cytokine profile, and/or any combinations thereof. By way of example only, for detecting the presence of an endogenous, intracellular ligand in a cell, the effector domain can be a detectable agent. For delivering a therapeutic agent to a diseased cell, the effector domain can be a therapeutic agent. In some embodiments, the effector domain can be an enzyme or a protein, whose function can be activated in a cell in the presence of an intracellular target ligand. Accordingly, the effector domain can be, without limitations, a protein, an enzyme, a nucleic acid, a therapeutic agent, a detectable agent, a growth factor, a transcription factor, an antibody, a liposome, a cytokine, and combinations thereof.

In some embodiments, the effector domain can be a nuclease enzyme. A nuclease is an enzyme capable of cleaving the phosphodiester bonds between the nucleotide subunits of nucleic acids. In some embodiments, the effector domain can be a DNA nuclease enzyme, e.g., a DNA endonuclease enzyme. In some embodiments, the DNA endonuclease enzyme can be an RNA-guided endonuclease enzyme (e.g., but not limited to CRISPR associated protein). An exemplary RNA-guided endonuclease enzyme is Cas9.

In some embodiments, the effector domain can be a recombinase enzyme. The term "recombinase" as used herein refers to a protein involved in recombination. As such, recombinases recognize and bind two specific DNA sequences termed "recombination sites" or "target sites" and mediate recombination between these two target sites. Accordingly, the term "recombinase" is meant to refer to any protein component of any recombinant system that mediates DNA rearrangements in a specific DNA locus. Naturally occurring recombinases recognize symmetric target sites comprising two identical sequences forming an inverted repeat. For example, recombinases from the tyrosine integrase family are characterized by having a tyrosine as the active site nucleophile that is utilized for DNA cleavage, whereas recombinases from the serine integrase family use a serine instead of a tyrosine. Examples of recombinases include, but are not limited to, a site-specific recombinase such as Cre recombinase, Flp recombinase, integrases, and/or invertases.

In some embodiments, the effector domain can be a therapeutic agent. The term "therapeutic agent" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent include, but are not limited to, steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzinostatin chromophore, and kedarcidin chromophore), heavy metal complexes (e.g., cisplatin), hormone antagonists (e.g., tamoxifen), non-specific (non-antibody) proteins (e.g., sugar oligomers), oligonucleotides (e.g., antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin, and attenuated diphtheria toxin), and transcription-based pharmaceuticals. In some embodiments, the effector domain is a toxin.

In some embodiments, the effector domain can be a reporter molecule. Exemplary reporter molecules include, but are not limited to, fluorescent proteins (FPs), e.g., green FP, red FP, cyan FP or yellow FP, luciferase, beta-galactosidase, beta-glucuronidase, β-lactamase, alkaline phosphatase, or peroxidase. Additional examples of reporter molecules can include fluorophores including but are not limited to a xanthene, coumarin, chromene, indole, isoindole, oxazole, BODIPY, a BODIPY derivative, imidazole, pyrimidine, thiophene, pyrene, benzopyrene, benzofuran, fluorescein, rhodamine, rhodol, phenalenone, acridinone, resorufin, naphthalene, anthracene, acridinium, α-napthol, β-napthol, dansyl, cyanines, oxazines, nitrobenzoxazole (NBD), dapoxyl, naphthalene imides, styryls, and the like. In one embodiment, the reporter molecule is a fluorescent protein.

In some embodiments, temporal control on the activity of a fusion protein comprising an intracellular target ligand-binding recognition domain linked to an effector domain can be incorporated by adding an ERT2 domain for sequestering the protein away from the nucleus until introduction of an intracellular target ligand (e.g., a Tamoxifen ligand). This can reduce background noise from some fusion proteins described herein (data not shown).

In some embodiments, the sensor systems described herein can further comprise an intracellular target ligand as described herein.

Sensor Systems for Genome Editing

In some embodiments, the inventors have fused destabilized nanobodies to Cas9 to perform genome targeting and editing under the control of desired antigens (e.g., FIGS. 7A-7D). Accordingly, a system for genome editing is also described herein. The system comprises (a) a nucleic acid guide designed to be complementary to a target nucleic acid sequence to be cut; and (b) a fusion molecule comprising: at least one target ligand-binding recognition domain linked to a nucleic acid-guided DNA endonuclease enzyme, wherein the target ligand-binding recognition domain specifically binds an intracellular target ligand and is configured such that (i) in the absence of the target ligand, the target ligand-binding recognition domain is destabilized and such that the fusion protein is destabilized and the DNA endonuclease enzyme is not active, or (ii) in the presence of the target ligand, the target ligand-binding recognition domain is stabilized upon binding of the target ligand, and the DNA endonuclease enzyme is active.

"Complementarity" of a nucleic acid guide refers to the ability of a nucleic acid guide to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

In general, a nucleic acid guide is a polynucleotide sequence having sufficient complementarity to a target polynucleotide sequence such that it hybridizes with the target sequence and direct sequence-specific binding of a nucleic acid-guided DNA endonuclease enzyme (that is linked to a target ligand-binding recognition domain described herein) to the target sequence. In some embodiments, the degree of complementarity between a guide sequence and its corresponding target sequence, when optimally aligned using a suitable alignment algorithm, can be about or more than about 50%, 60%, 75%, 80%, 85%, 90%, 95%, 97.5%, 99%, or more. Optimal alignment can be determined with the use of any suitable algorithm for aligning sequences, non-limiting examples of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a nucleic acid guide is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a nucleic acid guide is less than about 75, 50, 45, 40, 35, 30, 25, 20, 15, or 12 nucleotides in length. The ability of a nucleic acid guide sequence to direct sequence-specific binding of a nucleic acid-guided DNA endonuclease enzyme (that is linked to a target ligand-binding recognition domain described herein) to a target sequence can be assessed by any suitable assay. For example, the components (e.g., the nucleic acid guide and fusion molecule as described herein) of the systems for genome editing described herein, can be introduced to a host cell having the corresponding target sequence, such as by transfection with vectors encoding the components, followed by an assessment of preferential cleavage within the target sequence, such as by Surveyor® mutation detection kits. Similarly, cleavage of a target polynucleotide sequence can be evaluated in a test tube by providing the target sequence, components (e.g., the nucleic acid guide and fusion molecule as described herein) of the systems for genome editing described herein, including the nucleic acid guide sequence to be tested and a control guide sequence different from the test guide sequence, and comparing binding or rate of cleavage at the target sequence between the test and control guide sequence reactions.

A nucleic acid guide sequence can be selected to target any target sequence. In some embodiments, the target sequence can be a sequence within a genome of a cell.

Methods to design a nucleic acid guide (e.g., RNA guide) to target a specific sequence and/or to minimize off-target effects are known in the art, e.g., as described in U.S. Pat. No. 8,697,359, WO 2014/093701, WO 2014/144592, WO 2014/144288, WO 2014/152432, and WO 2013/176772, the contents of each of which are incorporated herein by reference in their entireties.

In some embodiments, the nucleic acid-guided endonuclease enzyme can be a CRISPR associated protein (e.g., but not limited to Cas9).

Components of the systems for genome editing, e.g., the nucleic acid guide and fusion molecule as described herein, can be introduced into cells by any art-recognized nucleic acid delivery methods or as described herein. For example, the nucleic acid guide and fusion molecule can be independently introduced into cells using expression vectors. Thus, expression vector systems comprising a nucleotide sequence encoding the nucleic acid guide, and a nucleotide sequence encoding the fusion molecule are also described herein. Alternatively, the nucleic acid guide and fusion molecule can be independently coupled to or encapsulated in a cell-permeable carrier prior to administration. An exemplary cell-permeable carrier is a liposome or a nanoparticle.

Detection of intracellular antigens can be used to activate genome editing in cells expressing a pathogenic antigen, for effects such as triggering apoptosis or activation of cellular mechanisms to counteract pathogen activity. Accordingly, a method of treating a disease or disorder caused by a mutation in a gene or by expression of a pathogen gene is also described herein. The method comprises introducing into cells a composition comprising or expressing a system described herein for genome editing with a nucleic acid guide designed to target a disease-causing mutation sequence or a mutation. In some embodiments, the method can comprise introducing into cells a composition comprising (a) a nucleic acid guide designed to be complementary to a target sequence comprising a disease-causing mutation or pathogen gene; and (b) a fusion molecule comprising: at least one pathogenic antigen-binding recognition domain linked to a nucleic acid-guided DNA endonuclease enzyme, wherein the pathogenic antigen-binding recognition domain specifically binds an intracellular pathogenic antigen and is configured such that (i) in the absence of the pathogenic antigen, the pathogenic antigen-binding recognition domain is destabilized and such that the fusion protein is destabilized and the DNA endonuclease enzyme is not activated to cut the target sequence, or (ii) in the presence of the pathogenic antigen, the pathogenic antigen-binding recognition domain is stabilized upon binding of the pathogenic antigen, and the DNA endonuclease enzyme is active to cut the target sequence.

The nucleic acid guide can be directly delivered into the cells as a nucleic acid molecule (e.g., using a carrier such as a nanoparticle), and/or be expressed in the cells using an expression vector comprising a nucleotide sequence that encodes the nucleic acid guide.

The fusion molecule can be directly delivered into the cells as a protein molecule (e.g., using a carrier such as a nanoparticle and/or a cell-penetrating peptide), and/or be expressed in the cells using an expression vector comprising a nucleotide sequence that encodes the fusion protein. In some embodiments where the fusion molecule is delivered into the cells as a protein, the fusion protein molecule can comprise a cell-penetrating peptide to facilitate intracellular protein delivery. As used herein, the term "cell-penetrating peptide," also known as a protein transduction domain or membrane translocation sequence, refers to a carrier peptide that is capable of crossing a biological membrane of a cell. Cell-penetrating peptides can translocate in vitro and/or in vivo the cell membranes and enter into cells and/or cell nuclei, and direct a conjugated molecule, such as a fusion protein described herein, to a desired cellular destination. In some embodiments, the cell penetrating peptide can comprise a nuclear localization signal (NLS) domain that directs the fusion protein into the nucleus of the cells. Accordingly, the cell-penetrating peptides can direct or facilitate penetration of the fusion molecules described herein across the plasma membrane into the cytoplasm or cytosol, and/or to a desired location within the cells, e.g., the nucleus, mitochondria, and/or endosome.

In some embodiments, the cells can be treated in vivo.

In some embodiments, the cells can be treated ex vivo and then transplanted into a subject in need thereof.

Sensor System-Encoding Expression Vectors or Systems

Expression vectors comprising a nucleotide sequence encoding one or more embodiments of the sensor systems described herein are also provided. In the expression vectors, the target ligand-binding recognition domain can be inserted in frame to the effector domain. In some embodiments, at least one target ligand-binding recognition domain can be inserted upstream to the effector domain. In other embodiments, at least one target ligand-binding recognition domain can be inserted downstream to the effector domain.

Any expression vector known in the art can be used to express the sensor systems described herein. The term "vectors" used interchangeably with "plasmid" refer to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments described herein, for example, but are not limited to, plasmids, episomes, bacteriophages or viral vectors, and such vectors may integrate into the host's genome or replicate autonomously in the particular cell. Other forms of expression vectors known by those skilled in the art which serve the equivalent functions can also be used. Expression vectors comprise expression vectors for stable or transient expression encoding the DNA.

In some embodiments, the expression vector further comprises a promoter. As used herein, a "promoter" or "promoter region" or "promoter element" used interchangeably herein refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

In some embodiments, the expression vector further comprises a regulatory sequence. The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, an optional operate sequence to control transcription, a sequence encoding suitable mRNA ribosomal binding sites, and sequences to control the termination of transcription and/or translation. Regulatory sequences are selected for the assay to control the expression of split-biomolecular conjugate in a cell-type in which expression is intended.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" or "operatively associated" are used interchangeably herein, and refer to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined.

In some embodiments, an expression vector is a viral vector. As used herein, the term "viral vector" refers to any form of a nucleic acid derived from a virus and used to transfer genetic material into a cell via transduction. The term encompasses viral vector nucleic acids, such as DNA and RNA, encapsidated forms of these nucleic acids, and viral particles in which the viral vector nucleic acids have been packaged. Examples of a viral vector include, but are not limited to, retroviruses, lentiviruses, adenoviruses, adeno-associated viruses, and combinations thereof.

Pharmaceutical Compositions

In some embodiments, the sensor systems and/or the expression vectors comprising the same can be administered in vivo. Accordingly, another aspect provides a pharmaceutical composition comprising (i) the sensor system according to one or more embodiments described herein or the sensor system-encoding expression vectors according to one or more embodiments described herein, and (ii) a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Depending on the selected administration route, the compositions or preparations can be in any form, e.g., a tablet, a lozenge, a suspension, a free-flowing powder, an aerosol, and a capsule. The term "pharmaceutically acceptable," as used herein, refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" refers to a pharmaceutically-acceptable material, composition or vehicle for administration of a sensor system or sensor system-comprising expression vector described herein. Pharmaceutically acceptable carriers include any and all solvents, dispersion media, coatings, antibacterial and antifungal agents, isotonic and absorption delaying agents, and the like which are compatible with the activity of the sensor system or sensor system-comprising expression vector and are physiologically acceptable to the subject. Some examples of materials which can serve as pharmaceutically-acceptable carriers include: (i) sugars, such as lactose, glucose and sucrose; (ii) starches, such as corn starch and potato starch; (iii) cellulose, and its derivatives, such as sodium carboxymethyl cellulose, methylcellulose, ethyl cellulose, microcrystalline cellulose and cellulose acetate; (iv) powdered tragacanth; (v) malt; (vi) gelatin; (vii) lubricating agents, such as magnesium stearate, sodium lauryl sulfate and talc; (viii) excipients, such as cocoa butter and suppository waxes; (ix) oils, such as peanut oil, cottonseed oil, safflower oil, sesame oil, olive oil, corn oil and soybean oil; (x) glycols, such as propylene glycol; (xi) polyols, such as glycerin, sorbitol, mannitol and polyethylene glycol (PEG); (xii) esters, such as ethyl oleate and ethyl laurate; (xiii) agar; (xiv) buffering agents, such as magnesium hydroxide and aluminum hydroxide; (xv) alginic acid; (xvi) pyrogen-free water; (xvii) isotonic saline; (xviii) Ringer's solution; (xix) ethyl alcohol; (xx) pH buffered solutions; (xxi) polyesters, polycarbonates and/or polyanhydrides; (xxii) bulking agents, such as polypeptides and amino acids (xxiii) serum component, such as serum albumin, HDL and LDL; (xxiv) C2-C12 alcohols, such as ethanol; and (xxv) other non-toxic compatible substances employed in pharmaceutical formulations. Wetting agents, coloring agents, release agents, coating agents, sweetening agents, flavoring agents, perfuming agents, preservative and antioxidants can also be present in the formulation. For compositions or preparations described herein to be administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Pharmaceutically acceptable carriers can vary in a preparation described herein, depending on the administration route and formulation. The compositions and preparations described herein can be delivered via any administration mode known to a skilled practitioner. For example, the compositions and preparations described herein can be delivered in a systemic manner, via administration routes such as, but not limited to, oral, and parenteral including intravenous, intramuscular, intraperitoneal, intradermal, and subcutaneous. In some embodiments, the compositions and preparations described herein are in a form that is suitable for injection. In other embodiments, the compositions and preparations described herein are formulated for oral administration.

When administering parenterally, a composition and preparation described herein can be generally formulated in a unit dosage injectable form (solution, suspension, emulsion). The compositions and preparations suitable for injection include sterile aqueous solutions or dispersions. The carrier can be a solvent or dispersing medium containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical carrier can be a buffered solution (e.g. PBS).

An oral composition can be prepared in any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the sensor system or sensor system-comprising expression vector can be suspended or dissolved in an oily phase combined with emulsifying or suspending agents. If desired, certain sweetening, flavoring, or coloring agents can be added. Liquid preparations for oral administration can also be prepared in the form of a dry powder to be reconstituted with a suitable solvent prior to use.

The compositions can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions described herein, however, any vehicle, diluent, or additive used should have to be biocompatible with the sensor systems or sensor system-comprising expression vectors described herein. Those skilled in the art will recognize that the components of the compositions should be selected to be biocompatible with respect to the sensor system or sensor system-comprising expression vector. This will present no problem to those skilled in chemical and pharmaceutical principles, or problems can be readily avoided by reference to standard texts or by simple experiments (not involving undue experimentation).

The terms "composition" or "pharmaceutical composition" used interchangeably herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed.

The amount of the sensor systems and/or expression vectors described herein used in the pharmaceutical compositions can range between 0.1-95% by weight of the preparation, or between 0.2-20% by weight in preparation or between 1 and 50% by weight in preparation.

Exemplary Methods of Use

The sensor systems, expression vectors encoding the same, and pharmaceutical compositions described herein can be used in various applications. In some embodiments, the sensor systems, expression vectors encoding the same, and pharmaceutical compositions described herein can be used to detect an intracellular target ligand in a cell. Accordingly, in one aspect, methods for detecting an intracellular target ligand in a cell are also provided herein. The method comprises (a) introducing to a cell the sensor system described herein; (b) detecting a detectable signal of the effector domain of the sensor system; and (c) determining the presence of an intracellular target ligand if a detectable signal of the effector domain is detected; or determining the absence of the target ligand if a detectable signal of the effector domain is not detected.

In some embodiments, the target ligand can be an intracellular, endogenous ligand.

In some embodiments, the sensor system described herein can be introduced into a cell by transfecting the cell with a sensor system-comprising expression vector described herein. The sensor system can be introduced into a cell by any methods for delivery of nucleic acid and/or proteins known in the art or described herein, including the methods used to perform gene therapy described below.

A detectable signal of the effector domain of the sensor system can be detected by any detection methods known in the art, depending on the types of detectable signals. Examples of a detectable signal include, but are not limited to, optical signals, therapeutic effects on cells (e.g., apoptosis or killing of a diseased cell), effector responses (e.g., biological response of an effector domain), gene editing, changes in cell phenotype, viability, and/or metabolism, changes in cytokine profile, and/or any combinations thereof. In some embodiments, an immunoassay, ELISA, immunostaining, microscopy, imaging, spectroscopy, immunofluorescence, western blot, PCR, RT-PCR, fluorescence in situ hybridization, sequencing, mass spectroscopy, metabolic assays, and any combinations thereof.

In some embodiments, the sensor systems, expression vectors encoding the same, and pharmaceutical compositions described herein can be used to control or regulate activity of an effector molecule in a cell or limit activity of an effector molecule to a specific cell. Accordingly, another aspect described herein provides a method of controlling activation of an effector protein in a manner that depends on the presence of an intracellular ligand in a cell. The method comprises: introducing to a cell the sensor system described herein or the sensor system-encoding expression vector described herein, wherein the effector domain of the sensor system is an effector protein, wherein: in the absence of the target intracellular ligand, the target ligand-binding recognition domain is destabilized and such that the fusion protein is destabilized and the effector protein is not active in the cell, or in the presence of the target intracellular ligand, the target ligand-binding recognition domain is stabilized upon binding of the target intracellular ligand, and the effector protein is active in the cell.

In some embodiments, the effector protein can be a DNA nuclease enzyme or a recombinase enzyme. In these embodiments, the target ligand can be a viral protein. Thus, the activity of DNA nuclease enzyme or recombinase enzyme can be limited to cells that contains ore are infected with a viral protein.

In some embodiments, the method can further comprise introducing to the cell a target intracellular ligand selected for the sensor system.

In some embodiments, the sensor systems, expression vectors encoding the same, and pharmaceutical compositions described herein can be used for targeted therapy. Accordingly, methods for delivery of a therapeutic agent or pro-drug agent to a target cell in a subject are also provided herein. The method comprises administering to a subject in need thereof the sensor system-comprising pharmaceutical composition described herein, wherein the effector domain of the sensor system is a therapeutic agent or pro-drug agent; and the target ligand-binding recognition domain of the sensor system is selected for specific binding to an intracellular ligand of a target cell to be treated. In a non-target cell without the intracellular ligand, the target ligand-binding recognition domain is destabilized and such that the fusion protein is destabilized and the therapeutic agent or pro-drug agent is not active in the non-target cell. In a target cell with the intracellular ligand, the target ligand-binding recognition domain is stabilized upon binding of the intracellular ligand, and the therapeutic agent or pro-drug agent is active in the target cell.

As used herein, the terms "administering," and "introducing" are used interchangeably herein and refer to the placement of the pharmaceutical compositions described herein into a subject by a method or route which results in at least partial localization of the sensor systems or sensor system-comprising expression vectors described herein at a desired site. The pharmaceutical composition described herein can be administered by any appropriate route which results in an effective treatment in the subject.

In some embodiments, the pharmaceutical composition described herein can be administered parenterally. The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. The phrases "systemic administration," "administered systemically", "peripheral administration" and "administered peripherally" as used herein mean the administration of the pharmaceutical compositions described herein and optionally other agents or material other than directly into the central nervous system, such that it enters the animal's system and, thus, is subject to metabolism and other like processes, for example, subcutaneous administration.

The pharmaceutical composition described herein can be administered to the subject in need thereof by any methods known in the art. For example, the sensor system-encoding expression vectors can be administered by any DNA delivery methods, including, e.g., but not limited to, virus-based delivery, plasmid-based delivery, and/or electroporation-based delivery. In some embodiments, the sensor systems described herein can be coupled to or encapsulated in a cell-permeable carrier prior to administration to the subject in need thereof. An exemplary cell-permeable carrier is a liposome or a nanoparticle.

The sensor system-comprising DNA expression systems described herein can be introduced into a subject's cells in several ways. There are transfection methods, including chemical methods such as calcium phosphate precipitation and liposome-mediated transfection, and physical methods such as electroporation. In general, transfection methods are not suitable for in vivo gene delivery. Genes can be delivered using "naked" DNA in plasmid form. There are also methods that use recombinant viruses. Current viral-mediated gene delivery methods employ retrovirus, adenovirus, herpes virus, pox virus, and adeno-associated virus (AAV) vectors. Of the more than one hundred gene therapy trials conducted, more than 95% used viral-mediated gene delivery. C. P. Hodgson, Bio/Technology 13, 222-225 (1995). Additional information about various viral-based delivery is described in the section "Exemplary DNA delivery methods" below.

Not only can the sensor systems described herein be used for cell-specific manipulations, they can also be used in many other applications. For example, in some embodiments, the sensor systems described herein can be used to reduce toxic effects with existing GFP-dependent systems. In these embodiments, dGBPs can be used to replace the wildtype GBP domain used in the existing Transcription Devices Dependent on GFP (T-DDOG) (FIG. 17A) as described in Tang et al. (Cell (2013) 154: 928-939) and in U.S. Patent Application No. US 2013/0230863, the contents of each of which are incorporated herein by reference, and CRE-DOG systems (FIG. 17B). In a transcription system, overexpression of transactivation domain can lead to squelching of transcription machinery and thereby cell toxicity (Gill and Ptashne, 1988). By replacing a wildtype GBP domain with a dGBP, the negative effects of transcription activation domains can be minimized by suppression of their expression until a cell expresses GFP. In addition, the background recombination seen with GFP-independent association of split Cre components can be further reduced by destabilizing the components in the absence of GFP. This approach can be generalized to any situation in which a reporter or other exogenous protein causes unwanted effects.

In some embodiments, the sensor systems described herein can be used as an improved protein localization probe. Besides being used as reagents to generate ligand-responsive (e.g., protein-responsive) effectors, destabilized fusion molecules (e.g., destabilized nanobodies) can also be used as improved probes for protein localization. Previously, by fusing nanobodies (no destabilizing modifications) to fluorophores, one could visualize the localization of target antigens or intracellular ligands in living cells (Rothbauer et al., 2006). In some embodiments, deigning a synthetic circuit with large fusion intrabody protein constructs and transcriptional feedback mechanism (Gross et al., 2013), the method requires that the targeted protein be excluded from the nucleus while bound to the antigen/ligand, and has been only demonstrated for proteins anchored away from the nucleus. In contrast, destabilized nanobody-fluorophores described herein would not be limited to extra-nuclear proteins as it is based on destabilization without antigen/ligand. Without wishing to be bound by theory, under ideal conditions, any unbound fluorophore could be sent for degradation, effectively suppressing background noise.

In some embodiments, the sensor systems described herein can be used for cell-specific genome editing, e.g., based on Cas9 fusion to the destabilized nanobodies.

In some embodiments, the sensor systems described herein can be used for cell-specific cell killing strategy, e.g., a destabilized nanobody fused to a toxin (e.g., but not limited to diphtheria toxin, ricin toxin or similar molecules).

In some embodiments, the sensor systems described herein can be used as a diagnostic tool, e.g., to label cells expressing an intracellular ligand of interest. This can be applied in clinical diagnosis, e.g., for detection of a tumor or an oncogene. For example, expression of a nanobody-detectable agent fusion (e.g., a nanobody-fluorescent protein fusion) in the presence of an intracellular ligand is indicative of cells expressing the intracellular ligand of interest.

Other applications of the sensor systems described herein include, but are not limited to cell-specific overexpression of one or more endogenous or exogenous genes of interest such as transcription factors, signaling molecules; optogenetic tools, etc.

Exemplary Methods of DNA Delivery

In one embodiment, a sequence encoding a sensor system described herein (termed as "sensor system-encoding sequence" hereafter) is operably linked to a vector. In general, as used herein, the term "vector" refers to any genetic element, such as a plasmid, phage, transposon, cosmid, chromosome, virus, virion, etc., that is capable of replication when associated with the proper control elements and that can transfer gene sequences to cells. Thus, the term includes cloning and expression vehicles, as well as viral vectors. By "recombinant vector" is meant a vector that includes a heterologous nucleic acid sequence, or "transgene," that is capable of expression in vivo.

In additional embodiments, it can be desirable to fuse the gene of interest to immunoglobulin molecules, for example the Fc portion of a mouse IgG2a with a noncytolytic mutation, to provide for sustained expression. Such a technique has been shown to provide for sustained expression of cytokines, especially when combined with electroporation. See e.g. Jiang et al. (2003) J. Biochem. 133:423-27; Adachi et al. (2002) Gene Ther. 9:577-83.

Plasmid-Directed Gene Delivery. The sensor system-encoding sequence can be delivered using non-viral plasmid-based nucleic acid delivery systems, as described in U.S. Pat. Nos. 6,413,942, 6,214,804, 5,580,859, 5,589,466, 5,763,270 and 5,693,622, all incorporated herein by reference in their entireties. Plasmids will include the gene of interest operably linked to control elements that direct the expression of the gene in a target cell, which control elements are well known in the art. Plasmid DNA can be guided by a nuclear localization signal or like modification.

Alternatively, plasmid vectors encoding the sensor systems described herein can be packaged in liposomes prior to delivery to a subject or to cells, as described in U.S. Pat. Nos. 5,580,859, 5,549,127, 5,264,618, 5,703,055, all incorporated herein by reference in their entireties. For a review of the use of liposomes as carriers for delivery of nucleic acids, see, Hug and Sleight (1991) Biochim. Biophys. Acta. 1097:1-17; Straubinger et al. (1983) in Methods of Enzymology Vol. 101, pp. 512-27; de Lima et al. (2003) Current Medicinal Chemistry, Volume 10(14): 1221-31. The DNA can also be delivered in cochleate lipid compositions similar to those described by Papahadjopoulos et al. (1975) Biochem. Biophys. Acta. 394:483-491. See also U.S. Pat. Nos. 4,663,161 and 4,871,488, incorporated herein by reference in their entireties.

Biolistic delivery systems employing particulate carriers such as gold and tungsten may also be used to deliver sensor system-comprising expression vectors described herein. The particles are coated with the DNA sequence to be delivered and accelerated to high velocity, generally under reduced pressure, using a gun powder discharge from a "gene gun." See, e.g., U.S. Pat. Nos. 4,945,050, 5,036,006, 5,100,792, 5,179,022, 5,371,015, and 5,478,744, all incorporated herein by reference in their entireties.

A wide variety of other methods can be used to deliver the vectors. Such methods include DEAE dextran-mediated transfection, calcium phosphate precipitation, polylysine- or polyornithine-mediated transfection, or precipitation using other insoluble inorganic salts, such as strontium phosphate, aluminum silicates including bentonite and kaolin, chromic oxide, magnesium silicate, talc, and the like. Other useful methods of transfection include electroporation, sonoporation, protoplast fusion, peptoid delivery, or microinjection. See, e.g., Sambrook et al (1989) Molecular Cloning, A Laboratory Manual, Cold Spring Harbor Laboratories, New York, for a discussion of techniques for transforming cells of interest; and Felgner, P. L. (1990) Advanced Drug Delivery Reviews 5:163-87, for a review of delivery systems useful for gene transfer. Exemplary methods of delivering DNA using electroporation are described in U.S. Pat. Nos. 6,132, 419; 6,451,002, 6,418,341, 6,233,483, U.S. Patent Publication No. 2002/0146831, and International Publication No. WO/0045823, all of which are incorporated herein by reference in their entireties.

Retroviral Gene Delivery. Retroviruses provide a convenient platform for gene delivery. A selected DNA sequence, e.g., encoding the sensor system described herein, can be inserted into a vector and packaged in retroviral particles using techniques known in the art. The recombinant virus can then be isolated and delivered to cells of the subject either in vivo or ex vivo. A number of retroviral systems have been described. See, e.g., U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Burns et al. (1993) Proc. Natl. Acad. Sci. USA 90:8033-37; Boris-Lawrie and Temin (1993) Curr. Opin. Genet. Develop. 3:102-09.

Replication-defective murine retroviral vectors are widely used gene transfer vectors. Murine leukemia retroviruses include a single stranded RNA molecule complexed with a nuclear core protein and polymerase (pol) enzymes, encased by a protein core (gag), and surrounded by a glycoprotein envelope (env) that determines host range. The genomic structure of retroviruses includes gag, pol, and env genes and 5' and 3' long terminal repeats (LTRs). Retroviral vector systems exploit the fact that a minimal vector containing the 5' and 3' LTRs and the packaging signal are sufficient to allow vector packaging, infection and integration into target cells, provided that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome.

Adenoviral Gene Delivery. In one embodiment, a nucleotide sequence encoding the sensor system described herein can be inserted into an adenovirus-based expression vector. Unlike retroviruses, which integrate into the host genome, adenoviruses persist extrachromosomally thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76).

The adenovirus genome is a linear double-stranded DNA molecule of approximately 36,000 base pairs with the 55-kDa terminal protein covalently bound to the 5' terminus of each strand. Adenoviral ("Ad") DNA contains identical Inverted Terminal Repeats ("ITRs") of about 100 base pairs with the exact length depending on the serotype. The viral origins of replication are located within the ITRs exactly at the genome ends.

Adenoviral vectors have several advantages in gene therapy. They infect a wide variety of cells, have a broad host-range, exhibit high efficiencies of infectivity, direct expression of heterologous genes at high levels, and achieve long-term expression of those genes in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. For all these reasons vectors derived from human adenoviruses, in which at least the E1 region has been deleted and replaced by a gene of interest, have been used extensively for gene therapy experiments in the pre-clinical and clinical phase.

Adenoviral vectors for use with the methods described herein can be derived from any of the various adenoviral serotypes, including, without limitation, any of the over 40 serotype strains of adenovirus, such as serotypes 2, 5, 12, 40, and 41. The adenoviral vectors used herein are replication-deficient and contain the DNA sequence of interest under the control of a suitable promoter, such as any of the promoters discussed below with reference to adeno-associated virus.

Other recombinant adenoviruses of various serotypes, and comprising different promoter systems, can be created by those skilled in the art. See, e.g., U.S. Pat. No. 6,306,652, incorporated herein by reference in its entirety.

Moreover, "minimal" adenovirus vectors as described in U.S. Pat. No. 6,306,652 will find use with the present invention. Such vectors retain at least a portion of the viral genome required for encapsidation (the encapsidation signal), as well as at least one copy of at least a functional part or a derivative of the ITR. Packaging of the minimal adenovirus vector can be achieved by co-infection with a helper virus or, alternatively, with a packaging-deficient replicating helper system.

Other useful adenovirus-based vectors for delivery of the sensor system-comprising expression system described herein include the "gutless" (helper-dependent) adenovirus in which the vast majority of the viral genome has been removed. Wu et al. (2001) Anesthes. 94:1119-32. Such "gutless" adenoviral vectors produce essentially no viral proteins, thus allowing gene therapy to persist for over a year after a single administration. Parks (2000) Clin. Genet. 58:1-11; Tsai et al. (2000) Curr. Opin. Mol. Ther. 2:515-23. In addition, removal of the viral genome creates space that can be used to insert control sequences that provide for regulation of transgene expression by systemically administered drugs (Burcin et al. (1999) Proc. Natl. Acad. Sci. USA 96:355-60), adding both safety and control of virally driven protein expression. These and other recombinant adenoviruses will find use with the present methods.

Adeno Associated Virus (AAT) Gene Delivery. One viral system that has been used for gene delivery is AAV. AAV is a parvovirus which belongs to the genus Dependovirus. AAV has several attractive features not found in other viruses. First, AAV can infect a wide range of host cells, including non-dividing cells. Second, AAV can infect cells from different species. Third, AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions, facilitating production, storage and transportation.

The AAV genome is a linear single-stranded DNA molecule containing approximately 4681 nucleotides. The AAV genome generally comprises an internal nonrepeating genome flanked on each end by inverted terminal repeats (ITRs). The ITRs are approximately 145 base pairs (bp) in length. The ITRs have multiple functions, including serving as origins of DNA replication and as packaging signals for the viral genome.

The internal non-repeated portion of the genome includes two large open reading frames, known as the AAV replication (rep) and capsid (cap) genes. The rep and cap genes code for viral proteins that allow the virus to replicate and package the viral genome into a virion. In particular, a family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

Adeno-associated virus (AAV) has been used with success in gene therapy. AAV has been engineered to deliver genes of interest by deleting the internal nonrepeating portion of the AAV genome (i.e., the rep and cap genes) and inserting a heterologous gene (in this case, the gene encoding the anti-inflammatory cytokine) between the ITRs. The heterologous gene is typically functionally linked to a heterologous promoter (constitutive, cell-specific, or inducible) capable of driving gene expression in the patient's target cells under appropriate conditions.

Recombinant AAV virions comprising a DNA sequence encoding the sensor system described herein can be produced using a variety of art-recognized techniques. In one embodiment, a rAAV vector construct is packaged into rAAV virions in cells co-transfected with wild-type AAV and a helper virus, such as adenovirus. See, e.g., U.S. Pat. No. 5,139,941.

Alternatively, plasmids can be used to supply the necessary replicative functions from AAV and/or a helper virus. In one embodiment of the present invention, rAAV virions are produced using a plasmid to supply necessary AAV replicative functions (the "AAV helper functions"). See e.g., U.S. Pat. Nos. 5,622,856 and 5,139,941, both incorporated herein by reference in their entireties. In another embodiment, a triple transfection method is used to produce rAAV virions. The triple transfection method is described in detail in U.S. Pat. Nos. 6,001,650 and 6,004,797, which are incorporated by reference herein in their entireties. The triple transduction method is advantageous because it does not require the use of an infectious helper virus during rAAV production, enabling production of a stock of rAAV virions essentially free of contaminating helper virus. This is accomplished by use of three vectors for rAAV virion production: an AAV helper function vector, an accessory function vector, and a rAAV expression vector. One of skill in the art will appreciate, however, that the nucleic acid sequences encoded by these vectors can be provided on two or more vectors in various combinations. Vectors and cell lines necessary for preparing helper virus-free rAAV stocks are commercially available as the AAV Helper-Free System (Catalog No. 240071) (Stratagene, La Jolla, Calif.).

The AAV helper function vector encodes AAV helper function sequences (i.e., rep and cap) that function in trans for productive rAAV replication and encapsidation. Preferably, the AAV helper function vector supports efficient rAAV virion production without generating any detectable replication competent AAV virions (i.e., AAV virions containing functional rep and cap genes). An example of such a vector, pHLP19, is described in U.S. Pat. No. 6,001,650. The rep and cap genes of the AAV helper function vector can be derived from any of the known AAV serotypes. For example, the AAV helper function vector may have a rep gene derived from AAV-2 and a cap gene derived from AAV-6. One of skill in the art will recognize that other rep and cap gene combinations are possible, the defining feature being the ability to support rAAV virion production.

The accessory function vector encodes nucleotide sequences for non-AAV-derived viral and/or cellular functions upon which AAV is dependent for replication (the "accessory functions"). The accessory functions include those functions required for AAV replication, including, without limitation, genes involved in activation of AAV gene transcription, stage specific AAV mRNA splicing, AAV DNA replication, synthesis of cap expression products, and AAV capsid assembly. Viral-based accessory functions can be derived from any of the well-known helper viruses such as adenovirus, herpesvirus (other than herpes simplex virus type-1), and vaccinia virus. In one embodiment, the accessory function plasmid pLadeno5 can be used. See U.S. Pat. No. 6,004,797. This plasmid provides a complete set of adenovirus accessory functions for AAV vector production, but lacks the components necessary to form replication-competent adenovirus.

Unlike stocks of rAAV vectors prepared using infectious helper virus, stocks prepared using an accessory function vector (e.g. the triple transfection method) do not contain contaminating helper virus because no helper virus is added during rAAV production. Even after purification, for example by CsCl density gradient centrifugation, rAAV stocks prepared using helper virus still remain contaminated with some level of residual helper virus. When adenovirus is used as the helper virus in preparing a stock of rAAV virions, contaminating adenovirus can be inactivated by heating to temperatures of approximately 60° C. for 20 minutes or more. This treatment effectively inactivates only the helper virus since AAV is extremely heat stable, while the helper adenovirus is heat labile. Although heat inactivating of rAAV stocks may render much of the contaminating adenovirus non-infectious, it does not physically remove the helper virus proteins from the stock. Such contaminating viral protein can elicit undesired immune responses in subjects and are to be avoided if possible. Contaminating adenovirus particles and proteins in rAAV stocks can be avoided by use of the accessory function vectors disclosed herein.

Recombinant AAV Expression Vectors. Recombinant AAV expression vectors can be constructed using standard techniques of molecular biology. rAAV vectors comprise a transgene of interest (e.g. a DNA sequence encoding a sensor system described herein) flanked by AAV ITRs at both ends. rAAV vectors are also constructed to contain transcription control elements operably linked to the transgene sequence, including a transcriptional initiation region and a transcriptional termination region. The control elements are selected to be functional in a mammalian target cell.

The nucleotide sequences of AAV ITR regions are known. See, e.g., Kotin (1994) Human Gene Therapy 5:793-801; Berns "Parvoviridae and their Replication" in Fundamental Virology, 2nd Edition, (B. N. Fields and D. M. Knipe, eds.) for the AAV-2 sequence. AAV ITRs used in the vectors of the invention need not have a wild-type nucleotide sequence, and may be altered, e.g., by the insertion, deletion or substitution of nucleotides. Additionally, AAV ITRs may be derived from any of several AAV serotypes, including without limitation, AAV-1, AAV-2, AAV-3, AAV-4, AAV-5, AAV-6, AAV-7 and AAV-8, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

The AAV expression vector harboring a transgene of interest (e.g. a DNA sequence encoding a sensor system described herein) bounded by AAV ITRs can be constructed by directly inserting the selected sequence(s) into an AAV genome that has had the major AAV open reading frames ("ORFs") excised. Other portions of the AAV genome can also be deleted, so long as enough of the ITRs remain to provide replication and packaging functions. Such constructs can be designed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-96; Vincent et al. (1990) Vaccines 90 (Cold Spring Harbor Laboratory Press); Carter (1992) Current Opinion in Biotechnology 3:533-39; Muzyczka (1992) Current Topics in Microbiol. and Immunol. 158:97-129; Kotin (1994) Human Gene Therapy 5:793-801; Shelling and Smith (1994) Gene Therapy 1:165-69; and Zhou et al. (1994) J. Exp. Med. 179:1867-75.

AAV ITR-containing DNA fragments can be ligated at both ends of a selected transgene using standard techniques, such as those described in Sambrook et al., supra.

Suitable host cells for producing rAAV virions from rAAV expression vectors include microorganisms, yeast cells, insect cells, and mammalian cells. Such host cells are preferably capable of growth in suspension culture, a bioreactor, or the like. The term "host cell" includes the progeny of the original cell that has been transfected with an rAAV virion. Cells from the stable human cell line, 293 (readily available through the American Type Culture Collection under Accession Number ATCC CRL1573) are preferred in the practice of the present invention. The human cell line 293 is a human embryonic kidney cell line that has been transformed with adenovirus type-5 DNA fragments (Graham et al. (1977) J. Gen. Virol. 36:59), and expresses the adenoviral Ela and Elb genes (Aiello et al. (1979) Virology 94:460). The 293 cell line is readily transfected, and provides a particularly convenient platform in which to produce rAAV virions.

Other Viral Vectors for Gene Delivery. Additional viral vectors useful for delivering a sensor system-comprising expression system described herein include those derived from the pox family of viruses, including vaccinia virus and avian poxvirus. By way of example, vaccinia virus recombinants expressing a sensor system described herein can be constructed as follows. DNA carrying the gene is inserted into an appropriate vector adjacent to a vaccinia promoter and flanking vaccinia DNA sequences, such as the sequence encoding thymidine kinase (TK). This vector is then used to transfect cells that are simultaneously infected with vaccinia. Homologous recombination serves to insert the vaccinia promoter and the gene into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can be used to deliver a sensor system-comprising expression vector described herein. Recombinant avipox viruses expressing immunogens from mammalian pathogens are known to confer protective immunity when administered to non-avian species. The use of avipox vectors in human and other mammalian species is advantageous with regard to safety because members of the avipox genus can only productively replicate in susceptible avian species. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors, can also be used for DNA delivery. Michael et al. (1993) J. Biol. Chem. 268:6866-69 and Wagner et al. (1992) Proc. Natl. Acad. Sci. USA 89:6099-6103.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%. When "0%" is used to describe the amount of a component, it is understood that this includes situations where only trace amounts of the component are present.

All numbering of the amino acid sequences of the immunoglobulins is according to the IMGT numbering scheme (IMGT, the international ImMunoGeneTics information system; Lefranc et al., 1999, *Nucleic Acids Res.* 27:209-212; Ruiz et al., 2000 *Nucleic Acids Res.* 28:219-221; Lefranc et al., 2001, *Nucleic Acids Res.* 29:207-209; Lefranc et al., 2003, *Nucleic Acids Res.* 31:307-310; Lefranc et al., 2005, *Dev Comp Immunol* 29:185-203).

As used herein, the term "peptidomimetic" means a peptide-like molecule that has the activity of the peptide on which it is structurally based. Such peptidomimetics include chemically modified peptides, peptide-like molecules containing non-naturally occurring amino acids, and peptoids, and have an activity such as the cardiac specificity of the peptide upon which the peptidomimetic is derived (see, for example, Goodman and Ro, Peptidomimetics for Drug Design, in "Burger's Medicinal Chemistry and Drug Discovery", Vol. 1 (ed. M. E. Wolff; John Wiley & Sons 1995), pages 803-861).

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a peptide described herein, as well as potential geometrical and chemical complementarity to a cognate receptor. Where no crystal structure of a peptide described herein is available, a structure can be generated using, for example, the program CONCORD (Rusinko et al., J. Chem. Inf. Comput. Sci. 29:251 (1989)). Another database, the Available Chemicals Directory (Molecular Design Limited, Informations Systems; San Leandro Calif.), contains about 100,000 compounds that are commercially available and also can be searched to identify potential peptidomimetics of a peptide described herein, for example, having specificity for the microbes.

The term "peptide" refers to a polymer of amino acids, or amino acid analogs, regardless of its size or function. In some embodiments, the term "peptide" refers to small polypeptides, e.g., a polymer of about 15-25 amino acids.

As used herein, the term "subject" refers to any living organism which can be administered to the pharmaceutical compositions of the present invention and in which cancer or a proliferative disorder can occur. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. As used herein, the terms "subject" and "individual" are used interchangeably and are intended to refer to an animal, for example a human, to whom treatment, including prophylactic treatment, with the pharmaceutical composition according to the present invention, is provided, including, but not limited to humans and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposion, affection.

The term "cell" used herein refers to any cell, prokaryotic or eukaryotic, including plant, yeast, worm, insect and mammalian. Mammalian cells include, without limitation; primate, human and a cell from any animal of interest, including without limitation; mouse, hamster, rabbit, dog, cat, transgenic animal domestic animals, such as equine, bovine, murine, ovine, canine, feline, etc. The cells may be a wide variety of tissue types without limitation such as; hematopoietic, neural, mesenchymal, cutaneous, mucosal, stromal, muscle spleen, reticuloendothelial, epithelial, endothelial, hepatic, kidney, gastrointestinal, pulmonary, T-cells etc. Stem cells, embryonic stem (ES) cells, ES-derived cells and stem cell progenitors are also included, including without limitation, hematopoietic, stromal, muscle, cardiovascular, hepatic, pulmonary, gastrointestinal stem cells, etc. Yeast cells may also be used as cells in this invention. Cells also refer not to a particular subject cell but to the progeny or potential progeny of such a cell because of certain modifications or environmental influences, for example differentiation, such that the progeny may not, in fact be identical to the parent cell, but are still included in the scope of the invention.

The cells can also be cultured cells, e.g. in vitro or ex vivo. For example, cells cultured in vitro in a culture medium. Alternatively, for ex vivo cultured cells, cells can be obtained from a subject, where the subject is healthy and/or affected with a disease. Cells can be obtained, as a non-limiting example, by biopsy or other surgical means know to those skilled in the art. Cells used in the invention can be present in a subject, e.g. in vivo. For the invention on use on in vivo cells, the cell is preferably found in a subject and display characteristics of the disease, disorder, or malignancy pathology As used herein, the terms "treat" or "treatment" or "treating" refers to both therapeutic treatment and prophylactic or preventative measures, wherein the object is to prevent or slow the development of the disease, such as slow down the development of a tumor, the spread of cancer, or reducing at least one effect or symptom of a condition, disease or disorder associated with inappropriate proliferation or a cell mass, for example cancer. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

All patents, patent applications, and publications identified in this document are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

EXAMPLES

The following examples are not intended to limit the scope of the invention, but are rather intended to be exemplary of certain embodiments.

Example 1

A Nanobody-Based, Single Component System for Labeling and Genetic Manipulation of Specific Cell Types The ability to target specific cell populations based upon expression of an intracellular biomolecule would greatly facilitate studies of basic biology, as well as therapeutic applications. Genetic manipulations are routinely performed on model organisms for which transgenesis and transient gene delivery methods are well established. However, such approaches rely on the availability of cell type-specific promoters, genomic loci that drive transgene expression in the desired cell types, and/or transgenic driver lines. No existing technologies yet allow genetic access to specific cell types based upon the expression of endogenous, specific gene products. Such technology would provide an unprecedented level of access in model organisms, as well as greatly increase the possibilities for genetic manipulations in non-model organisms.

Binary expression strategies are a powerful approach to the manipulation of activities in specific cell types. In such strategies, a "driver" molecule is expressed under a cell type-specific promoter, and it interacts with a responder element to drive target gene expression. The driver molecule can be a transcription factor that binds its cognate upstream activating sequence (UAS), resulting in transcription of a target gene under UAS control (Brand and Perrimon, 1993), (Butala et al., 2009) (Schonig et al., 2010). The driver molecule can also be a site-specific DNA recombinase that recognizes its cognate binding sequences to induce DNA recombination events, leading to outcomes such as gene activation or deletion, e.g. Cre/LoxP (Orban et al., 1992) and Flp/FRT systems (Dymecki, 1996). Binary systems are powerful for two main reasons. First, since expression of the driver molecule is separated from that of the target gene, different cell-specific driver constructs can be combined with different responder-target gene constructs, providing for efficiency and flexibility in experimental design. Second, in the context of transgenic animals, the use of an innocuous driver makes it more likely that the transgenic driver lines will have normal development and behavior.

Driver molecules have been selected for their natural biological activities, and are usually exogenous to the system under study. In contrast to the existing technologies, the inventors have developed general strategies employing an intracellular product, exogenous or endogenous, as driver molecules as long as strategies exist to exploit their presence for "driving" the desired molecular output. The inventors previously demonstrated this using GFP as a dimerizer to scaffold the formation of biologically active transcription complexes (Tang et al., 2013). However, the dimerizer-based GFP-dependent system requires multiple components to drive target gene output. For example, in order for GFP to induce transcription of Cre, at least 3 components must be delivered and expressed in GFP-labeled cells (Tang et al., 2013). Rather than using GFP as a dimerizer, a binary system that used GFP as a single driver molecule would be a simpler approach. In such a system, GFP would interact with a single component to directly induce the activity of a protein of interest. This concept could be generalized such that cell type-specificity would not be conferred by GFP, but by some other, endogenous cell type-specific protein. If successful, this method would provide unprecedented control of any cell type that expresses a specific protein. Moreover, this strategy would not require a pool of transgenic animals with exogenous genes expressed in specific cell types, thus enabling genetic manipulation of specific cell types in non-model organisms.

A concept that can be employed to develop such a strategy is one that makes a protein's stability dependent upon its interaction with another molecule. This concept has been applied to, for example, protein domains that are stable only upon binding to an exogenous small molecule or only after interacting with light (Banaszynski et al., 2006; Bonger et al., 2014). These applications have been aimed towards generating temporal control of proteins, and require the delivery of drugs or light to the target cell type. The existing technologies have not explored use of endogenous intracellular proteins to induce protein stabilization for applications such as labeling and manipulation of specific cell types.

In this Example, the inventors showed that intracellular antigens can be used as stabilizing agents to enable spatial control of output protein activity with cellular precision. For example, mutagenesis was used to derive a GFP-binding nanobody (GBP) that is destabilized until it binds to its antigen, GFP. This mutant nanobody could destabilize multiple fusion proteins with a variety of activities, including, e.g., fluorescent proteins and DNA-modifying enzymes. These fusion constructs were applied to show their utility for detecting and manipulating antigen-expressing cells in mice. This approach was generalized by showing that the destabilizing mutations of the GFP nanobody could be grafted onto other nanobodies that target other antigens, to rapidly generate antigen-specific sensors and effectors. The utility of this system for detecting and manipulating living cells was, in part, based on coincident expression of multiple antigens as well as for initiating genome editing in response to the presence of a pathogenic antigen. The technology described herein is a powerful approach to label and manipulate cells based on expressed intracellular antigens, for a wide variety of potential uses across biological disciplines.

Results

Single chain antigen recognition domains, e.g., derived from Camelid antibodies ("nanobodies"), constitute an attractive class of protein binders to evaluate the idea that intracellular cell type-specific proteins can activate engineered protein activities (FIG. 1A). Nanobodies can have affinity and specificity, and have been shown to be readily expressed as soluble proteins within cells. They have a conserved protein backbone structure with the potential to be selected to bind a variety of antigens in living cells (Muyldermans, 2013).

To investigate whether it is possible to modify a nanobody such that its intracellular protein level becomes strongly dependent on binding to its target antigen, the GFP-GBP1 complex (Kirchhofer et al., 2010) was used for proof-of-concept experiments (FIGS. 1A-1C). Error-prone PCR was used to mutagenize the GBP1 coding sequence and a library of GBP1 variants was created in a mouse leukemia virus (MLV) retroviral vector. Inserted GBP1 variants were placed N-terminal to, and in frame with, e.g., TagBFP, a blue fluorescent protein derived from Entacmaea quadricolor (Subach et al., 2008). To assess infection by all MLV vectors, the red fluorescent protein t-HcRed (Gurskaya et al., 2001) was co-expressed with each mutant GBP1-TagBFP via an internal ribosomal entry site (IRES). TagBFP and t-HcRed bears little amino acid similarity to Aequorea-derived GFP and its derivatives. 293T cells were infected with the MLV mutant GBP1-TagBFP library, and were then subjected to fluorescence-activating cell sorting (FACS). The cells that were infected (HcRed+), but had low expression of TagBFP, carried putatively destabilized GBP1 variants, and so were isolated. These isolated cells were propagated and infected with recombinant adeno-associated virus (rAAV) expressing GFP. A second round of FACS was carried out to isolate infected cells that now showed high TagBFP fluorescence. Sorted cells were proliferated and then subjected to genomic extraction and PCR to isolate GBP1 variants. GBP1 variants were then screened individually for enhanced TagBFP expression in the presence of yellow fluorescent protein (YFP), a GFP derivative known to also interact with GBP1 (Rothbauer et al., 2008; Tang et al., 2013). A number of GBP1 variants that showed YFP-dependent blue fluorescence were isolated. Some variants showed aggregation of TagBFP in punctate regions within the cell in the absence of YFP, but became soluble in the cytoplasm when co-expressed with YFP (data not shown). This indicate that YFP binding prevents destabilization of GBP1-TagBFP variants, most of which aggregate when unstable.

A Highly Destabilized Nanobody that is Responsive to Antigen Binding

Figure 8:
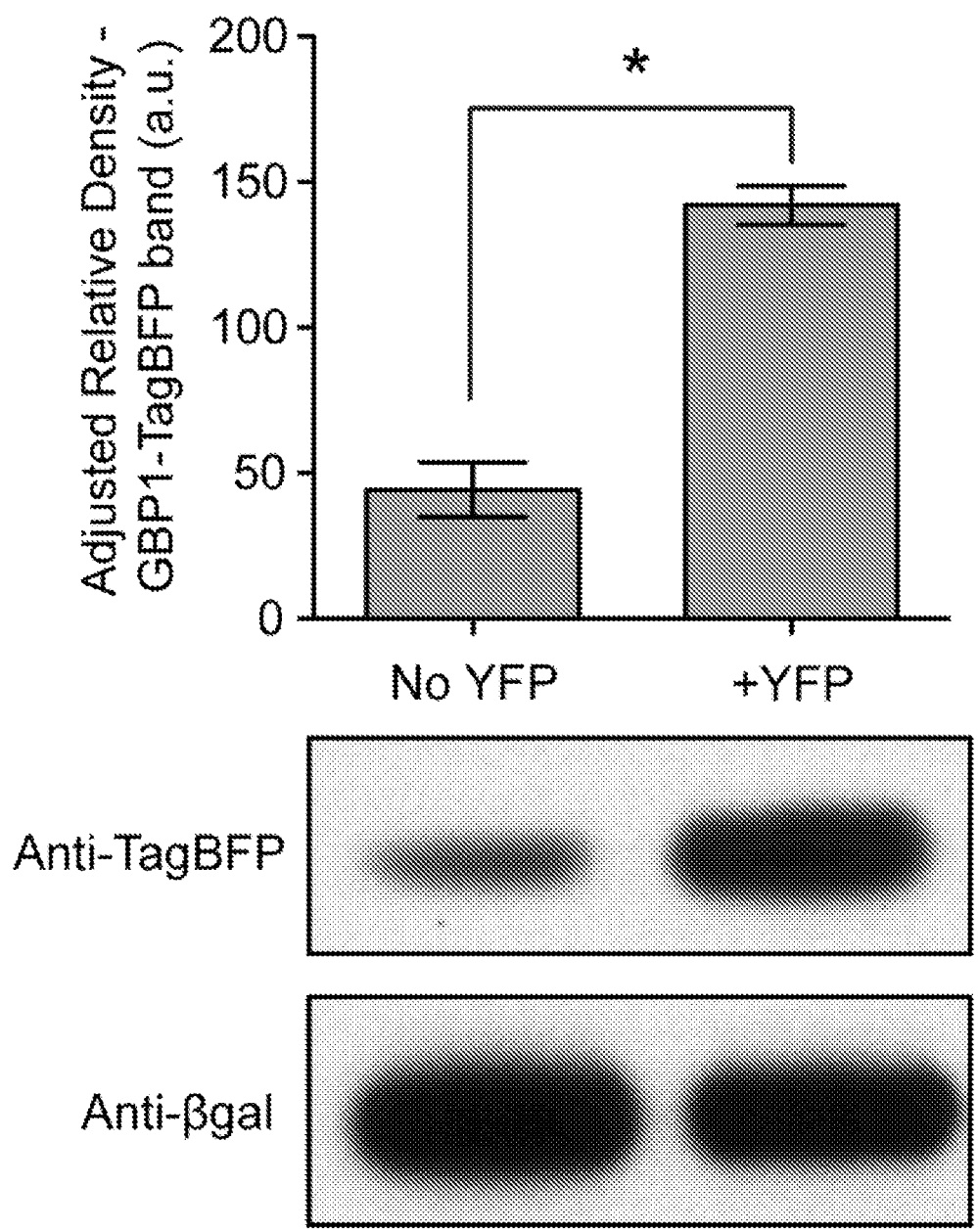
FIG. 8 shows that YFP stabilizes wildtype GBP1 protein in cells. 293T cells transfected with MMLV-GBP1-TagBFP, CAG-nlacZ and filler plasmid or CAG-YFP were harvested 2 days post transfection and whole cell lysate were blotted for anti-TagBFP as well as anti-βgal (same experiment as in FIG. 1D). Densitometry measurements of western blot bands were plotted as the relative density of anti-TagBFP bands compared to that of anti-βgal bands in the same lane. a.u. is arbitrary unit. n=3. Asterisk represents p<0.001. Plot is mean+/− standard deviation. Results are representative of at least 3 independent experiments.

A GBP1 variant carrying at least 6 amino acid changes (A25V, E63V, S73R, S98Y, Q109H, S117F) gave little to no TagBFP fluorescence and no signs of aggregation in the absence of YFP (FIG. 1E). This variant is herein referred to as destabilized GBP1 (dGBP1). By western blot analysis and fluorescence imaging, it was determined that the protein level of dGBP1-TagBFP was strongly induced by YFP and GFP (FIGS. 1D and 1E; data not shown). Some or all of the six mutations found in dGBP1 were responsible for the YFP-induced phenotype, since wildtype GBP1-TagBFP showed abundant protein level and fluorescence even in the absence of YFP (FIGS. 1D and 1E). Surprisingly, an enrichment of wildtype GBP1-TagBFP protein was detected in the presence of YFP (FIG. 1D and FIG. 8). Taken together, a highly destabilized nanobody was isolated that shows a sharp increase in fluorophore-tagged protein level when co-expressed with its cognate antigen.

Figures 2A, 2B, 2C:
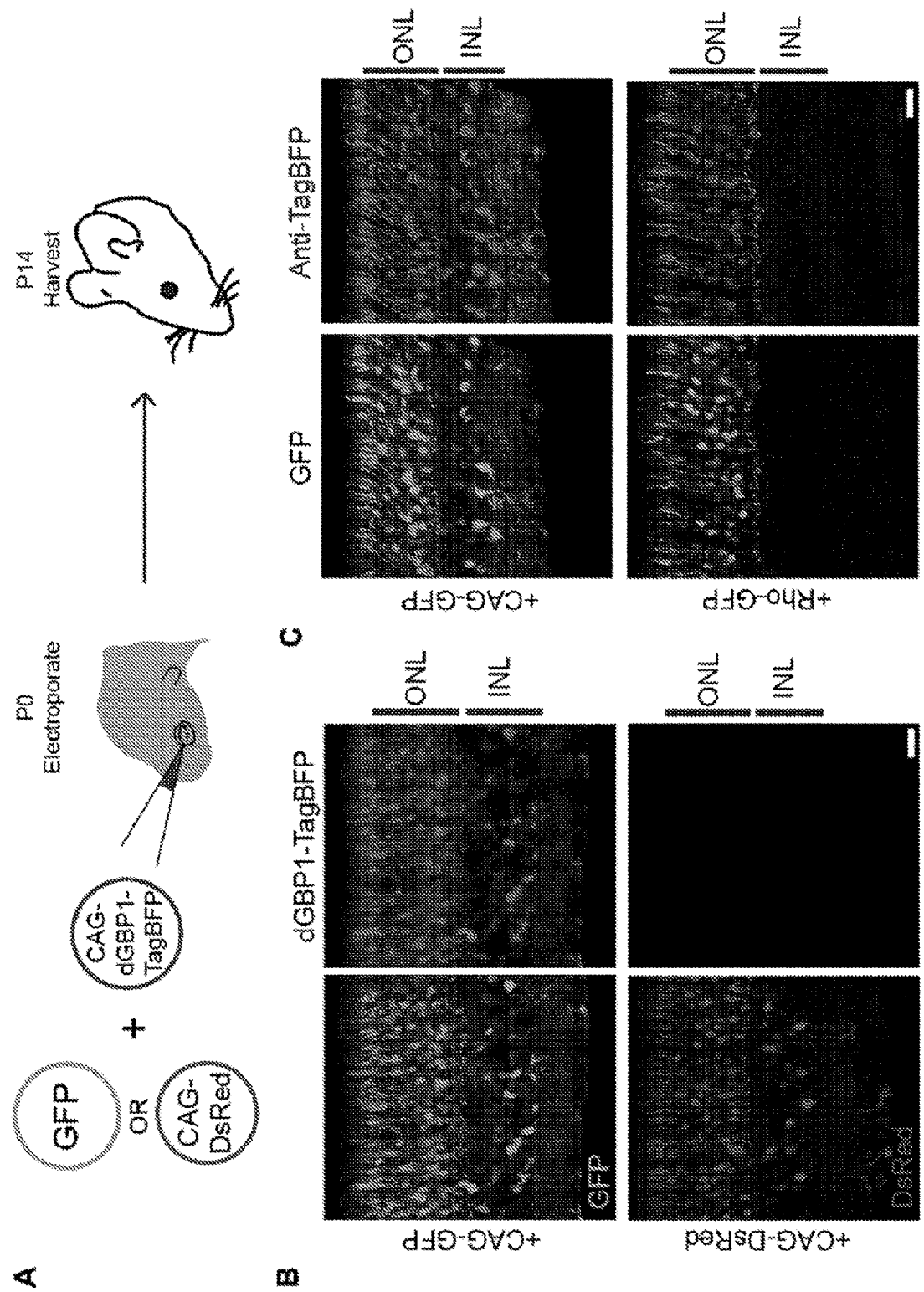
FIGS. 2A-2H contain experimental data showing detection of antigen-expressing cells with destabilized nanobody in vivo.
Figures 2D, 2E, 2F, 2G, 2H:
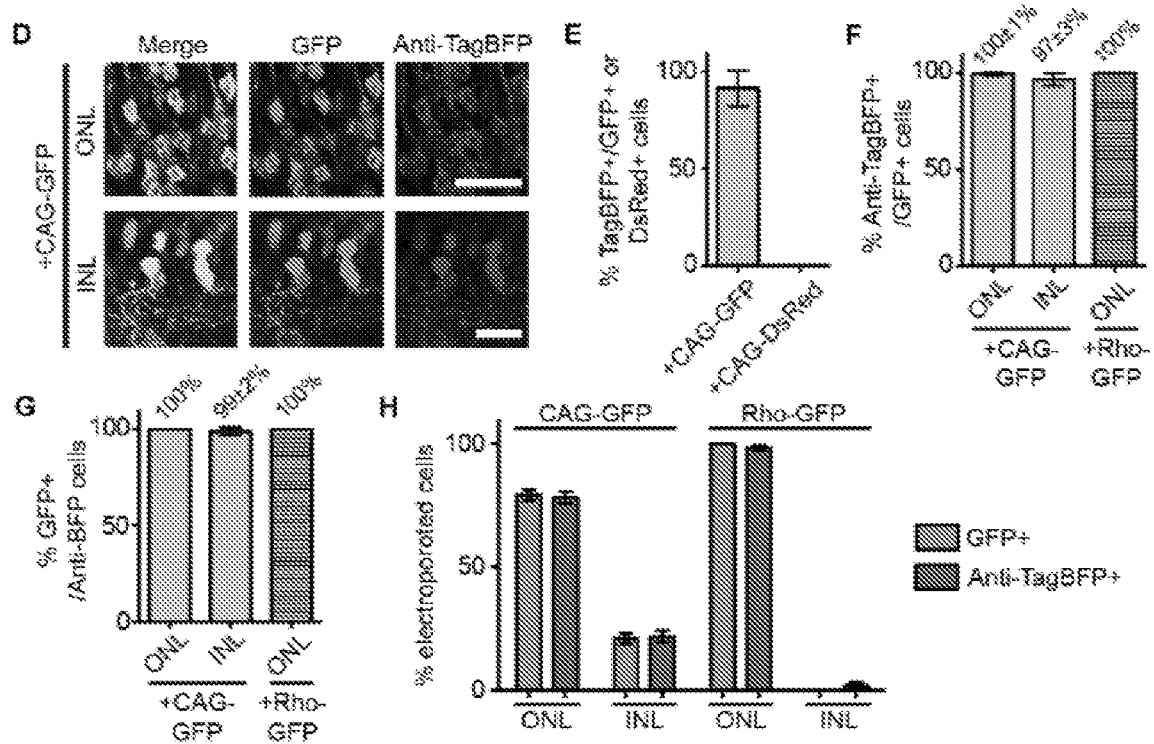
Figures 9A, 9B, 9C, 9D, 9E:
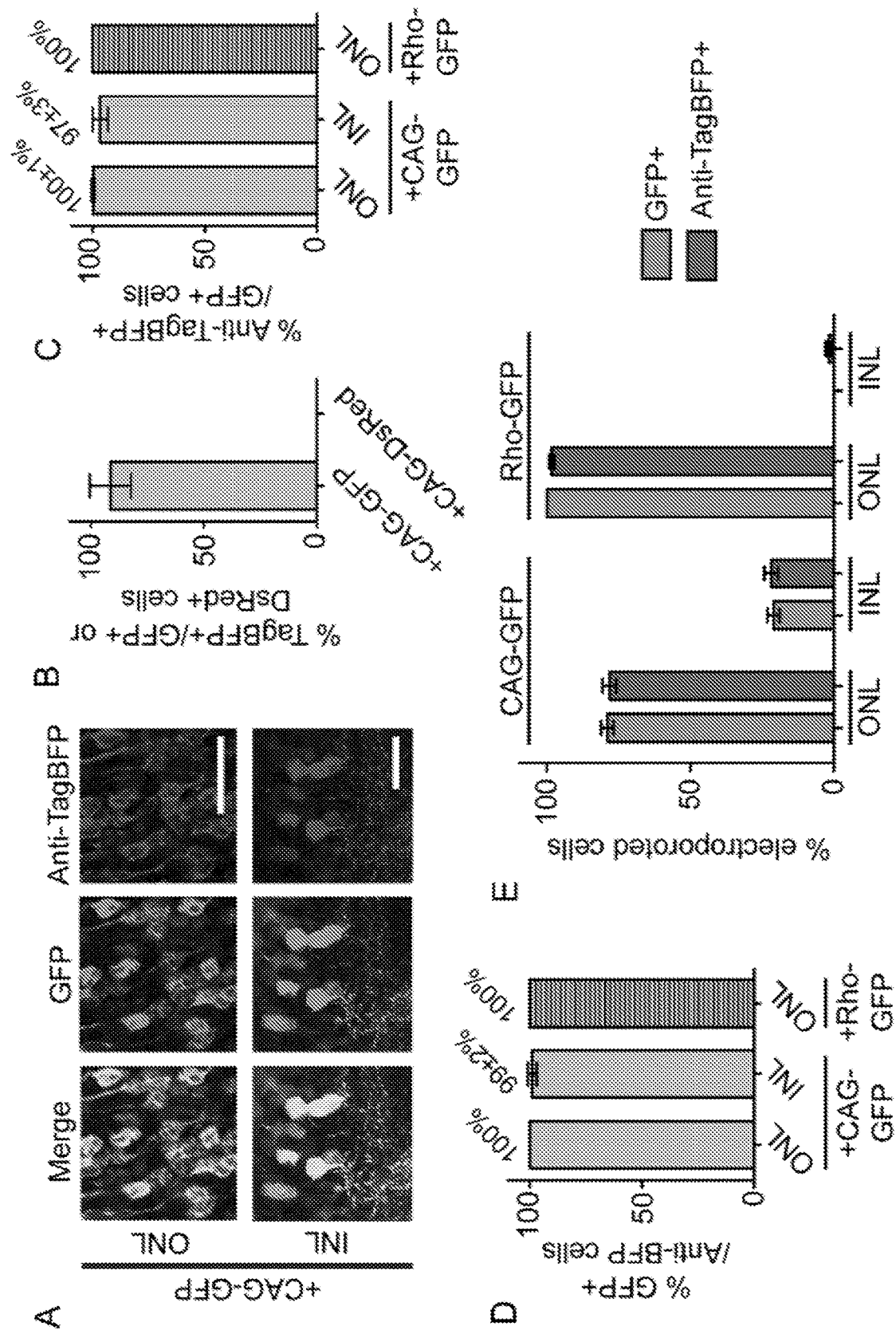
FIGS. 9A-9E show detailed analysis of dGBP1-TagBFP in vivo electroporation results. Refer to FIGS. 2A-2C and Methods for experimental setup.

Detection of Antigen-Expressing Cells with a Destabilized Sensor Against GFP in the Mouse To determine whether dGBP1 protein stability is similarly dependent on GFP binding in vivo, the destabilized nanobody was introduced into the mouse retina or any target site in an animal model. The retina was chosen based on the ease with which one can deliver plasmid DNA to the system, as well as the availability of cell-specific promoter elements for manipulating transgene expression pattern (Matsuda and Cepko, 2004). However, any tissue or site can be targeted by selection of appropriate promoter elements and delivery routes. dGBP1-TagBFP was electroporated into the neonatal mouse retina, along with different promoter-GFP constructs, and TagBFP expression examined upon tissue maturation (FIG. 2A). dGBP1-TagBFP fluorescence was indeed absent in electroporated retinas without GFP expression, but fluorescence and protein level was present either broadly when CAG-GFP was expressed, or only in rod photoreceptors when delivered Rho-GFP was expressed (FIGS. 2B-2C and FIGS. 9A-9E). Replacement of GFP with DsRed resulted in loss of TagBFP fluorescence (FIGS. 2B and 9B, Table 1). Surprisingly, the efficiency of TagBFP stabilization and GFP co-localization of TagBFP positive cells were nearly 100% (FIG. 9B, Table 1 and 9C, Table 2). The efficiency of T-DDOG systems was, at its highest, 85% in similarly designed electroporation experiments (Tang et al., 2013). This difference likely reflects, in part, that the new binary approach requires fewer components to be co-delivered and co-expressed. Further, the GFP specificity of TagBFP expressing cells is close to or at 100% (FIG. 9D, Table 2). These results show that dGBP1 can be used to impose GFP-dependent control on fusion protein expression in animals. Since GFP-expressing cells were able to be independently visualized with high fidelity, these results further serve as a demonstration that a destabilized nanobody can be used as a tool to detect antigen-expressing cells in vivo.

TABLE 1

Quantitative summary of experimental data related to FIG. 9B

| Panel | Condition | n (retinas) | Total n (GFP+ or DsRed+ cells) | % TagBFP+ given GFP+ or DsRed+ cells in ONL[a] | SD |
|---|---|---|---|---|---|
| S2B | +CAG-GFP | 3 | 305 | 91 | 9 |
|  | +CAG-DsRed | 3 | 304 | 0 | 0 |

[a]Value derived from average of parameter measured per retina. At least 100 GFP+ or DsRed+ cells were sampled from each retina in the ONL.

TABLE 2

Quantitative summary of results related to FIGS. 9C and 9D

| Panel | Promoter for GFP | Layer analyzed | n (retinas) | Total n (cells) | % Anti-TagBFP+ given GFP+ cells[a] | SD |
|---|---|---|---|---|---|---|
| S2C | CAG | ONL | 3 | 240 | 100 | 1 |
|  | CAG | INL | 3 | 133 | 97 | 3 |
|  | Rho | ONL | 3 | 307 | 100 | 0 |

| Panel | Promoter for GFP | Layer analyzed | n (retinas) | Total n (cells) | % GFP+ cells given Anti-TagBFP+ cells[a] | SD |
|---|---|---|---|---|---|---|
| S2D | CAG | ONL | 3 | 231 | 100 | 0 |
|  | CAG | INL | 3 | 133 | 99 | 2 |
|  | Rho | ONL | 3 | 300 | 100 | 0 |

[a]Value derived from average of parameter measured per retina. At least 100 and 30 cells were sampled from each retina in the ONL and INL, respectively.

TABLE 3

Quantitative summary of ONL/INL distribution related to FIG. 9E

| Panel | Promoter for GFP | Cells counted | n (retinas) | Total n (cells) | % cells in ONL[a] | % cells in INL[a] | SD |
|---|---|---|---|---|---|---|---|
| S2E | CAG | GFP+ | 3 | 894 | 79 | 21 | 2 |
|  | CAG | Anti-TagBFP+ | 3 | 814 | 78 | 22 | 2 |
|  | Rho | GFP+ | 3 | 930 | 100 | 0 | 0 |
|  | Rho | Anti-TagBFP+ | 3 | 879 | 98 | 2 | 1 |

[a]Value derived from average of parameter measured per retina. All cells within a 20 µm thick retina slice (>100 cells) were counted per retina.

Figures 3A, 3B, 3C, 3D, 3E, 3F:
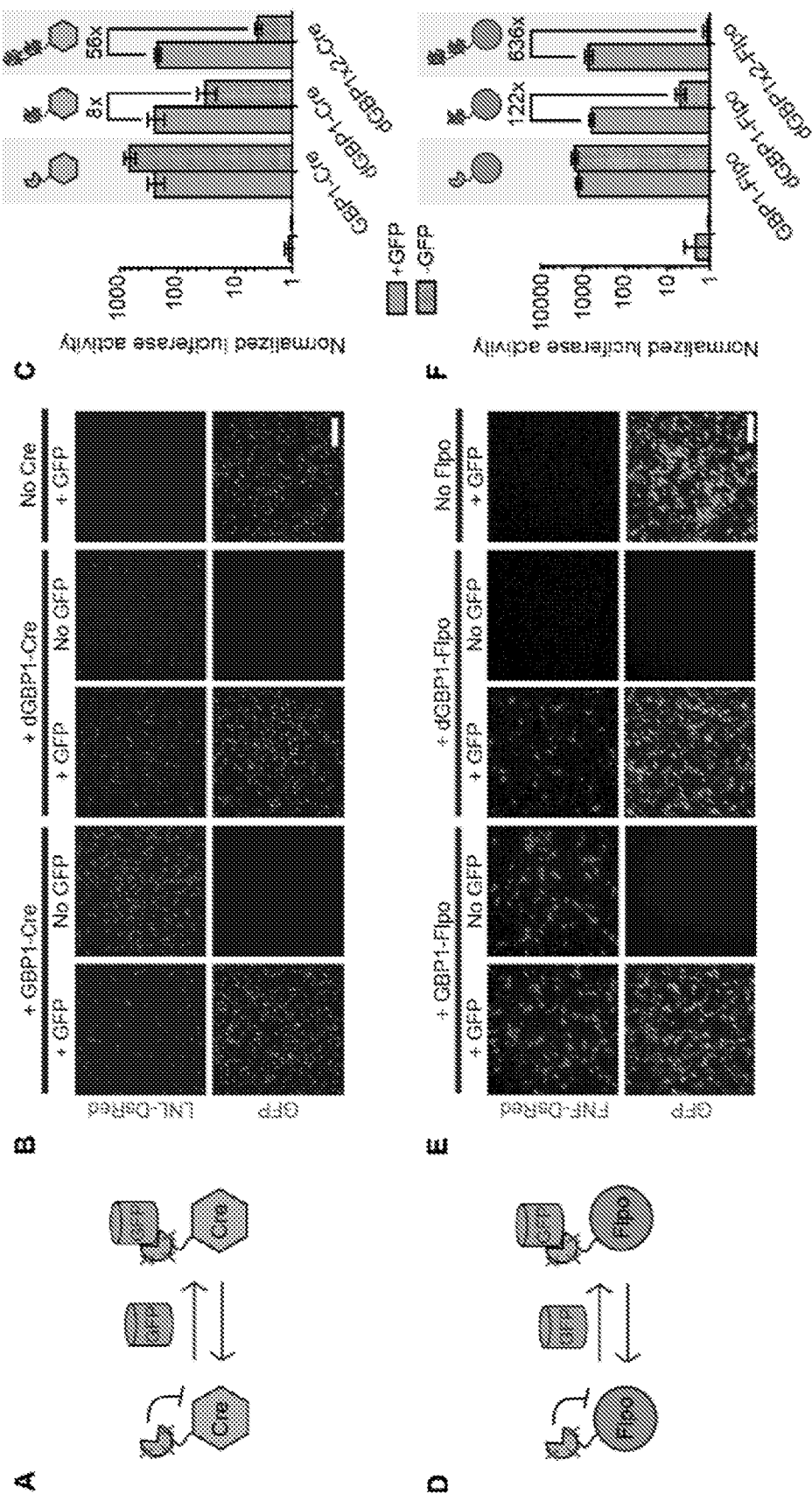
FIGS. 3A-3H contain experimental data showing generation and optimization of antigen-responsive effectors. Plasmids encoding wildtype or destabilized GBP1 fusion to Cre or Flpo were transfected into 293T cells along with loxP-Neo-loxP- (LNL-) or FRT-Neo-FRT-(FNF-) reporters.
Figure 3G:
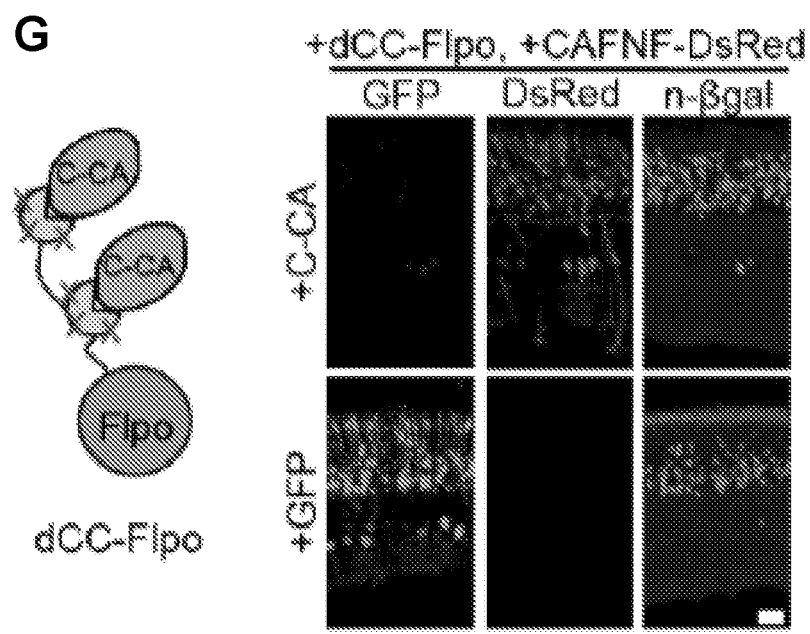

Antigen Binding to Destabilized Nanobody can Control the Activity of Nanobody-Fused Proteins In Vitro and In Vivo It was next sought to determine whether the destabilizing effect of dGBP1 could be extended to fusion protein partners beyond TagBFP. dGBP1 effects on the site-specific recombinases Cre and Flp, which are commonly used as cell-specific driver enzymes in model organisms (Luo et al., 2008), were first evaluated. dGBP1 was fused to Cre and codon-optimized Flp (Flpo) (Raymond and Soriano, 2007), creating dGBP1-Cre and dGBP1-Flpo, respectively (FIGS. 3A and 3D). Recombinase activity was determined by use of DsRed or luciferase reporters that were transcriptionally inactive until Cre or Flp-dependent excision of a transcription stop cassette flanked by loxP or FRT, respectively. Indeed, dGBP1-Cre and -Flpo gave GFP-dependent recombinase activity in 293T cells (FIGS. 3B, 3C, 3E, 3F and 10A-10B).

In some embodiments, the background recombination can build up over time. For example, with dGBP1-Cre, strategies were developed to reduce the background. In some embodiments, increasing the number of dGBP1 domains fused to Cre or Flpo was able to reduce GFP-independent recombination without noticeably affecting GFP-dependent recombination (FIGS. 3C, 3F and 10A-10B). In contrast, replacement of dGBP1 with wildtype GBP1 as one of the repeating units gave relatively higher background signal (FIGS. 10A-10B). Among the test constructs, the best-performing construct over the assayed period was dGBP1x2-Flpo, with little to no accumulated background signal and 636-fold induction by GFP (FIG. 3F). Taken together, these results indicate that dGBP1 is capable of conferring GFP-dependent control over different fusion protein partners, and that the background activity can be optimized or minimized by multimerization of destabilized nanobodies.

Figures 4A, 4B, 4C:
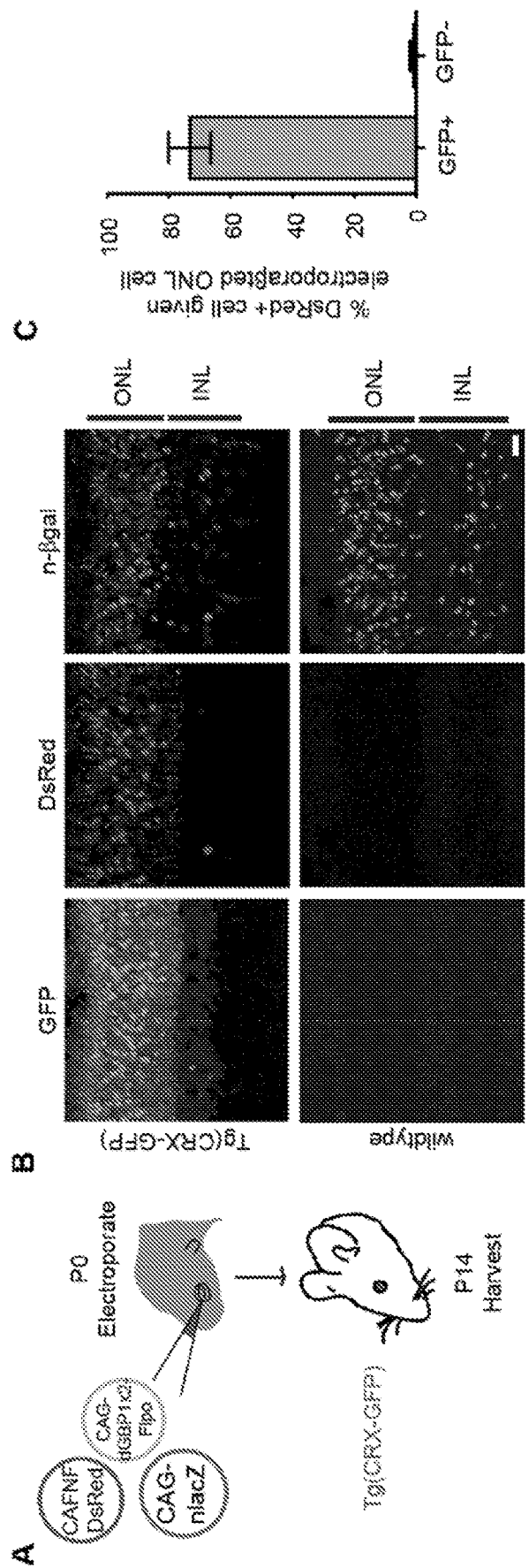
FIGS. 4A-4C contain experimental data showing in vivo gene manipulation of antigen-expressing cells with destabilized nanobody-Flpo fusion protein.

The tight regulation of Flpo activity by tandem dGBP1 repeats, as well as its robust recombinase activity induction by GFP, indicates that one could apply this tool in GFP lines for cell-specific manipulation of genes. To investigate this further, dGBP1×2-Flpo encoding plasmids along with Flp-dependent DsRed reporter as well as broadly-driven nlacZ (which expresses nuclear β-galactosidase (n-βgal)) electroporation marker plasmid were electroporated into the retinas of Tg(CRX-GFP) positive mouse pups (Samson et al., 2009) (FIG. 4A). Indeed, DsRed was induced only in Tg(CRX-GFP) positive retinas, but not in the electroporated retinas of GFP negative littermates (FIGS. 4B and 4C). Thus, this shows the practicality of using destabilized nanobody fusion proteins to conduct cell-specific gene manipulation in animals.

Mapping the Destabilizing Mutations in dGBP1

Figure 12A:
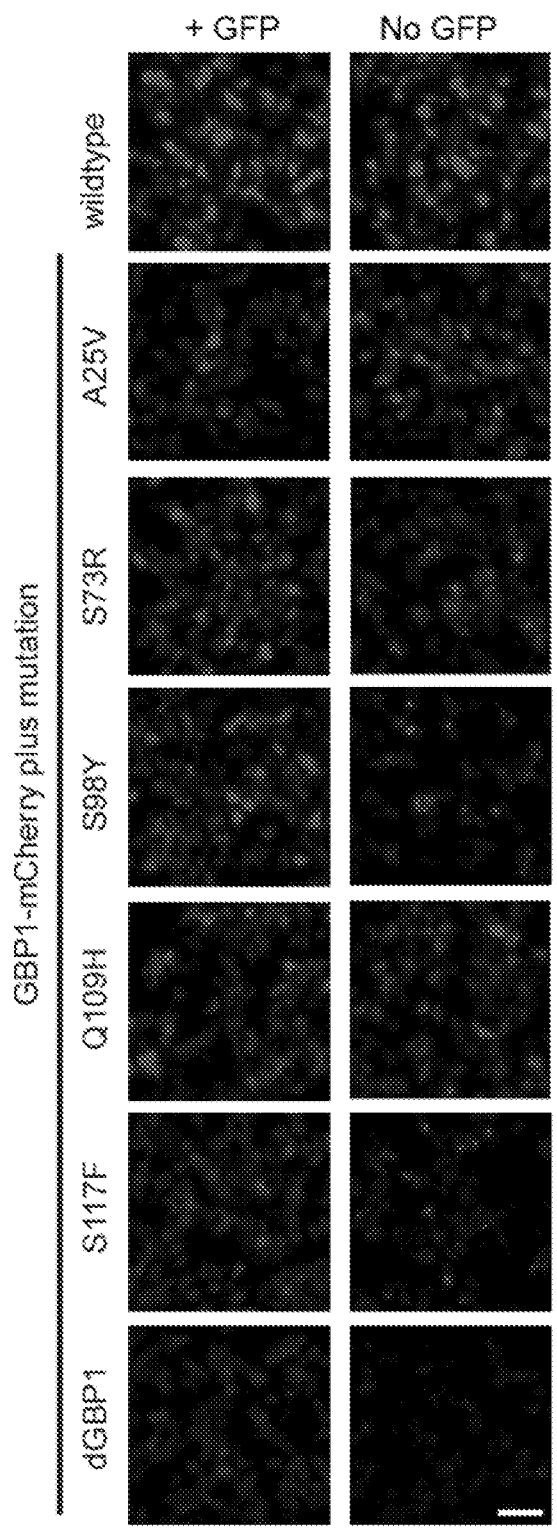
FIGS. 12A-12B show mapping mutations sufficient for dGBP1 destabilization.
Figure 12B:
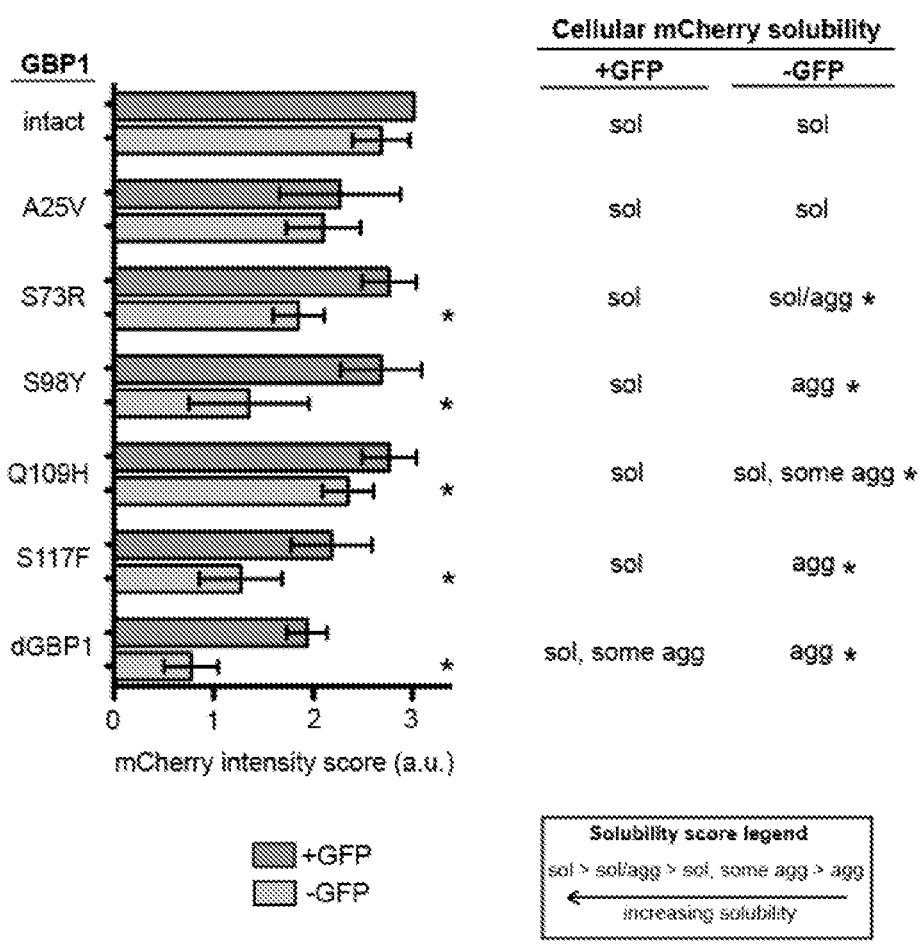

The inventors have also found that dGBP1 fusion to Discosoma-derived mCherry (dGBP1-mCherry) also showed antigen-inducible stabilization properties (FIGS. 11A-11B and 12A-12B). However, dGBP1-mCherry fusion protein did not disappear without GFP, as was observed for TagBFP. Instead, dGBP1-mCherry appeared to form aggregates within the cell. This property was exploited to use dGBP1-mCherry as a sensitized reporter to map the key residues involved in GBP1 stability, by comparing the level of fluorescence and aggregation of the fusion proteins in cells. Individual mutations were evaluated for their necessity in creating aggregates, and it was found that S98Y and S117F were strongly involved in the destabilization effect. This observation was supported by sufficiency experiments, whereby each of these same mutations was able to destabilize mCherry (FIGS. 12A-12B). In addition to these residues, S73R and Q109H also showed notable destabilizing effects in single mutant analyses (FIGS. 12A-12B). Interestingly, GFP addition was able to rescue the destabilization phenotype of all mutants (FIGS. 12A-12B). Thus, a subset of the dGBP1 mutations had clear destabilizing effects on fusion protein stability, both alone and in combination with other destabilizing mutations.

Generality of Destabilizing Mutations on Other Nanobodies

Further analysis revealed that all six mutations found in dGBP1 are located within the conserved framework regions of the nanobody scaffold (FIG. 5A). Also, analysis of the GFP/GBP1 crystal structure (Kirchhofer et al., 2010) suggested that the mutated residues are not involved in antigen binding. Given that nanobodies are highly conserved in their framework sequences, it is contemplated that the mutations found in dGBP1 can be transferred to other nanobodies for rapid generation of antigen-dependent protein sensors and effectors, without having to spend laborious efforts selecting and/or screening for a destabilized nanobody of interest. To this end, a series of grafting experiments were performed, transferring dGBP1 mutations to the corresponding framework residue positions of other nanobodies. The results indicate that a significant subset of nanobodies could be mutated to become antigen-inducible in protein level. Presented herein are two examples showing the feasibility of the mutation grafting strategy for rapid generation of antigen-dependent sensors and effectors.

The effects of transferring dGBP1 mutations to two nanobodies, VHH9 and CA1698 (Oyen et al., 2013) were investigated. VHH9 targets the C-terminal domain of Human Immunodeficiency Virus-1 (HIV-1) capsid protein (C-CA), whiles CA1698 targets the E. Coli Dihydrofolate Reductase (DHFR) enzyme. When fused to TagBFP, wildtype VHH9 and CA1698 showed diffuse and soluble TagBFP distribution in human cells, as well as abundant fusion protein level, regardless of the presence of its corresponding antigen (FIGS. 5B and 5D). The six dGBP1 mutations, hereafter referred to as the dG1-A code, were then transferred to both TagBFP-fused nanobodies, generating dVHHdG1-A-TagBFP and dCA1698dG1-A-TagBFP. Relative to their wildtype nanobody counterparts, both dVHHdG1-A-TagBFP and dCA1698dG1-A-TagBFP showed a sharp drop in fluorescence as well as fusion protein level in the absence of their corresponding antigens (FIGS. 5B and 5C, data not shown for dCA1698dG1-A-TagBFP). The extent of destabilization was strong, but not complete; faint fluorescent puncta were occasionally observed in cells overexpressing the fusion proteins (FIG. 5B; data not shown for dCA1698dG1-A-TagBFP). Co-expression of dVHHdG1-A-TagBFP with HIV-1 C-CA led to increased blue fluorescence diffusely distributed in cells, as well as a sharp increase in protein level, suggesting stabilization by HIV-1 C-CA binding (FIGS. 5B and 5C). In contrast, although dCA1698G1-A-TagBFP also showed increase in TagBFP fluorescence and appearance of diffuse fluorescence distribution in cells, a significant amount of strongly fluorescent puncta were observed, indicating aggregation of the DHFR/dCA1689G1-A-TagBFP complex (data not shown). It was speculated that the dG1-A code adversely affected CA1698-TagBFP's ability to respond to antigen binding, and so it was next sought to determine whether transfer of fewer destabilizing mutations would improve the antigen-induced phenotype. This new code, dG1-B, includes the three most destabilizing mutations mapped in dGBP1: S73R, S98Y and S117F (FIGS. 11A-11B and 12A-12B). It was determined that dCA1698dG1-B-TagBFP was again strongly destabilized in fluorescence as well as in protein level when expressed without DHFR (FIGS. 5D and 5E). However, unlike dCA1698dG1-A-TagBFP, co-expression of dCA1698dG1-B-TagBFP with DHFR resulted in predominately diffuse TagBFP fluorescence, with little sign of aggregation (FIGS. 5D and 5E). This result thus further validates the dGBP1 mutant mapping experiment establishing that all or some combination of S73R, S98Y and S117F were sufficiently destabilizing mutations. It further shows that although not all nanobodies may have tolerated dGBP1 mutations equally well, a more refined mutation code can be identified in a straightforward manner to generate properly responding antigen-responsive nanobody fusion proteins. Further, mutations found to destabilize a nanobody from the Arabian camel, C. dromedarius (dGBP1) could surprisingly exert very similar effects on nanobodies from the Alpaca, V. pacos (VHH9) as well as the Llama, I. glama (CA1698) (FIG. 5A).

Figures 6A, 6B, 6C, 6D:
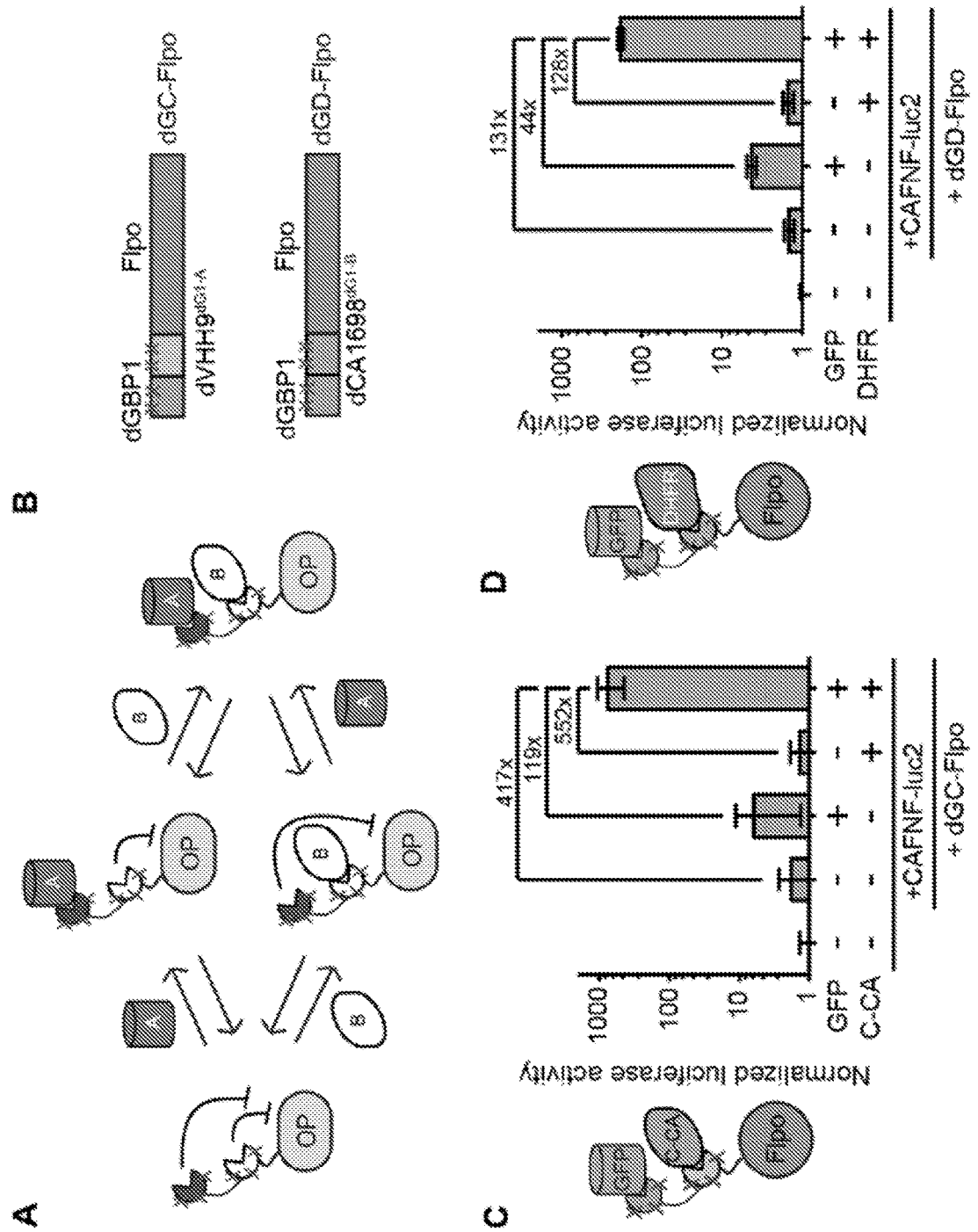
FIGS. 6A-6D show coincidence antigen detection in cells by double fusion of destabilized nanobodies targeting different antigens.

Dual Control of Fusion Protein Activity Based on Coincidental Expression of Antigens The ability to control fusion protein activity with tandemly fused destabilized nanobodies (FIGS. 3C and 3F), as well as the ability to rapidly generate destabilized nanobodies targeting different antigens (FIGS. 5A-5E), prompted the inventors to consider whether it would be possible to impose dual regulation of fusion protein activity simply by fusing the output protein to two destabilized nanobodies each targeting a different antigen (FIG. 6A). To investigate this, the second dGBP1 of dGBP1x2-Flpo was replaced with either VHH9 (dGC-Flpo) or CA1698 (dGD-Flpo) (FIG. 6B). Strong Flpo recombination was able to trigger only when either HIV-1 C-CA or DHFR were co-transfected with GFP into cells (FIGS. 6C and 6D). This result shows the feasibility of using destabilizing nanobody fusion proteins to manipulate genes selectively in cells expressing two antigens.

Intracellular Antigen Induced Genome Editing via the CRISPR/Cas9 System

Figures 7A, 7B, 7C, 7D:
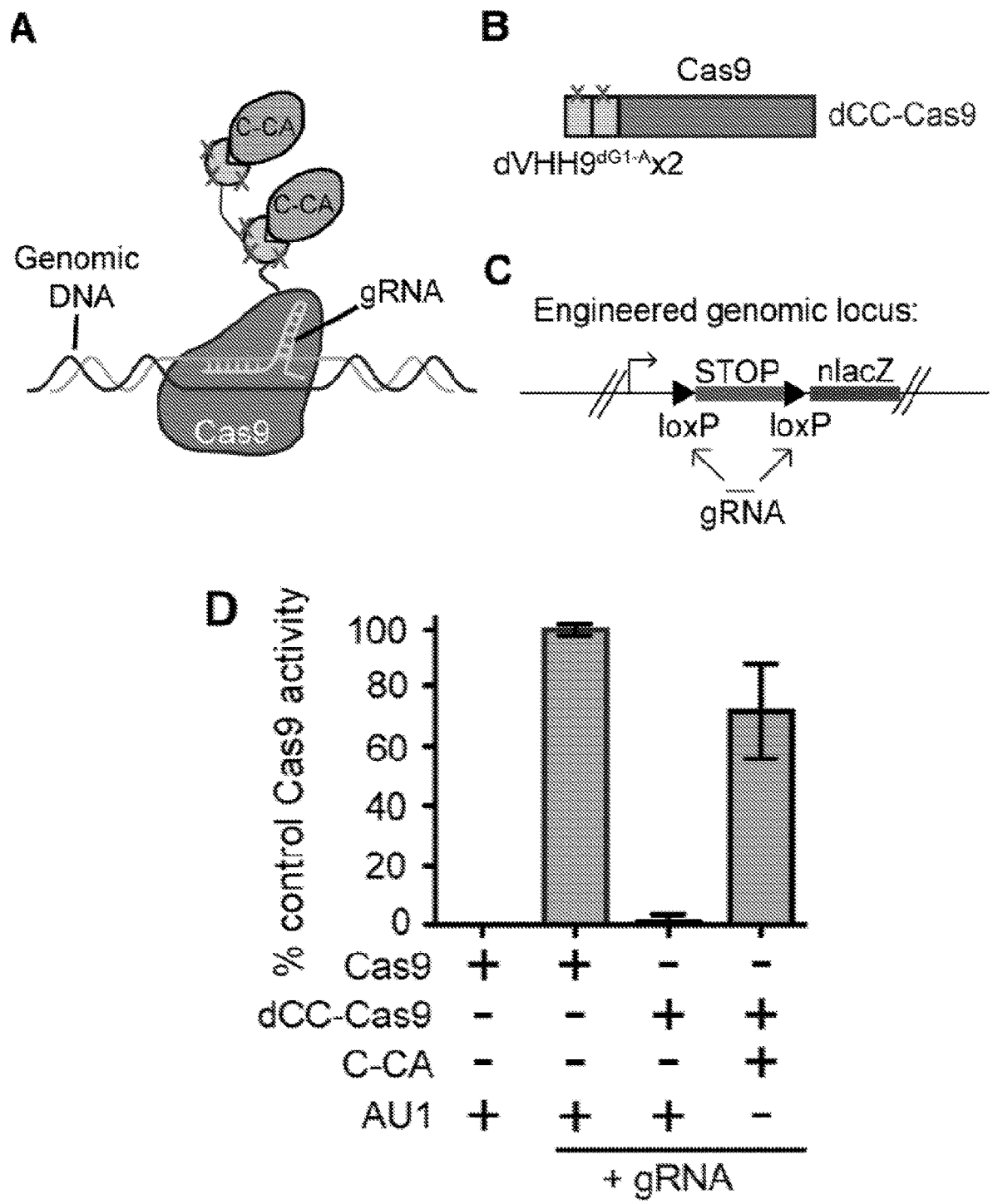
FIGS. 7A-7D contain experimental data showing that intracellular antigen can trigger genome editing via destabilized nanobodies.

To further investigate the range of activities that could be regulated by destabilizing nanobodies, it was next sought to determine whether it was possible to fuse destabilized nanobodies to Cas9 and perform genome targeting and editing under the control of desired antigens (FIG. 7A). A fusion was created between two dVHHG1-A and Cas9 (dCC-Cas9) and its ability to execute targeted genome editing was assessed. An engineered human cell line that expresses β-galactosidase upon removal of a stop cassette was engineered, and a guide RNA that can specifically target the loxP sites and delete the stop cassette (dCC-Cas9-LoxPgRNA) was designed (FIGS. 7B and 7C). Co-expression of HIV-1 C-CA with dCC-Cas9 and loxPgRNA triggered genome-editing events, while little to no β-galactosidase expression was detected in the absence of HIV-1 C-CA (FIG. 7D). The efficiency of HIV-1 C-CA-dependent genome editing approached that of control Cas9 (FIG. 7D). This result demonstrated the feasibility of using the intracellular epitopes of pathogens to initiate genome editing or targeting in infected cells.

Discussion

One aspect presented herein relates to a general strategy that uses intracellularly expressed proteins to induce an engineered biological activity. Mutations were created in a GFP nanobody that led to its stability only when bound to GFP, and these mutations can be transferred to nanobodies that bind other antigens. These destabilized nanobodies were used as fusion partners with proteins with desirable biological activities, such as fluorescent proteins, recombinases and the genome editing enzyme, e.g., Cas9. Destabilized nanobody fusion proteins were able to selectively label and manipulate genes in antigen-expressing cells in mice. In addition, fusions were engineered to be dependent upon the intersection of expression of more than one antigen, providing for more precision in the choice of cell types for gene manipulation. The technology described herein shows the feasibility of rapidly designing intracellular epitope-responsive sensors and effectors with a residue code that can be grafted across conserved binding protein scaffolds regardless of antigen identity.

This Example has provided several advances in the development of protein-inducible systems. First, the inventors simplified the use of an intracellular protein with no defined regulatory abilities, GFP, as a driver molecule that can activate a sensor or effector activity via a single fusion protein. Thus, one could now treat the GFP-dGBP1 system as a form of binary system analogous to GAL4/UAS and Cre/loxP system. The simplification enhanced the efficiency of activation compared to previous dimerizer systems (Tang et al., 2013). It is contemplated that this system will overcome potential issues from excessive target levels, as seen in dimerizer systems (Tang et al., 2013). The system was shown to regulate the activity of several popular fluorescent proteins and DNA modifying enzymes, demonstrating the utility of such an approach for generating protein-responsive sensors and effectors. The tools described herein can be immediately applicable for studies in the mouse by making use of existing transgenic GFP reporter lines for cell-specific manipulation studies. Notably, the reagents make it quite simple to perform intersectional genetics using GFP and Flp or Cre driver lines, by using GFP to directly turn on Cre or Flpo recombination.

Second, the inventors demonstrated that mutagenesis screens could be employed to discover protein mutations that confer antigen-induced stabilization effects. This provides a tool for the screening of other nanobodies and/or protein scaffold binders (Wurch et al., 2012) to generate additional destabilizing systems controlled by intracellular antigens. Third, the inventors showed that destabilizing mutations can be grafted from one conserved protein scaffold or antibody framework to another, regardless of antigen identity. Surprisingly, both recipient nanobodies were derived from different species from that of GBP1 (FIG. 5A), indicating the broad transferability of the mutations discovered herein. Thus, this strategy allows for rapid generation of protein sensors and responders without going through laborious screens to discover relevant mutations or evolve antigen-binding specificity. Ultimately, the ability to turn any intracellular protein target into a synthetic switch can allow the use of wildtype animals for cell-specific manipulation studies.

Generality to Different Fusion Proteins, and Intersectional Control

Despite having virtually no background signal associated with the dGBP1-TagBFP construct, fusion of dGBP1 to other proteins can have variable success. Fusion to mCherry led to aggregation of the fusion protein in cells, and dGBP1-Cre fusion displayed a significant number of background recombination events. The background noise issue with Cre fusion constructs can be addressed by different engineering approaches. For example, it can be desirable to incorporate temporal control on the activity of dGBP1-Cre fusion protein by adding an ERT2 domain for sequestering the protein away from the nucleus until introduction of the Tamoxifen ligand.

A caveat of the destabilized sensor/effector approach compared to transcription activation of a gene could be that the translated protein may retain partial functional activities like fluorescence or DNA-modifying activities. The different amount of background fluorescence seen with different fluorescent proteins as fusion partners may be due to differences in the way different destabilized nanobody-fusion partner constructs interact when linked together. Nevertheless, a simple way to reduce background effector activity includes, e.g., increasing the number of destabilized nanobodies fused to the fusion partner. This approach indeed works well to suppress leakage of Cre and especially Flpo and CRISPR/Cas9 activity (FIGS. 4A-4C and FIGS. 7A-7D). Screening for additional destabilizing mutant combinations or further mutagenesis of dGBP1 fused to highly stable fusion partners can further enhance the antigen-specificity of sensor/effector activities.

The finding presented herein that one could fuse an effector protein to two destabilized nanobodies led to the development of an intersectional strategy for manipulating genes in cells, based on the co-expression of two different antigens bound to distinct nanobodies fused to the effector protein, Flpo (FIGS. 6A-6D). The intersectional strategy can provide precise manipulation of desired cell types based on endogenous molecules. This could either replace and/or complement existing intersectional genetic schemes dependent on the availability of cell-specific promoters and/or transgenic lines expressing driver molecules.

Detection of Intracellular Antigens for Genome Editing

The ability of a viral antigen, the HIV C-CA protein, to trigger genome editing events in human cells indicate that one could design various antigen-specific Cas9 effectors for genome editing and targeting events only in cells expressing the targeted antigen. One possible application of this technology can be to activate genome editing only in cells expressing a pathogenic antigen, for effects such as triggering apoptosis or activation of cellular mechanisms to counteract pathogen activity. In addition, a concern with expression of Cas9 and gRNA in cells is non-specific genome editing effects from targeting of undesired genomic loci. A combination of strategies is being developed to address this concern (Hsu et al., 2014; Sander and Joung, 2014). The novel strategy as presented herein of destabilizing Cas9 activity until its genome targeting abilities is desired in the presence of an antigen can provide an additional layer of protection against undesired effects on normal genomic content.

Alternative Example Applications of Destabilized Nanobodies Beyond Cell-Specific Manipulations as an Improved Protein Localization Probe Not only can the sensor systems described herein be used for cell-specific manipulations, they can also be used in many other applications. For example, in some embodiments, the sensor systems described herein can be used to reduce toxic effects with existing GFP-dependent systems. In these embodiments, dGBPs can be used to replace the wildtype GBP domain used in the existing Transcription Devices Dependent on GFP (T-DDOG) as described in Tang et al. (Cell (2013) 154: 928-939) and in U.S. Patent Application No. US 2013/0230863, the contents of each of which are incorporated herein by reference, and CRE-DOG systems. In a transcription system, overexpression of transactivation domain can lead to squelching of transcription machinery and thereby cell toxicity (Gill and Ptashne, 1988). By replacing a wildtype GBP domain with a dGBP, the negative effects of transcription activation domains can be minimized by suppression of their expression until a cell expresses GFP. In addition, the background recombination seen with GFP-independent association of split Cre components can be further reduced by destabilizing the components in the absence of GFP.

In some embodiments, the sensor systems described herein can be used as an improved protein localization probe. In addition to being used as reagents to generate antigen-dependent effectors, destabilized nanobodies also can be exploited as improved probes for protein localization. By fusing nanobodies to fluorophores, one can visualize the localization of target antigens in living cells (Rothbauer et al., 2006). However, a caveat of this approach is that good signal-to-noise detection of target protein localization requires the nanobody-fluorophore be restricted in localization to the site of interactions. Recently, this issue was addressed by designing a synthetic circuit with large fusion intrabody protein constructs and transcriptional feedback mechanism (Gross et al., 2013). However, this method requires that the targeted protein be excluded from the nucleus while bound to the antigen, and so has been only demonstrated for proteins anchored away from the nucleus. In comparison, destabilized nanobody-fluorophores are not limited to extra-nuclear proteins as it is based on destabilization without antigen. It is contemplated that under ideal conditions, any unbound fluorophore can be sent for degradation, effectively suppressing background noise. Therefore, elimination of aggregation phenotype seen in nanobodies receiving the destabilizing mutations is desirable to such application.

In some embodiments, the sensor systems described herein can be used for cell-specific genome editing, e.g., based on Cas9 fusion to the destabilized nanobodies.

In some embodiments, the sensor systems described herein can be used for cell-specific cell killing strategy, e.g., a destabilized nanobody fused to a toxin (e.g., but not limited to diphtheria toxin, ricin toxin or similar molecules).

In some embodiments, the sensor systems described herein can be used as a diagnostic tool, e.g., to label cells expressing an intracellular ligand of interest. This can be applied in clinical diagnosis, e.g., for detection of a tumor. For example, expression of a nanobody-detectable agent fusion (e.g., a nanobody-fluorescent protein fusion) in the presence of an intracellular ligand is indicative of cells expressing the intracellular ligand of interest.

Other applications of the sensor systems described herein include, but are not limited to cell-specific overexpression of one or more endogenous or exogenous genes of interest such as transcription factors, signaling molecules; optogenetic tools, etc.

Generalizing the Destabilization Mutation Code to other Nanobodies

The major GBP1 residues contributing to destabilization have been mapped to S73, C98 and S117. All residues fall in the relatively conserved framework regions of the nanobody scaffold. S73 is exposed to the hydrophilic environment. C98 is involved in disulfide bond formation in the scaffold when in the extracellular environment. S117 is on the C-terminal end of the nanobody. With both VHH9 and CA1698, sub-mapping experiments further indicate that C98 and S117 can be sufficient to confer antigen-inducible stabilization (FIGS. 5A-5E, data not shown for VHH9). Studies on CA1698 indicate that not all nanobodies can tolerate the full set of dGBP1 mutations. However, the inventors showed that introduction of a refined subset of dGBP1 mutations could adequately destabilize the CA1698, enabling rapid generation of antigen-sensors and effectors.

A particularly surprising finding is that mutations that destabilized a nanobody derived from the Arabian camel (GBP1) were able to be successfully transferred to nanobodies from Alpaca (VHH9) and Llama (CA1698), to generate antigen-specific sensors and effectors. These three Camelid species represent major sources of nanobodies. Thus, the dGBP1 destabilization code as well as mutation grafting approach can be extended to a broad collection of nanobodies, for rapid generation of intracellular antigen-inducible control. It is contemplated that by studying the crystal structures of the nanobody-antigen complex, in combination with mutagenesis screens described herein, a common set of rules and mutations can be identified and applied to predictively destabilize any nanobody at will, with desirable antigen-inducible effects, based on the presence of intracellular epitopes, with enormous implications for basic biology and medicine.

Example 2

Generality of Destabilizing Mutations on Other Nanobodies

Since all six mutations identified in dGBP1 are located within the non-hypervariable regions of the nanobody scaffold, and were not directly involved in antigen binding, it was next sought to determine if the mutations found in dGBP1 could be transferred to other nanobodies for generation of antigen-dependent protein sensors and effectors. The six mutations were able to destabilize all tested nanobody fusion proteins. In some tested nanobody fusion proteins, antigen-dependent changes in the fusion protein in terms of level and subcellular localization were detected (data not shown).

Figures 13A, 13B, 13C, 13D, 13E, 13F:
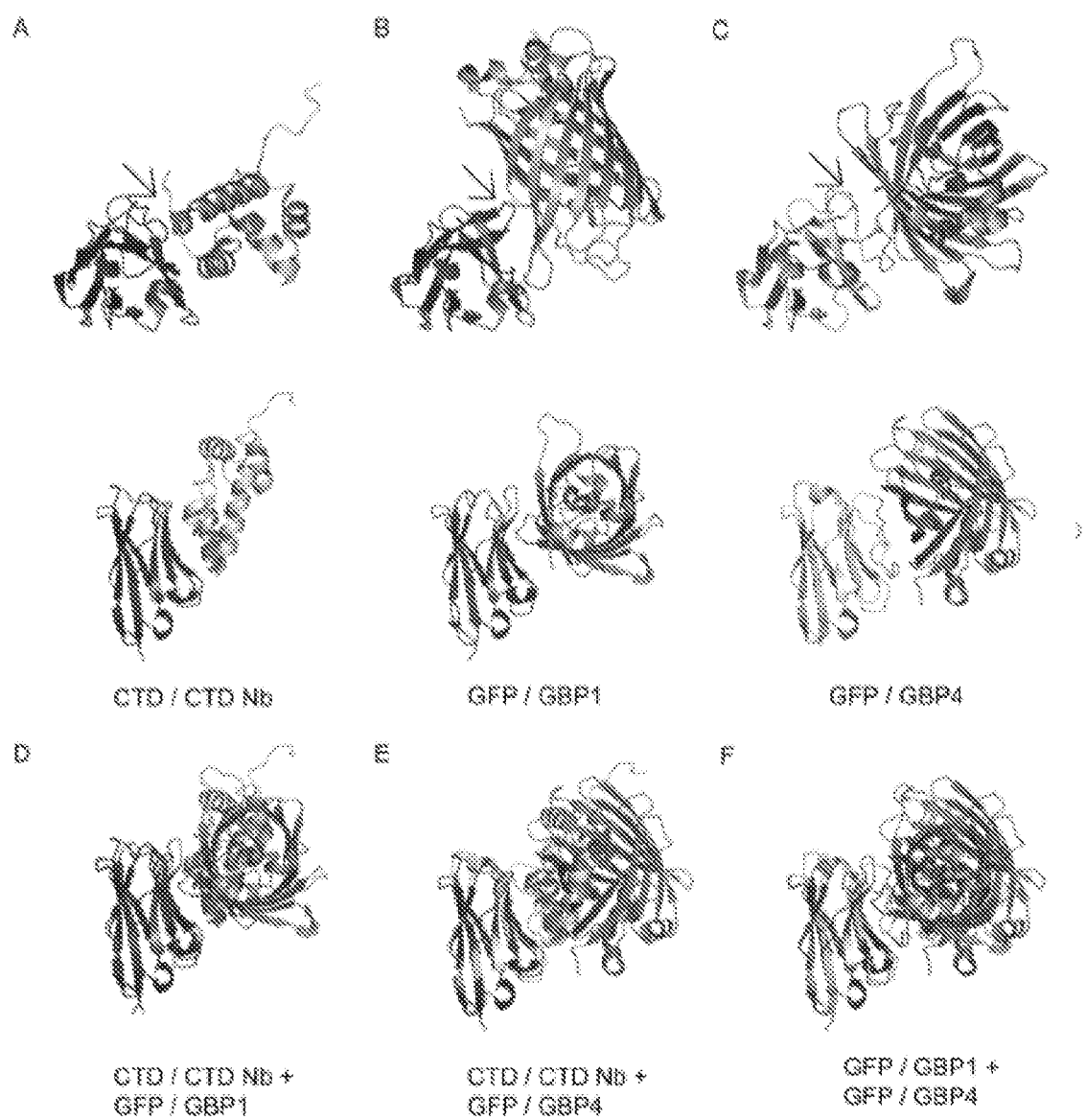
FIGS. 13A-13F show structural alignment of three antigen-nanobody complexes.

It is contemplated that the transferability of the six GBP1 destabilizing mutations to other nanobodies to produce a desirable antigen/ligand-dependent nanobody fusion protein stabilization effect depends, at least in part, on the binding interaction between the nanobody and the antigen/ligand. Crystal structures of the nanobody-antigen complexes were evaluated. It was found that GFP bound to GBP1 via interactions with the CDR2 and CDR3 loops and with FR2 and FR3 (FIG. 13B). This GBP1-GFP complex interaction differs from the other nanobodies tested, such as that of a GBP4-GFP complex (FIG. 13C). Unlike in GBP1-GFP complex, the antigen/ligand-nanobody binding in the other tested nanobodies (e.g., GBP4-GFP) occurs primarily at an elongated CDR3 loop region, pushing the antigen/ligand away from FR2, FR3 and CDR2.

A survey through published crystal structures revealed that some antigen-nanobody complexes do share a similar binding relationship as between GBP1 and GFP. For example, the HIV C-terminal domain (CTD or C-CA) nanobody (Nb) also has a relatively short CDR3 loop, resulting in interactions with CTD (or C-CA) at FR2, FR3 and CDR2, as did GBP1 with GFP (FIG. 13A). Thus, when the dGBP1 mutations were grafted to the CTD Nb (or termed as C-CA Nb) (FIGS. 14A-14E), the 6 dGBP1 mutations destabilized CTD Nb-mCherry, or dCTD Nb-mCherry, to a similar extent as dGBP1-mCherry, with reduced mCherry fluorescence compared to wildtype and widespread aggregations seen throughout the cells (FIGS. 14B and 14C). Surprisingly, the aggregation was eliminated by co-expression with CTD, indicating that the CTD/CTD Nb complex becomes stabilized upon complex formation (FIG. 14B). Western blot analysis further showed that CTD stabilizes dCTD Nb-mCherry expression (FIG. 14E). With mCherry antibody, the presence of a protein fragment slightly smaller in size than the expected dGBP1-mCherry fusion protein was also detected. This could possibly be a degradation product liberating mCherry from dGBP1.

The 6 dGBP1 mutations were roughly divided into an N- and C-terminal group (N-terminal: A25V, E63V, S73R. C-terminal: C/S98Y, Q109H, S117F) to determine whether each group alone could confer CTD Nb with destabilizing phenotypes. The C-terminal group alone gave visibly detectable destabilization of CTD Nb, e.g., in the form of aggregations and exclusion from nucleus (FIG. 14D). This destabilizing phenotype can be rescued by CTD co-expression (FIG. 14D). In some embodiments, destabilizing residues at C/S98Y and S117F can be sufficient to confer a nanobody with destabilizing phenotypes, as described in a residue mapping experiment of dGBP1 (FIGS. 11A-11B, and 12A-12B). Taken together, the findings described herein indicate the feasibility of transferring protein-destabilizing mutations to different nanobodies that target different antigens, for rapid generation of intracellular antigen/ligand-inducible control.

To discern what is common amongst GBP1 and CTD Nb that permits these nanobodies to behave in a desired antigen-induced stabilization fashion in response to dGBP1 destabilizing mutations, it was speculated that the mode of binding between the antigen and nanobody can explain why certain nanobodies receive the dGBP1 mutations when others cannot. Each nanobody structure is divided into multiple secondary structure regions such as loops, alpha helices and beta strands. The crystal structure of many available antigen-nanobody complexes were analyzed to create a matrix and each nanobody secondary structure region for putative contact sites with the antigen was scored. Principal component analysis was then performed to cluster antigen-nanobody complexes. It was discovered that principal component 1 (PC1) separates the nanobodies that were able to receive the dGBP1 mutations with favorable antigen-inducible expression from the nanobodies that did not respond with antigen-inducibility. Further analysis shows that the secondary structure regions that contribute to the PC1 axis are involved in antigen binding. GBP1 and CTD Nb were found to interact with their respective antigens via very similar surfaces. This analysis indicates that antigen-nanobody complexes utilizing this type of interaction are more responsive to receiving the dGBP1 mutations to create antigen-inducible expression and predicts specific antigen-nanobody complexes as likely candidates for creating antigen-responsive sensors and effectors. Using the prediction generated by this analysis as a guide for choosing nanobodies for introducing dGBP1 mutations, it was found that the DHFR-binding nanobody (DHFR Nb) can also be turned into a ligand-inducible domain with 3 or 6 of the 6 dGBP1 mutations; without DHFR antigen expression, the DHFR Nb-TagBFP construct shows loss of fluorescence and fluorescent aggregates, whereas with DHFR antigen expression, the TagBFP fusion protein becomes soluble in cells (Table 4).

TABLE 4 dGBP1 mutations confer DHFR nanobody with clear ligand stabilizable phenotype

|  | wildtype Nb | | 6 dGBP1 mutations | | 3 major dGBP1 mutations - S73R, S/C98F, S117F | |
| --- | --- | --- | --- | --- | --- | --- |
|  | TagBFP intensity | Aggregation? | TagBFP intensity | Aggregation? | TagBFP intensty | Aggregation? |
| with DHFR | +++ | − | +++ | + | +++ | − |
| no DHFR | +++ | − | ++ | +++ | ++ | +++ |

Transfecte 293T cells.

Example 3

Effector Functions Controllable by Destabilized Nanobodies

It was next sought to determine whether intracellular antigens can influence the activity of other effector molecules. The inventors showed that CTD or C-CA can control genome editing via Cas9 destabilization (FIGS. 15A-15D and 16) and both GFP and CTD can inhibit protein synthesis via attenuated Diphtheria toxin (Table 5).

TABLE 5

GFP and CTD can both induce attenuated Diphtheria toxin ability via their respective destabilized nanobodies

| | Intensity of CAG-mCherry | |
| --- | --- | --- |
| | dGBP1x2-tox176 | dCTDNbx2-tox176 |
| with GFP | + | |
| no GFP | ++ | |
| with CTD | | + |
| no CTD | | ++ | n = 2-3. tox176 is an attenuated Diphtheria toxin that inhibits protein translation. CAG-mCherry serves to assay protein level. Cells examined 1-2 days post-transfection Example 4

Mechanism of Destabilization

Proteins are generally degraded through the ubiquitin pathway, the lysosome, and/or phagocytosis. In some embodiments, the ubiquitin pathway can mediate the destabilization effects seen in the sensor systems described herein. As a proof-of-concept, an ubiquitin ligase blocker or other blocker that inhibits the specific branches of the degradation pathway can be used to determine its effects on the destabilization of the fusion proteins describe herein. Pulse-chase experiments and subcellular-localization analysis of nanobody-halo fusion proteins with or without blocker can address its mechanism of removal.

In some embodiments, as compared to transcription activation of a gene, the effector protein product can be produced and potentially exert its effector effects before being subjected to degradation. The different amount of background fluorescence observed with different fluorescent proteins as fusion partners can be due to differences in the rate at which different dGBP1-fusion partner constructs were degraded (e.g., by sending to the proteasome).

One way to enhance the efficiency of degradation of the sensor systems described herein can be increasing the number of destabilized nanobodies fused to a fusion partner of interest (e.g., an effector domain). Indeed, this approach works well to suppress leakage of Cre and especially Flpo activity (FIGS. 10A-10B). Alternatively or additionally, screening for additional destabilizing mutant combinations and/or further mutagenesis of dGBP1 fused to highly stable fusion partners can further enhance the degradation efficiency.

Example 5

Grafting dGBP1 Mutations Across Aanobodies

As shown in the Examples above, the major contributing GBP1 residues involved in destabilization have been mapped to S73, C98 and/or 5117. All residues fall in the relatively conserved framework regions of the nanobody scaffold. S73 is exposed to the hydrophilic environment. C98 is involved in disulfide bond formation in the scaffold. S117 is on the very end of the nanobody. In the case of HIV CTD Nb, sub-mapping experiment further indicate that C98 and S117 can be sufficient to confer antigen-inducible stabilization. In some embodiments, the relative destabilizing contributions of Q109H can also be negligible when transferred across nanobodies.

All other tested nanobodies receiving the dGBP1 mutations seemed to be destabilized (data not shown). However, the ability of an antigen/ligand to reverse the destabilized phenotype upon nanobody binding vary with the mode of antigen-nanobody binding. Without wishing to be bound by theory, a key difference between the antigen binding mode of GBP1, CTD Nb and the other nanobodies tested is the existence of an elongated loop structure in the CDR3 region that pushes these other antigens away from FR2 and CDR2 of the other nanobodies. The antigen probably acts like a staple in the case of GBP1 and CTD Nb to stabilize any destabilizing effects conferred by C98 and S117. When the antigen/ligand is bound primarily to the CDR3 loop, however, the antigen binds away from the backbone structure and so there is no stapling effect, resulting in continued destabilization of the entire structure.

To determine effects of destabilizing mutations on antigen-nanobody binding modes, one can repeat the mutagenesis screen on selected candidates within each clade of complexes, and then to compare and contrast isolated mutations within clade and across clades. Upon arrival at a common set of residues and residue mutations within and between clades, single, and/or combinations of mutations can be grafted between nanobodies to assess whether a clade-specific or universal mutation codes can be arrived at for generating antigen/ligand-inducible protein stabilization.

An alternative way to design a universal destabilized nanobody scaffold can be to graft the hypervariable CDR loops onto a common destabilized scaffold.

Exemplary Materials and Methods for Examples 1-5

Animals. All animal experiments performed were approved by the Institutional Animal Care and Use Committee at Harvard University. Time pregnant CD1 (Charles River Breeding Laboratories, Boston, Mass.) were used for the electroporation experiment. Tg(CRX-GFP) (Samson et al., 2009) was bred in C57/BL6J background. For experiments transgenic mice were either crossed to CD1, C57/BL6J or littermates to produce pups.

Generation of mutagenized GBP1 Library. GBP1 and vector flanking sequences were PCR amplified from the pBMN-GBP1-TagBFP vector (described below). A SphI site was inserted between the GBP1 and TagBFP sequences, creating an AC amino-acid linker. For mutagenesis, GBP1 and vector flanking sequences were PCR amplified from the pBMN-GBP1-TagBFP vector using forward primer

```
5' GACCATCCTCTAGACTGCCGGATCCGCCACCATGGCCGACGTGCAGC
TCGTGGAAT-3'
``` and reverse primer

```
5' TGTTCTCCTTAATCAGCTCGCTCATGCATGCAGAACTAACAGTCACT
TGTGTGCCC-3'.
```

The amplified products were gel extracted and randomly mutagenized using primers flanking the GBP1 coding sequence, which were forward primer

```
5' GACCATCCTCTAGACTGCCGGATCCGCCACC-3'
``` and reverse primer

```
5'-TGTTCTCCTTAATCAGCTCGCTCATGCATGC-3'.
```

The GeneMorph II Random Mutagenesis Kit was used to introduce balanced mutation rates for different nucleotides (Agilent). Duplicates of low, medium, and high mutation reactions were cloned into the pBMN vector by Gibson Assembly in frame with TagBFP, maintaining an SphI linker. The pBMN backbone was digested with BamHI and SphI to receive the inserts, which were inserted using the Gibson reaction, and transformation of DH5-alpha cells was carried out. Transformants were grown in 200 mL LB cultures overnight, and DNA was purified by Maxiprep kits (QIAGEN). An aliquot of each culture that grew well was plated, and GBP1 inserts were sequenced. The medium mutagenesis library was used to generate VSV-G coated MLV viruses (Yee et al., 1994), which were used to infect 293T cells.

Selection of Destabilized GBP1 variants. 293T cells infected with MLV carrying GBP1 mutants were sorted by FACS for either low, medium, or high red fluorescence (from the IRES t-HcRed) and for absence of blue fluorescence (for putative destabilized TagBFP). Next, sorted cells were plated and allowed for expansion in culture. Cells were then infected with a 2/8 AAV-EF1a-GFP virus, and allowed to grow for 24 hours. Cells were then sorted for red fluorescence and either high or very high blue fluorescence. Sorted cells were then seeded into T25 flasks and allowed to grow to confluence. Next, DNA from cells was extracted using the DNeasy kit (QIAGEN). Next, GBP sequences were PCR amplified using flanking GBP sequences (above) and Phusion polymerase (New England Biolabs). PCR products were gel purified and cloned back into the pBMN vector using Gibson Assembly. The ligation product was purified, transformed, and grown for 1 hour in SOC at 37° C. and seeded onto Carbenicillin plates. Two hundred colonies were randomly picked and sequenced. Plasmids from clones were individually transfected into 96 well plates of 293T cells with or without CAG-YFP to assay for TagBFP fluorescence.

Molecular Biology. DNA constructs were generated with standard molecular biology and example constructs are listed as below.

Nanobody sequences—Nanobodies used were: GBP1 (Kirchhofer et al., 2010), VHH9 (PDB Identifier: 2XT1) and CA1698 (Oyen et al., 2013).

Miscellaneous Plasmids—pCAG-GFP (Addgene plasmid 11150) (Matsuda and Cepko, 2004), pCAG-YFP (Addgene plasmid 11180) (Matsuda and Cepko, 2004), pCAG-DsRed (Addgene 11151) (Matsuda and Cepko, 2004). pRho-GFP-IRES-AP (referred to as Rho-GFP in main text) (Emerson and Cepko, 2011). pCAG-nlacZ (Cepko lab, Harvard Medical School), pCAGEN (Addgene plasmid 11160) (Matsuda and Cepko, 2004). pCALNL-DsRed (Addgene plasmid 13769) (Matsuda and Cepko, 2004). pCAFNF-DsRed (Addgene plasmid 13771) (Matsuda and Cepko, 2004). pCAG-GAPDH-AU1 (Emerson and Cepko, 2011). pBMN DHFR (DD)-YFP (Addgene plasmid #29325) (Iwamoto et al., 2010). pX330-U6-Chimeric BB-CBh-hSpCas9 (Addgene plasmid #42230) (Cong et al., 2013). pRL-TK (Promega, 4E2241).

Plasmid construction—All DNA constructs were generated with standard techniques:

pBMN-GBP1-TagBFP—A GBP1-TagBFP construct inserted into a BamHI/NotI digested pBMN-DHFR(DD)-YFP vector (Addgene plasmid 29325), replacing the DHFR(DD)-YFP insert and generating pBMN-GBP1-TagBFP vector. This becomes the host vector for mutagenized GBP1 inserts.

pBMN-dGBP1-Cre and pBMN-dGBP1-Flpo-pBMN-dGBP1-TagBFP was digested with SphI/SalI, liberating TagBFP as well as the IRES-t-HcRed element. PCR-amplified Cre and Flpo fragments were then inserted into the digested vector via Gibson Assembly.

pBMN-GBP1-Cre and pBMN-GBP1-Flpo—PCR fragments of GBP1 were inserted into BspEI/SphI digested pBMN-dGBP1-Cre and pBMN-dGBP1-Flpo by Gibson Assembly, resulting in pBMN-GBP1-Cre and pBMN-GBP1-Flpo. dGBP1 sequence was removed by BspEI/SphI digest.

pBMN-dGBP1x2-Cre, pBMN-dGBP1-GBP1-Cre, pBMN-dGBP1x2-Flpo, pBMN-dGBP1-GBP1-Flpo—pBMN-dGBP1-Cre or -Flpo plasmids were digested with SphI. gBlock fragment encoding a codon modified dGBP1 was inserted into this site via Gibson Assembly, generating pBMN-dGBP1x2-Cre or -Flpo. Using a GBP1 gBlock fragment instead of dGBP1 gives pBMN-dGBP1-GBP1-Cre or -Flpo.

pCALNL-luc2—An EcoRI/NotI flanked fragment bearing luc2 was sub-cloned into EcoRI/NotI digested pCALNL-DsRed, giving pCALNL-luc2 and removing DsRed from the construct.

pCAFNF-luc2—An EcoRI-Kozak-luc2-NotI DNA fragment liberated from pCALNL-luc2 (Tang et al., 2013) was sub-cloned into EcoRI/NotI digested pCAFNF-DsRed vector, giving pCAFNF-luc2.

pCAG-dGBP1-mCherry—PCR amplified mCherry was inserted into a SphI/NotI digested pCAG-dGBP1-TagBFP vector, resulting in replacement of TagBFP with mCherry. The vector became pCAG-dGBP1-mCherry.

Wildtype and mutant nanobodies in pCAG vector—all wildtype and variant sequences were synthesized as gBlocks and inserted into EcoRI/SphI digested pCAG-dGBP1-mCherry vector via Gibson Assembly. The inserted fragment thus replaced dGBP1.

pCAG-VHH9-TagBFP, pCAG-CA1698-TagBFP, pCAG-dVHH9$^{G1-A}$-TagBFP and pCAG-CA1698$^{G1-B}$-TagBFP—A gBlock fragment carrying either the VHH9 or CA1698 nanobody coding sequence, codon optimized for mammalian cell expression, was inserted into an EcoRI/SphI digested pCAG-TagBFP vector via Gibson Assembly, resulting in pCAG-VHH9-TagBFP or pCAG-CA1698-TagBFP. To destabilize VHH9 and CA1698, mutations were introduced into residue positions that aligned with the dGBP1 mutation positions. Equivalent residues were easy to identify since surrounding amino acid sequences were highly conserved. For G1-A code, the dGBP1 mutations were A25V, E63V, S73R, S98Y, Q109H and S117F. For G1-B code, the dGBP1 mutations were S73R, S98Y and S117F. gBlocks carrying these mutations in the respective nanobodies were introduced into the EcoRI/SphI digested pCAG-TagBFP vector via Gibson Assembly, giving either pCAG-VHH9G1-A-TagBFP or pCAG-CA1698G1-B-TagBFP.

pCAG-dGC-Flpo and pCAG-dGD-Flpo—A gBlock fragment carrying either dVHH9G1-A or CA1698G1-B coding sequence were inserted into SphI digested pCAG-dGBP1-Flpo vector via Gibson Assembly, giving either pCAG-dGC-Flpo or pCAG-dGD-Flpo, respectively.

pCAG-C-CA and pCAG-DHFR—A gBlock fragment carrying either the HIV C-CA coding sequence (encoding residue 146-231 of HIV-1 gag polyprotein) or E. coli DHFR coding sequence was inserted into EcoRT/NotI digested pCAG-GFP vector via Gibson Assembly; C-CA or DHFR replaced GFP in the cassette.

pX330-dCC-Cas9-loxPgRNA—The pX330 vector was modified to contain XhoI and BsrGI sites 5' to the Cas9 sequence. A dVHH9dG1-Ax2 gBlock fragment was amplified by PCR and digested by XhoI and BsrGI, followed by Gibson Assembly with the XhoI/BsrGI digested and modified pX330 vector, giving pdCC-Cas9. The guide RNA that targets the LoxP sites was inserted into the BbsI sites of the dCC-Cas9 constructs as previously described (Wang et al., 2014).

pX330-loxPgRNA—The guide RNA that targets the LoxP sites was inserted into the BbsI sites of the modified pX330 construct as previously described (Wang et al., 2014).

Cell culture and Transfection. 293T cells were seeded onto 24 or 96 well plates and used for transfection when the cells reached between 60-95% confluency, usually 1-2 days later. Transfection is achieved with polyethyleneimine (PEI) at a 1:4 DNA amount: PEI volume ratio. Between 100 and 400 ng total DNA were transfected into single wells of 96 well plates for fluorescence analysis of destabilized mutants. Around 70 ng total DNA were transfected into single wells of 96 well plates for luciferase analysis. Around 400 to 520 ng total DNA were transfected into single wells of 24 well plates for fluorescence imaging and western blot analysis.

Luciferase assay. In all experiments, 20 ng CALNL-luc2 or CAFNF-luc2 and 3 ng pRL-TK were included. Plasmids encoding CAG-driven XFP and destabilized nanobody fusion constructs were transfected at amounts adjusted for their molarity. pCAGEN was added to adjust the total DNA amount to around 70 ng. Cells were harvested at the appropriate time for Dual-luciferase assay (Promega) according to manufacturer's instructions. Lysates were pipetted into 96-well plates and read in a Spectra Max Paradigm plate reader (Molecular Devices). The linear range of detection for the plate reader was determined with serial dilutions of QuantiLum recombinant luciferase (Promega). Transfection amounts were then adjusted to give readings within the linear range of detection for the instrument. Readings were normalized against a specific condition such that the background reporter activity gives a value of 1. All transfection conditions were independently repeated at least 3 times and in assayed in one to three replicates in transfection wells and/or plate reader well.

Western Blot. 293T cells were seeded onto 24 well plates and transfected with the relevant constructs plus a constant amount of CAG-nlacZ plasmid, which served as a transfection control. Transfected 293T cells were lysed in 6xSDS PAGE loading buffer (350 mM Tris-HCl, pH8, 30% glycerol, 10% SDS, 600 mM DTT, 0.01% Bromophenol Blue) and stored at −20° C. until used for SDS PAGE and Western blot. Transferred blots were cut into two pieces for blotting with anti-TagBFP or anti-βgal.

In vivo electroporation. P0-P2 mouse pups were microinjected with plasmids into their subretinal space and subjected to electroporation (Matsuda and Cepko, 2004). For electroporation of CD1 mice, plasmids encoding CAG-dGBP1-TagBFP were injected along with CAG-DsRed, CAG-GFP or Rho-GFP. For electroporation of Tg(CRX- GFP) mice, plasmids encoding CAG-dGBP1x2-Flpo, CAFNF-DsRed and CAG-nlacZ were blindly injected into Tg(CRX-GFP) and wild type littermates. Electroporated retinas were harvested at P14, immunostained for TagBFP or βgal antibodies in the far-red channel, and imaged by confocal microscopy.

Retinal Histology. Isolated mouse retinas were fixed at room temperature for 30 minutes in 4% paraformaldehyde/PBS solution. Retinas were then transferred to 30% sucrose in PBS, and subsequently into a 1:1 mixture of 30% sucrose/PBS and OCT for sectioning. 20 µm retinal cryosections were cut on a Leica CM3050 cryostat (Leica Microsystems).

Retinal immunohistochemistry. Retinal cryosections were incubated in blocking solution (3% normal goat serum, 1% BSA, 0.1% Triton-X, 0.02% SDS in PBS) for 1 hour and stained for primary antibody overnight at 4° C. Immunostained cryosections were washed three times in PBS and stained for secondary antibodies in blocking solution for 2 hours at room temperature. Slides were then washed in PBS and mounted for imaging in Fluoromount-G (Southern Biotechnology Associates; 0100-01).

Antibodies. Antibodies used were rabbit anti-TagRFP (also targets TagBFP; 1:1000 dilution for both immunoblot and immunohistochemistry) (AB233, Evrogen), mouse anti-βgal (1:50 dilution for immunoblot) (40-1a supernatant, Developmental Studies Hybridoma Bank), chicken anti-βgal (1:1000 dilution for immunohistochemistry) (ab9361, Abcam), rabbit-anti-GFP (1:500 dilution for immunohistochemistry) (A-6455, Invitrogen). Secondary antibodies raised against the appropriate species were acquired from Jackson ImmunoResearch or Invitrogen.

General Microscopy and Image Analysis. Retinal section images were acquired on a Zeiss LSM780 confocal microscope, on a 40× oil immersion objective. Images were analyzed and processed on Imaris, ImageJ and/or Photoshop software. Cell culture images were acquired on a Leica DMI3000B microscope, using a 5×, 10× or 20× objective. Whenever possible, image settings were adjusted for saturation. Whenever samples were to be compared within an experiment, image settings and processing were kept constant. Imaris, Image J and/or Photoshop software were used for image processing and analysis. Images from in vivo electroporation were smoothened on Imaris using the median filter as 3×3×1 pixel dimension or on Photoshop using the blue function at 1 pixel. Image level was adjusted in Photoshop. Electroporated and immunostained retinas were quantified as 20 µm thick retinal cryosections imaged via confocal microscopy. Regions of dense electroporation were selected for quantification. Quantification approaches were described previously (Tang et al., 2013).

CRISPR experiment. The human LoxLacZ cell line was obtained from Allele Biotech (SKU: ABP-RP-CLA-CLOXE), and cultured as instructed in the product manual. Cas9 activity was assessed by detecting βgal-expressing cells in wells transfected with pX330-dCC-Cas9 and either pCAG-C-CA or pCAG-GAPDH-AU1 control construct (simply called AU1 in the main text). In addition, pCAG-mCherry is included as a transfection marker. For X-gal staining, cells were fixed on ice with 0.5% Glutaraldehyde for 5 min. X-gal staining was performed as previously described. Cells were left at room temperature overnight for color development. Images were acquired by Keyence BZ9000 microscope. The number of mCherry+ and X-gal+ cells was quantified by Fiji software. The normalized Cas9 activity is calculated by dividing individual replicate values of specific conditions by the average number of X-gal+ cells induced by pX330-loxPgRNA alone.

Densitometry analysis. The western blot bands were quantified using densitometry. The anti-TagBFP immunopositive bands (~39.5 kDa, migrating close to 38 kDa marker band), anti-βgal immunopositive bands (~120 kDa, migrating between 98 and 198 kDa marker bands) as well as control bands at empty lanes were quantified to arrive at the adjusted relative density for anti-TagBFP bands.

dGBP1 mutation mapping analysis. To map the effects of individual dGBP1 mutations on protein stability, the fluorescent intensity and solubility of mCherry tagged with various GBP1 variants were scored. A semi-quantitative approach was used to score mCherry intensity, based on a six point scale ranging from 0 to 3, with 0.5 points given. For solubility scores, a 4 point score ranging from "soluble" (mCherry diffusely distributed in cytoplasm), "soluble, some aggregate" (mostly diffuse mCherry expression but some instances of mCherry aggregation), "soluble/aggregate" (mixture of diffuse mCherry and aggregating mCherry), and "aggregate" (strongly aggregating mCherry) was used. As a reference point for both intensity and solubility scores, the intensity of variants to that of either GBP1-mCherry and/or dGBP1-mCherry controls was compared. Scores were assessed across replicates and in independent experiments.

dCTD-CRISPR/Cas9 Methods:

1. Plasmid Construction

The Px330 vector was modified to contain XhoI and BsrGI sites 5' to the Cas9 sequence. The dCTDx2 fragments were synthesized as double strand DNA (G-blocks, IDT), amplified by PCR and digested by XhoI and BsrGI. The dCTD-Cas9 constructs were generated by subcloning dGBPx2 and dCTDx2 fragments into the modified Px330 vector. The sequences of dGBPx2, dCTDx2 and primers are listed below.

| dCTDx2 | >dCTDx2 |
|---|---|
| | ggaagtggcagtggtATGGCGCAGGTGCAGCTGGTGGAAAGCGGCGGCG |
| | GCCTGGTGCAGGCGGGCGGCAGCCTGCGCCTGAGCTGCGTGGCG |
| | AGCGGCAGCTTTTTTATGAGCAACGTGATGGCGTGGTATCGCCAG |
| | GCGCCGGGCAAAGCGCGCGAACTGATTGCGGCGATTCGCGGCGG |
| | CGATATGAGCACCGTGTATGTGGATAGCGTGAAAGGCCGCTTTAC |
| | CATTCGCCGCGATGATGATAAAAACATTCTGTATCTGCAGATGAA |
| | CGATCTGAAACCGGAAGATACCGCGATGTATTATTATAAAGCGAG |
| | CGGCAGCAGCTGGGGCCATGGCACCCAGGTGACCGTGAGCTTTGC |
| | ATGCATGGCTCAAGTCCAACTCGTCGAGTCTGGTGGCGGACGGGT |
| | GCAGGCTGGCGGATCTCTGAGACTGAGCTGTGTCGCCAGCGGCAG |
| | CTTCTTCATGTCCAACGTCATGGCCTGGTACAGACAGGCCCCTGG |
| | CAAGGCCAGAGAGCTGATCGCTGCTATCAGAGGCGGCGACATGA |
| | GCACCGTGTACGTCGACAGCCAGAAGGGCAGATTCACCATCCGGA |
| | GGGACGACGACAACGAACATCCTGTACCTGCAAATGAACGACCTG |
| | AAGCCCGAGGACACCGCCATGTACTACTACAAGGCCTCCGGCAGC |
| | TCTTGGGGCACGGAACACAAGTCACGGTCTCCTTC |

| Primer Name | Sequences (5'-3') | Note |
| --- | --- | --- |
| 5F-strand | aatcactttttttcaggttGGACTCGAGaatTGTACAATGGACTATAAGGACCACGACG | To obtain the modified Px330 vector, 5F-Strand and annealed, treated with Polynucleotide Kinase (PNK), and ligated into AgeI digested Px330 vector via Gibson assembly. |
| 5R-strand | CGTCGTGGTCCTTATAGTCCATTGTACAattCTCGAGtCCaacctgaaaaaaagtgatt | |
| CTD-amplify F | ggaagtggcagtggtATGgcgc | To amplify the 2XdCTD fragment. |
| CTD-amplify-R | tccagaaccactgccGAAGGAG | |
| 2XCTD-5-F | aattCTCGAGgccaccATGgctgcaggtgcagctgg | To amplify the 2XdCTD fragment for subcloning. |
| 2XCTD-5-R2 | attTGTACAgcatgcGAAGGAGACCGTGACTTGTGTT | |

2. Reporter Cell Line

The Human LoxLacZ cell line was obtained from Allele Biotech (SKU: ABP-RP-CLACLOXE), and cultured as instructed in the product manual.

3. X-gal Staining

Cells were fixed on ice with 0.5% Glutaraldehyde for 5 min. X-gal staining was performed as previously described. Cells were left at room temperature overnight for color development.

4. Imaging, Data Quantification and Statistics

Images were acquired by Keyence BZ9000 microscope. The number of mCherry+, and X-gal+ cells was quantified by Fiji software. A two-tailed Student's t test was used to compare differences between control and experimental values.

Statistical Analysis. Two-tailed Student's t test assuming unequal variance was used for all comparisons. $p<0.05$ is judged as statistically significant.

REFERENCES

Banaszynski, L. A., Chen, L. C., Maynard-Smith, L. A., Ooi, A. G., and Wandless, T. J. (2006). A rapid, reversible, and tunable method to regulate protein function in living cells using synthetic small molecules. Cell 126, 995-1004.

Bonger, K. M., Rakhit, R., Payumo, A. Y., Chen, J. K., and Wandless, T. J. (2014). General method for regulating protein stability with light. ACS Chem Biol 9, 111-115.

Brand, A. H., and Perrimon, N. (1993). Targeted gene expression as a means of altering cell fates and generating dominant phenotypes. Development 118, 401-415.

Butala, M., Zgur-Bertok, D., and Busby, S. J. (2009). The bacterial LexA transcriptional repressor. Cell Mol Life Sci 66, 82-93.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Dymecki, S. M. (1996). Flp recombinase promotes site-specific DNA recombination in embryonic stem cells and transgenic mice. Proc Natl Acad Sci USA 93, 6191-6196.

E. R., Ellis-Davies, G. C., McGee, A. W., Sabatini, B. L., et al. (2013). Recombinant probes for visualizing endogenous synaptic proteins in living neurons. Neuron 78, 971-985.

Emerson, M. M., and Cepko, C. L. (2011). Identification of a retina-specific Otx2 enhancer element active in immature developing photoreceptors. Dev Biol 360, 241-255.

Gill, G., and Ptashne, M. (1988). Negative effect of the transcriptional activator GAL4. Nature 334, 721-724.

Gross, G. G., Junge, J. A., Mora, R. J., Kwon, H. B., Olson, C. A., Takahashi, T. T., Liman, Gurskaya, N. G., Fradkov, A. F., Terskikh, A., Matz, M. V., Labas, Y. A., Martynov, V. I., Yanushevich, Y. G., Lukyanov, K. A., and Lukyanov, S. A. (2001). GFP-like chromoproteins as a source of far-red fluorescent proteins. FEBS Lett 507, 16-20.

Hsu, P. D., Lander, E. S., and Zhang, F. (2014). Development and applications of CRISPR-Cas9 for genome engineering. Cell 157, 1262-1278.

Iwamoto, M., Bjorklund, T., Lundberg, C., Kirik, D., and Wandless, T. J. (2010). A general chemical method to regulate protein stability in the mammalian central nervous system. Chem Biol 17, 981-988.

Kirchhofer, A., Helma, J., Schmidthals, K., Frauer, C., Cui, S., Karcher, A., Pellis, M., Kirchhofer, A., Helma, J., Schmidthals, K., Frauer, C., Cui, S., Karcher, A., Pellis, M., Muyldermans, S., Casas-Delucchi, C. S., Cardoso, M. C., et al. (2010). Modulation of protein properties in living cells using nanobodies. Nat Struct Mol Biol 17, 133-138.

Luo, L., Callaway, E. M., and Svoboda, K. (2008). Genetic dissection of neural circuits. Neuron 57, 634-660.

Matsuda, T., and Cepko, C. L. (2004). Electroporation and RNA interference in the rodent retina in vivo and in vitro. Proc Natl Acad Sci USA 101, 16-22.

Matsuda, T., and Cepko, C. L. (2004). Electroporation and RNA interference in the rodent retina in vivo and in vitro. Proc Natl Acad Sci USA 101, 16-22.

Muyldermans, S. (2013). Nanobodies: natural single-domain antibodies. Annu Rev Biochem 82, 775-797.

Muyldermans, S., Casas-Delucchi, C. S., Cardoso, M. C., et al. (2010). Modulation of protein properties in living cells using nanobodies. Nat Struct Mol Biol 17, 133-138.

Orban, P. C., Chui, D., and Marth, J. D. (1992). Tissue- and site-specific DNA recombination in transgenic mice. Proc Natl Acad Sci USA 89, 6861-6865.

Oyen, D., Wechselberger, R., Srinivasan, V., Steyaert, J., and Barlow, J. N. (2013). Mechanistic analysis of allosteric and non-allosteric effects arising from nanobody binding to two epitopes of the dihydrofolate reductase of *Escherichia coli*. Biochim Biophys Acta 1834, 2147-2157.

Oyen, D., Wechselberger, R., Srinivasan, V., Steyaert, J., and Barlow, J. N. (2013). Mechanistic analysis of allosteric and non-allosteric effects arising from nanobody binding to two epitopes of the dihydrofolate reductase of *Escherichia coli*. Biochim Biophys Acta 1834, 2147-2157.

Raymond, C. S., and Soriano, P. (2007). High-efficiency FLP and PhiC31 site-specific recombination in mammalian cells. PLoS One 2, e162.

Rothbauer, U., Zolghadr, K., Muyldermans, S., Schepers, A., Cardoso, M. C., and Leonhardt, H. (2008). A versatile nanotrap for biochemical and functional studies with fluorescent fusion proteins. Mol Cell Proteomics 7, 282-289.

Rothbauer, U., Zolghadr, K., Tillib, S., Nowak, D., Schermelleh, L., Gahl, A., Backmann, N., Conrath, K., Muyldermans, S., Cardoso, M. C., et al. (2006). Targeting and tracing antigens in live cells with fluorescent nanobodies. Nat Methods 3, 887-889.

Samson, M., Emerson, M. M., and Cepko, C. L. (2009). Robust marking of photoreceptor cells and pinealocytes with several reporters under control of the Crx gene. Dev Dyn 238, 3218-3225.

Samson, M., Emerson, M. M., and Cepko, C. L. (2009). Robust marking of photoreceptor cells and pinealocytes with several reporters under control of the Crx gene. Dev Dyn 238, 3218-3225.

Sander, J. D., and Joung, J. K. (2014). CRISPR-Cas systems for editing, regulating and targeting genomes. Nat Biotechnol 32, 347-355.

Schonig, K., Bujard, H., and Gossen, M. (2010). The power of reversibility regulating gene activities via tetracycline-controlled transcription. Methods Enzymol 477, 429-453.

Subach, O. M., Gundorov, I. S., Yoshimura, M., Subach, F. V., Zhang, J., Gruenwald, D., Souslova, E. A., Chudakov, D. M., and Verkhusha, V. V. (2008). Conversion of red fluorescent protein into a bright blue probe. Chem Biol 15, 1116-1124.

Tang, J. C., Szikra, T., Kozorovitskiy, Y., Teixiera, M., Sabatini, B. L., Roska, B., and Cepko, C. L. (2013). A nanobody-based system using fluorescent proteins as scaffolds for cell-specific gene manipulation. Cell 154, 928-939.

Tang, J. C., Szikra, T., Kozorovitskiy, Y., Teixiera, M., Sabatini, B. L., Roska, B., and Cepko, C. L. (2013). A nanobody-based system using fluorescent proteins as scaffolds for cell-specific gene manipulation. Cell 154, 928-939.

Wang, S., Sengel, C., Emerson, M. M., and Cepko, C. L. (2014). A gene regulatory network controls the binary fate decision of rod and bipolar cells in the vertebrate retina. Dev Cell 30, 513-527.

Wurch, T., Pierre, A., and Depil, S. (2012). Novel protein scaffolds as emerging therapeutic proteins: from discovery to clinical proof-of-concept. Trends Biotechnol.

Yee, J. K., Miyanohara, A., LaPorte, P., Bouic, K., Burns, J. C., and Friedmann, T. (1994). A general method for the generation of high-titer, pantropic retroviral vectors: highly efficient infection of primary hepatocytes. Proc Natl Acad Sci USA 91, 9564-9568.

Example 6

Detection and Manipulation of Live Antigen-Expressing Cells Using Conditionally Stable Manobodies Many applications in biology and medicine require the ability to target a subset of cells in a population based upon specific cellular characteristics. Although this can be achieved by exploiting transcriptional elements that are selectively active in a subset of cells, cell-specific promoters or knock-in alleles are often not available, and it is difficult to generate them. Alternatively, other features that distinguish cells, such as expression of a specific RNA or protein, may be exploited. Recently, it has become possible to utilize specific intracellular proteins to drive desired molecular events, using RNA-based binders in cells (Auslander et al., 2014; Culler et al., 2010; Kennedy et al., 2014; Saito et al., 2011), and protein-based binders in cells and animals (Tang et al., 2015; Tang et al., 2013). While current methods are promising, protein-responsive systems are continually evolving. A major need for widespread adoption is generalizable strategies that enable rapid conversion of diverse classes of binders into protein-responsive tools.

Antibodies are widely adopted probes for protein detection. Their popularity derives from their superior specificity and high affinity, achieved in large part by the stringent selection in an immunized animal. Nanobodies (Nbs), the antigen recognition portions of single chain antibodies found in camelids (Hamers-Casterman et al., 1993) and cartilaginous fishes (Greenberg et al., 1995), bind their cognate antigens with high affinity and specificity, and have the added advantage over heterotetrameric antibodies in that they are very stable in the intracellular environment. Fusions between Nbs and proteins with desirable activities have enabled a number of applications in living cells (Caussinus et al., 2012; Irannejad et al., 2013; Kirchhofer et al., 2010; Rothbauer et al., 2006; Tang et al., 2015; Tang et al., 2013). Despite these successes, it has been difficult to take advantage of Nbs for live cell applications requiring cell-specificity, as genetically expressed Nb-fusion proteins are stable and active even in cells that do not express the cognate antigens. This is a general problem that applies to any class of protein-based binder.

To address this issue, it was reasoned that the Nb portion of a single Nb-fusion protein could be modified to be unstable in living cells, but could become stable when bound to antigen (FIG. 1A). A similar approach has been used to create small molecule-dependent domains, for temporal control or tuning of protein activity (Banaszynski et al., 2006). Here, the isolation of destabilized Nbs (dNbs) is reported using a strategy that is generalizable to other types of protein-based binders. A dNb was isolated whose destabilizing mutations fell within the structurally conserved framework region of Nbs. These destabilizing mutations could simply be transferred to other Nbs to rapidly generate antigen-dependent stability. dNbs were able to destabilize multiple fusion partners having a variety of activities, including fluorescent proteins, site-specific recombinases and genome editing enzymes. These reagents were used to optogenetically control neural activities in specific cell types, as well as detect and isolate Human immunodeficiency virus (HIV) infected cells based upon expression of the HIV-1 capsid protein. Thus, this work offers a generalizable strategy to label and manipulate specific cell populations in cellular and animal systems, with specificity endowed by protein expression and/or specific cellular features.

Results

Isolation and Characterization of a Destabilized Nb

Figure 1F:
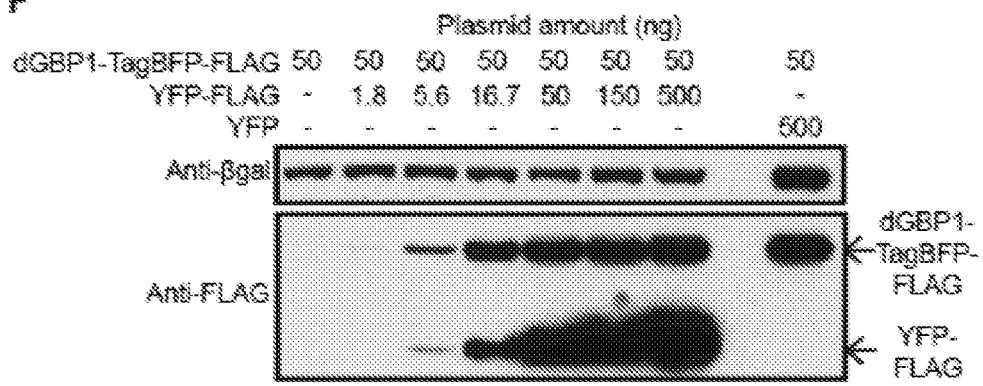
Figure 1G:
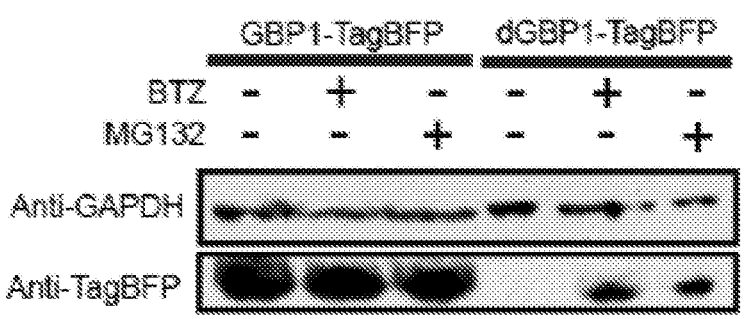
Figure 1H:
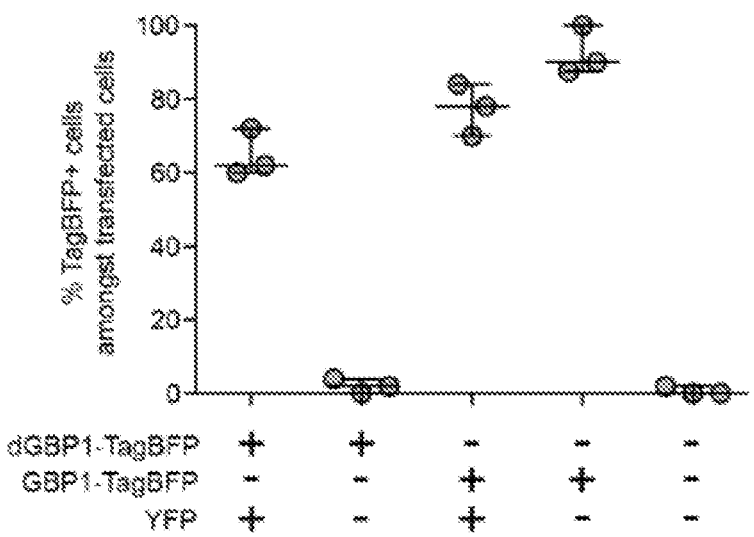

To test whether it is possible to modify a Nb such that its intracellular protein level is strongly dependent upon antigen co-expression, the GFP-binding Nb, GBP1, was used for proof-of-concept experiments (Kirchhofer et al., 2010; Rothbauer et al., 2006) (FIG. 1B, 1C). A murine leukemia virus (MLV) library encoding mutagenized variants of GBP1 fused to the blue fluorescent protein, TagBFP (Subach et al., 2008) was generated. HcRed (Gurskaya et al., 2001) was co-expressed via an IRES to report infection. TagBFP and t-HcRed bear little amino acid similarity to Aequorea-derived GFP and its derivatives. 293T cells were infected with this library, and combined FACS with super-infection by a GFP-encoding AAV to isolate GBP1-TagBFP variants whose blue fluorescence depended upon GFP expression (FIG. 1B). GBP1 variants were then individually screened for enhanced TagBFP expression in the presence of yellow fluorescent protein (YFP), a GFP derivative known to also interact with GBP1 (Rothbauer et al., 2008; Tang et al., 2013). Strikingly, many variants showed fusion TagBFP aggregates within the cell when YFP is absent, but became soluble in the cytoplasm when YFP is present (data not shown). Notably, a GBP1 variant carrying 6 amino acid changes (A25V, E63V, S73R, S98Y, Q109H, S117F) gave little to no TagBFP fluorescence and no signs of aggregation in the absence of YFP. The study was then focused on this variant, which will hereafter be referred to as destabilized GBP1 (dGBP1). dGBP1-TagBFP showed strong fluorescence and protein level when co-expressed with GFP or YFP, but became weakly detectable or undetectable when antigen was absent (FIGS. 1D, 1E and 1H). In contrast, unmodified GBP1-TagBFP showed strong fluorescence and protein level regardless of antigen co-expression (FIGS. 1D, 1E). In an electroporation experiment using the mouse retina, dGBP1-TagBFP fluorescence and protein level were detected only upon GFP co-expression in vivo (FIGS. 2A-2H). Taken together, these data show that one can create a highly destabilized Nb whose protein level is dependent upon co-expression with its cognate antigen in vitro and in vivo.

Nb-based, antigen-dependent systems were previously created that use the antigen as a scaffold for the assembly of split protein domains or fragments (Tang et al., 2015; Tang et al., 2013). Complex assembly can be inhibited when excessive antigen levels saturate antigen-binding sites in Nb-fusion proteins (Tang et al., 2015; Tang et al., 2013). In contrast, a single polypeptide, dNb-fusion protein should not suffer the same limitation. Indeed, YFP promoted dGBP1-TagBFP stability in a dose-dependent manner, with no adverse effects even when YFP plasmid was transfected at 10-fold excess of dGBP1-TagBFP plasmid (FIG. 1F). To investigate the mechanism of dNb destabilization, dGBP1-TagBFP-transfected 293T cells were treated with the ubiquitin proteasome inhibitors, MG132 or Bortezomib (BTZ) (Kisselev et al., 2012). dGBP1-TagBFP protein was evident following addition of either inhibitor and was absent without inhibitors, indicating that it was degraded by the ubiquitin proteasome system (UPS) (FIG. 1G).

Generation of Additional dNbs by Mutation Transfer

Discosoma-derived mCherry fused to dGBP1 (dGBP1-mCherry) also showed antigen-dependent stabilization. Unlike dGBP1-TagBFP (FIG. 1E), some aggregation of dGBP1-mCherry occurred inside cells when antigen was absent (FIGS. 11A-11B). dGBP1-mCherry was used as a sensitized reporter to map the key residues involved in GBP1 stability, by comparing the level of fluorescence and aggregation of the fusion proteins in cells. (FIGS. 11A-11B & 12A-12B). C/S98Y and S117F showed strong destabilizing effects, as seen in both sufficiency and necessity experiments. S73R and Q109H also had destabilizing effects in single mutant analyses. GFP rescued the destabilization phenotype of all mutants. Thus, specific single dGBP1 mutations had clear destabilizing effects, which could be enhanced by combination with other destabilizing mutations.

Figure 3H:
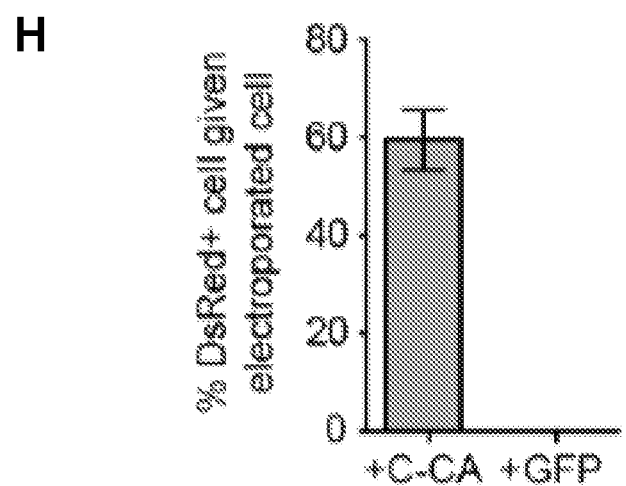

The dGBP1 mutations mapped onto the structurally conserved framework regions of Nbs (Muyldermans, 2013), and 99-100% of Nbs (n=76) shared the same residue as GBP1 at each of the 3 most destabilizing positions (3major: S73R, C/S98Y, S117F) (FIG. 5A; FIG. 19A). Further, a survey across 76 unique Nb-antigen interfaces, gathered from a total of 102 crystal structures, indicated that Nb positions corresponding to those of dGBP1 A25V, S73R, S98Y and S117F were universally located outside of all Nb-antigen interfaces (FIG. 19B). Nb positions corresponding to dGBP1 Q109H fell outside of 99%, or 75 of 76 unique Nb-antigen interfaces. Positions equivalent to dGBP1 E63V were found in 22%, or 17 of 76 unique Nb-antigen interfaces, and in close proximity to the interface in 9%, or 7 of 76 of the cases. Given these results, it was hypothesized that the destabilizing framework mutations could be transferred across Nbs to rapidly create antigen-dependent stability. Next, all dGBP1 mutations (6mut) and the 3maj mutations were transferred to Nbs targeting the HIV-1 capsid protein (aCA) and *Escherichia coli* dihydrofolate reductase (aDHFR), respectively. dNbs created by mutation transfer behaved similarly as dGBP1 in that TagBFP fusion fluorescence and protein level both depended upon expression of the cognate antigen (FIGS. 5B-5E). Destabilization also depended on degradation by the UPS (FIG. 5F). To further establish generality, the 3major mutations were transferred to 9 Nbs that recognize epitopes of intracellular origin (FIG. 5G). All dNb-TagBFPs showed strongly reduced fluorescence relative to their unmodified Nb counterparts and occasionally formed faint fluorescent puncta in cells overexpressing the fusion proteins (FIGS. 5B, 5D and 5G). Importantly, whereas no unmodified Nb showed >2 fold increase in TagBFP fluorescence in response to antigen co-expression, 8 of 9, or 89% of dNbs, passed this threshold (FIG. 5G). Notably, mutations that destabilized a *Camelus dromedarius* Nb (GBP1) had very similar effects on Nbs derived from *Vicugna pacos* and *Llama glama*, indicating that destabilizing mutations can be transferred across Nbs from different camelid species to create antigen-dependence (FIGS. 5A, 5G and 24).

Generation, Optimization and Uses of Antigen-Specific Effectors

To explore if additional fusion proteins could be rendered antigen-dependent, dNbs were engineered onto two popular site-specific recombinases, Cre and codon-optimized Flp (Flpo)(Luo et al., 2008), (Raymond and Soriano, 2007). Both enzymes were rendered GFP-dependent after fusion to dGBP1, but not GBP1 (FIG. 3C-3F). By increasing the number of dGBP1 domains fused to either enzyme, residual GFP-independent recombination of the initial fusions was decreased without affecting GFP-dependent recombination (FIGS. 3C, 3F & 10A-10B). Notably, Flpo fused to tandemly repeated dGBP1 (dGBP1x2-Flpo, or Flp dependent on GFP (Flp-DOG)) had insignificant background signal and 636-fold induction by GFP (FIG. 10B). The inventors rapidly constructed an Flpo dependent upon the C-terminal portion of HIV-1 CA (C-CA) using mutation transfer. This construct was functional in vitro and in vivo (FIG. 10C andl OD). Further, both GFP- and C-CA-dependent Flpo responded to antigen in a dose-dependent manner (FIGS. 10C-10D). Thus, dNbs can confer antigen-dependent control over different types of effector proteins, and can adequately reduce the activity of a highly sensitive enzyme when antigen is absent.

The ability to control Flpo activity with tandem dNb-fusions raised the possibility of imposing dual regulation on effector protein activity using two dNbs, each targeting a different antigen (FIGS. 3H, 6C and FIG. 6A). This was tested by generating Flpo fused to dGBP1 and aCA dNb6mut (dGC-Flpo) or dGBP1 and aDHFR dNb3major (dGD-Flpo). Strong Flpo recombination was triggered only when both antigens were present (FIGS. 3H, 6C). This shows the feasibility of using dNb-fusion proteins to create synthetic circuits whereby dual inputs are integrated entirely at the protein level.

It was next tested whether it was possible to perform genome targeting and editing under the control of specific antigen(s) (FIG. 7A). A fusion was created between two aCA dNb6mut and Cas9 (dCC-Cas9) and delivered the construct to an engineered human cell line that expresses β-galactosidase upon removal of a loxP-stop-loxP cassette. A guide RNA was also delivered that can specifically target the loxP sites, leading to Cas9-mediated deletion of the stop cassette (dCC-Cas9-loxPgRNA) (FIGS. 7B-7C). Co-expression of C-CA with dCC-Cas9 and loxPgRNA triggered genome-editing events, while little to no ß-galactosidase expression was detected when C-CA was absent (FIG. 7D). The efficiency of C-CA-dependent genome editing approached that of control Cas9 (FIG. 7D). This result demonstrated the feasibility of using intracellular epitopes to initiate genome editing or targeting.

Retrofitting Transgenic GFP Mouse Lines for Cell-Specific Manipulation of Gene Expression and Neural Activity To evaluate the usefulness of dNbs, dNb-fusion proteins were applied in situations where the antigen level could not be controlled. GFP and its derivatives (Tsien, 1998) are widely used to label cell types, with specificity dependent upon cellular features such as gene transcription (Chalfie et al., 1994) or neuronal connectivity (Beier et al., 2011; DeFalco et al., 2001; Ekstrand et al., 2014; Lo and Anderson, 2011; Wickersham et al., 2007). Genetic manipulation of GFP-labeled cells can reveal their functions, but current approaches require delivery of 2 or more aGFP Nb-fusion proteins (Tang et al., 2015; Tang et al., 2013). Electroporation and AAV were used to deliver the one-component Flp-DOG along with Flp-dependent constructs to the retinas of Tg(CRX-GFP) (Samson et al., 2009) and cerebella of Tg(GAD67-GFP) (Tamamaki et al., 2003) lines, respectively. In both instances, robust Flpo recombination was detected in GFP+ tissues, but not in GFP-negative tissues labeled with electroporation, infection or injection markers (FIGS. 20A-20C; FIGS. 4A-4C; FIGS. 21A-21E). AAV-delivered Flp-DOG was used to induce ChR2-mCherry expression in GABAergic Purkinje cells (PCs) of Tg(GAD67-GFP) cerebella (FIG. 20C).

Figures 20A, 20B, 20C, 20D:
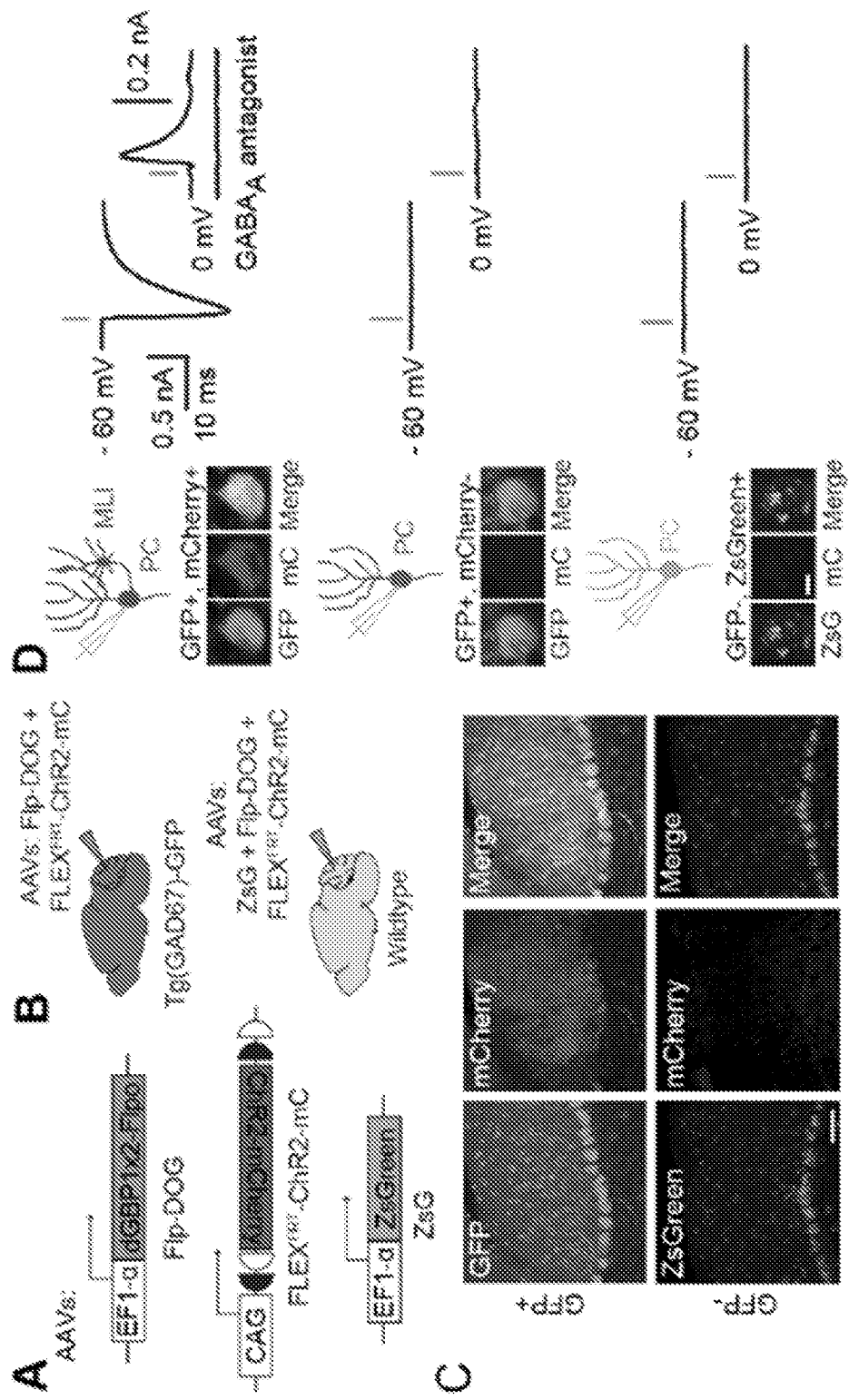
FIGS. 20A-20D Applying Flp-DOG for optogenetic manipulation of transgenic GFP-labeled cell types in the mouse cerebellum.
Figures 21A, 21B, 21C, 21D, 21E, 21F:
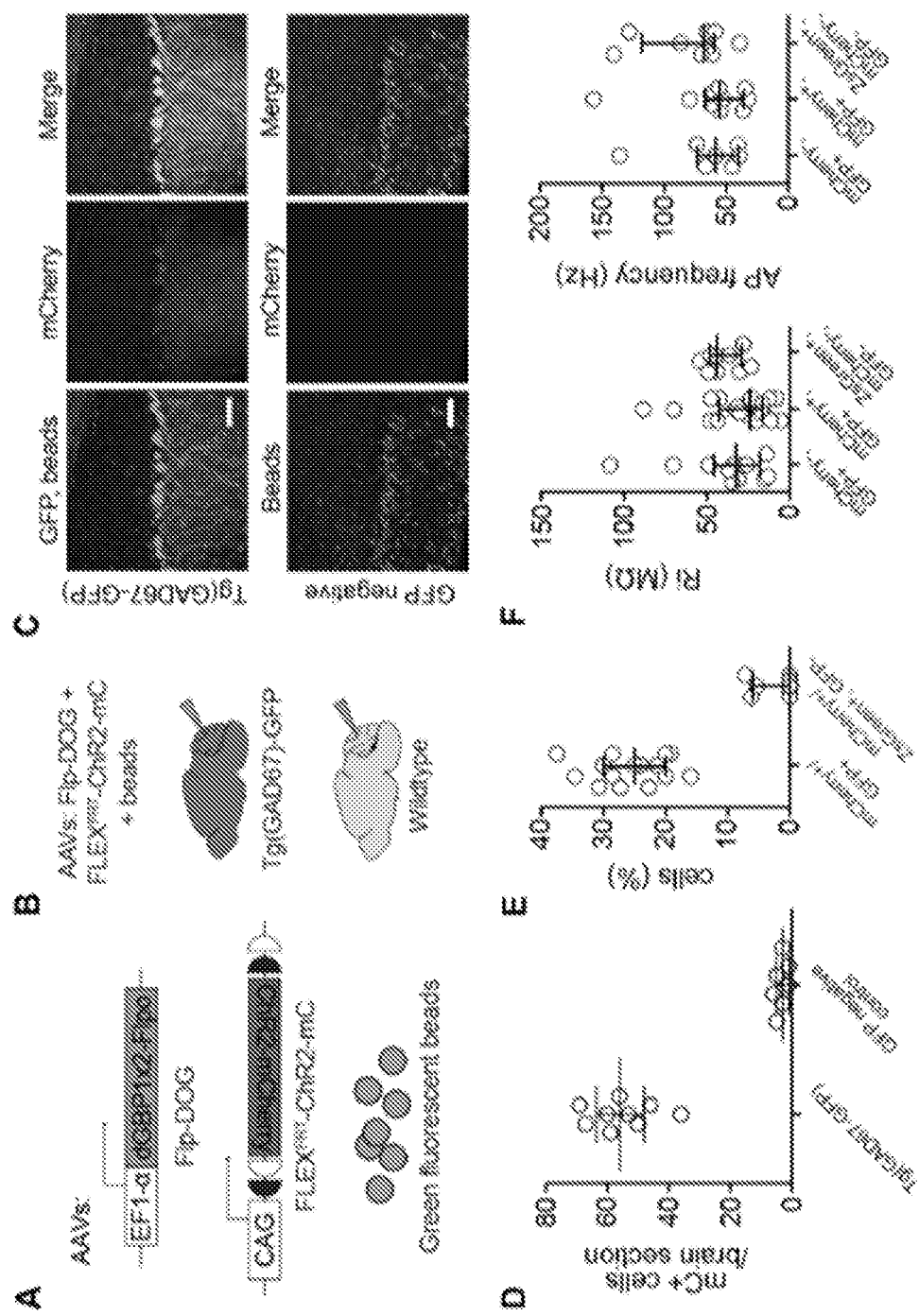
FIGS. 21A-21F Characterization of mouse cerebella infected with AAV-Flp-DOG.

Under conditions in which infection did not alter spontaneous firing frequency or input resistance, excitatory photocurrents and synaptic inhibitory currents were evoked in ChR2-mCherry+ PCs, with inhibitory inputs from neighboring ChR2-mCherry+ neurons that contacted the recorded PCs (FIG. 20; FIG. 21F). GFP+ neurons that did not express ChR2-mCherry, as well as control ZsGreen+ neurons in GFP-negative animals, never showed light-evoked photocurrents, indicating antigen-specificity of the system (FIG. 20D). Thus, Flp-DOG provides a much simpler approach to manipulate GFP-defined cell types over pre-existing methods. Overall, these results demonstrate that dNb-fusion proteins enable functional manipulation of antigen-expressing cells in vivo.

Detection of HIV-1 Reactivated Human Cells by Flow Cytometry

Figures 22A, 22B:
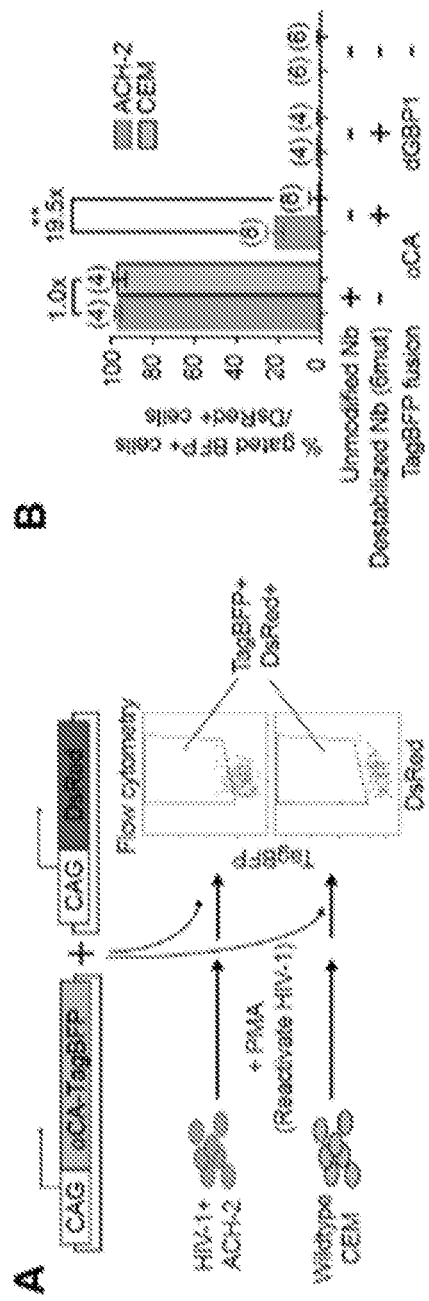
FIGS. 22A-22B show detection of HIV-1 reactivate cells with a CA-specific sensor.

Next, it was tested whether dNbs could be used to detect and isolate live, antigen-expressing cells. ACH-2 (Folks et al., 1989), a human T-cell line chronically infected with HIV-1, is widely used to study HIV-1 persistence (Clouse et al., 1989). Destabilized aCA fused to either TagBFP or TagRFP (Matz et al., 1999) were expressed in ACH-2 or the uninfected parental cell line (CEM), under conditions in which HIV-1 was reactivated with PMA (Poli et al., 1990) (FIG. 22A and FIGS. 23A-23D). Fluorescence was detected by flow cytometry of the destabilized fusions selectively in ACH-2, but not CEM cells (FIG. 22B and FIG. 23B). ACH-2-specific fluorescence was dependent upon CA recognition, as the effect was not observed with dGBP1-TagBFP. Importantly, unmodified aCA Nb-TagBFP fluoresced strongly in both cell lines and could not be used to distinguish between the two (FIG. 23B). As positive controls, it was confirmed that aCA dNb6mut 250-TagBFP could be stabilized by C-CA co-expression in CEM cells (data not shown) and that the HIV-1 CA antigen was specifically detected by immunofluorescence in ACH-2, but not CEM cells (FIG. 23D). Thus, dNbs make possible detection of intracellular viral epitopes without the need for cell fixation or membrane permeabilization, enabling live monitoring of intracellular viral protein expression and specific isolation of infected live cells with a choice of spectrally distinct fluorescent proteins.

Provided herein is a straightforward and generalizable approach to convert a class of protein-based binders, the Nbs, into conditional reagents that can regulate biological activities within cells that express a specific protein. Importantly, these conditional reagents perform their tasks within living cells, thereby greatly expanding the utility of Nbs and, perhaps, of other classes of intracellular protein binders. This strategy generates cell type-specificity by exploiting the intracellular protein expression pattern in animals or pathogen-infected cells. These conditional reagents were isolated either by using the generalizable screening strategy described here, or by introducing a common set of destabilizing mutations to an ever-expanding repertoire of Nbs (De Meyer et al., 2014; Fridy et al., 2014). Previously, laborious screening was required to isolate pairs of Nb-fusion proteins that could reconstitute an activity when they co-occupied an antigen (Tang et al., 2015; Tang et al., 2013). The ability to create single polypeptide, protein-responsive sensors and effectors marks an important advance, as it greatly simplifies design, promotes generalizability, improves performance and enables easier delivery.

Utility of Antigen-Specific Sensors and Effectors in Cellular and Animal Systems An important aspect of this work is the demonstration that the conditional Nb-based sensors and effectors were effective even when the experimenter did not choose the antigen levels. This was true for experiments conducted in human cell culture and in mice. Importantly, the detection of HIV-1 CA+ cells was achieved using a dNb that was rapidly generated by mutation transfer rather than by isolation from a screen. Although the proportion of CA+ cells detected by the dNb sensor was approximately ⅓ to ½ of that detected by a mouse monoclonal antibody, the efficiency of antigen detection may be improved by optimization of the dNb fusion construct or of the gene delivery protocol. In future work, one may create fusion proteins that specifically manipulate or kill infected cells, e.g. by fusing a conditional Nb to a cellular toxin.

Studies of model organisms often take advantage of transgenic lines that express an exogenous protein in specific cell types (Luo et al., 2008). Driver molecules, such as transcription factors and site-specific recombinases, can respond to the introduction of DNA cassettes to enable the manipulation of gene expression in a cell type-specific manner. Here, GFP was used, which has no naturally known regulatory abilities, as a novel driver molecule. The GFP/dGBP1 binary system is thus analogous to the popular GAL4/UAS, Cre/loxP and Flp/FRT systems. Flp-DOG is immediately useful for studies in model organisms such as the mouse, by making use of existing transgenic GFP reporter lines (>1,000 lines in the mouse)(Chalfie, 2009; Gong et al., 2003; Heintz, 2004; Siegert et al., 2009; Tang et al., 2015; Tang et al., 2013) or virally labeled neural circuits (Beier et al., 2011; DeFalco et al., 2001; Ekstrand et al., 2014; Lo and Anderson, 2011; Schwarz et al., 2015; Wickersham et al., 2007) for cell-specific manipulation studies. In addition, one can combine GFP and the popular Cre recombinase for intersectional Cre+Flp cell targeting studies (Dymecki et al., 2010; Fenno et al., 2014). Beyond fluorescent proteins, endogenous proteins should be usable as driver molecules to trigger sensor or effector activity. This scenario would enable one to selectively target specific cell types in wildtype animals for experimentation, without requiring any knowledge of cell type-specific promoters or creation of knock-in alleles. This approach would especially benefit studies of non-model organisms, with the only demand being a method to introduce genetic constructs, e.g. via viral vectors.

Optimization of Antigen-Dependent Sensors and Effectors

Although dGBP1-TagBFP showed virtually no background signal, fusions of dGBP1 to some fusion partners gave significant background signals. Background signals could be addressed by simply increasing the number of dNbs fused to the protein partner. Additional engineering efforts could further reduce background activity of particular fusion constructs. For example, background activity of dGBP1-Cre could be further controlled by fusion to an ERT2 domain to create small-molecule dependency (Feil et al., 1997). Lastly, one could perform additional screens to isolate novel destabilizing mutant combinations that enhance the antigen-specificity of a wider variety of sensor/effector fusion partners. Such an approach could help eliminate the background fluorescent aggregates seen with some dNb-fluorescent protein fusions.

Possible Applications with dNb-Based Sensors and Effectors

The fusion of protein binders to fluorescent proteins enables visualization of antigen localization in living cells. Optimal signal-to-noise detection requires that the fluorescent fusion proteins be strictly co-localized with the antigen. This may not occur if the number of fluorescent fusion proteins exceeds the number of target antigens. One can address this by designing a transcriptional feedback mechanism to control the level of a fluorescent fusion protein (Gross et al., 2013). This method requires that the antigen be localized outside of the nucleus. The use of dNb fluorescent protein fusions is not limited by this requirement, as the mechanism for background reduction involves protein degradation rather than transcriptional feedback. Indeed, it was found that a dNb-TagBFP construct became strictly localized to the nucleus upon co-expression with its NLS-tagged antigen (data not shown).

The finding that one could fuse an effector protein to two dNbs led to the development of a strategy wherein two different antigens bound to distinct dNbs could stabilize the effector protein, Flpo. Dual antigen dependence may enable one to precisely target specific cell populations in ways similar to established intersectional strategies, but using proteins that do not necessarily have any defined regulatory abilities (Dymecki et al., 2010; Luo et al., 2008).

Demonstrated herein is the ability to integrate dNb with CRISPR/Cas technology to perform genome editing selectively in antigen-expressing cells. A concern with the expression of Cas9 and gRNA in cells is that there is non-specific genome editing, and several methods are being developed to address this problem (Hsu et al., 2014; Sander and Joung, 2014). The strategy developed here, wherein dNb-Cas9 activity is suppressed until antigen can stabilize the fusion protein, offers a novel strategy to reduce off-targeting events.

Generation of Additional Destabilized Binder Systems with Wcreens and/or Mutation Transfer The screening strategy described here opens the door to creating protein-responsive reagents useful for control of fusion protein activity in specific cell populations. A key feature of this screen is the use of AAVs to deliver the antigen to cells. Virtually all MLV-infected cells in culture can be super-infected by AAV, and the cells remain viable for subsequent culture expansion and FACS. In principle, the screening strategy can be extended to generate a diversity of protein-responsive, destabilized binders based on the Nb scaffold or other protein scaffolds (Wurch et al., 2012). (Helma et al., 2015; Wurch et al., 2012)

Over the past 20 years, ~100 crystal structures featuring Nb-antigen complexes have been solved. This resource was leveraged to establish a phylogenetic and structural basis for transferring destabilizing mutations across Nbs. Strikingly, all successfully modified Nbs were derived from camelid species different from that of GBP1, demonstrating the broad transferability of the mutations discovered here. As one would expect, dNb-363 TagBFPs generated by mutation transfer showed a spectrum of fluorescence fold change in response to antigen co-expression. This is likely due to multiple factors, including variable Nb affinity for antigen, variable antigen stability, and variable Nb stability even before destabilization. In addition, Nbs might have variable tolerance to the destabilization mutations tested. Thus, although the high percentage of successful mutation transfers indicate that the strategy is generally applicable, it would be beneficial to derive novel combinations of destabilizing mutations that are even better tolerated across Nbs. Lastly, although dNb generation may be limited by the availability of Nbs isolated from immunized animals, additional Nbs and dNbs may be isolated from in vitro screening technologies that are constantly being improved upon.

Beyond Nbs, multiple classes of artificially derived binding proteins that are amenable to expression in living cells are being developed for antigen-recognition (Helma et al., 2015; Wurch et al., 2012). As epitope-specific binders are typically generated by varying loops or surfaces on a common structural scaffold, it should be possible to generate epitope-responsive properties by incorporating a common set of mutations onto conserved and non-epitope binding regions of the scaffold. Future developments building upon this work should expand our ability to rapidly generate sensors and effectors against a diversity of intracellular epitopes, for cell- or antigen-specific applications in biology and medicine.

Materials and Methods

Animals—The Institutional Animal Care and Use Committee at Harvard University approved all animal experiments. Timed pregnant CD1 (Charles River Breeding Laboratories, Boston, Mass.) were used for electroporation experiments. Tg(CRX GFP)(Samson et al., 2009) and Tg(GAD67-GFP)(Tamamaki et al., 2003) were kept on a C57/BL6J background.

Miscellaneous Plasmids—pCAG-GFP (Addgene plasmid 11150)39, pCAG-YFP (Addgene plasmid 11180)39, pCAG-DsRed (Addgene 11151)39. pRho-GFP-IRES-AP (referred to as Rho-GFP)40. pCAG-nlacZ (Cepko lab, Harvard Medical School), pCAGEN (Addgene plasmid 11160)39. pCALNL-DsRed (Addgene plasmid 13769)39. pCAFNF-DsRed (Addgene plasmid 13771)39. pCALNL-luc28. pRL-TK (Promega, 4E2241).

Antibodies: Antibodies used were rabbit anti-TagRFP (also targets TagBFP; 1:5,000 dilution for immunoblot, 1:1,000 for immunohistochemistry) (AB233, Evrogen), mouse anti-βgal (1:50 for immunoblot) (40-1a supernatant, Developmental Studies Hybridoma Bank), chicken anti-βgal (1:1,000 for immunohistochemistry) (ab9361, Abcam), rabbit anti-GFP (1:500 for immunohistochemistry) (A-6455, Invitrogen), rabbit anti-GAPDH (1:10,000 for immunoblot) (A300-641A, Bethyl Laboratories, Inc.), mouse anti-FLAG M2 (1:1,000 for immunoblot) (F1804, Sigma-Aldrich), mouse anti-KC57-RD1 (5 ul per 1 million cells) (6604667, Beckman Coulter). Secondary antibodies used were goat anti-chicken Alexa Fluor 647 (1:500 of 50% glycerol stock) (102371, Jackson ImmunoResearch Laboratories Inc), goat anti-rabbit DyLight 649 (1:500 of 50% glycerol stock) (111-495-144, Jackson ImmunoResearch Laboratories Inc.), anti-rabbit or anti-mouse IgG-Horseradish Peroxidase (GE Healthcare).

Screen for dGBP1—

Generation of mutagenized GBP1 Library—GBP1 and flanking vector sequences were PCR amplified from the pBMN-GBP1-TagBFP vector (described below). A SphI site was inserted between the GBP1 and TagBFP sequences, creating an AC amino-acid linker. For mutagenesis, GBP1 was amplified by PCR to add 5' and 3' overhangs corresponding to vector sequence flanking GBP1 in the desired pBMN-GBP1-TagBFP construct. The amplified products were then randomly mutagenized using primers targeting the overhang sequences that flank GBP1. The primers were:

```
Forward primer
5'GACCATCCTCTAGACTGCCGGATCCGCCACC-3'

Reverse primer
5'-TGTTCTCCTTAATCAGCTCGCTCATGCATGC-3'.
```

The GeneMorph II Random Mutagenesis Kit was used to introduce balanced mutation rates for different nucleotides, and at high, medium or low mutation frequency (Agilent). Mutagenized GBP1 DNA was inserted into a BamHI/SphI-digested, pBMN-GBP1-TagBFP vector by Gibson Assembly. This created an in-frame fusion with TagBFP bridged by the SphI linker. Transformed DH5α were grown overnight and harvested for DNA purification using Maxiprep kits (QIAGEN). An aliquot of each culture that grew well was plated, and GBP1 inserts were sequenced. Between 9,000-160,000 colonies were produced per library preparation, with 85% of sequenced colonies carrying a unique combination of GBP1 mutations. A library using the medium mutation rate was used to generate an MLV library using VSV-G for an envelope (Yee et al., 1994).

Selection of candidate GBP mutants—293T cells infected with the MLV library encoding GBP1 mutants were sorted by FACS for presence of red fluorescence (from IRES t-HcRed) and for absence of blue fluorescence (from putative destabilized TagBFP). As a control, 293T cells infected with MLV encoding unmodified GBP1 was used to establish gating for TagBFP expression. Sorted cells were plated and allowed to expand in culture. Cells were then infected with AAV-EF1α-GFP 2/8 virus (Tang et al., 2015). 24 h later, cells were sorted for red fluorescence and high blue fluorescence. Sorted cells were then seeded into T25 flasks and allowed to grow to confluence. Next, cellular DNA was extracted using the DNeasy kit (QIAGEN). GBP1 variants were PCR amplified by Phusion polymerase (New England Biolabs), using primer targeting vector sequences flanking GBP1. PCR products were inserted into the pBMN vector with Gibson Assembly. One hundred bacterial colonies were picked and sequenced. Plasmids from clones were individually transfected into 96 well plates of 293T cells with or without CAG-YFP to assay for TagBFP fluorescence. Almost all isolated GBP1-TagBFP variants showed YFP-dependent fluorescence, but many had either TagBFP aggregation or high background fluorescence in the absence of YFP. The only clone that showed a complete lack of TagBFP fusion fluorescence when YFP was absent was named dGBP1 (A25V, E63V, S73R, C/S98Y, Q109H, S117F).

General strategy for cloning Nbs and antigens into pCAG vector: All antigen and Nb protein sequences, except YFP, were acquired from Protein Data Bank (PDB). Protein sequences were backtranslated into DNA sequences, using codons optimized for *Mus musculus*. The list of tested Nbs and their antigens are listed in FIG. 24. In general, an antigen sequence was synthesized as gBlock fragments, which were inserted into an EcoRI/NotI digested pCAG vector via Gibson Assembly, giving pCAG-antigen plasmids used for co-expression of antigen in cells. In general, Nb sequences were synthesized as gBlock fragments, and individually inserted into an EcoRI/SphI digested pCAG TagBFP vector via Gibson Assembly, giving pCAG-Nb-TagBFP plasmids. To destabilize Nbs, mutations were introduced into residue positions that aligned with the dGBP1 mutation positions. Equivalent residues were easy to identify since surrounding amino acid sequences were highly conserved. For 6mut combo, the dGBP1 mutations were A25V, E63V, S73R, C/S98Y, Q109H and S117F. For 3major combo, the dGBP1 mutations were S73R, S98Y and S117F. Note that C/S98Y in GBP1 was originally a cysteine, but was mutated to serine in earlier studies to avoid complications with disulfide bond formation.

Construction of selected DNA constructs:

pBMN-GBP1-TagBFP—A GBP1-TagBFP construct was inserted into a BamHI/NotI 778 digested pBMN DHFR (DD)-YFP (a gift from Thomas Wandless; Addgene plasmid #29325)(Iwamoto et al., 2010), replacing the DHFR(DD)-YFP insert and generating pBMN GBP1-TagBFP. This became the host vector for mutagenized GBP1 inserts.

pBMN-dGBP1-Cre and pBMN-dGBP1-Flpo—pBMN-dGBP1-TagBFP were digested with SphI/SalI, liberating TagBFP as well as the IRES-t-HcRed element. PCR-amplified Cre and Flpo fragments were then inserted into the digested vector via Gibson Assembly.

pBMN-GBP1-Cre and pBMN-GBP1-Flpo—PCR fragments of GBP1 were inserted into BspEI/SphI digested pBMN-dGBP1-Cre and pBMN-dGBP1-Flpo by Gibson Assembly, resulting in pBMN-GBP1-Cre and pBMN-GBP1-Flpo, respectively. dGBP1 sequence was removed by BspEI/SphI digest.

pBMN-dGBP1x2-Cre, pBMN-dGBP1-GBP1-Cre, pBMN-dGBP1x2-Flpo, pBMN-dGBP1-GBP1-Flpo—pBMN-dGBP1-Cre or -Flpo plasmids were digested with SphI. A gBlock fragment encoding a codon modified dGBP1 was inserted into this site via Gibson Assembly, generating pBMN-dGBP1x2-Cre or -Flpo. Using a GBP1 gBlock fragment instead of dGBP1 gave pBMN-dGBP1-795 GBP1-Cre or Flpo.

pCAFNF-luc2—An EcoRI-Kozak-luc2-NotI DNA fragment liberated from pCALN luc2(Tang et al., 2015) was sub-cloned into EcoRI/NotI digested pCAFNF-DsRed vector, giving pCAFNF-luc2.

pCAG-dGBP1-TagBFP—Using PCR, an AgeI-Kozak-dGBP1-TagBFP-NotI was generated from pBMN-dGBP1-TagBFP. This fragment was sub-cloned into AgeI/NotI digested pCAG-GFP, giving pCAG-dGBP1-TagBFP and removing GFP from the construct.

pCAG-dGBP1-TagBFP-FLAG—A gBlock fragment encoding Kozak-TagBFP-FLAG was inserted into SphI/NotI digested pCAG-dGBP1-TagBFP via Gibson Assembly, giving pCAG-dGBP1-TagBFP-FLAG and removing untagged TagBFP from the construct pCAG-YFP-FLAG—A gBlock fragment encoding Kozak-YFP-FLAG was inserted into EcoRI/NotI digested pCAG-αCA-dNb6mut-TagBFP, giving pCAG-YFP-FLAG and removing aCA dNb6mut-TagBFP from the construct.

pCAG-dGBP1-mCherry—PCR amplified mCherry was inserted into a SphI/NotI digested pCAG-dGBP1-TagBFP vector, resulting in replacement of TagBFP with mCherry. The vector became pCAG-dGBP1-mCherry.

pCAG-GBP1-mCherry—A gBlock fragment encoding GBP1 was inserted into EcoRT/SphI digested pCAG-dGBP1-mCherry vector, resulting in replacement of dGBP1 with GBP1. The vector became pCAG-GBP1-mCherry.

pCAG-αCA-Nb-TagBFP, pCAG-αDHFR-Nb-TagBFP, pCAG-αCA-dNb6mut—TagBFP and pCAG-αCA-dNb3major-TagBFP—A gBlock fragment carrying either the aCA Nb or αDHFR Nb coding sequence was inserted into an EcoRI/SphI digested pCAG-TagBFP vector via Gibson Assembly, resulting in pCAG-αCA-Nb-TagBFP or pCAG-αDHFR-Nb-TagBFP. gBlocks carrying these mutations in the respective Nbs were introduced into the EcoRI/SphI digested pCAG-TagBFP vector via Gibson Assembly, giving either pCAG-αCA-dNb6mut-TagBFP or pCAG-αDHFR-dNb3major-TagBFP.

pCAG-dGC-Flpo and pCAG-dGD-Flpo—A gBlock fragment carrying either αCA-dNb6mut or aDHFR-dNb3major coding sequence were inserted into SphI digested pCAG-dGBP1 1 Flpo vector (Tang, C. Y. J, Cepko lab) via Gibson Assembly, giving either pCAG-dGC833 Flpo or pCAG-dGD-Flpo, respectively.

pCAG-dGBP1x2-Flpo—An AgeI-Kozak-dGBP1x2-Flpo-NotI fragment was generated by PCR using pBMN-dGBP1x2-Flpo as a template. This fragment was sub-cloned into AgeI/NotI-digested pCAG vector, giving pCAG-dGBP1x2-Flpo.

pCAG-αCA-dNb6mutx2-Flpo—Two gBlock fragments, together encoding αCA-dNb6mutx2, was inserted into EcoRI/SphI-digested pCAG-dGBP1x2-Flpo, giving pCAG-αCA841dNb6mutx2-Flpo and replacing dGBP1x2 from the construct.

pCAG-αCA-dNb6mut-TagRFP—A gBlock fragment carrying the TagRFP coding sequence was inserted into SphI/NotI digested pCAG-αCA-dNb6mut-TagBFP via Gibson Assembly, giving pCAG-αCA-dNb6mut-TagRFP and removing TagBFP from the construct.

pAAV-EF1α-dGBP1x2-Flpo-NW—An BamHI-Kozak-dGBP1x2-Flpo-EcoRI PCR fragment was inserted into BamHI/EcoRI digested pAAV-EF1α-N-CretrcintG (Tang et al., 2015), giving pAAV-EF1α-dGBP1x2-Flpo. The WPRE element was subsequently removed from this plasmid via EcoRV/AfeI digest and re-ligation, giving pAAV-EF1α-dGBP1x2-Flpo-NW.

pAAV-CAG-FLEXFRT-ChR2(H134R)-mCherry—A Chr2(H134R)-mCherry DNA fragment was digested with NheI and inserted into NheI digested pAAV-CAG-FRTed-SynGFPreverse-WPRE (Pivetta et al., 2014) (a gift from Sylvia Arber)(Pivetta et al., 2014). A clone with ChR2 (H134R)-mCherry inserted in the reverse direction relative to CAG promoter were chosen, giving pAAV-FLEXFRT-ChR2(H134R)-mCherry.

pCAG-C-CA and pCAG-DHFR—A gBlock fragment carrying either the HIV-1 C-CA coding sequence (encoding residue 278-352 of HIV-1 gag polyprotein) or E. coli DHFR coding sequence was inserted into EcoRI/NotI digested pCAG-GFP vector via Gibson Assembly; C-CA or DHFR replaced GFP in the cassette.

Cell culture data—For sample size, the results were reproduced in at least 3 independent experiments (equal to at least 3 biological replicates, or transfected wells). This is a sufficient sample size for demonstrating reproducibility of the findings. For statistical analysis, the number of independent experiments (equal to biological replicates) was increased to 8.

Cell culture and transfection—293T cells were seeded onto 24 or 96 well plates and used for transfection when the cells reached between 60-95% confluency, usually 1-2 days later. Transfections were achieved with polyethyleneimine 873 (PEI) at a 1:4 DNA mass:PEI volume ratio. PEI stock was 1 mg/ml. A total of between 100 and 400 ng of DNA were transfected into single wells of 96 well plates for fluorescence analysis of destabilized mutants. Approximately 70 ng total DNA were transfected into single wells of 96 well plates for luciferase analysis. Approximately 400 to 520 ng of total DNA were transfected into single wells of 24 well plates for fluorescence imaging and western blot analysis.

Cell Culture Fluorescence Imaging Experiments—

General information—All cell culture images were acquired on a Leica DMI3000B microscope, using a 5×, 10× or 20× objective. pCAG-YFP was used in place of pCAG884 GFP to induce dGBP1-TagBFP stability in order to avoid fluorescence bleedthrough from brightly fluorescent GFP signals into the TagBFP channel.

YFP-specificity of dGBP1-TagBFP fluorescence—293T cells seeded in 96 well plates were transfected with 200 ng pBMN-GBP1-TagBFP, pBMN-dGBP1-TagBFP, or pCAGEN along with 27.5 ng of pCAG-YFP or pCAGEN. Cells were imaged for fluorescence 2 days post-transfection.

Antigen-specific DsRed activation with Flpo constructs—All transfection conditions were adjusted to 180 ng total DNA and transfected into 293T cells in 96 well plates. 50 ng of pBMN-based plasmids encoding dGBP1-Cre, dGBP1-Flpo, dGBP1x2-Cre, dGBP1x2-Flpo, dGBP1-GBP1-Cre, or dGBP1-GBP1-Flpo were used. 100 ng of pCALNL-DsRed or pCAFNF-DsRed were used as reporter readouts of Cre or Flpo recombination, respectively. 30 ng of pCAG-GFP or pCAG-YFP were used for antigen co-expression conditions, whereas the same amount of pCAGEN replaces GFP or YFP plasmids in negative control conditions. Cells transfected with Cre- or Flpo-899 fusion constructs were imaged for 22 or 50 h post-transfection, respectively. Flpo-fusion constructs were less active and thus required a longer incubation time to detect signal.

Mapping of dGBP1 Mutations—

Transfection—293T cells seeded in 96 well plates were transfected with 75 ng pCAG905 driven GBP1 variant constructs along with 75 ng of either pCAG-GFP or pCA-GEN. Cells were imaged 17 h post-transfection.

Analysis—To map the effects of individual dGBP1 mutations on protein stability, the fluorescent intensity and solubility of mCherry tagged with various GBP1 variants was scored by eye. A semi-quantitative approach was used to score mCherry intensity, based on a six point scale ranging from 0 to 3, with 0.5 point increments. For solubility scores, a 4 point score was used, ranging from "soluble" (mCherry diffusely distributed in cytoplasm), "soluble, some aggregate" (mostly diffuse mCherry expression but some instances of mCherry aggregation), "soluble/aggregate" (mixture of diffuse mCherry and aggregating mCherry), and "aggregate" (strongly aggregating mCherry). As a reference point for both intensity and solubility scores, the intensity of variants was compared to that of either GBP1-mCherry and/or dGBP1-mCherry controls. Scores were assessed across replicates and in independent experiments.

Mapping of dGBP1 Mutations Across Nanobody-Antigen Interfaces

The inventors exhaustively searched the Protein Data Bank (PDB) and, at the time of analysis, identified 77 unique camelid single-chain antibody fragments (VHH or VH, here collectively referred to as nanobodies (Nbs)) that have been co-crystallized with their respective antigens. One structure (PDB ID 3J6A) was removed from the analysis because it was a low-resolution structure produced by cryo-electron microscopy. The PDBePISA online server tool was used to evaluate whether residue positions equivalent to those of dGBP1 mutations are located outside of antigen-Nb interfaces across different crystallized complexes. PDBePISA produces an analysis of buried surface area (BSA), defined as the solvent-accessible surface area of the corresponding residue that is buried upon interface formation, in Å2. An Nb residue was considered to be in the interface with the antigen if its BSA value is above 0 A2. It was confirmed that this metric is a reliable indicator of an Nb residue's proximity to the antigen by examining all structures by eye using tools such as PyMol. In a few cases the Nb bound to more than one antigen. The inventors took this into consideration by analyzing the interfaces formed between an Nb and each of the two antigens. A protein alignment was used to determine the residue positions corresponding to the mutations located in dGBP1. The same 76 Nbs were used to determine the extent of GBP1 residue conservation across Nbs. Analysis across 76 unique Nb-antigen interfaces, and a total of 102 uniquely crystallized interfaces, indicated that Nb positions corresponding to those of dGBP1 A25V, S73R, S98Y and S117F were universally located outside of all Nb-antigen interfaces (FIG. 19B). Nb positions corresponding to dGBP1 Q109H fell outside of 99%, or 75 of 76 unique Nb-antigen interfaces. Positions equivalent to dGBP1 E63V were directly found in 22%, or 17 of 76 unique Nb-antigen interfaces, and in close proximity to the interface in 9%, or 7 of 76 of the cases.

16 identical or highly similar Nb-antigen complexes had been crystallized under similar or differing conditions, allowing the validation of the mutation mapping results by comparing across identical or related crystal structures. There was agreement in mutation mapping results between redundant or similar crystal structures for 94%, or 16 of 17 unique Nb952 antigen interfaces. The lone exception concerned a unique Nb (PDB ID 4KRM and 4KRL). The Q109H equivalent position in the Nb of structure 4KRL was identified to be at the interface. This discrepancy may be explained by the fact that the two structures were crystallized under very different pH conditions.

Selection of Nbs and Antigens for Mutation Transfer Experiment

For the mutation transfer experiment, 18 Nbs were tested that, when fused to TagBFP, showed strong blue fluorescence and soluble, diffuse localization in 293T cells. Some available nanobodies were too problematic to be included for analysis because they recognized problematic antigens such as the Ricin toxin. Nevertheless, Nbs that bound to proteins originating from both intracellular and extracellular locations were selected. A pCAG expression vector was used to express antigen deposited in PDB for each crystal structure. During analysis, a strong correlation was observed between dNbs that failed to be stabilized by antigen (<2-fold TagBFP fluorescence induction by antigen) and the use of extracellular epitopes. dNbs targeting extracellular epitopes were thus excluded from evaluation of mutation transfer generality.

To determine whether the antigen used for TagBFP stabilization assays derived from intracellular or extracellular proteins, the annotation and literature reports of each antigen's cellular localization were studied.

Nb Destabilizing Mutation Transfer Experiments:

Transfection—293T cells seeded in 96 well plates were transfected with the following plasmid mix: 50 ng of CAG-driven Nb-TagBFP or dNb-TagBFP fusion constructs, 75 ng of CAG-driven DsRed (CAG-DsRed), and either 150 ng of CAG-driven antigen corresponding to the Nb of interest, or an equivalent amount of empty vector (pCAGEN) in negative control conditions. The DNA mix was transfected with PEI at a ratio of 1:4 (DNA μg:PEI μl) ratio. 16-24 h post-transfection, DsRed and TagBFP fluorescence images were acquired on a Leica DMI3000B microscope, using a 20× objective. DsRed served as a marker of transfected cells, and guided the imaging of TagBFP fluorescence regardless of condition.

Image Analysis: Cell culture images were processed on ImageJ. DsRed and TagBFP images were converted to 8-bit. DsRed images were adjusted with the threshold function, converted to binary images, and processed with the "fill holes" and "watershed" functions to create individual regions of interests (ROI) that represent single cells. Processed DsRed binary images were used to guide measurement of mean pixel intensity of TagBFP images in the regions of interests (ROI). Measurements were only made on ROIs that had areas larger than 0.01 inches$^2$. To measure background fluorescence of TagBFP images, 5-15 squares were drawn in areas devoid of cells and collectively measured for a single mean pixel intensity value per image. This background value was subtracted from individual pixel intensity measurements from each ROI. This background subtraction approach occasionally produced negative values. Negative values were set to zero to enable scaling of data. This manipulation did not affect the representation of the data, since we used the median to represent center of spread and all median values were found to be above zero. Data from each experiment were divided by the median value of the corresponding "unmodified Nb, no antigen condition", and multiplied by 100 to get a percentage of wildtype fluorescence level. Fold induction was obtained by dividing the median normalized TagBFP fluorescence reading in the "with antigen" condition by the equivalent value in the "without antigen" condition. TagBFP fluorescence measurements and fold induction values were analyzed from at least 3 micrographs, taken from 3 independent experiments. Heat map showing normalized TagBFP fluorescence values was generated in Excel. For each condition, all three replicate values are shown in a series of 3 horizontal colored bars. The color gradient was chosen to emphasize changes between 0 and 40%, because most dNb-TagBFP constructs gave values in this range. Graphs were plotted as the median TagBFP pixel intensity. Values were plotted inPrism (Graphpad).

Luciferase Assay Experiments—

General information—In all experiments, 20 ng CALNL-luc2 or CAFNF-luc2 and 3 ng pRL-TK were included in transfection mixture delivered to 293T cells seeded in 96 well plates. Plasmids encoding CAG-driven XFP and dNb fusion constructs were transfected at amounts adjusted for their molarity. pCAGEN was added to adjust the total DNA amount to approximately 70 ng. Cells were harvested at the appropriate time for Dual luciferase assay (Promega) according to manufacturer's instructions. Lysates were pipetted into 96-well plates and read in a Spectra Max Paradigm plate reader (Molecular Devices). The linear range of detection for the plate reader was determined with serial dilutions of QuantiLum recombinant luciferase (Promega). Transfection amounts were then adjusted to give readings within the linear range of detection for the instrument. All transfection conditions were independently repeated at least 3 times and were assayed in one to three replicates in terms of transfection wells (biological replicates) and/or plate reader well (technical replicates). Luciferase readings were processed similarly to previous studies (Tang et al., 2015; Tang et al., 2013). Fold induction was determined by dividing the mean normalized luciferase activity of the "with antigen" condition by that of the "without antigen" condition.

Antigen-specificity of Flpo constructs—All transfection conditions were adjusted to include a total of 180 ng DNA. 45-50 ng of pBMN-based plasmids encoding GBP1-Cre, GBP1-Flpo, dGBP1-Cre, dGBP1-Flpo, dGBP1x2-Cre or dGBP1x2-Flpo were tested for Cre or Flpo-dependent recombination of luciferase reporter. 20 ng of pCAG-GFP was used for co-expression conditions, whereas the same amount of pCAGEN replaced GFP plasmids in negative control conditions. Cre or Flpo transfected cells were harvested at 15 or 36 h post-transfection, respectively. Readings were normalized against a specific condition such that the background reporter activity gave a value of 1.

Flpo recombination dependent on two different antigens—A total of 57 ng DNA was transfected. 4 ng of pCAG-dGD-Flpo or pCAG-dGC-Flpo were tested for Flp-dependent recombination, along with 15 ng pCAG-GFP and/or 15 ng pCAG-C-CA or pCAG-DHFR. pCAGEN was used as a filler for antigen-expressing plasmids in all cases. Cells were harvested 16 h post-transfection.

Dose-dependency of Flpo constructs—All transfection conditions were adjusted to 178 ng total DNA. 5 ng of pCAG-dGBP1x2-Flpo or pCAG-αCA-dNb6mutx2-Flpo were used. CAG-DsRed was used as a filler plasmid to substitute for the antigen-expressing plasmid. Antigen-expressing plasmids were tested at a range from 150 ng to 0.6 ng. pCAG-GFP and pCAG-C-CA were used to test for antigen-dependency of dGBP1x2-Flpo and αCA-dNb6mutx2-Flpo, respectively. CAG-DsRed was used as a filler plasmid to substitute for the antigen-expressing plasmid. Transfected cells were harvested for luciferase assay at 24 h post-transfection. Normalized luciferase activity of a transfection condition dropping out antigen-expressing plasmid and Flpo-expressing plasmid was subtracted from readings of all other conditions in the same experiment.

Western Blot Experiments—

General information—293T cells were seeded onto 24 well plates and transfected using PEI. pCAG-nlacZ was used as a transfection loading marker. Transfected 293T cells were lysed in 6×SDS PAGE loading buffer (350 mM Tris-HCl (pH=8), 30% glycerol, 10% SDS, 600 mM DTT, 0.01% Bromophenol Blue), heated to 95° C. for 5 min, and stored at −20° C. until used for western blot analysis. When necessary, transferred blots were cut into two pieces for blotting with different antibodies.

Antigen-dependent stabilization of dNb-TagBFP—To demonstrate the ability of YFP to stabilize dGBP1, 400 ng pBMN-GBP1-TagBFP or pBMN-dGBP1-TagBFP were transfected into 293T cells along with 55 ng of pCAG-YFP or pCAGEN. 60 ng of pCAG nlacZ was included in all conditions as a transfection marker. Cells were harvested for western blot 2 days post-transfection. To test the ability of C-CA to stabilize destabilized αCA-dNb6mut, 100 ng pCAG-αCA-Nb-TagBFP or pCAG-αCA-dNb6mut-TagBFP were transfected into 293T cells along with 125 ng pCAG-C-CA or pCAGEN. 200 ng pCAG nlacZ was also included in the mix. To test the ability of DHFR to stabilize destabilized aDHFR-dNb3major, 100 ng pCAG-αDHFR-Nb-TagBFP or pCAG-αDHFR-dNb3major-TagBFP were transfected into 293T cells along with 375 ng pCAG-DHFR or pCAGEN. 50 ng pCAG-nlacZ were also included in the mix. Cells transfected with C-CA or DHFR test constructs were harvested 16 h post-transfection.

Proteasome inhibition experiment—To test whether dGBP1 degradation was dependent on the UPS, 293T cells were transfected with 400 ng pBMN-GBP1-TagBFP or pBM dGBP1-TagBFP. 60 ng pCAG-nlacZ were added as a transection marker, while 60 ng pCAGEN were added as a filler plasmid. 20-24 h post-transfection. Cells were treated with 10 µM MG132 (C2211, Sigma Aldrich) or 10 nM Bortezomib (sc-217785, Santa Cruz Biotech) for 20 h before harvesting for western 1081 blot. To test whether the degradation of αCA-dNb6mut-TagBFP was dependent on ubiquitin proteasome action, 293T cells were transfected with CAG-driven plasmids encoding 150 ng αCA-Nb-TagBFP or αCA-dNb6mut-TagBFP, along with 300 ng pCAG-nlacZ. 10 h post-transfection, cells were treated with 10 µM MG132 for 6 h. Cells were then harvested for western blot.

Dose experiment—To assay for dose dependency of dGBP1-TagBFP-FLAG on YFP, a total of 750 ng of DNA were transfected into 293T cells. All transfections conditions included 200 ng pCAG-nlacZ, and 50 ng pCAG-dGBP1-TagBFP-FLAG. pCAG-YFP FLAG was used in the range of 1.8 ng to 500 ng. In one condition, 500 ng pCAG-YFP was used in place of pCAG-YFP-FLAG. pCAG-DsRed was used as a filler plasmid to adjust for pCAG-YFP-FLAG removal, up to 500 ng. Transfected cells were harvested 24 h post-transfection for western blot. Mouse-Anti-FLAG was used to detect the presence of both dGBP1-TagBFP-FLAG (41 kDa) and YFP-FLAG (28 kDa). dGBP1-TagBFP FLAG stabilized by untagged YFP helped confirm that the 28 kDa protein was YFP-FLAG rather than a degradation product of dGBP1-TagBFP-FLAG.

In vivo data—In all in vivo experiments, biological replicates are defined in terms of cells, retinas or animals. Technical replicates are defined in terms of whole brain sections. The biological replicates are a sufficient sample size for demonstrating reproducibility of these findings. As an exception, 2 biological replicates were used for injection of green fluorescent beads/AAV mix into GFP and wildtype mouse brains. However, this was deemed sufficient as the results basically replicated previous findings in an equivalent experiment using a slightly different injection mix (FIG. 22). For statistical analysis, data consisting of 7-21 cells was used.

In Vivo Electroporation Experiments—

General information—Postnatal day 0 (P0) or P2 mouse pups were microinjected with plasmids into their subretinal space and subjected to electroporation (Matsuda and Cepko, 2004). Testing of dGBP1-TagBFP in vivo—1.33 µg/µl pCAG-dGBP1-TagBFP were injected into CD1 mice along with 1.33 µg/µl of pCAG-DsRed, pCAG-GFP or pRho-GFP. Electroporated CD1 retinas were harvested at P14, immunostained for anti-TagBFP antibodies in the far-red channel, and imaged by confocal microscopy.

Testing of αCA-dNb6mutx2-Flpo in vivo—0.33 µg/µl pCAG-αCA-dNb6mutx2-Flpo, 0.42 µg/µlpCAFNF-DsRed and 0.42 µg/µl pCAG-nlacZ were injected into CD1 retinas along with 0.5 µg/µl of either pCAG-C-CA or pCAG-GFP.

Electroporation of Tg(CRX-GFP) mice—A plasmid mixture, including 0.33 µg/µl pCAG dGBP1x2-Flpo, 0.49 µg/µl pCAFNF-DsRed and 0.66 µg/µl pCAG-nlacZ were injected into Tg(CRX-GFP) and wildtype littermates, with the person doing the injections blind to the genotype of injected pup. Electroporated retinas were harvested at P14.

Retinal Histology—Isolated mouse retinas were fixed at room temperature for 30 minutes in 4% paraformaldehyde (PFA)/phosphate buffered saline (PBS) solution. Retinas were then transferred to 30% sucrose in PBS, and subsequently into a 1:1 mixture of 30% sucrose/PBS and Optimal Cutting Temperature compound (OCT) for sectioning. 20 µm retinal cryosections were cut on a Leica CM3050 cryostat (Leica Microsystems).

Retinal immunohistochemistry: Retinal cryosections were incubated in blocking solution (3% normal goat serum, 1% BSA, 0.1% Triton-X, 0.02% SDS in PBS) for 1 hour and stained for primary antibody overnight at 4° C. Immunostained cryosections were washed three times in PBS and stained for secondary antibodies in blocking solution for 2 h at room temperature. Slides were then washed in PBS and mounted for imaging in Fluoromount-G (Southern Biotechnology Associates; 0100-01). Retinal section images were acquired on a Zeiss LSM780 confocal microscope, on a 40× oil immersion objective.

Analysis—Electroporated and immunostained retinas were quantified as 20 µm thick retinal cryosections imaged via confocal microscopy. Regions of dense electroporation were selected for quantification. Quantification approaches were described previously (Tang et al., 2013).

AAV production and injections—AAV (2/1) virus preparations were made from pAAV EF1α-dGBP1x2-Flpo-NW and pAAV-CAG-FLEXFRT-ChR2-mCherry. All AAVs were injected in the range of 1013-1014 genome copies/ml, assayed by PCR of AAV vectors at Boston Children's Hospital (Zhigang He lab). Primers targeted the ITR region of AAV vectors, and were:

```
Forward-
5'-GACCTTTGGTCGCCCGGCCT-3',

Reverse-
5'-GAGTTGGCCACTCCCTCTCTGC-3'
```

Brain Injections and Electrophysiology

Intracranial virus injection. For AAV infection of cerebella, Tg(GAD67-GFP) mice and GFP-negative littermates of either sex aged 3-4 weeks were anesthetized with ketamine/xylazine/acepromazine at 100, 2.5 and 3 mg per kg of body weight, respectively, and a continuous level of deep anesthesia was maintained with 5% isoflurane. A total volume of 200 nl of the following viral constructs: AAV-2/1-EF1α-dGBP1x2-Flpo-NW, AAV-2/1-FLEXFRT-ChR2 (H134R)-mCherry, AAV-2/8-ZsGreen (Tang et al., 2015) (GFP-negative mice only) were injected into cerebellar cortex using a stereotactic device. For some experiments, 20 nl of green fluorescent beads (Lumafluor) were injected instead of AAV 2/8-ZsGreen to monitor successful injection. 3 weeks later, brain tissue was fixed for immunohistochemistry, or prepared for electrophysiology.

Cerebellar histology. Mice were transcardially perfused with 4% PFA in PBS (pH=7.4) and the brains were post-fixed overnight at 4° C. in the same solution. Parasagittal vermal slices of the cerebellum were cut at 50 µm thickness on a Leica VT1000S vibratome. Slices were then mounted on Superfrost slides (VWR) using Prolong Diamond mounting medium (Invitrogen). Images were acquired with an Olympus FV1000 or FV1200 confocal microscope.

Slice preparation for electrophysiology. Mice were anaesthetized with ketamine/xylazine/acepromazine at 200, 5 and 6 mg per kg of body weight. Anaesthetized mice were intracardially perfused and processed to generate parasagittal cerebellar slices for electrophysiology as previous described (Tang et al., 2015).

Electrophysiological recordings. Slices were superfused with ~32° C. warm ACSF at a flow rate of ~3 ml/min in a recording chamber heated by an inline heater (Warner instruments). PCs were visualized using an Olympus BX51WI microscope equipped with differential interference contrast (DIC). GFP+ and ChR2-mCherry+ were imaged using a custom two-photon laser-scanning microscope with 750 nm illumination. Visually guided recordings were performed with ~2 MΩ (PCs) borosilicate glass pipettes (Sutter Instrument). The internal solution for voltage-clamp recordings contained the following (in mM): 140 cesium methanesulfonate, 15 HEPES, 0.5 EGTA, 2 TEA-Cl, 2 MgATP, 0.3 NaGTP, 10 phosphocreatine-tris2, and 2 QX 314-Cl (pH adjusted to 7.2 with CsOH). Recordings were performed with a 700B Axoclamp amplifier (Molecular Devices) and were controlled with custom software written in Matlab. ChR2-mCherry+ cells were excited using a 473 nm wavelength blue laser (OptoEngine) coupled through the excitation pathway of the microscope. Laser light was focused onto slices through a 40× water-immersion objective. Brief light pulses (0.5-1 ms) at an intensity of ~3-10 mW/mm2 evoked ChR2-mediated photocurrents. Light-evoked synaptic currents were blocked by bath application of the GABAA receptor blocker SR 95531 (Tocris). For cerebellar data, statistical significance was assessed with one-way ANOVA. Statistical significance was assumed when P<0.05.

Quantifications. To quantify the specificity of AAV-delivered dGBP1x2-Flpo in the brain, ChR2-mCherry+ cells were compared between GFP+ cells in Tg(GAD67-GFP) brains injected with AAV-EF1α-dGBP1x2-Flpo-NW and AAV-CAG-FLEXFRT-ChR2-mCherry, and ZsGreen+ cells in wildtype brains injected with AAV-EF1α-ZsGreen, AAV-EF1α-dGBP1x2-Flpo-NW and AAV-CAG-FLEXFRT-ChR2-mCherry. To further rule out the confounding effect of injecting AAV-ZsGreen into only the wildtype brains, the number of ChR2-mCherry+ cells were counted in Tg(GAD67-GFP) and wildtype whole brain sections that both were co-injected with green fluorescent beads (along with AAV-EF1α-dGBP1x2-Flpo-NW and AAV-CAG-FLEXFRT-ChR2-mCherry). Both approaches tested for the specificity of AAV-delivered dGBP1x2-Flpo.

CRISPR experiment: The human LoxP-LacZ cell line was obtained from Allele Biotech (SKU: ABP-RP-CLA-CLOXE), and cultured as instructed in the product manual. Cas9 activity was assessed by detecting βgal-expressing cells in wells transfected with pX330-dCC-Cas9 and either pCAG-C-CA or pCAG-GAPDH-AU1 control construct (simply called AU1 in the main text). In addition, pCAG-mCherry is included as a transfection marker. For X-gal staining, cells were fixed on ice with 0.5% Glutaraldehyde for 5 min. X-gal staining was performed as previously described. Cells were left at room temperature overnight for color development. Images were acquired by Keyence BZ9000 microscope. The number of mCherry+ and X-gal+ cells was quantified by Fiji software. The normalized Cas9 activity was calculated by dividing individual replicate values of specific conditions by the average number of X-gal+ cells induced by pX330-loxPgRNA alone.

HIV-1 Sensor Experiments:

Cell culture: ACH-2(Folks et al., 1989) or CEM cells were cultured with 10 nM Phorbol 12-myristate 13-acetate (PMA) in complete RPMI 1640 medium for three days prior to transfection (Folks et al., 1989; Fujinaga et al., 1995). $3 \times 10^6$ cells were seeded in 6 well plates. Cells were kept in the same medium after transfection for two days. A total of 2 µg DNA was transfected with X-tremeGene HP (Roche) into each well. TagBFP transfection mixtures consisted of 0.25 µg plasmids of either CAG-driven αCA-Nb-TagBFP, αCA1227 dNb6mut-TagBFP, or dGBP1-TagBFP, along with 1.75 µg pCAG-DsRed. TagRFP transfection mixtures consisted of 0.25 µg plasmids of either CAG-driven αCA-dNb6mut-TagRFP or C-CA along with 1.75 µg of pCAG-GFP. Cells were fixed in 4% PFA for 30 minutes at room temperature. Cells were washed twice with 2% heat-inactivated fetal calf serum in PBS, and finally re-suspended in PBS to be used for flow cytometry. For immunofluorescence with flow cytometry, cells were fixed and permeabilized using the CytoFix/CytoPerm kit (BD Biosciences). The antibody KC57-RD1 (6604667, Beckman Coulter), which recognizes the 24 kDa protein, also known as CA, of HIV-1 core antigen, was used to detect CA.

Analysis: Flow cytometry data were analyzed using FlowJo (FlowJo, LLC). Cells were gated to remove dead cells and doublets. DsRed+ gate was determined by comparison to PMS-stimulated but un-transfected ACH-2 and CEM samples. Stimulated ACH-2 and CEM cells transfected with only pCAG-DsRed and filler plasmids were used to determine TagBFP- or TagRFP-negative signals to be gated out of TagBFP+ or TagRFP+ population. Between 70-350 gated DsRed+ cells were analyzed per condition per experiment. The "% gated TagBFP cells given DsRed+ cell" parameter was determined by dividing the number of cells that were dual-positive for TagBFP and DsRed by the total number of gated DsRed cells and the "% gated TagRFP cells/transfected cell" parameter was determined by dividing TagBFP and GFP dual-positive cells by the total number of GFP+ cells. Fold induction was determined by dividing the total number of TagBFP+/DsRed+ or TagRFP+/GFP+ cells counted in ACH-2 cells by that counted in CEM cells. Two-tailed Mann-Whitney test assuming unequal variance was used for testing of statistical significance. $P<0.05$ is judged as statistically significant.

General Microscopy and Image Analysis—

General information—Images were analyzed and processed on Imaris (Bitplane), ImageJ (Schneider et al., 2012) and/or Adobe Photoshop software. Whenever possible, image settings were adjusted for saturation. Whenever samples were to be compared within an experiment, image settings and processing were kept constant. Imaris, Image J and/or Photoshop software were used for image processing and analysis. Images from in vivo electroporation were smoothened on Imaris using the median filter as 3×3×1 pixel dimension or on Photoshop using the blue function at 1 pixel. Image level was adjusted in Photoshop.

References for Example 6

Auslander, S., Stucheli, P., Rehm, C., Auslander, D., Hartig, J. S., and Fussenegger, M. (2014). A general design strategy for protein-responsive riboswitches in mammalian cells. Nat Methods 11, 1154-1160.

Banaszynski, L. A., Chen, L. C., Maynard-Smith, L. A., Ooi, A. G., and Wandless, T. J. (2006). A rapid, reversible, and tunable method to regulate protein function in living cells using synthetic small molecules. Cell 126, 995-1004.

Beier, K. T., Saunders, A., Oldenburg, I. A., Miyamichi, K., Akhtar, N., Luo, L., Whelan, S. P., Sabatini, B., and Cepko, C. L. (2011). Anterograde or retrograde transsynaptic labeling of CNS neurons with vesicular stomatitis virus vectors. Proc Natl Acad Sci USA 108, 15414-15419.

Caussinus, E., Kanca, O., and Affolter, M. (2012). Fluorescent fusion protein knockout mediated by anti-GFP nanobody. Nat Struct Mol Biol 19, 117-121.

Chalfie, M. (2009). GFP: Lighting up life. Proc Natl Acad Sci USA 106, 10073-10080.

Chalfie, M., Tu, Y., Euskirchen, G., Ward, W. W., and Prasher, D. C. (1994). Green fluorescent protein as a marker for gene expression. Science 263, 802-805.

Clouse, K. A., Powell, D., Washington, I., Poli, G., Strebel, K., Farrar, W., Barstad, P., Kovacs, J., Fauci, A. S., and Folks, T. M. (1989). Monokine regulation of human immunodeficiency virus-1 expression in a chronically infected human T cell clone. Journal of immunology (Baltimore, Md.: 1950) 142, 431-438.

Culler, S. J., Hoff, K G., and Smolke, C. D. (2010). Reprogramming cellular behavior with RNA controllers responsive to endogenous proteins. Science 330, 1251-1255.

De Meyer, T., Muyldermans, S., and Depicker, A. (2014). Nanobody-based products as research and diagnostic tools. Trends Biotechnol 32, 263-270.

DeFalco, J., Tomishima, M., Liu, H., Zhao, C., Cai, X., Marth, J. D., Enquist, L., and Friedman, J. M. (2001). Virus-assisted mapping of neural inputs to a feeding center in the hypothalamus. Science 291, 2608-2613.

Dymecki, S. M., Ray, R. S., and Kim, J. C. (2010). Mapping cell fate and function using recombinase-based intersectional strategies. Methods Enzymol 477, 183-213.

Ekstrand, M. I., Nectow, A. R., Knight, Z. A., Latcha, K. N., Pomeranz, L. E., and Friedman, J. M. (2014). Molecular profiling of neurons based on connectivity. Cell 157, 1230-1242.

Feil, R., Wagner, J., Metzger, D., and Chambon, P. 1345 (1997). Regulation of Cre recombinase activity by mutated estrogen receptor ligand-binding domains. Biochemical and biophysical research communications 237, 752-757.

Fenno, L. E., Mattis, J., Ramakrishnan, C., Hyun, M., Lee, S. Y., He, M., Tucciarone, J., Selimbeyoglu, A., Berndt, A., Grosenick, L., et al. (2014). Targeting cells with single vectors using multiple-feature Boolean logic. Nat Methods 11, 763-772.

Folks, T. M., Clouse, K. A., Justement, J., Rabson, A., Duh, E., Kehrl, J. H., and Fauci, A. S. (1989). Tumor necrosis factor alpha induces expression of human immunodeficiency virus in a chronically infected T-cell clone. Proc Natl Acad Sci USA 86, 2365-2368.

Fridy, P. C., Li, Y., Keegan, S., Thompson, M. K., Nudelman, I., Scheid, J. F., Oeffinger, M., Nussenzweig, M. C., Fenyo, D., Chait, B. T., et al. (2014). A robust pipeline for rapid production of versatile nanobody repertoires. Nat Methods 11, 1253-1260.

Fujinaga, K., Zhong, Q., Nakaya, T., Kameoka, M., Meguro, T., Yamada, K., and Ikuta, K. (1995). Extracellular Nef protein regulates productive HIV-1 infection from latency. Journal of immunology (Baltimore, Md.: 1950) 155, 5289-5298.

Gong, S., Zheng, C., Doughty, M. L., Losos, K., Didkovsky, N., Schambra, U. B., Nowak, N. J., Joyner, A., Leblanc, G., Hatten, M. E., et al. (2003). A gene expression atlas of the central nervous system based on bacterial artificial chromosomes. Nature 425, 917-925.

Greenberg, A. S., Avila, D., Hughes, M., Hughes, A., McKinney, E. C., and Flajnik, M. F. (1995). A new antigen receptor gene family that undergoes rearrangement and extensive somatic diversification in sharks. Nature 374, 168-173.

Gross, G. G., Junge, J. A., Mora, R. J., Kwon, H. B., Olson, C. A., Takahashi, T. T., Liman, E. R., Ellis-Davies, G. C., McGee, A. W., Sabatini, B. L., et al. (2013). Recombinant probes for visualizing endogenous synaptic proteins in living neurons. Neuron 78, 971-985.

Gurskaya, N. G., Fradkov, A. F., Terskikh, A., Matz, M. V., Labas, Y. A., Martynov, V. I., Yanushevich, Y. G., Lukyanov, K. A., and Lukyanov, S. A. (2001). GFP-like chromoproteins as a source of far-red fluorescent proteins. FEBS Lett 507, 16-20.

Hamers-Casterman, C., Atarhouch, T., Muyldermans, S., Robinson, G., Hamers, C., Songa, E. B., Bendahman, N., and Hamers, R. (1993). Naturally occurring antibodies devoid of light chains. Nature 363, 446-448.

Heintz, N. (2004). Gene expression nervous system atlas (GENSAT). Nat Neurosci 7, 483. Helma, J., Cardoso, M. C., Muyldermans, S., and Leonhardt, H. (2015). Nanobodies and recombinant binders in cell biology. J Cell Biol 209, 633-644.

Hsu, P. D., Lander, E. S., and Zhang, F. (2014). Development and 1380 applications of CRISPR-Cas9 for genome engineering. Cell 157, 1262-1278.

Irannejad, R., Tomshine, J. C., Tomshine, J. R., Chevalier, M., Mahoney, J. P., Steyaert, J., Rasmussen, S. G., Sunahara, R. K., El-Samad, H., Huang, B., et al. (2013) Conformational biosensors reveal GPCR signalling from endosomes. Nature 495, 534-538.

Iwamoto, M., Bjorklund, T., Lundberg, C., Kirik, D., and Wandless, T. J. (2010). A general chemical method to regulate protein stability in the mammalian central nervous system. Chem Biol 17, 981-988.

Kennedy, A. B., Vowles, J. V., d'Espaux, L., and Smolke, C. D. (2014). Protein-responsive ribozyme switches in eukaryotic cells. Nucleic Acids Res 42, 12306-12321.

Kirchhofer, A., Helma, J., Schmidthals, K., Frauer, C., Cui, S., Karcher, A., Pellis, M., Muyldermans, S., Casas-Delucchi, C. S., Cardoso, M. C., et al. (2010). Modulation of protein properties in living cells using nanobodies. Nat Struct Mol Biol 17, 133-138.

Kisselev, A. F., van der Linden, W. A., and Overkleeft, H. S. (2012). Proteasome inhibitors: an expanding army attacking a unique target. Chem Biol 19, 99-115.

Lo, L., and Anderson, D. J. (2011). A Cre-dependent, anterograde transsynaptic viral tracer for mapping output pathways of genetically marked neurons. Neuron 72, 938-950.

Luo, L., Callaway, E. M., and Svoboda, K. (2008). Genetic dissection of neural circuits. Neuron 57, 634-660.

Matsuda, T., and Cepko, C. L. (2004). Electroporation and RNA interference in the rodent retina in vivo and in vitro. Proc Natl Acad Sci USA 101, 16-22.

Matz, M. V., Fradkov, A. F., Labas, Y. A., Savitsky, A. P., Zaraisky, A. G., Markelov, M. L., and Lukyanov, S. A. (1999). Fluorescent proteins from non-bioluminescent Anthozoa species. Nat Biotechnol 17, 969-973.

Muyldermans, S. (2013). Nanobodies: natural single-domain antibodies. Annu Rev Biochem 82, 775-797.

Pivetta, C., Esposito, M. S., Sigrist, M., and Arber, S. (2014). Motor-circuit communication matrix from spinal cord to brainstem neurons revealed by developmental origin. Cell 156, 537-548.

Poli, G., Kinter, A., Justement, J. S., Kehrl, J. H., Bressler, P., Stanley, S., and Fauci, A. S. (1990). Tumor necrosis factor alpha functions in an autocrine manner in the induction of human immunodeficiency virus expression. Proc Natl Acad Sci USA 87, 782-785.

Raymond, C. S., and Soriano, P. (2007). High-efficiency 1413 FLP and PhiC31 site-specific recombination in mammalian cells. PLoS One 2, e162.

Rothbauer, U., Zolghadr, K., Muyldermans, S., Schepers, A., Cardoso, M C., and Leonhardt, H. (2008). A versatile nanotrap for biochemical and functional studies with fluorescent fusion proteins. Mol Cell Proteomics 7, 282-289.

Rothbauer, U., Zolghadr, K., Tillib, S., Nowak, D., Schermelleh, L., Gahl, A., Backmann, N., Conrath, K., Muyldermans, S., Cardoso, M. C., et al. (2006). Targeting and tracing antigens in live cells with fluorescent nanobodies. Nat Methods 3, 887-889.

Saito, H., Fujita, Y., Kashida, S., Hayashi, K., and Inoue, T. (2011). Synthetic human cell fate regulation by protein-driven RNA switches. Nat Commun 2, 160.

Samson, M., Emerson, M M., and Cepko, C. L. (2009). Robust marking of photoreceptor cells and pinealocytes with several reporters under control of the Crx gene. Dev Dyn 1425 238, 3218-3225.

Sander, J. D., and Joung, J. K. (2014). CRISPR-Cas systems for editing, regulating and targeting genomes. Nat Biotechnol 32, 347-355.

Schneider, C. A., Rasband, W. S., and Eliceiri, K. W. (2012). NIH Image to ImageJ: 25 years of image analysis. Nat Methods 9, 671-675.

Schwarz, L. A., Miyamichi, K., Gao, X. J., Beier, K. T., Weissbourd, B., DeLoach, K. E., Ren, J., Ibanes, S., Malenka, R. C., Kremer, E. J., et al. (2015). Viral-genetic tracing of the input-output organization of a central noradrenaline circuit. Nature 524, 88-92.

Siegert, S., Scherf, B. G., Del Punta, K., Didkovsky, N., Heintz, N., and Roska, B. (2009). Genetic address book for retinal cell types. Nat Neurosci 12, 1197-1204.

Subach, O. M., Gundorov, I. S., Yoshimura, M., Subach, F. V., Zhang, J., Gruenwald, D., Souslova, E. A., Chudakov, D. M., and Verkhusha, V. V. (2008). Conversion of red fluorescent protein into a bright blue probe. Chem Biol 15, 1116-1124.

Tamamaki, N., Yanagawa, Y., Tomioka, R., Miyazaki, J., Obata, K., and Kaneko, T. (2003). Green fluorescent protein expression and colocalization with calretinin, parvalbumin, and somatostatin in the GAD67-GFP knock-in mouse. J Comp Neurol 467, 60-79.

Tang, J. C., Rudolph, S., Dhande, O. S., Abraira, V. E., Choi, S., Lapan, S. W., Drew, I. R., Drokhlyansky, E., Huberman, A. D., Regehr, W. G., et al. (2015). Cell type-specific manipulation with GFP-dependent Cre recombinase. Nat Neurosci 18, 1334-1341.

Tang, J. C., Szikra, T., Kozorovitskiy, Y., Teixiera, M., Sabatini, B. 1445 L., Roska, B., and Cepko, C. L. (2013). A nanobody-based system using fluorescent proteins as scaffolds for cell-specific gene manipulation. Cell 154, 928-939.

Tsien, R. Y. (1998). The green fluorescent protein. Annu Rev Biochem 67, 509-544.

Wickersham, I. R., Lyon, D. C., Barnard, R. J., Mori, T., Finke, S., Conzelmann, K. K., Young, J. A., and Callaway, E. M. (2007). Monosynaptic restriction of transsynaptic tracing from single, genetically targeted neurons. Neuron 53, 639-647.

Wurch, T., Pierre, A., and Depil, S. (2012). Novel protein scaffolds as emerging therapeutic proteins: from discovery to clinical proof-of-concept. Trends Biotechnol.

Yee, J. K., Miyanohara, A., LaPorte, P., Bouic, K., Burns, J. C., and Friedmann, T. (1994). A general method for the generation of high-titer, pantropic retroviral vectors: highly efficient infection of primary hepatocytes. Proc Natl Acad Sci USA 91, 9564-9568.

SEQUENCE LISTING

MADVQLVESGGALVQPGGSLRLSCAASGFPVNR-YSMRWYRQAPGKEREWVAGMSSAGDRSSYEDSVK-GRFTISRDDARNTVYLQMNSLKPEDTAVYYSNVNV-GFEYWGQGTQVTVSS (SEQ ID NO: 1, wherein in some embodiments, the amino acid residue S at position 98 can be replaced by an amino acid residue C)

MAQVQLVESGGGLVQAGGSLRLSCAASGSFFMS-NVMAWYRQAPGKARELIAAIRGGDMS TVYDDSVK-GRFTITRDDDKNILYLQMNDLKPEDTAMYYCKASG-SSWGQGTQVTVSS (SEQ ID NO: 2, wherein in some embodiments, the amino acid residue C at position 98 can be replaced by an amino acid residue S)

What is claimed is:

1. A sensor system comprising a fusion protein molecule comprising at least one target ligand-binding recognition domain linked to an effector domain, wherein the target ligand-binding recognition domain is a nanobody, that specifically binds an intracellular target ligand and is configured such that
   (i) in the absence of the target ligand, the target ligand-binding recognition domain is destabilized and such that the fusion protein is destabilized and the effector domain is not active, or
   (ii) in the presence of the target ligand, the target ligand-binding recognition domain is stabilized upon binding of the target ligand, and the effector domain is active, wherein the nanobody has a framework region mutated at one or more sites consisting essentially of the sites corresponding to S73, S98 and S117 relative to wild-type nanobody corresponding to SEQ ID NO: 1 to one or more of S73R, S98Y and/or S117F relative to wild-type nanobody corresponding to SEQ ID NO: 1.

2. The sensor system of claim 1, wherein the target ligand is a polypeptide, a nucleic acid, or a combination thereof.

3. The sensor system of claim 1, wherein the effector domain is a protein, an enzyme, a nucleic acid, a therapeutic agent, a detectable agent, or a combination thereof.

4. The sensor system of claim 1, wherein the effector domain is a recombinase enzyme, a toxin, a DNA nuclease enzyme, or a fluorescent protein.

5. The sensor system of claim 1, wherein the target ligand-binding recognition domain is a nanobody against a GFP protein, a nanobody against HIV C-terminal domain (CTD) or a nanobody against dihydrofolate reductase.

6. The sensor system of claim 1, further comprising the target ligand.

7. The sensor system of claim 6, wherein the target ligand is an endogenous, intracellular target ligand.

8. An expression vector comprising a nucleotide sequence encoding the sensor system of claim 1, wherein nucleotide sequence encoding the nanobody is linked in frame to nucleotide sequence encoding the effector domain.

9. The expression vector of claim 8, wherein the nucleotide sequence encoding the nanobody is linked upstream to nucleotide sequence encoding the effector domain or downstream to nucleotide sequence encoding the effector domain.

10. A method of detecting an intracellular target ligand comprising:
   a. introducing to a cell the sensor system of claim 1;
   b. detecting a detectable signal of the effector domain of the sensor system; and
   c. determining the presence of an intracellular target ligand if a detectable signal of the effector domain is detected; or
   determining the absence of the intracellular target ligand if a detectable signal of the effector domain is not detected.

11. The method of claim 10, wherein the target ligand is a polypeptide, a nucleic acid, or a combination thereof.

12. A method for delivery of a therapeutic agent or pro-drug agent to a target cell in a subject comprising
   administering to a subject in need thereof a composition comprising the sensor system of claim 1, wherein the effector domain of the sensor system is a therapeutic agent or pro-drug agent; and the target ligand-binding recognition domain of the sensor system specifically binds an intracellular target ligand of a target cell to be treated,
   wherein:
   in a non-target cell without the target ligand, the target ligand-binding recognition domain is destabilized and such that the fusion protein is destabilized and the therapeutic agent or pro-drug agent is not active in the non-target cell, or
   in a target cell with the target ligand, the target ligand-binding recognition domain is stabilized upon binding of the target ligand, and the therapeutic agent or pro-drug agent is active in the target cell.

13. A system for genome editing comprising:
   a nucleic acid guide designed to be complementary to a target nucleic acid sequence to be cut; and
   a fusion protein molecule comprising:
   at least one target ligand-binding recognition domain linked to a nucleic acid-guided DNA endonuclease enzyme, wherein the target ligand-binding recognition domain is a nanobody, that specifically binds an intracellular target ligand and is configured such that
   (i) in the absence of the target ligand, the target ligand-binding recognition domain is destabilized and such that the fusion protein is destabilized and the DNA endonuclease enzyme is not active, or
   (ii) in the presence of the target ligand, the target ligand-binding recognition domain is stabilized upon binding of the target ligand, and the DNA endonuclease enzyme is active, wherein the nanobody has a framework region mutated at one or more sites consisting essentially of the sites corresponding to S73, S98 and S117 relative to wild-type nanobody corresponding to SEQ ID NO: 1 to one or more of S73R, S98Y and/or S117F relative to wild-type nanobody corresponding to SEQ ID NO: 1.

14. The system of claim 13, wherein the nucleic acid guide is RNA.

15. The system of claim 13, wherein the nucleic acid-guided endonuclease enzyme is CRISPR associated protein.

16. The system of claim 15, wherein the CRISPR associated protein is Cas9.

\* \* \* \* \*